(12) United States Patent
Cai et al.

(10) Patent No.: US 11,785,839 B2
(45) Date of Patent: Oct. 10, 2023

(54) ORGANIC LIGHT-EMITTING MATERIALS CONTAINING CYANO-SUBSTITUTED LIGAND

(71) Applicant: BEIJING SUMMER SPROUT TECHNOLOGY CO., LTD., Beijing (CN)

(72) Inventors: Wei Cai, Beijing (CN); Ming Sang, Beijing (CN); Chi Yuen Raymond Kwong, Beijing (CN); Chuanjun Xia, Beijing (CN); Zhen Wang, Beijing (CN); Tao Wang, Beijing (CN); Hongbo Li, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 639 days.

(21) Appl. No.: 16/750,282

(22) Filed: Jan. 23, 2020

(65) Prior Publication Data
US 2020/0251666 A1 Aug. 6, 2020

(30) Foreign Application Priority Data

Feb. 1, 2019 (CN) .......................... 201910077079.0

(51) Int. Cl.
| | | |
|---|---|---|
| H10K 85/00 | (2023.01) | |
| H10K 85/30 | (2023.01) | |
| C07F 15/00 | (2006.01) | |
| C07D 405/10 | (2006.01) | |
| C09K 11/06 | (2006.01) | |
| H10K 50/11 | (2023.01) | |

(52) U.S. Cl.
CPC ......... *H10K 85/342* (2023.02); *C07D 405/10* (2013.01); *C07F 15/0033* (2013.01); *C09K 11/06* (2013.01); *C09K 2211/1029* (2013.01); *C09K 2211/1088* (2013.01); *C09K 2211/185* (2013.01); *H10K 50/11* (2023.02)

(58) Field of Classification Search
CPC ............. H01L 51/0085; H01L 51/5012; H01L 51/5016; H01L 2251/5384; C07D 405/10; C07D 213/57; C07D 401/04; C07D 405/04; C07D 409/04; C07D 421/04; C07D 491/048; C07D 213/16; C07F 15/0033; C07F 7/0816; C09K 11/06; C09K 2211/1029; C09K 2211/1088; C09K 2211/185; Y02E 10/549; C07B 2200/05; H10K 85/342; H10K 50/11; H10K 2101/10; H10K 2101/90; H10K 85/30
USPC ........................................................ 428/690
See application file for complete search history.

(56) References Cited

U.S. PATENT DOCUMENTS

| | | |
|---|---|---|
| 5,703,436 A | 12/1997 | Forrest et al. |
| 5,707,745 A | 1/1998 | Forrest et al. |
| 5,844,363 A | 12/1998 | Gu et al. |
| 6,097,147 A | 8/2000 | Baldo et al. |
| 6,303,238 B1 | 10/2001 | Thompson et al. |
| 7,279,704 B2 | 10/2007 | Walters et al. |
| 7,968,146 B2 | 6/2011 | Wagner et al. |
| 8,946,697 B1 | 2/2015 | Ma et al. |
| 2003/0230980 A1 | 12/2003 | Forrest et al. |
| 2004/0121184 A1 | 6/2004 | Thompson et al. |
| 2004/0172116 A1 | 9/2004 | Seifert et al. |
| 2010/0244004 A1* | 9/2010 | Xia .................. C09K 11/06 546/4 |
| 2012/0292601 A1* | 11/2012 | Kottas .............. H01L 51/0085 546/4 |
| 2013/0181190 A1 | 7/2013 | Ma et al. |
| 2014/0175408 A1 | 6/2014 | Lin et al. |
| 2014/0231755 A1 | 8/2014 | Xia et al. |
| 2014/0252333 A1 | 9/2014 | Watanabe et al. |
| 2015/0137096 A1 | 5/2015 | Xia et al. |
| 2015/0171349 A1 | 6/2015 | Ma et al. |
| 2015/0236276 A1 | 8/2015 | Boudreault et al. |
| 2015/0315222 A1 | 11/2015 | Boudreault et al. |
| 2015/0349273 A1 | 12/2015 | Hung et al. |
| 2016/0049599 A1 | 2/2016 | Ma et al. |
| 2016/0079546 A1 | 3/2016 | Park et al. |
| 2016/0093815 A1 | 3/2016 | Ma et al. |
| 2016/0093816 A1 | 3/2016 | Ma et al. |

(Continued)

FOREIGN PATENT DOCUMENTS

| | | |
|---|---|---|
| CN | 1374315 A | 10/2002 |
| CN | 1646548 A | 7/2005 |

(Continued)

OTHER PUBLICATIONS

CAS reg. No. 2458812-89-8, Aug. 16, 2020. (Year: 2020).*
German First Office Action dated Jan. 29, 2021 received Feb. 3, 2021, for German Patent Application No. 102020101561.5 and its English translation.
Japanese First Office Action, dated Jan. 6, 2021 for Japanese Application No. 2020-011825 and its English translation.
Korean First Office Action, dated Sep. 13, 2021 for Korean Application No. 10-2020-0008644 and its English translation.

(Continued)

*Primary Examiner* — Douglas J Mc Ginty
(74) *Attorney, Agent, or Firm* — BARNES & THORNBURG LLP; Jeffrey R. Stone

(57) ABSTRACT

An organic light-emitting material containing cyano-substituted ligand is disclosed. The organic light-emitting material is a metal complex containing a cyano-substituted ligand, which can be used as a light-emitting material in a light-emitting layer of an organic electroluminescent device. These new complexes can provide better device performance, e.g., narrower full width at half maximum, lower voltage values, and higher quantum efficiency, and the like. An electroluminescent device and a compound formulation containing the metal complex, and a compound capable of being used to prepare the metal complex are also disclosed.

22 Claims, 2 Drawing Sheets

(56) References Cited

U.S. PATENT DOCUMENTS

| | | |
|---|---|---|
| 2016/0133860 A1 | 5/2016 | Boudreault et al. |
| 2016/0141522 A1 | 5/2016 | Ma et al. |
| 2016/0155963 A1 | 6/2016 | Hwang et al. |
| 2016/0359122 A1 | 12/2016 | Boudreault et al. |
| 2017/0084849 A1 | 3/2017 | Tsai et al. |
| 2017/0263872 A1 | 9/2017 | Ma et al. |
| 2017/0365801 A1 | 12/2017 | Margulies et al. |
| 2018/0019406 A1 | 1/2018 | Lee et al. |
| 2018/0026208 A1 | 1/2018 | Tsai et al. |
| 2018/0097185 A1 | 4/2018 | Su et al. |
| 2018/0102487 A1 | 4/2018 | Tsai et al. |
| 2018/0190914 A1 | 7/2018 | Tsai et al. |
| 2018/0254417 A1 | 9/2018 | Ma et al. |
| 2018/0287070 A1 | 10/2018 | Ji et al. |
| 2019/0245153 A1 | 8/2019 | Kottas et al. |
| 2020/0091442 A1 | 3/2020 | Cai et al. |
| 2021/0280802 A1* | 9/2021 | Wang ............... C07F 15/0033 |
| 2022/0162244 A1* | 5/2022 | Sang ............... H01L 51/0072 |
| 2022/0181560 A1* | 6/2022 | Wang ............... H01L 51/0085 |
| 2022/0259239 A1* | 8/2022 | Cai ............... H01L 51/0085 |
| 2023/0109178 A1* | 4/2023 | Dai ............... H10K 85/342 |
| | | 257/40 |

FOREIGN PATENT DOCUMENTS

| | | |
|---|---|---|
| CN | 102439019 A | 5/2012 |
| CN | 102898477 A | 1/2013 |
| CN | 103102371 A | 5/2013 |
| CN | 104419415 A | 3/2015 |
| CN | 105367606 A | 3/2016 |
| CN | 108164564 A | 6/2018 |
| EP | 1238981 A2 | 11/2002 |
| EP | 2730583 A1 | 5/2014 |
| JP | 2008069221 A | 3/2008 |
| JP | 2020066622 A | 4/2020 |
| JP | 6978105 B2 | 12/2021 |
| KR | 20170142949 A | 12/2017 |
| KR | 20180069860 A | 6/2018 |
| KR | 1020180069860 A | 6/2018 |
| KR | 102434251 B1 | 8/2022 |
| WO | 2003/084972 A1 | 10/2003 |
| WO | 2009/069442 A1 | 6/2009 |

OTHER PUBLICATIONS

Pawar, Ab et al., Cobalt-Catalyzed C—H Cyanation of (Hetero)arenes and 6-Arylpurines with N-Cyanosuccinimide as a New Cyanating Agent, Organic Letters, 2015年, vol. 17, pp. 660-663.

Tani, N et al., Antifungal activities of novel non-azole molecules against S. cerevisiae and C. albicans., European Journal of Medicinal Chemistry, 2012年, vol. 47, pp. 270-277.

Yalcin, E et al., Novel fluorene/fluorenone DNA and RNA binders as efficient non-toxic ds-RNA selective fluorescent probes, Tetrahedron, 2018年, vol. 74, pp. 535-543.

Office Action/Search Report issued by the Chinese Patent Office in application No. 201910077079.0, dated May 24, 2022. English translation attached.

Tang, et al., "Organic electroluminescent diodes", Appl. Phys. Letter, 51, 913(1987), pp. 913-915.

Joyama, et al., "Highly efficient organic light-emitting diodes from delayed fluorescence", Nature, vol. 492, Dec. 13, 2012, pp. 234-239.

Chinese Office Action, dated Dec. 26, 2022, for Chinese Application No. 201910077079.0.

English translation of Chinese Office Action, dated Dec. 26, 2022, for Chinese Application No. 201910077079.0.

Japanese Office Action, dated Oct. 11, 2022, for Japanese Application No. 2021-179210.

English translation of Japanese Office Action, dated Oct. 11, 2022, for Japanese Application No. 2021-179210.

Korean Office Action, dated Mar. 23, 2023, for Korean Application No. 10-2022-0100661.

English translation of Korean Office Action, dated Mar. 23, 2023, for Korean Application No. 10-2022-0100661.

* cited by examiner

ORGANIC LIGHT-EMITTING MATERIALS CONTAINING CYANO-SUBSTITUTED LIGAND

TECHNICAL FIELD

The present disclosure relates to a compound for using in an organic electronic device, such as an organic light-emitting device. In particular, it relates to a metal complex containing a cyano-substituted ligand, and an electroluminescent device and a compound formulation containing the metal complex.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. The present disclosure laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

Cyano substitution is not often introduced into phosphorescent metal complexes, such as iridium complexes. US20140252333A1 discloses a series of iridium complexes substituted with cyano-phenyl, and as a result, the effect brought by the cyano group is not clearly indicated. In addition, since the cyano group is a very electron-withdrawing substituent, it is also used to blue-shift the emission spectrum of phosphorescent metal complexes, such as disclosed in US20040121184A1.

SUMMARY

The present disclosure aims to provide a series of technical solutions to solve at least part of the above problems.

One object of the present disclosure is to provide a metal complex comprising a ligand $L_a$ represented by Formula 1:

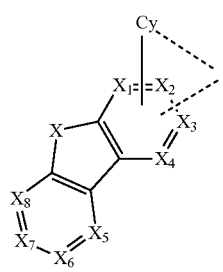

Formula 1 wherein, Cy is a substituted or unsubstituted aryl or heteroaryl group having 5 to 24 ring atoms;

wherein, Cy is connected to a metal through a metal-carbon bond or a metal-nitrogen bond;

wherein, $X_1$ to $X_4$ are each independently selected from C, $CR_{x1}$ or N, and at least one of $X_1$ to $X_4$ is C and connected to Cy; when more than one of $X_1$ to $X_4$ is $CR_{x1}$, the $R_{x1}$ may be the same or different;

wherein, $X_5$ to $X_8$ are each independently selected from $CR_{x2}$ or N; when more than one of $X_5$ to $X_8$ is $CR_{x2}$, the $R_{x2}$ may be the same or different;

wherein, X is selected from the group consisting of O, S, Se, $NR_{x3}$, $CR_{x4}R_{x5}$ and $SiR_{x6}R_{x7}$;

wherein, $R_{x1}$, $R_{x2}$, $R_{x3}$, $R_{x4}$, $R_{x5}$, $R_{x6}$ and $R_{x7}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

wherein, at least one of $R_{x1}$ and $R_{x2}$ is a cyano group;

any two adjacent substituents can optionally be joined to form a ring;

$X_1$, $X_2$, $X_3$ or $X_4$ is connected to the metal through a metal-carbon bond or a metal-nitrogen bond.

A second object of the present disclosure is to provide an electroluminescent device, which includes an anode, a cathode, and an organic layer disposed between the anode and the cathode, wherein the organic layer comprises the metal complex according to the first object of the present disclosure.

A third object of the present disclosure is to provide a compound formulation, which comprises the metal complex according to the first object of the present disclosure.

A fourth object of the present disclosure is to provide a compound that can be used for preparing the metal complex according to the first object of the present disclosure.

The novel metal complex having a cyano-substituted ligand disclosed by the present disclosure can be used as a light-emitting material in an electroluminescent device. When used in electroluminescent devices, these novel compounds can provide better device performance, e.g., narrower full width at half maximum, lower voltage values, and higher quantum efficiency, and the like.

The present invention discloses a series of novel cyano-substituted metal complexes which unexpectedly show many characteristics, such as high efficiency, low voltage, and no obvious blue-shifted or red-shifted luminescence. The most unexpected is that they have a very narrow peak width of emitted light. These advantages will greatly help to improve the level and color saturation of green light devices.

DETAILED DESCRIPTION

Figure 1:
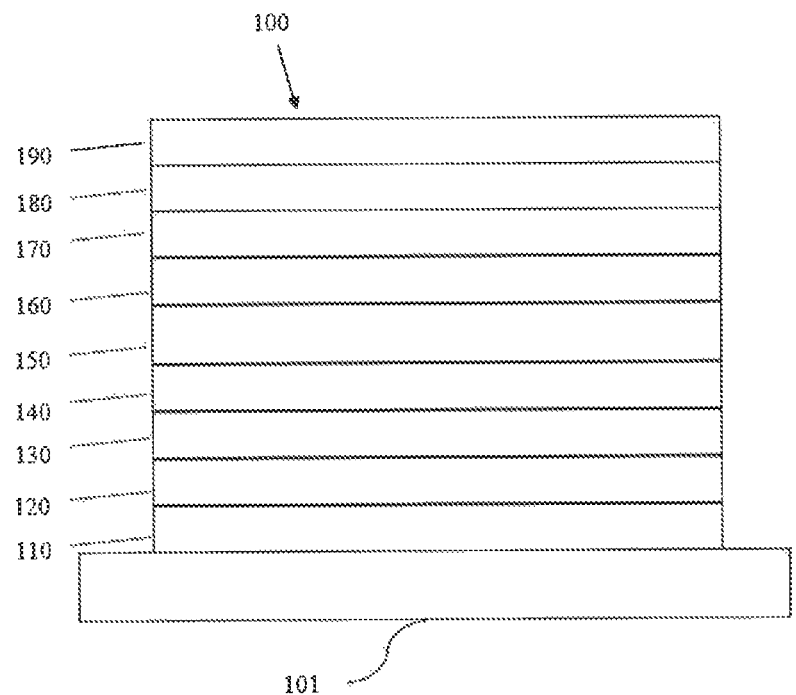
FIG. 1 is a schematic diagram of an organic light-emitting device that may contain a metal complex and a compound formulation disclosed herein.

OLEDs can be fabricated on various types of substrates such as glass, plastic, and metal foil. FIG. 1 schematically shows the organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
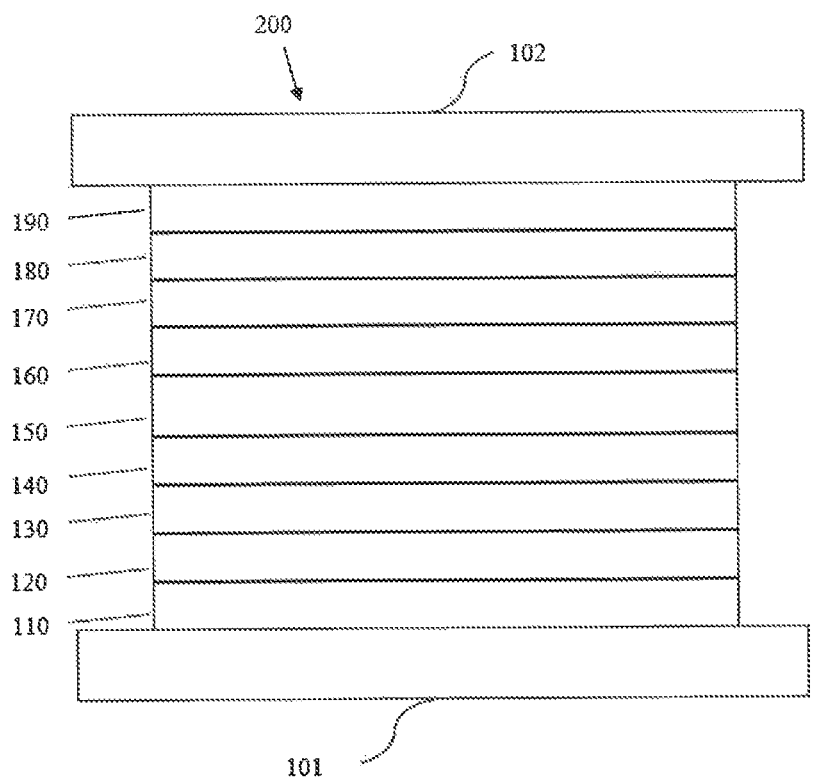
FIG. 2 is a schematic diagram of another organic light-emitting device that may contain a metal complex and a compound formulation disclosed herein.
Figure 3:
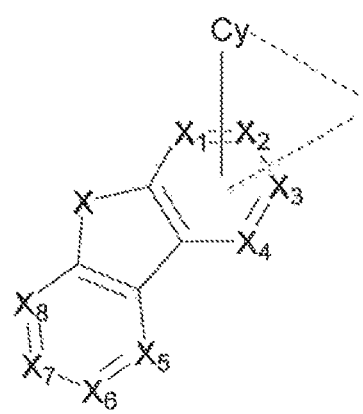
FIG. 3 is a diagram showing a ligand $L_a$ represented by Formula 1 as disclosed herein.

An OLED can be encapsulated by a barrier layer. FIG. 2 schematically shows the organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass and organic-inorganic hybrid layers. The barrier layer should be placed directly or indirectly outside of the OLED device. Multilayer thin film encapsulation was described in U.S. Pat. No. 7,968,146, which is herein incorporated by reference in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, and 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing 2 to 15 carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing 2 to 15 carbon atoms. Additionally, the alkynyl group may be optionally substituted.

Aryl or aromatic group—as used herein includes noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein includes aromatic and non-aromatic cyclic groups. Heteroaromatic also means heteroaryl. Preferred non-aromatic heterocyclic groups are those containing 3 to 7 ring atoms which include at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein includes noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

The alkyl, cycloalkyl, alkenyl, alkynyl, arylalkyl, heterocyclic group, aryl, and heteroaryl may be unsubstituted or may be substituted with one or more substituents selected from the group consisting of deuterium, halogen, alkyl, cycloalkyl, arylalkyl, alkoxy, aryloxy, amino, cyclic amino, silyl, alkenyl, cycloalkenyl, heteroalkenyl, alkynyl, aryl, heteroaryl, an acyl group, a carbonyl group, a carboxylic acid group, an ether group, an ester group, a nitrile group, an isonitrile group, a thioalkyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions. When a substitution in the compounds mentioned in this disclosure represents multiple substitutions (including di, tri, tetra substitutions etc.), that means the substituent may exist at a plurality of available substitution positions on its linking structure, the substituents present at a plurality of available substitution positions may be the same structure or different structures.

In the compounds mentioned in this disclosure, the expression that adjacent substituents can be optionally joined to form a ring is intended to be taken to mean that two radicals are linked to each other by a chemical bond. This is illustrated by the following scheme:

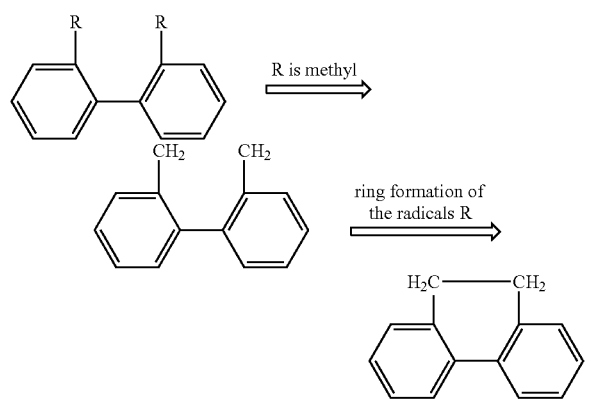

Furthermore, the expression that adjacent substituents can be optionally joined to form a ring is also intended to be taken to mean that in the case where one of the two radicals represents hydrogen, the second radical is bonded at a position to which the hydrogen atom was bonded, with formation of a ring. This is illustrated by the following scheme:

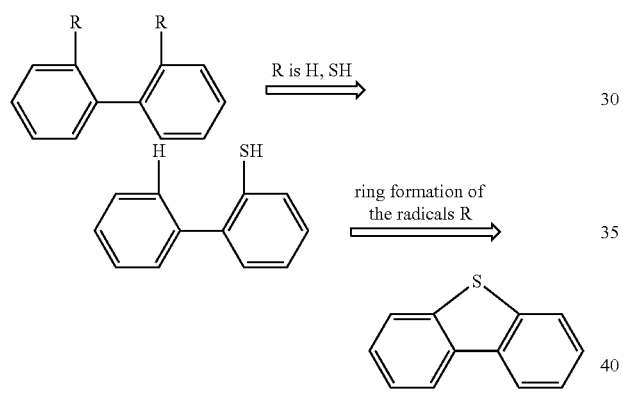

According to an embodiment of the present disclosure, a metal complex having a $L_a$ ligand is disclosed, wherein $L_a$ comprises a structure represented by Formula 1:

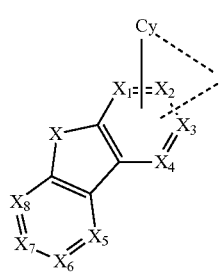

Formula 1 wherein, Cy is a substituted or unsubstituted aryl or heteroaryl group having 5 to 24 ring atoms;

wherein, Cy is bonded to a metal through a metal-carbon bond or a metal-nitrogen bond;

wherein, $X_1$ to $X_4$ are each independently selected from C, $CR_{x1}$ or N, and at least one of $X_1$ to $X_4$ is C and connected to Cy; when more than one of $X_1$ to $X_4$ is $CR_{x1}$, the $R_{x1}$ may be the same or different;

wherein, $X_5$ to $X_8$ are each independently selected from $CR_{x2}$ or N; when more than one of $X_5$ to $X_8$ is $CR_{x2}$, the $R_{x2}$ may be the same or different;

X is selected from the group consisting of O, S, Se, $NR_{x3}$, $CR_{x4}R_{x5}$ and $SiR_{x6}R_{x7}$;

wherein, $R_1$, $R_{x2}$, $R_{x3}$, $R_{x4}$, $R_{x5}$, $R_{x6}$ and $R_{x7}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

wherein, at least one of $R_{x1}$ and $R_{x2}$ is a cyano group;

any two adjacent substituents can optionally be joined to form a ring;

$X_1$, $X_2$, $X_3$ or $X_4$ is connected to the metal through a metal-carbon bond or a metal-nitrogen bond.

According to an embodiment of the present disclosure, Cy is any structure selected from the group consisting of:

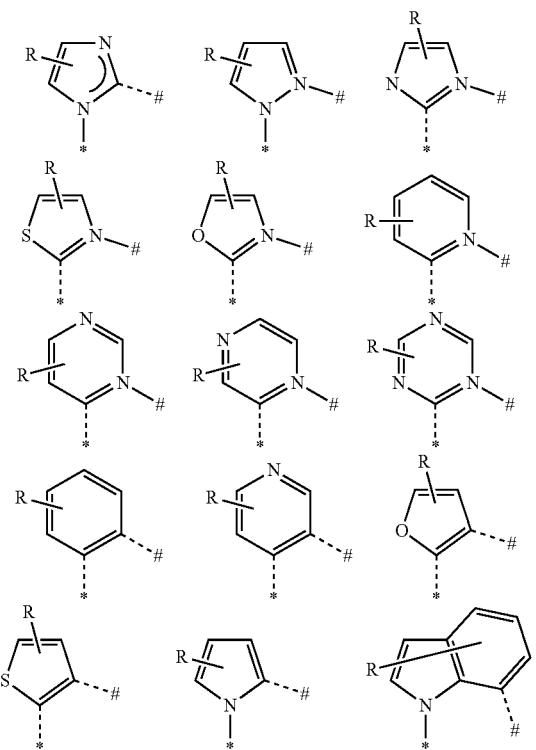

-continued

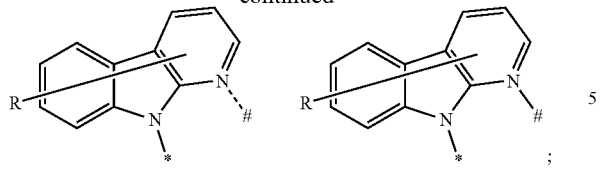

wherein

R may represent mono-substitution, up to the maximum available multi-substitution, or no substitution; when more than one R exists in any of the above structures, the R may be the same or different;

wherein, R is independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

any two adjacent substituents can optionally be joined to form a ring;

wherein, "#" represents a position at which the metal is connected, and "*" represents a position at which $X_1$, $X_2$, $X_3$ or $X_4$ is connected.

According to an embodiment of the present disclosure, the metal complex has a general formula of $M(L_a)_m(L_b)_n(L_c)_q$, wherein $L_a$ is a first ligand coordinated to the metal M, and $L_b$ and Lc are a second ligand and a third ligand coordinated to the metal M, respectively, wherein $L_b$ and Le may be the same or different; $L_a$, $L_b$ and $L_c$ can optionally be linked to form a multidentate ligand;

wherein, m is 1, 2 or 3, n is 0, 1 or 2, q is 0, 1 or 2, and m+n+q is equal to the oxidation state of M;

wherein, the metal M is selected from the group consisting of Cu, Ag, Au, Ru, Rh, Pd, Os, Ir, and Pt; preferably, wherein, the metal M is selected from Pt, Os or Ir;

wherein, $L_a$ is independently selected from the group consisting of:

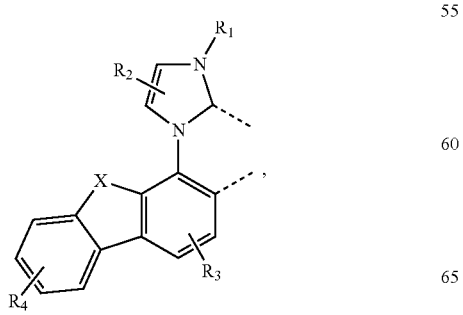

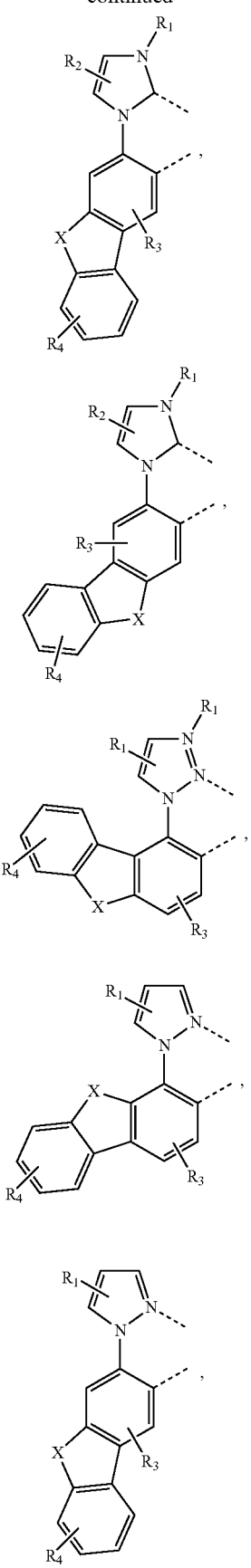

-continued
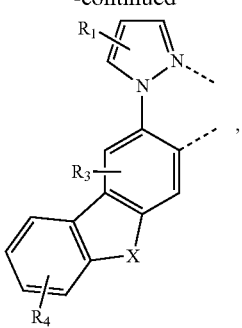
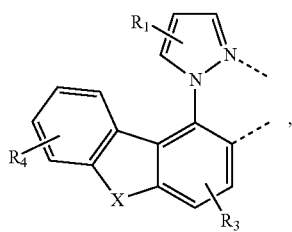
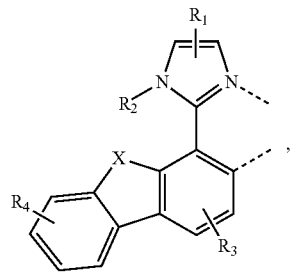
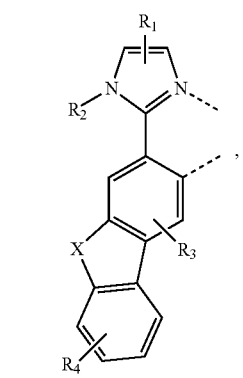
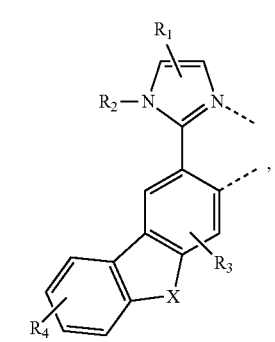
-continued
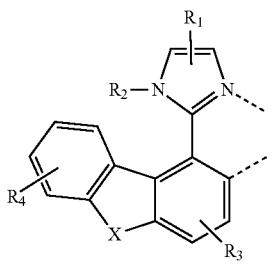
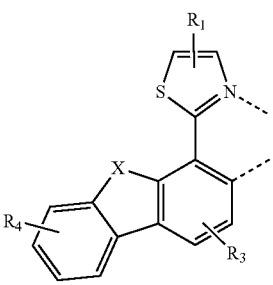
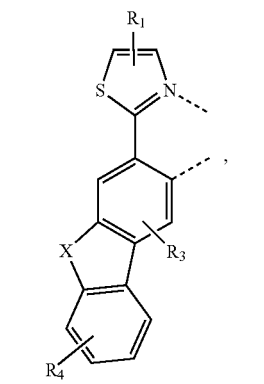
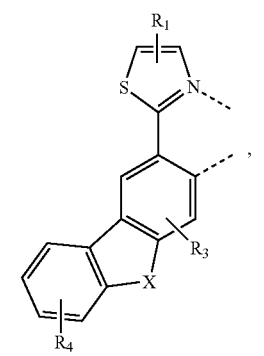
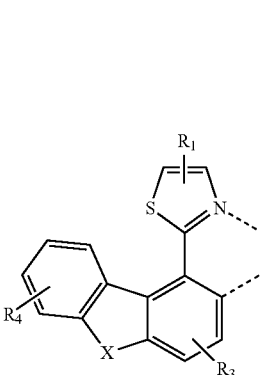

-continued
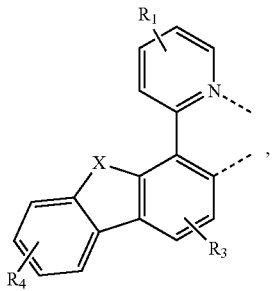
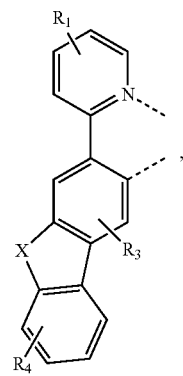
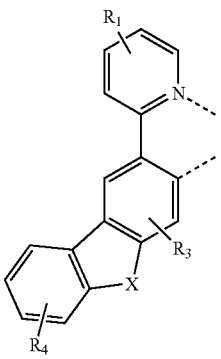
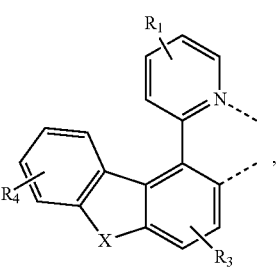
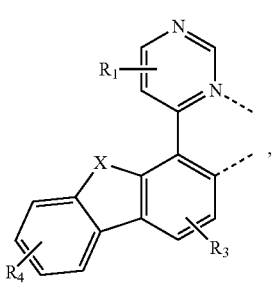
-continued
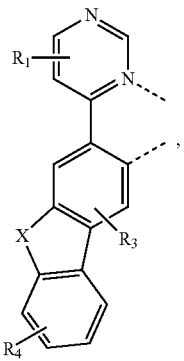
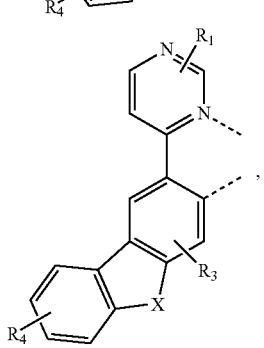
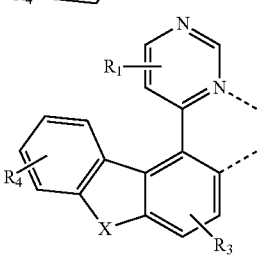
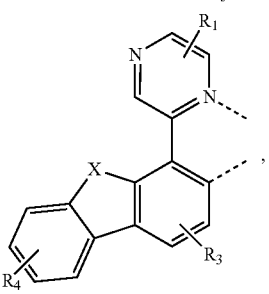
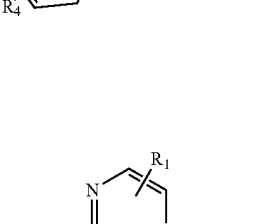
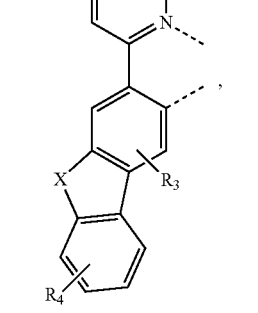

-continued
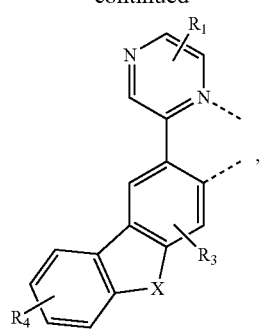
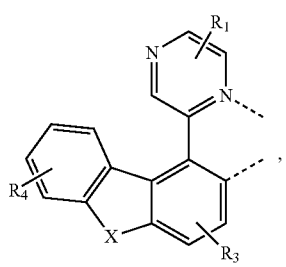
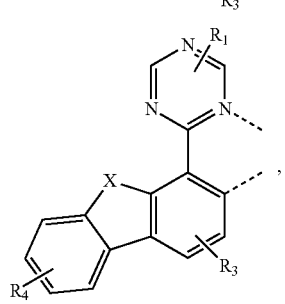
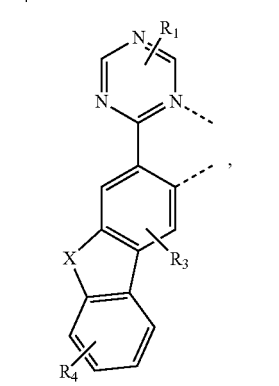
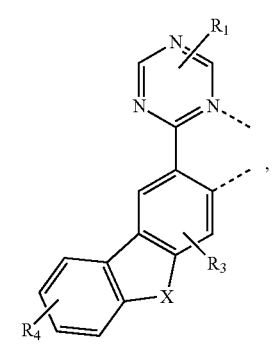
-continued
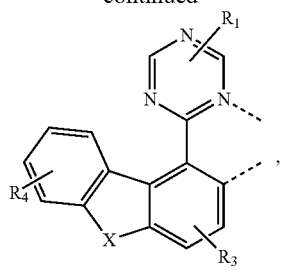
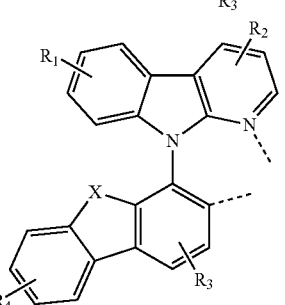
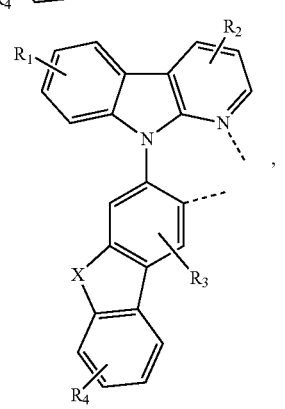
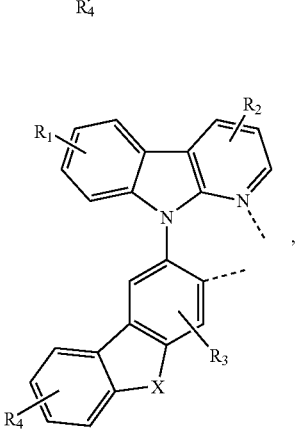
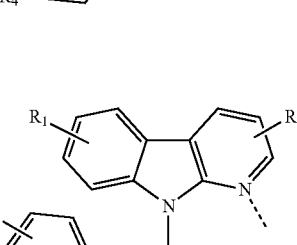

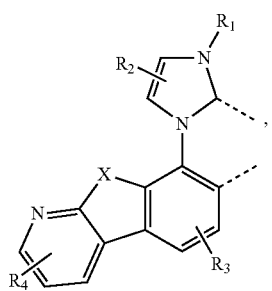
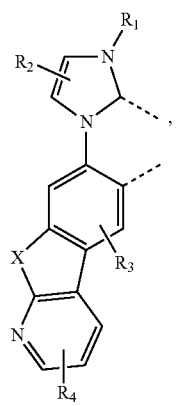
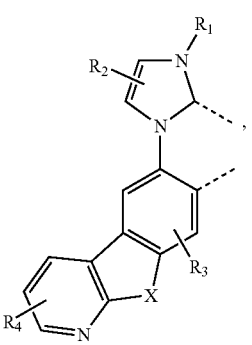
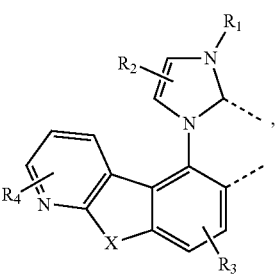
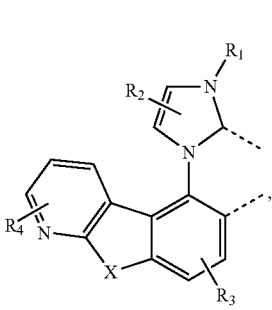
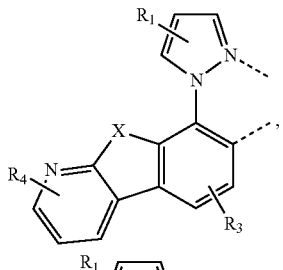
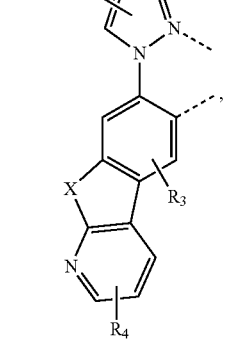
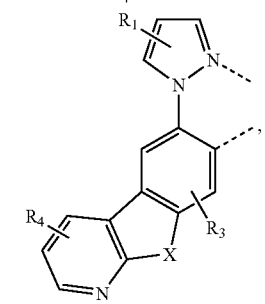
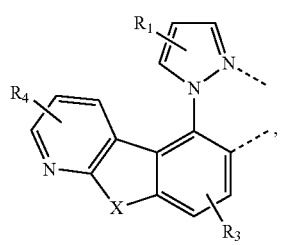
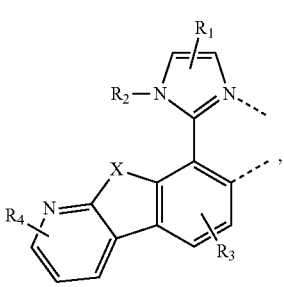

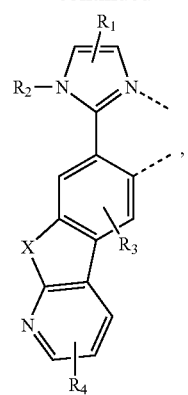
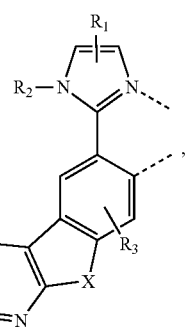
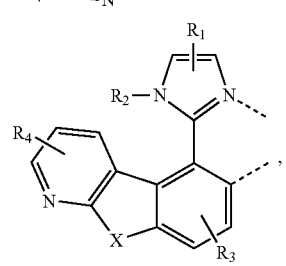
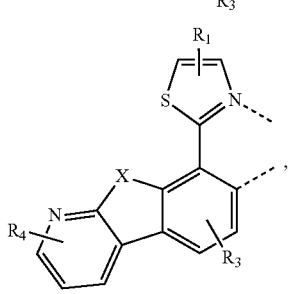
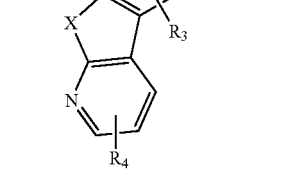
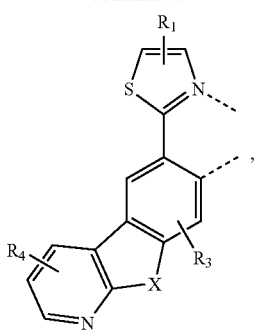
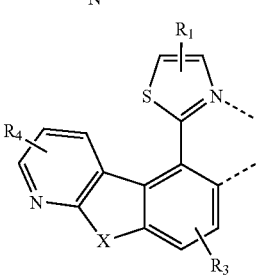
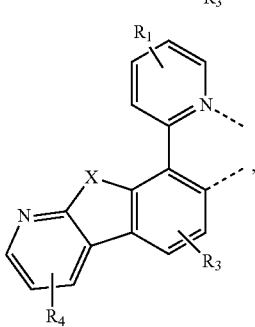
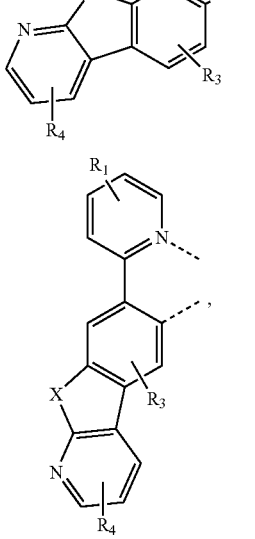
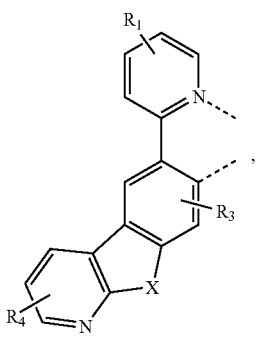

-continued
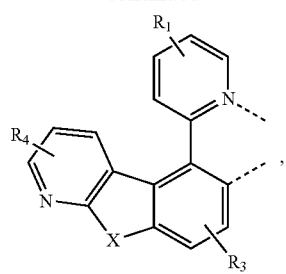
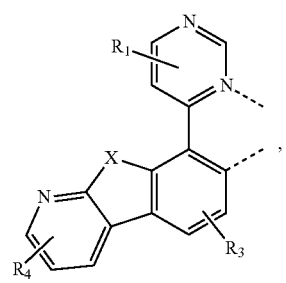
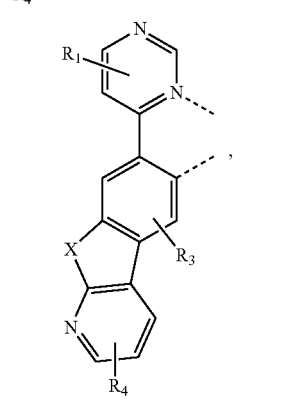
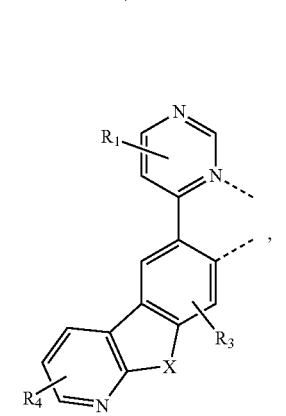
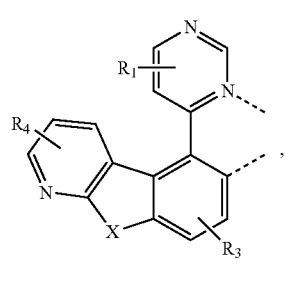
-continued
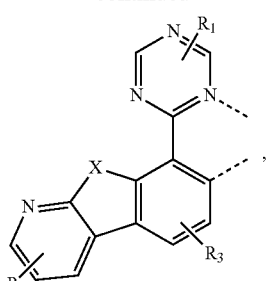
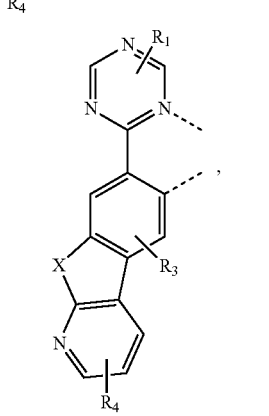
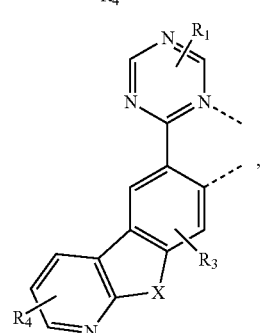
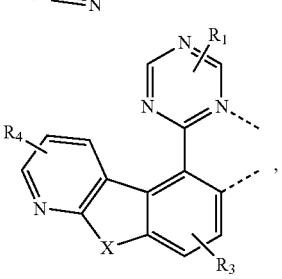
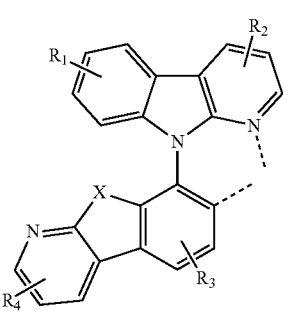

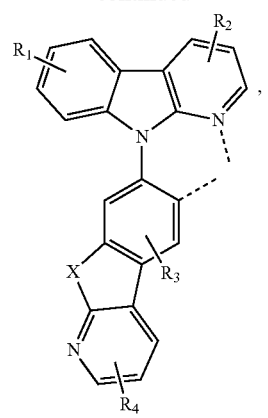
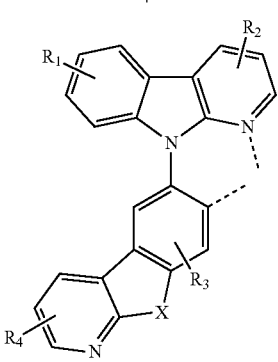
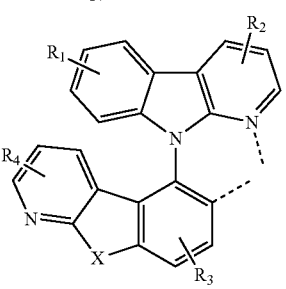
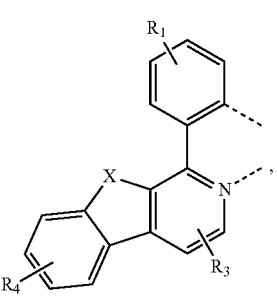
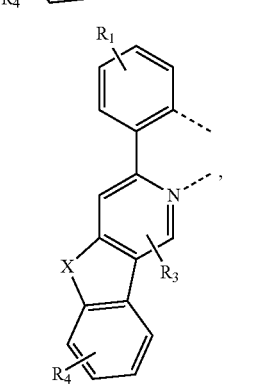
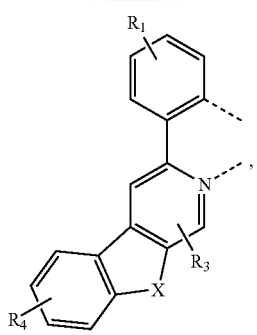
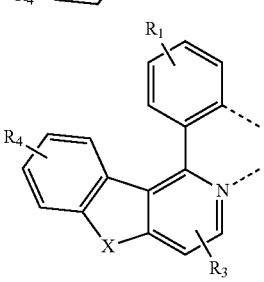
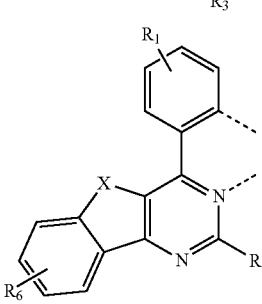
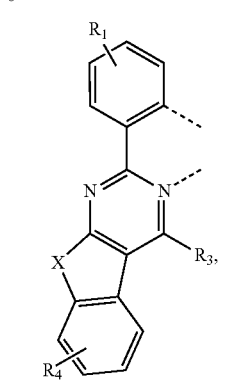
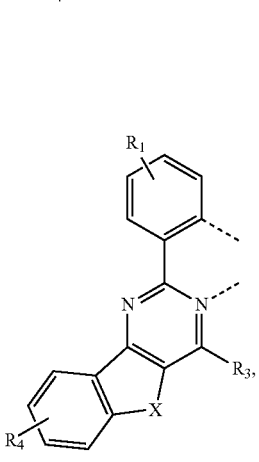

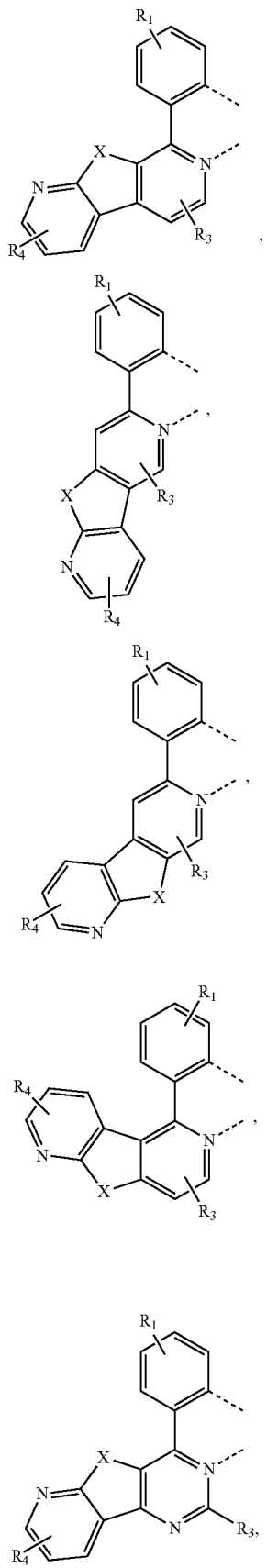

wherein, in the structure of $L_a$,

X is selected from the group consisting of O, S, Se, N, $CR_{x4}R_{x5}$ and $SiR_{x6}R_{x7}$;

$R_1$, $R_2$, $R_3$ and $R_4$ may represent mono-, di-, tri- or tetra-substitution, or no substitution;

$R_1$, $R_2$, $R_3$, $R_4$, $R_{x3}$, $R_{x4}$, $R_{x5}$, $R_{x6}$ and $R_{x7}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

wherein, at least one of $R_3$ and $R_4$ is a cyano group;

any two adjacent substituents can optionally be joined to form a ring;

wherein, $L_b$ and $L_c$ are independently selected from the group consisting of:

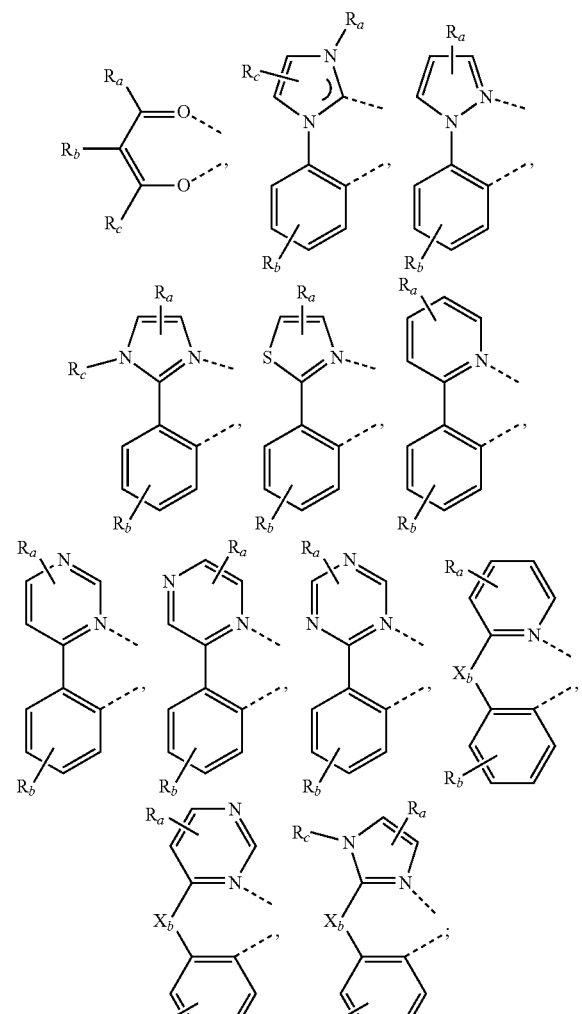

wherein $R_a$, $R_b$, and $R_c$ may represent mono-, di-, tri- or tetra-substitution, or no substitution;

$X_b$ is selected from the group consisting of: O, S, Se, $NR_{N1}$, and $CR_{C1}R_{C2}$;

$R_a$, $R_b$, $R_c$, $R_{N1}$, $R_{C1}$ and $R_{C2}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

any two adjacent substituents can optionally be joined to form a ring.

According to an embodiment of the present disclosure, in the structural formula of the ligand $L_a$, X is selected from 0, S or Se.

According to an embodiment of the present disclosure, the metal complex has any one of the structures according to Formula 2 to Formula 10:

Formula 2

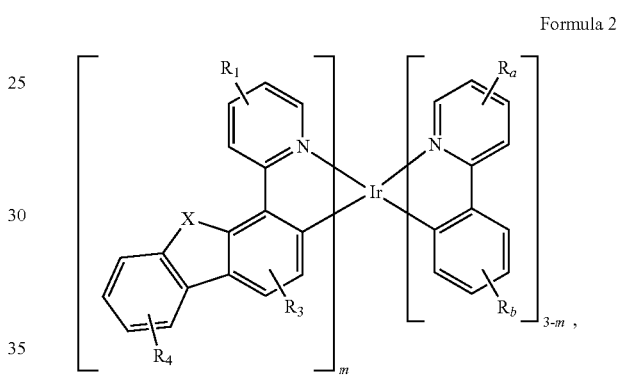

Formula 3

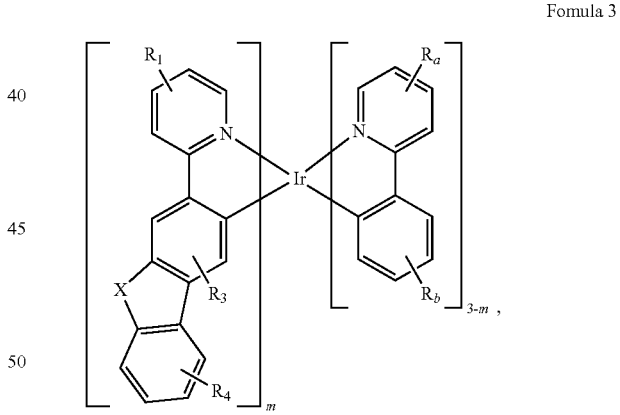

Formula 4

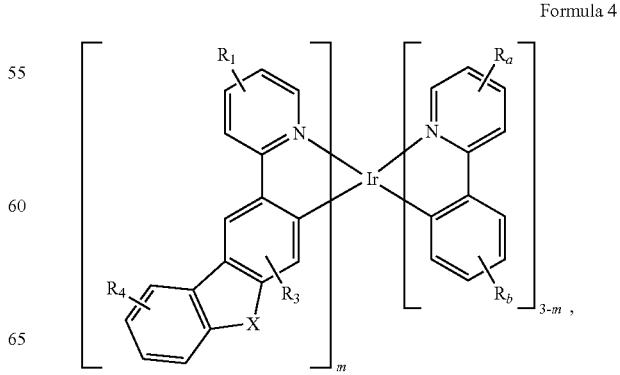

Formula 5
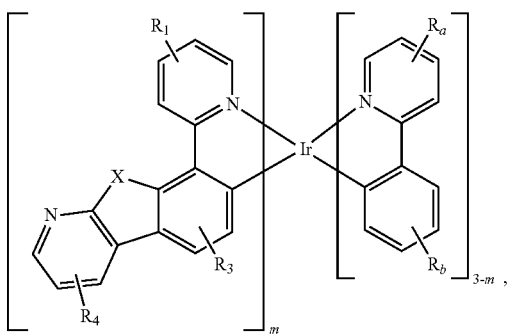

Formula 6
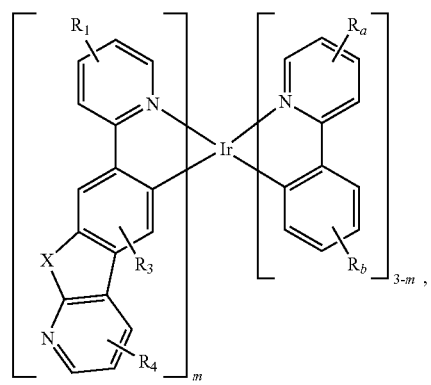

Formula 7
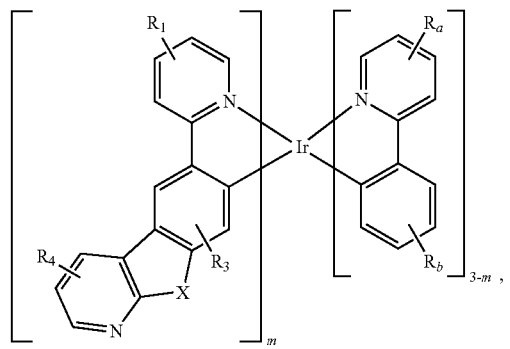

Formula 8
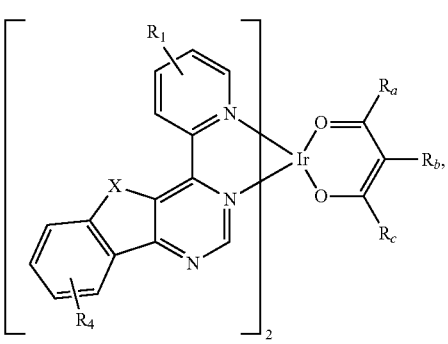

Formula 9
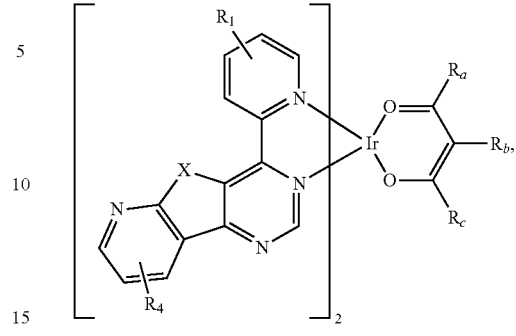

Formula 10
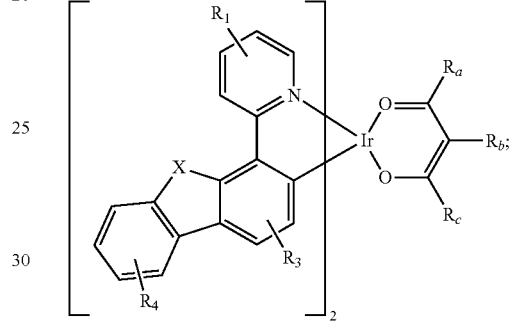

wherein m is 1, 2 or 3;

X is selected from O, S or Se;

$R_1$, $R_3$, and $R_4$ may represent mono-, di-, tri- or tetra-substitution, or no substitution;

$R_a$, $R_b$, and $R_c$ may represent mono-, di-, tri- or tetra-substitution, or no substitution;

$R_1$, $R_3$, $R_4$, $R_a$, $R_b$ and $R_c$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

wherein, at least one of $R_3$ and $R_4$ is a cyano group;

any two adjacent substituents can optionally be joined to form a ring.

According to an embodiment of the present disclosure, the metal complex has the structure of Formula 2-a:

Formula 2-a

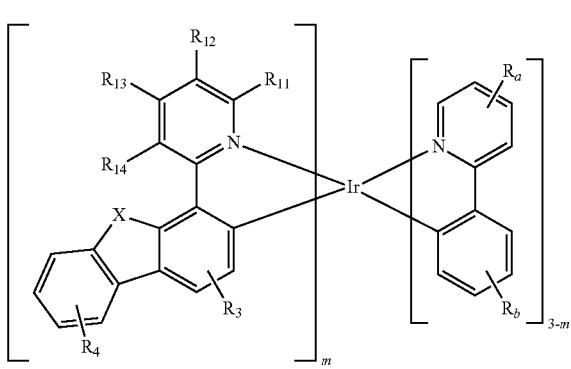

wherein, m is 1, 2 or 3;

X is selected from O, S or Se;

$R_3$ and $R_4$ may represent mono-, di-, tri- or tetra-substitution, or no substitution;

$R_a$, $R_b$, and $R_c$ may represent mono-, di-, tri- or tetra-substitution, or no substitution;

wherein, $R_{11}$, $R_{12}$, $R_{13}$, $R_{14}$, $R_3$, $R_4$, $R_a$, and $R_b$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

wherein, at least one of $R_3$ and $R_4$ is a cyano group;

any two adjacent substituents can optionally be joined to form a ring.

According to an embodiment of the present disclosure, when at least one of $R_{11}$, and $R_{14}$ in Formula 2-a is not hydrogen, $R_{12}$ and $R_{13}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof.

According to an embodiment of the present disclosure, when $R_{11}$ and $R_{14}$ in Formula 2-a are both hydrogen, $R_{12}$ and $R_{13}$ are each independently selected from the group consisting of hydrogen, deuterium, halogen, a substituted or unsubstituted alkyl group having 1-20 carbon atoms, a substituted or unsubstituted heteroalkyl group having 1-20 carbon atoms, a substituted or unsubstituted alkoxy group having 1-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof; and the total number of carbon atoms in $R_{12}$ and $R_{13}$ is less than or equal to 1.

According to an embodiment of the present disclosure, at least one of $X_5$ to $X_8$ in the Formula 1 is $CR_{x2}$, and the $R_{x2}$ is a cyano group.

According to an embodiment of the present disclosure, $X_5$ to $X_8$ in the Formula 1 are each independently selected from $CR_{x2}$, and at least one of the $R_{x2}$ is a cyano group.

According to an embodiment of the present disclosure, $R_4$ may represent mono-, di-, tri- or tetra-substitution; when more than one $R_4$ exists, the $R_4$ may be the same or different; $R_4$ is selected from the group consisting of deuterium, halogen, a substituted or unsubstituted alkyl group having 1-20 carbon atoms, a substituted or unsubstituted cycloalkyl group having 3-20 ring carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a cyano group, and combinations thereof; and at least one $R_4$ is a cyano group.

According to an embodiment of the present disclosure, the ligand $L_a$ is selected from the group consisting of $L_{a1}$ to $L_{a575}$. The specific structures of $L_{a1}$ to $L_{a575}$ are described in claim 8.

According to an embodiment of the present disclosure, the ligand $L_a$ is selected from the group consisting of $L_{a1}$ to $L_{a957}$. The specific structures of $L_a$ to $L_{a957}$ are described in claim 8.

According to an embodiment of the present disclosure, the hydrogen in $L_a$ can be partially or fully deuterated.

According to an embodiment of the present disclosure, the hydrogen on the aryl group in $L_a$ can be partially or fully deuterated.

According to an embodiment of the present disclosure, the hydrogen on the alkyl group in $L_a$ can be partially or fully deuterated.

According to an embodiment of the present disclosure, the hydrogen in $L_a$ can be partially or fully deuterated, and the ligand $L_a$ is selected from the group consisting of $L_{a958}$ to $L_{a1019}$, wherein the specific structures of $L_{a958}$ to $L_{a1019}$ are described in claim 10.

According to an embodiment of the present disclosure, the metal complex has the Formula $IrL_a(L_b)_2$ or $Ir(L_a)_2L_b$, wherein $L_a$ is one or two selected from $L_a$ to $L_{a575}$, and $L_b$ is one or two selected from the group consisting of $L_{b1}$-$L_{b41}$, wherein the specific structures of $L_{b1}$-$L_{b41}$ are described in claim 11.

According to an embodiment of the present disclosure, the metal complex has the Formula $IrL_a(L_b)_2$ or $Ir(L_a)_2L_b$, wherein $L_a$ is one or two selected from $L_{a1}$ to $L_{a1019}$, and $L_b$ is one or two selected from the group consisting of:
$L_{b1}$
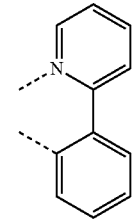
$L_{b2}$
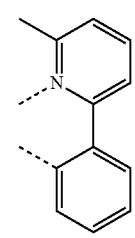
$L_{b3}$
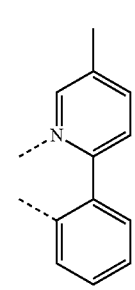
$L_{b4}$
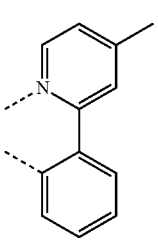
$L_{b5}$
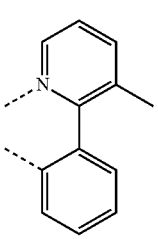
$L_{b6}$
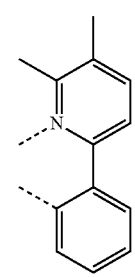
-continued
$L_{b7}$
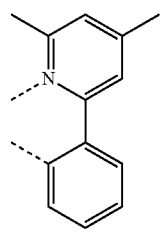
$L_{b8}$
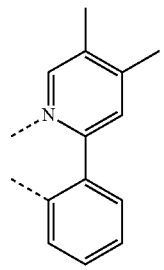
$L_{b9}$
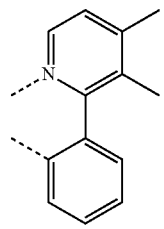
$L_{b10}$
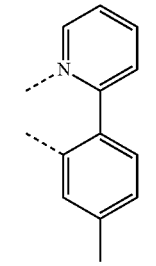
$L_{b11}$
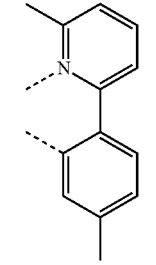
$L_{b12}$
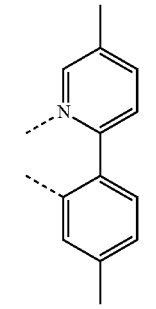

L_b13 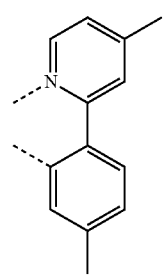
L_b14 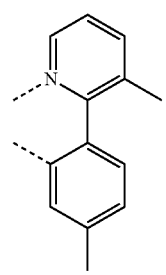
L_b15 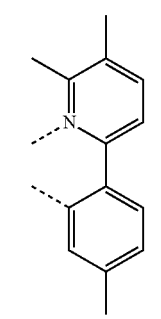
L_b16 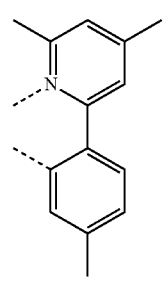
L_b17 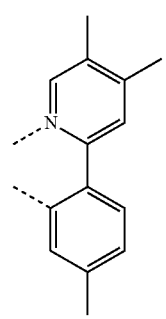
L_b18 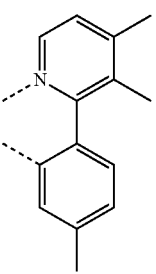
L_b19 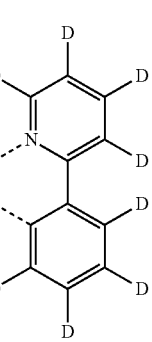
L_b20 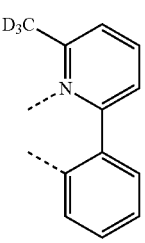
L_b21 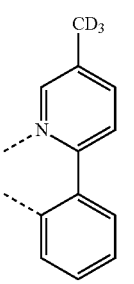
L_b22 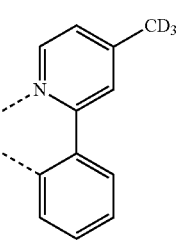
L_b23 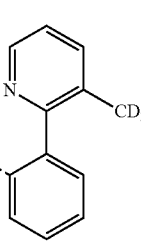

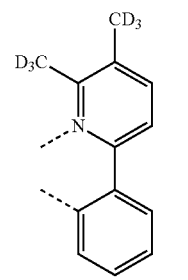 L$_{b24}$
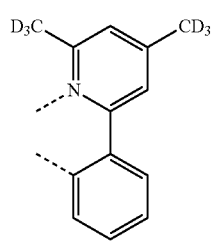 L$_{b25}$
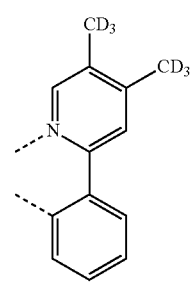 L$_{b26}$
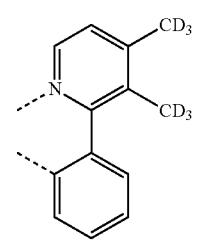 L$_{b27}$
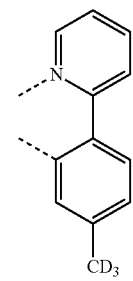 L$_{b28}$
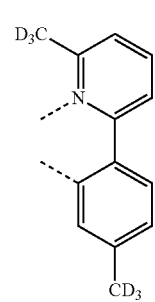 L$_{b29}$
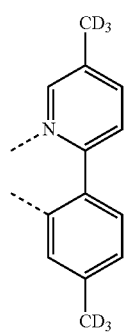 L$_{b30}$
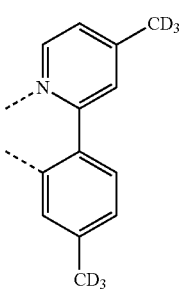 L$_{b31}$
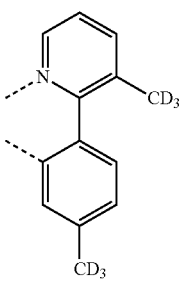 L$_{b32}$
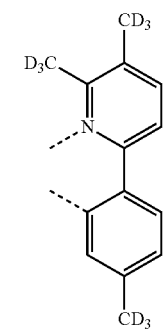 L$_{b33}$
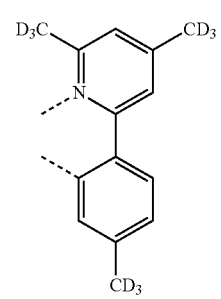 L$_{b34}$

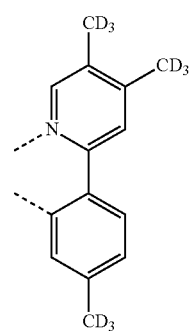
L<sub>b35</sub>
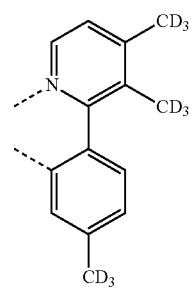
L<sub>b36</sub>
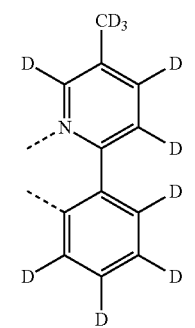
L<sub>b37</sub>
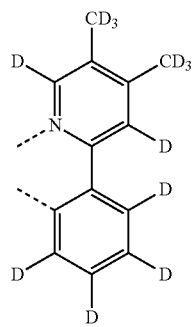
L<sub>b38</sub>
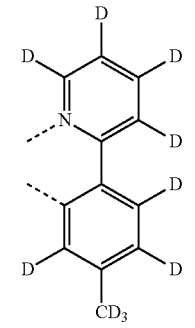
L<sub>b39</sub>
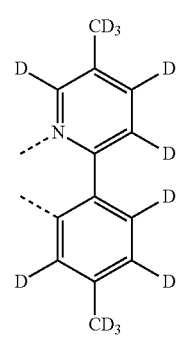
L<sub>b40</sub>
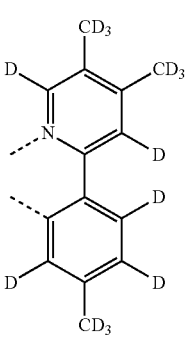
L<sub>b41</sub>
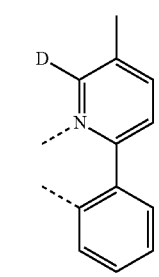
L<sub>b42</sub>
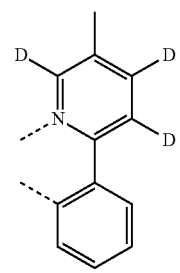
L<sub>b43</sub>
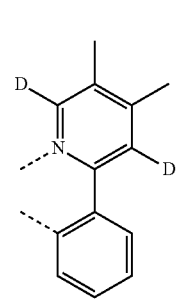
L<sub>b44</sub>

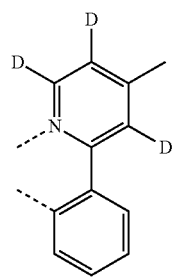 L<sub>b45</sub>
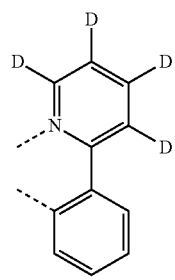 L<sub>b46</sub>
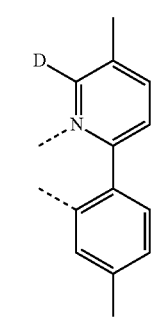 L<sub>b47</sub>
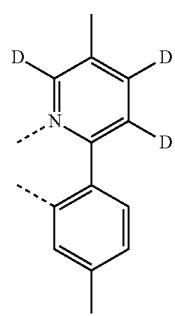 L<sub>b48</sub>
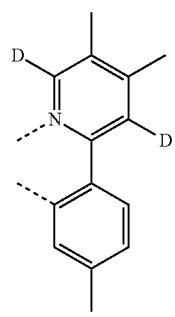 L<sub>b49</sub>
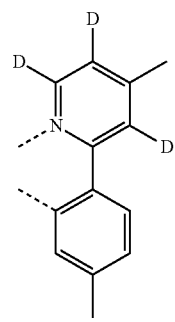 L<sub>b50</sub>
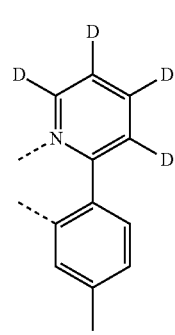 L<sub>b51</sub>
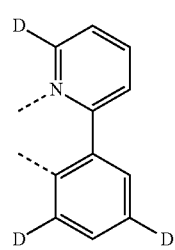 L<sub>b52</sub>
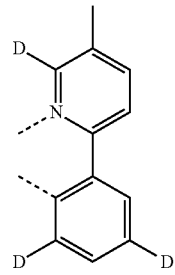 L<sub>b53</sub>
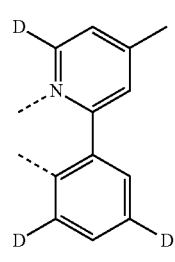 L<sub>b54</sub>

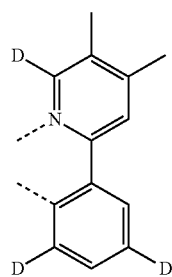 L<sub>b55</sub>
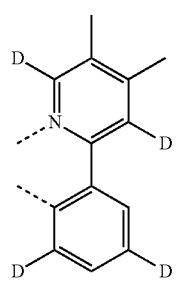 L<sub>b56</sub>
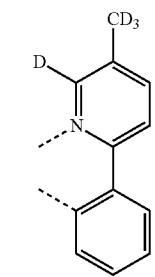 L<sub>b57</sub>
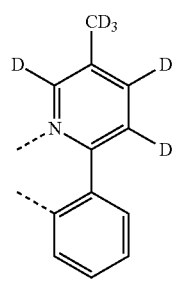 L<sub>b58</sub>
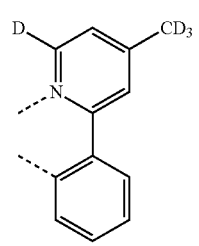 L<sub>b59</sub>
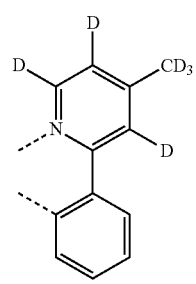 L<sub>b60</sub>
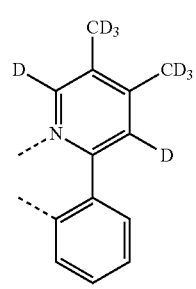 L<sub>b61</sub>
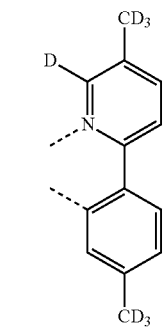 L<sub>b62</sub>
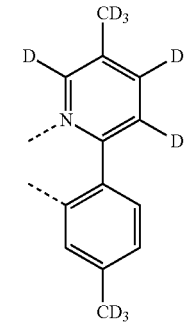 L<sub>b63</sub>
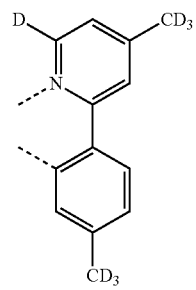 L<sub>b64</sub>

L_{b65} 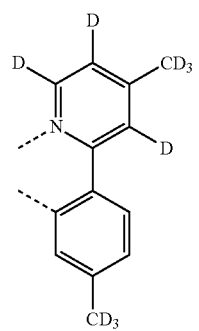
L_{b66} 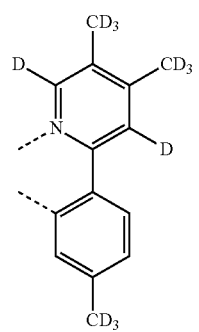
L_{b67} 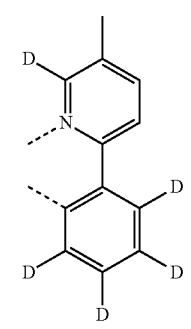
L_{b68} 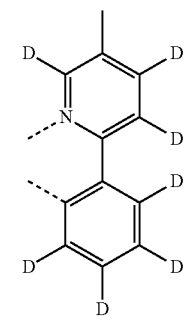
L_{b69} 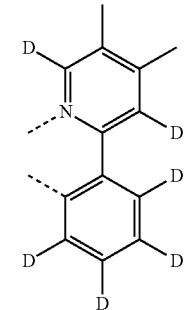
L_{b70} 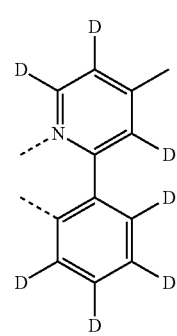
L_{b71} 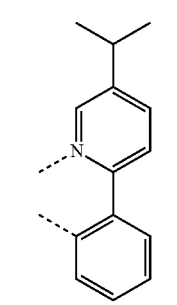
L_{b72} 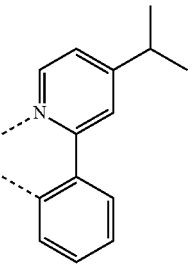
L_{b73} 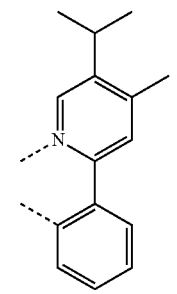
L_{b74} 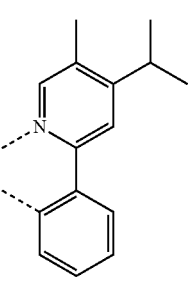

-continued

L<sub>b75</sub>
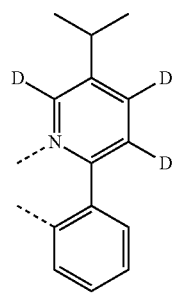

L<sub>b76</sub>
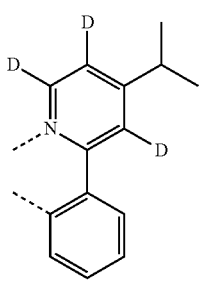

L<sub>b77</sub>
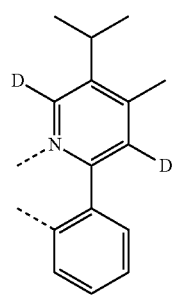

L<sub>b78</sub>
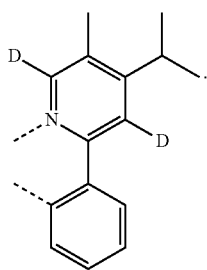

According to an embodiment of the present disclosure, the metal complex has the Formula $Ir(L_a)_2L_c$ or $IrL_a(L_c)_2$, wherein $L_a$ is one or two selected from $L_{a1}$ to $L_{a1019}$, and L is one or two selected from the group consisting of $L_c$ to $L_{c360}$, wherein the specific structures of $L_{c1}$ to $L_{c360}$ are described in claim 12.

According to an embodiment of the present disclosure, the metal complex has a structure represented by any one selected from Metal complex 1 to Metal complex 316:

Wherein Metal complex 1 to Metal complex 226 have the structure of $IrL_a(L_b)_2$, wherein the two $L_b$ are the same, wherein $L_a$ and $L_b$ correspond to the structures as shown in the following table, respectively:

| Metal complex | $L_a$ | $L_b$ | Metal complex | $L_a$ | $L_b$ |
|---|---|---|---|---|---|
| 1 | $L_{a1}$ | $L_{b1}$ | 2 | $L_{a2}$ | $L_{b1}$ |
| 3 | $L_{a3}$ | $L_{b1}$ | 4 | $L_{a4}$ | $L_{b1}$ |
| 5 | $L_{a121}$ | $L_{b1}$ | 6 | $L_{a122}$ | $L_{b1}$ |
| 7 | $L_{a123}$ | $L_{b1}$ | 8 | $L_{a137}$ | $L_{b1}$ |
| 9 | $L_{a138}$ | $L_{b1}$ | 10 | $L_{a139}$ | $L_{b1}$ |
| 11 | $L_{a153}$ | $L_{b1}$ | 12 | $L_{a154}$ | $L_{b1}$ |
| 13 | $L_{a155}$ | $L_{b1}$ | 14 | $L_{a169}$ | $L_{b1}$ |
| 15 | $L_{a170}$ | $L_{b1}$ | 16 | $L_{a171}$ | $L_{b1}$ |
| 17 | $L_{a221}$ | $L_{b1}$ | 18 | $L_{a222}$ | $L_{b1}$ |
| 19 | $L_{a293}$ | $L_{b1}$ | 20 | $L_{a294}$ | $L_{b1}$ |
| 21 | $L_{a295}$ | $L_{b1}$ | 22 | $L_{a297}$ | $L_{b1}$ |
| 23 | $L_{a298}$ | $L_{b1}$ | 24 | $L_{a299}$ | $L_{b1}$ |
| 25 | $L_{a313}$ | $L_{b1}$ | 26 | $L_{a314}$ | $L_{b1}$ |
| 27 | $L_{a415}$ | $L_{b1}$ | 28 | $L_{a416}$ | $L_{b1}$ |
| 29 | $L_{a467}$ | $L_{b1}$ | 30 | $L_{a468}$ | $L_{b1}$ |
| 31 | $L_{a487}$ | $L_{b1}$ | 32 | $L_{a488}$ | $L_{b1}$ |
| 33 | $L_{a507}$ | $L_{b1}$ | 34 | $L_{a508}$ | $L_{b1}$ |
| 35 | $L_{a516}$ | $L_{b1}$ | 36 | $L_{a517}$ | $L_{b1}$ |
| 37 | $L_{a527}$ | $L_{b1}$ | 38 | $L_{a528}$ | $L_{b1}$ |
| 39 | $L_{a547}$ | $L_{b1}$ | 40 | $L_{a548}$ | $L_{b1}$ |
| 41 | $L_{a576}$ | $L_{b1}$ | 42 | $L_{a577}$ | $L_{b1}$ |
| 43 | $L_{a592}$ | $L_{b1}$ | 44 | $L_{a593}$ | $L_{b1}$ |
| 45 | $L_{a640}$ | $L_{b1}$ | 46 | $L_{a652}$ | $L_{b1}$ |
| 47 | $L_{a692}$ | $L_{b1}$ | 48 | $L_{a693}$ | $L_{b1}$ |
| 49 | $L_{a704}$ | $L_{b1}$ | 50 | $L_{a842}$ | $L_{b1}$ |
| 51 | $L_{a854}$ | $L_{b1}$ | 52 | $L_{a896}$ | $L_{b1}$ |
| 53 | $L_{a962}$ | $L_{b1}$ | 54 | $L_{a966}$ | $L_{b1}$ |
| 55 | $L_{a970}$ | $L_{b1}$ | 56 | $L_{a973}$ | $L_{b1}$ |
| 57 | $L_{a974}$ | $L_{b1}$ | 58 | $L_{a975}$ | $L_{b1}$ |
| 59 | $L_{a976}$ | $L_{b1}$ | 60 | $L_{a978}$ | $L_{b1}$ |
| 61 | $L_{a985}$ | $L_{b1}$ | 62 | $L_{a987}$ | $L_{b1}$ |
| 63 | $L_{a988}$ | $L_{b1}$ | 64 | $L_{a999}$ | $L_{b1}$ |
| 65 | $L_{a1003}$ | $L_{b1}$ | 66 | $L_{a1010}$ | $L_{b1}$ |
| 67 | $L_{a1}$ | $L_{b3}$ | 68 | $L_{a2}$ | $L_{b3}$ |
| 69 | $L_{a3}$ | $L_{b3}$ | 70 | $L_{a4}$ | $L_{b3}$ |
| 71 | $L_{a121}$ | $L_{b3}$ | 72 | $L_{a122}$ | $L_{b3}$ |
| 73 | $L_{a123}$ | $L_{b3}$ | 74 | $L_{a137}$ | $L_{b3}$ |
| 75 | $L_{a138}$ | $L_{b3}$ | 76 | $L_{a139}$ | $L_{b3}$ |
| 77 | $L_{a293}$ | $L_{b3}$ | 78 | $L_{a294}$ | $L_{b3}$ |
| 79 | $L_{a297}$ | $L_{b3}$ | 80 | $L_{a298}$ | $L_{b3}$ |
| 81 | $L_{a576}$ | $L_{b3}$ | 82 | $L_{a577}$ | $L_{b3}$ |
| 83 | $L_{a592}$ | $L_{b3}$ | 84 | $L_{a593}$ | $L_{b3}$ |
| 85 | $L_{a640}$ | $L_{b3}$ | 86 | $L_{a652}$ | $L_{b3}$ |
| 87 | $L_{a692}$ | $L_{b3}$ | 88 | $L_{a693}$ | $L_{b3}$ |
| 89 | $L_{a704}$ | $L_{b3}$ | 90 | $L_{a842}$ | $L_{b3}$ |
| 91 | $L_{a854}$ | $L_{b3}$ | 92 | $L_{a896}$ | $L_{b3}$ |
| 93 | $L_{a962}$ | $L_{b3}$ | 94 | $L_{a966}$ | $L_{b3}$ |
| 95 | $L_{a970}$ | $L_{b3}$ | 96 | $L_{a973}$ | $L_{b3}$ |
| 97 | $L_{a974}$ | $L_{b3}$ | 98 | $L_{a975}$ | $L_{b3}$ |
| 99 | $L_{a976}$ | $L_{b3}$ | 100 | $L_{a978}$ | $L_{b3}$ |
| 101 | $L_{a985}$ | $L_{b3}$ | 102 | $L_{a987}$ | $L_{b3}$ |
| 103 | $L_{a988}$ | $L_{b3}$ | 104 | $L_{a999}$ | $L_{b3}$ |
| 105 | $L_{a1003}$ | $L_{b3}$ | 106 | $L_{a1010}$ | $L_{b3}$ |
| 107 | $L_{a1}$ | $L_{b4}$ | 108 | $L_{a2}$ | $L_{b4}$ |
| 109 | $L_{a3}$ | $L_{b4}$ | 110 | $L_{a4}$ | $L_{b4}$ |
| 111 | $L_{a121}$ | $L_{b4}$ | 112 | $L_{a122}$ | $L_{b4}$ |
| 113 | $L_{a123}$ | $L_{b4}$ | 114 | $L_{a137}$ | $L_{b4}$ |
| 115 | $L_{a138}$ | $L_{b4}$ | 116 | $L_{a139}$ | $L_{b4}$ |
| 117 | $L_{a293}$ | $L_{b4}$ | 118 | $L_{a294}$ | $L_{b4}$ |
| 119 | $L_{a297}$ | $L_{b4}$ | 120 | $L_{a298}$ | $L_{b4}$ |
| 121 | $L_{a576}$ | $L_{b4}$ | 122 | $L_{a577}$ | $L_{b4}$ |
| 123 | $L_{a592}$ | $L_{b4}$ | 124 | $L_{a593}$ | $L_{b4}$ |
| 125 | $L_{a640}$ | $L_{b4}$ | 126 | $L_{a652}$ | $L_{b4}$ |
| 127 | $L_{a692}$ | $L_{b4}$ | 128 | $L_{a693}$ | $L_{b4}$ |
| 129 | $L_{a704}$ | $L_{b4}$ | 130 | $L_{a842}$ | $L_{b4}$ |
| 131 | $L_{a854}$ | $L_{b4}$ | 132 | $L_{a896}$ | $L_{b4}$ |
| 133 | $L_{a962}$ | $L_{b4}$ | 134 | $L_{a966}$ | $L_{b4}$ |
| 135 | $L_{a970}$ | $L_{b4}$ | 136 | $L_{a973}$ | $L_{b4}$ |
| 137 | $L_{a974}$ | $L_{b4}$ | 138 | $L_{a975}$ | $L_{b4}$ |
| 139 | $L_{a976}$ | $L_{b4}$ | 140 | $L_{a978}$ | $L_{b4}$ |
| 141 | $L_{a985}$ | $L_{b4}$ | 142 | $L_{a987}$ | $L_{b4}$ |
| 143 | $L_{a988}$ | $L_{b4}$ | 144 | $L_{a999}$ | $L_{b4}$ |
| 145 | $L_{a1003}$ | $L_{b4}$ | 146 | $L_{a1010}$ | $L_{b4}$ |
| 147 | $L_{a1}$ | $L_{b8}$ | 148 | $L_{a2}$ | $L_{b8}$ |
| 149 | $L_{a3}$ | $L_{b8}$ | 150 | $L_{a4}$ | $L_{b8}$ |
| 151 | $L_{a121}$ | $L_{b8}$ | 152 | $L_{a122}$ | $L_{b8}$ |
| 153 | $L_{a123}$ | $L_{b8}$ | 154 | $L_{a137}$ | $L_{b8}$ |

-continued

| Metal complex | $L_a$ | $L_b$ | Metal complex | $L_a$ | $L_b$ |
|---|---|---|---|---|---|
| 155 | $L_{a138}$ | $L_{b8}$ | 156 | $L_{a139}$ | $L_{b8}$ |
| 157 | $L_{a293}$ | $L_{b8}$ | 158 | $L_{a294}$ | $L_{b8}$ |
| 159 | $L_{a297}$ | $L_{b8}$ | 160 | $L_{a298}$ | $L_{b8}$ |
| 161 | $L_{a576}$ | $L_{b8}$ | 162 | $L_{a577}$ | $L_{b8}$ |
| 163 | $L_{a592}$ | $L_{b8}$ | 164 | $L_{a593}$ | $L_{b8}$ |
| 165 | $L_{a640}$ | $L_{b8}$ | 166 | $L_{a652}$ | $L_{b8}$ |
| 167 | $L_{a692}$ | $L_{b8}$ | 168 | $L_{a693}$ | $L_{b8}$ |
| 169 | $L_{a704}$ | $L_{b8}$ | 170 | $L_{a842}$ | $L_{b8}$ |
| 171 | $L_{a854}$ | $L_{b8}$ | 172 | $L_{a896}$ | $L_{b8}$ |
| 173 | $L_{a962}$ | $L_{b8}$ | 174 | $L_{a966}$ | $L_{b8}$ |
| 175 | $L_{a970}$ | $L_{b8}$ | 176 | $L_{a973}$ | $L_{b8}$ |
| 177 | $L_{a974}$ | $L_{b8}$ | 178 | $L_{a975}$ | $L_{b8}$ |
| 179 | $L_{a976}$ | $L_{b8}$ | 180 | $L_{a978}$ | $L_{b8}$ |
| 181 | $L_{a985}$ | $L_{b8}$ | 182 | $L_{a987}$ | $L_{b8}$ |
| 183 | $L_{a988}$ | $L_{b8}$ | 184 | $L_{a999}$ | $L_{b8}$ |
| 185 | $L_{a1003}$ | $L_{b8}$ | 186 | $L_{a1010}$ | $L_{b8}$ |
| 187 | $L_{a1}$ | $L_{b30}$ | 188 | $L_{a2}$ | $L_{b30}$ |
| 189 | $L_{a3}$ | $L_{b30}$ | 110 | $L_{a4}$ | $L_{b30}$ |
| 191 | $L_{a121}$ | $L_{b30}$ | 192 | $L_{a122}$ | $L_{b30}$ |
| 193 | $L_{a123}$ | $L_{b30}$ | 194 | $L_{a137}$ | $L_{b30}$ |
| 195 | $L_{a138}$ | $L_{b30}$ | 196 | $L_{a139}$ | $L_{b30}$ |
| 197 | $L_{a293}$ | $L_{b30}$ | 198 | $L_{a294}$ | $L_{b30}$ |
| 199 | $L_{a297}$ | $L_{b30}$ | 200 | $L_{a298}$ | $L_{b30}$ |
| 201 | $L_{a576}$ | $L_{b30}$ | 202 | $L_{a577}$ | $L_{b30}$ |
| 203 | $L_{a592}$ | $L_{b30}$ | 204 | $L_{a593}$ | $L_{b30}$ |
| 205 | $L_{a640}$ | $L_{b30}$ | 206 | $L_{a652}$ | $L_{b30}$ |
| 207 | $L_{a692}$ | $L_{b30}$ | 208 | $L_{a693}$ | $L_{b30}$ |
| 209 | $L_{a704}$ | $L_{b30}$ | 210 | $L_{a842}$ | $L_{b30}$ |
| 211 | $L_{a854}$ | $L_{b30}$ | 212 | $L_{a896}$ | $L_{b30}$ |
| 213 | $L_{a962}$ | $L_{b30}$ | 214 | $L_{a966}$ | $L_{b30}$ |
| 215 | $L_{a970}$ | $L_{b30}$ | 216 | $L_{a973}$ | $L_{b30}$ |
| 217 | $L_{a974}$ | $L_{b30}$ | 218 | $L_{a975}$ | $L_{b30}$ |
| 219 | $L_{a976}$ | $L_{b30}$ | 220 | $L_{a978}$ | $L_{b30}$ |
| 221 | $L_{a985}$ | $L_{b30}$ | 222 | $L_{a987}$ | $L_{b30}$ |
| 223 | $L_{a988}$ | $L_{b30}$ | 224 | $L_{a999}$ | $L_{b30}$ |
| 225 | $L_{a1003}$ | $L_{b30}$ | 226 | $L_{a1010}$ | $L_{b30}$ |

Wherein Metal complex 227 to Metal complex 274 have the structure of $Ir(L_a)_2L_c$, wherein the two $L_a$ are the same, wherein $L_a$ and $L_c$ correspond to the structures as shown in the following table, respectively:

| Metal complex | $L_a$ | $L_c$ | Metal complex | $L_a$ | $L_c$ |
|---|---|---|---|---|---|
| 227 | $L_{a323}$ | $L_{c1}$ | 228 | $L_{a324}$ | $L_{c1}$ |
| 229 | $L_{a328}$ | $L_{c1}$ | 230 | $L_{a329}$ | $L_{c1}$ |
| 231 | $L_{a333}$ | $L_{c1}$ | 232 | $L_{a334}$ | $L_{c1}$ |
| 233 | $L_{a338}$ | $L_{c1}$ | 234 | $L_{a339}$ | $L_{c1}$ |
| 235 | $L_{a343}$ | $L_{c1}$ | 236 | $L_{a344}$ | $L_{c1}$ |
| 237 | $L_{a348}$ | $L_{c1}$ | 238 | $L_{a349}$ | $L_{c1}$ |
| 239 | $L_{a353}$ | $L_{c1}$ | 240 | $L_{a354}$ | $L_{c1}$ |
| 241 | $L_{a358}$ | $L_{c1}$ | 242 | $L_{a359}$ | $L_{c1}$ |
| 243 | $L_{a363}$ | $L_{c1}$ | 244 | $L_{a364}$ | $L_{c1}$ |
| 245 | $L_{a368}$ | $L_{c1}$ | 246 | $L_{a369}$ | $L_{c1}$ |
| 247 | $L_{a373}$ | $L_{c1}$ | 248 | $L_{a374}$ | $L_{c1}$ |
| 249 | $L_{a388}$ | $L_{c1}$ | 250 | $L_{a389}$ | $L_{c1}$ |
| 251 | $L_{a323}$ | $L_{31}$ | 252 | $L_{a324}$ | $L_{31}$ |
| 253 | $L_{a328}$ | $L_{31}$ | 254 | $L_{a329}$ | $L_{31}$ |
| 255 | $L_{a333}$ | $L_{31}$ | 256 | $L_{a334}$ | $L_{31}$ |
| 257 | $L_{a338}$ | $L_{31}$ | 258 | $L_{a339}$ | $L_{31}$ |
| 259 | $L_{a343}$ | $L_{31}$ | 260 | $L_{a344}$ | $L_{31}$ |
| 261 | $L_{a348}$ | $L_{31}$ | 262 | $L_{a349}$ | $L_{31}$ |
| 263 | $L_{a353}$ | $L_{31}$ | 264 | $L_{a354}$ | $L_{31}$ |
| 265 | $L_{a358}$ | $L_{31}$ | 266 | $L_{a359}$ | $L_{31}$ |
| 267 | $L_{a363}$ | $L_{31}$ | 268 | $L_{a364}$ | $L_{31}$ |
| 269 | $L_{a368}$ | $L_{31}$ | 270 | $L_{a369}$ | $L_{31}$ |
| 271 | $L_{a373}$ | $L_{31}$ | 272 | $L_{a374}$ | $L_{31}$ |
| 273 | $L_{a388}$ | $L_{31}$ | 274 | $L_{a389}$ | $L_{31}$ |

Wherein Metal complex 275 to Metal complex 316 have the structure of $Ir(L_a)_3$, wherein the three $L_a$ are the same, wherein $L_a$ corresponds to the structures as shown in the following table:

| Metal complex | $L_a$ |
|---|---|
| 275 | $L_{a1}$ |
| 276 | $L_{a2}$ |
| 277 | $L_{a3}$ |
| 278 | $L_{a121}$ |
| 279 | $L_{a122}$ |
| 280 | $L_{a137}$ |
| 281 | $L_{a138}$ |
| 282 | $L_{a293}$ |
| 283 | $L_{a297}$ |
| 284 | $L_{a298}$ |
| 285 | $L_{a487}$ |
| 286 | $L_{a488}$ |
| 287 | $L_{a507}$ |
| 288 | $L_{a508}$ |
| 289 | $L_{a547}$ |
| 290 | $L_{a548}$ |
| 291 | $L_{a576}$ |
| 292 | $L_{a577}$ |
| 293 | $L_{a640}$ |
| 294 | $L_{a641}$ |
| 295 | $L_{a652}$ |
| 296 | $L_{a653}$ |
| 297 | $L_{a692}$ |
| 298 | $L_{a693}$ |
| 299 | $L_{a704}$ |
| 300 | $L_{a842}$ |
| 301 | $L_{a854}$ |
| 302 | $L_{a896}$ |
| 303 | $L_{a962}$ |
| 304 | $L_{a966}$ |
| 305 | $L_{a970}$ |
| 306 | $L_{a973}$ |
| 307 | $L_{a974}$ |
| 308 | $L_{a975}$ |
| 309 | $L_{a976}$ |
| 310 | $L_{a978}$ |
| 311 | $L_{a985}$ |
| 312 | $L_{a987}$ |
| 313 | $L_{a988}$ |
| 314 | $L_{a999}$ |
| 315 | $L_{a1003}$ |
| 316 | $L_{a1010}$. |

According to an embodiment of the present disclosure, a compound selected from the group consisting of Compound 1 to Compound 136 is also disclosed. Wherein, the specific structures of Compound 1 to Compound 136 are described in claim 14.

According to an embodiment of the present disclosure, an electroluminescent device is also disclosed, which includes:

an anode, a cathode, and an organic layer disposed between the anode and the cathode, wherein the organic layer comprises a metal complex comprising the ligand $L_a$ represented by Formula 1:

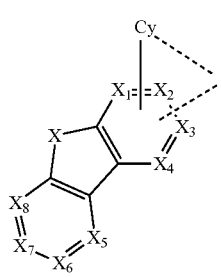

Formula 1 wherein, Cy is a substituted or unsubstituted aryl or heteroaryl group having 5 to 24 ring atoms;

the Cy is bonded to a metal through a metal-carbon bond or a metal-nitrogen bond;

$X_1$ to $X_4$ are each independently selected from C, $CR_{x1}$ or N, and at least one of $X_1$ to $X_4$ is C which is connected to the Cy; when more than one of $X_1$ to $X_4$ is $CR_{x1}$, the $R_{x1}$ may be the same or different;

$X_5$ to $X_8$ are each independently selected from $CR_{x2}$ or N; when more than one of $X_5$ to $X_8$ is $CR_{x2}$, the $R_{x2}$ may be the same or different;

X is selected from the group consisting of O, S, Se, $NR_{x3}$, $CR_{x4}R_{x5}$ and $SiR_{x6}R_{x7}$;

$R_{x1}$, $R_{x2}$, $R_{x3}$, $R_{x4}$, $R_{x5}$, $R_{x6}$ and $R_{x7}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

wherein, at least one of $R_{x1}$ and $R_{x2}$ is a cyano group;

any two adjacent substituents can optionally be joined to form a ring;

$X_1$, $X_2$, $X_3$ or $X_4$ are connected to the metal through a metal-carbon bond or a metal-nitrogen bond.

According to an embodiment of the present disclosure, in the electroluminescent device, the organic layer is a light-emitting layer, and the metal complex is a light-emitting material.

According to an embodiment of the present disclosure, in the electroluminescent device, the organic layer further includes a host material.

According to an embodiment of the present disclosure, in the electroluminescent device, the organic layer further includes at least two host materials.

According to an embodiment of the present disclosure, the host material comprises at least one chemical group selected from the group consisting of benzene, biphenyl, pyridine, pyrimidine, triazine, carbazole, azacarbazole, indolocarbazole, dibenzothiophene, azadibenzothiophen, dibenzofuran, azadibenzofuran, dibenzoselenophene, azadibenzoselenophene, triphenylene, azatriphenylene, fluorene, silicon-fluorene, naphthalene, quinoline, isoquinoline, quinazoline, quinoxaline, phenanthrene, azaphenanthrene, and combinations thereof.

According to an embodiment of the present disclosure, the electroluminescent device is incorporated into a device selected from the group consisting of a consumption product, an electronic component module, an organic light-emitting device and a lighting panel.

According to another embodiment of the present disclosure, a compound formulation is also disclosed, which comprises a metal complex. The specific structure of the metal complex is shown in any one of the foregoing embodiments.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, dopants disclosed herein may be used in combination with a wide variety of hosts, transport layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

Synthesis examples of the materials:

The method for preparing the compound of the present disclosure is not limited, and the following compounds are exemplified as typical but non-limiting examples. The synthetic route and preparation method of which are as follows:

Synthesis Example 1: Synthesis of Compound $IrL_{a1}(L_{b1})_2$ (Metal Complex 1)

Step 1:

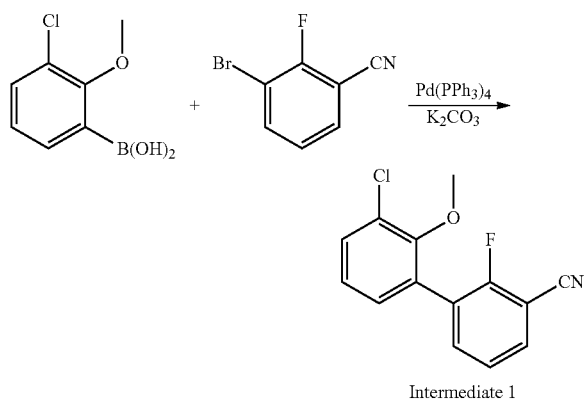

Intermediate 1

To a dried 1000 mL round bottom flask, 3-chloro-2-methoxyphenylboronic acid (20.00 g, 107.29 mmol), 2-fluoro-3-bromobenzonitrile (20.43 g, 102.20 mmol), tetrakis(triphenylphosphine)palladium (Pd(PPh$_3$)$_4$) (4.39 g, 3.74 mmol), potassium carbonate (32.48 g, 235.40 mmol), 1,4-dioxane (500 mL) and water (100 mL) were sequentially added. The reaction system was then replaced with N$_2$ three times and protected by N$_2$, then it was heated in a heating mantle and stirred under reflux for 12 h. After the reaction was cooled, it was extracted with ethyl acetate, washed with saturated brine three times, dried over anhydrous magnesium sulfate, and concentrated under reduced pressure. The crude product was purified by column chromatography, eluting with 5% (v/v) ethyl acetate (EA)/petroleum ether (PE), to give 22 g of white product intermediate 1 (74.8% yield).

Step 2:

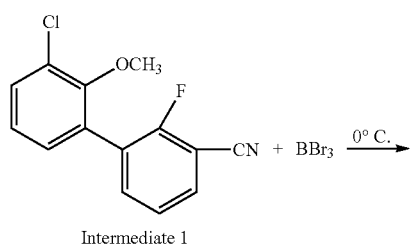

Intermediate 1

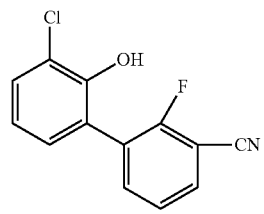

Intermediate 2

In a dried 500 mL three-necked flask, intermediate 1 (22.00 g, 84.30 mmol) and dichloromethane (350 mL) were added. The reaction system was then replaced with N$_2$ three times and protected by N$_2$, and then stirred in an ice bath at 0° C. for 5 minutes. Boron tribromide was added dropwise thereto. After the completion of the addition, the reaction was warmed up to room temperature and stirred for 12 h. After the reaction was completed, the reaction was quenched with ice-water in an ice bath and neutralized with a saturated aqueous solution of sodium bicarbonate. A large amount of white solid product was precipitated, which was directly filtered, washed with water three times, and dried under reduced pressure to obtain 19.7 g of white solid product intermediate 2 (94.4% yield).

Step 3:

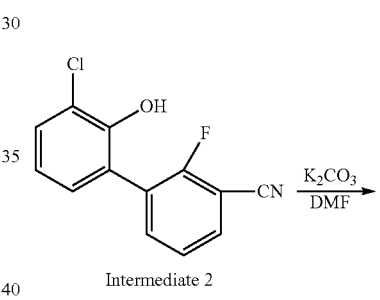

Intermediate 2

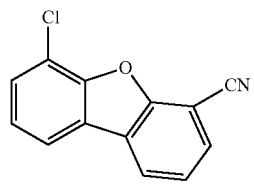

Intermediate 3

In a dried 500 mL round-bottomed flask, intermediate 2 (19.7 g, 79.6 mmol), potassium carbonate (32.9 g, 238.8 mmol) and DMF (300 mL) were added successively, and then the reaction was heated in a heating mantle at 100° C. and stirred for 12 h. After the reaction was completed, it was cooled and filtered through celite. The organic phase was washed with saturated brine, extracted twice with ethyl acetate, dried over anhydrous magnesium sulfate, and concentrated under reduced pressure. The crude product was purified by column chromatography, eluting with a 20% (v/v) dichloromethane/petroleum ether solution to give 11 g of intermediate 3 as a white solid (60.7% yield).

Step 4:

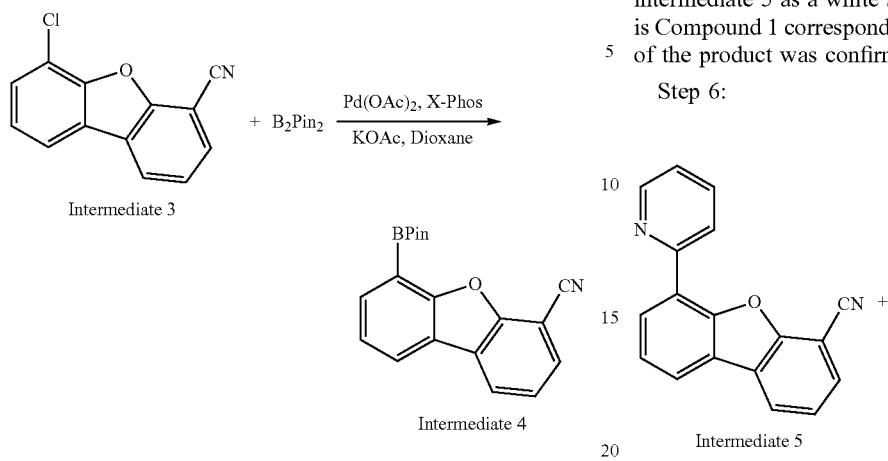

In a dried 500 mL round bottom flask, intermediate 3 (9.60 g, 42.19 mmol), bis(pinacolato)diboron (13.93 g, 54.86 mmol), X-Phos (0.99 g, 2.10 mmol), palladium acetate (0.47 g, 2.10 mmol), potassium acetate (10.30 g, 105.00 mmol) and dioxane (200 mL) were added successively. The reaction system was then replaced with $N_2$ three times and protected by $N_2$, heated at 100° C. and stirred overnight. After the reaction was completed, it was filtered through celite and anhydrous magnesium sulfate, and washed twice with ethyl acetate. The organic phase was collected and concentrated under reduced pressure to obtain a crude product, which was directly used in the next step.

Step 5:

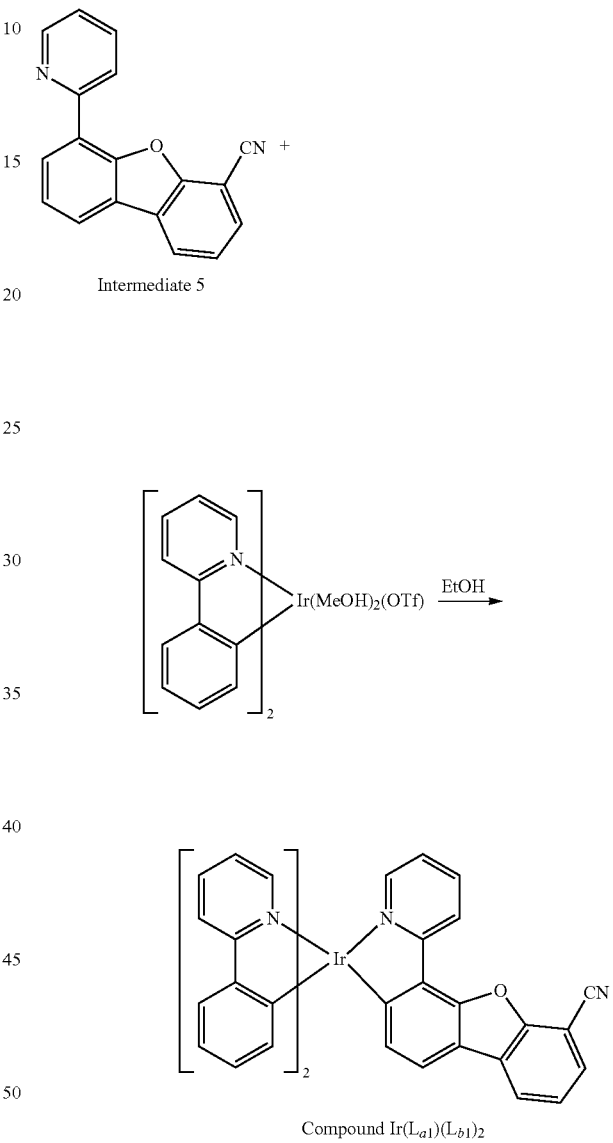

In a dried 500 mL round bottom flask, intermediate 4 (crude product), 2-bromopyridine (6.23 g, 39.45 mmol), Pd(PPh₃)₄ (2.07 g, 1.79 mmol), sodium carbonate (9.49 g, 89.50 mmol), dioxane (250 mL) and water (50 mL) were added successively. The reaction system was then replaced with $N_2$ three times and protected by $N_2$, heated at 100° C. and reacted for 12 h. After the reaction was completed, it was extracted with ethyl acetate, washed with saturated brine three times, dried over anhydrous magnesium sulfate, and concentrated under reduced pressure. The crude product was purified by column chromatography by eluting with a gradient of PE:EA=10:1 to 5:1 (v/v) to obtain 11.4 g of intermediate 5 as a white solid (98% yield). Intermediate 5 is Compound 1 corresponding to ligand $L_a$, and the structure of the product was confirmed by NMR and GCMS.

Step 6:

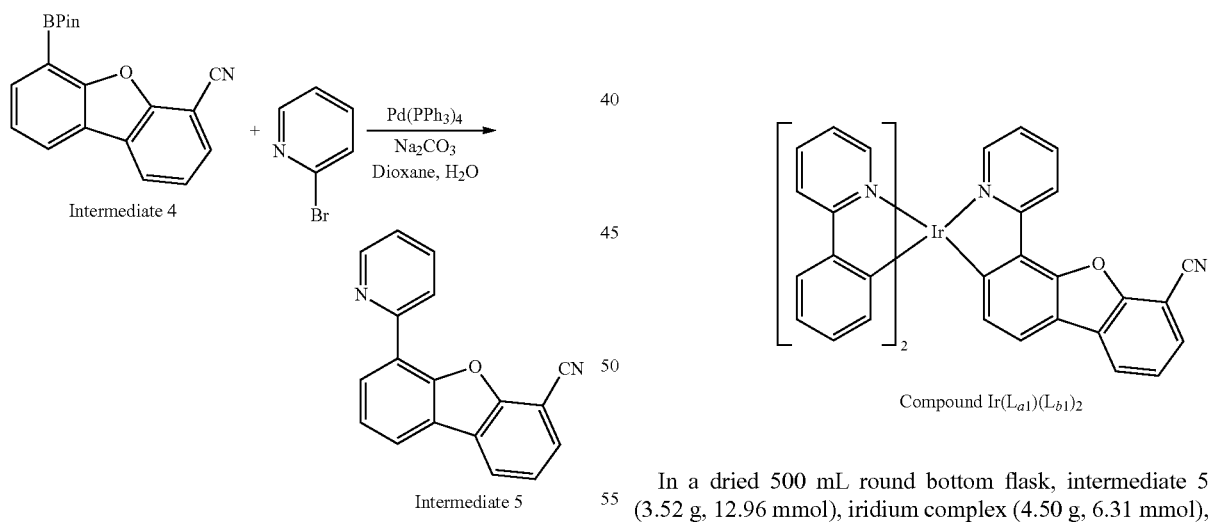

Compound Ir(L$_{a1}$)(L$_{b1}$)$_2$

In a dried 500 mL round bottom flask, intermediate 5 (3.52 g, 12.96 mmol), iridium complex (4.50 g, 6.31 mmol), and ethanol (250 mL) were added successively. The reaction system was then replaced with $N_2$ three times and protected by $N_2$, and then heated to reflux for 24 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a1}$(L$_{b1}$)$_2$ (Metal complex 1) as a yellow solid (1.5 g, 28.7% yield). The product was identified as the target product with a molecular weight of 770.

Synthesis Example 2: Synthesis of Compound IrL$_{a4}$(L$_{b1}$)$_2$ (Metal Complex 4)

Step 1:

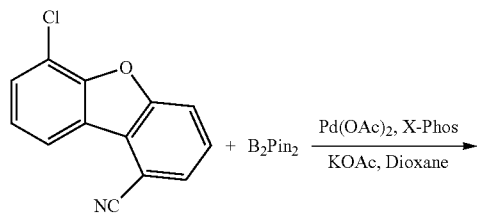

In a dried 500 mL round bottom flask, 6-chloro-dibenzofuran-1-nitrile (4.6 g, 20.2 mmol), bis(pinacolato)diboron (5.9 g, 23.2 mmol), palladium acetate (0.14 g, 0.6 mmol), potassium acetate (2.97 g, 30.3 mmol), X-Phos (0.58 g, 1.21 mmol) and 1,4-dioxane (90 mL) were added successively. The reaction system was then replaced with N$_2$ three times and protected by N$_2$, heated to reflux and stirred overnight. After the reaction was completed, it was filtered through celite and anhydrous magnesium sulfate, and washed twice with ethyl acetate. The organic phase was collected and concentrated under reduced pressure to obtain intermediate 6, which was directly used in the next step.

Step 2:

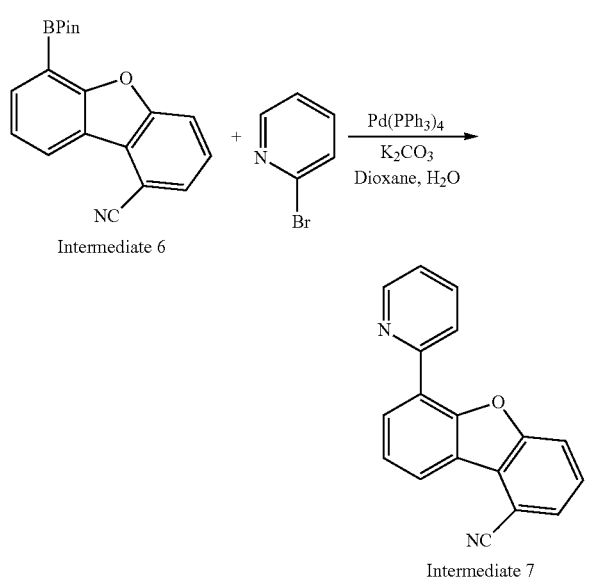

In a dried 500 mL round bottom flask, intermediate 6 (6.4 g, 20.2 mmol), 2-bromopyridine (3.2 g, 20.2 mmol), Pd(PPh$_3$)$_4$ (1.4 g, 1.2 mmol), potassium carbonate (4.2 g, 30.3 mmol), 1,4-dioxane (90 mL) and water (30 mL) were added successively. The reaction system was then replaced with N$_2$ three times and protected by N$_2$, heated at 100° C. and reacted for 12 h. After the reaction was completed, it was extracted with ethyl acetate, washed with saturated brine three times, dried over anhydrous magnesium sulfate, and concentrated under reduced pressure. The crude product was purified by column chromatography by eluting with a gradient of PE:EA=20:1 to 10:1 (v/v) to obtain 4 g of intermediate 7 as a white solid (74% yield). Intermediate 7 is compound 4 corresponding to ligand L$_a$, and the structure of the product was confirmed by NMR and GCMS.

Step 3:

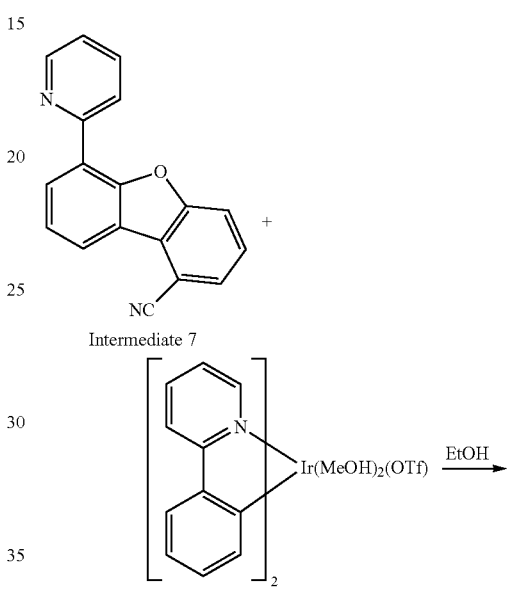

In a dried 500 mL round bottom flask, intermediate 7 (2.9 g, 11.0 mmol), iridium complex (4.0 g, 5.5 mmol), and ethanol (250 mL) were added successively. The reaction system was then replaced with N$_2$ three times and protected by N$_2$, and then heated to reflux for 24 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a4}$(L$_{b1}$)$_2$ (Metal complex 4) as a yellow solid (1.5 g, 36% yield). The product structure was identified as the target product with a molecular weight of 770.

Synthesis Example 3: Synthesis of Compound IrL$_{a2}$(L$_{b1}$)$_2$ (Metal Complex 2)

Step 1:

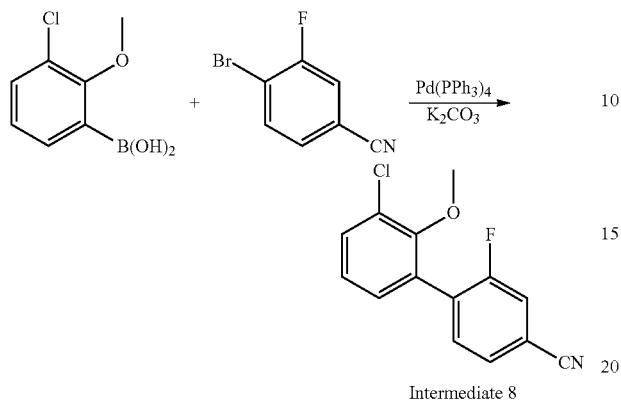

Intermediate 8

To a dried 1000 mL round bottom flask, 3-chloro-2-methoxyphenylboronic acid (12.00 g, 64.37 mmol), 2-fluoro-3-bromobenzonitrile (12.26 g, 61.31 mmol), tetrakis(triphenylphosphine)palladium (Pd(PPh$_3$)$_4$) (3.25 g, 3.05 mmol), potassium carbonate (18.61 g, 134.80 mmol), 1,4-dioxane (500 mL) and water (100 mL) were added successively. The reaction system was then replaced with N$_2$ three times and protected by N$_2$, then it was heated in a heating mantle and stirred under reflux for 12 h. After the reaction was cooled, it was extracted with ethyl acetate, washed with saturated brine three times, dried over anhydrous magnesium sulfate, and concentrated under reduced pressure. The crude product was purified by column chromatography, eluting with 5% (v/v) ethyl acetate (EA)/petroleum ether (PE), to give 13.2 g of intermediate 8 as a white product (82.5% yield).

Step 2:

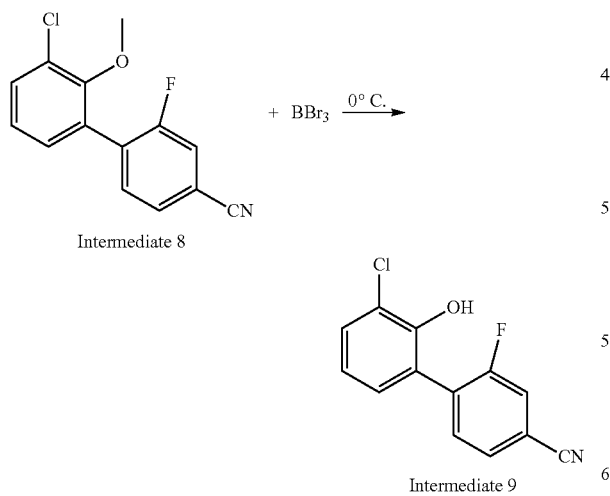

In a dried 500 mL three-necked flask, intermediate 8 (13.20 g, 50.50 mmol), and 350 mL of dichloromethane were added successively. The reaction system was then replaced with N$_2$ three times and protected by N$_2$, and stirred in an ice bath at 0° C. for 5 minutes. Boron tribromide (19.0 g, 75.74 mmol) was added dropwise slowly. After the completion of the addition, the reaction was warmed up to room temperature and stirred for 12 h. After the reaction was completed, the reaction was quenched with ice-water in an ice bath and neutralized with a saturated aqueous solution of sodium bicarbonate. A large amount of white solid product was precipitated, which was directly filtered, washed with water three times, and dried under reduced pressure to obtain 11.75 g of intermediate 9 as a white solid (94% yield).

Step 3:

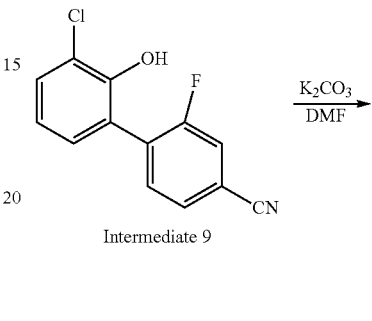

Intermediate 9

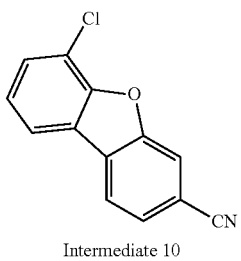

Intermediate 10

In a dried 500 mL round-bottomed flask, intermediate 9 (11.75 g, 47.47 mmol), potassium carbonate (19.6 g, 142.4 mmol), and DMF (300 mL) were added successively. The mixture was then heated in a heating mantle at 100° C. and stirred for 12 h. After the reaction was completed, it was cooled and filtered through celite. The organic phase was washed with saturated brine, extracted twice with ethyl acetate, dried over anhydrous magnesium sulfate, and concentrated under reduced pressure. The crude product was purified by column chromatography, eluting with a 20% (v/v) dichloromethane (DCM/petroleum ether(PE)) to give 7.09 g of intermediate 10 as a white solid (65.7% yield).

Step 4:

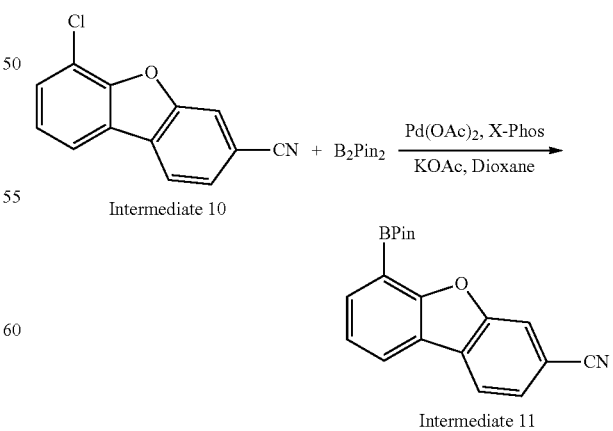

Intermediate 11

In a dried 500 mL round bottom flask, intermediate 10 (4.10 g, 18.02 mmol), bis(pinacolato)diboron (5.95 g, 23.42 mmol), X-Phos (0.43 g, 0.90 mmol), palladium acetate (0.20 g, 0.90 mmol), potassium acetate (4.46 g, 45.00 mmol) and dioxane (100 mL) were added successively. The reaction system was then replaced with N₂ three times and protected by N₂, heated at 100° C. and stirred overnight. After the reaction was completed, it was filtered through celite and anhydrous magnesium sulfate, and washed twice with ethyl acetate. The organic phase was collected and concentrated under reduced pressure to obtain crude product intermediate 11, which was directly used in the next step.

Step 5:

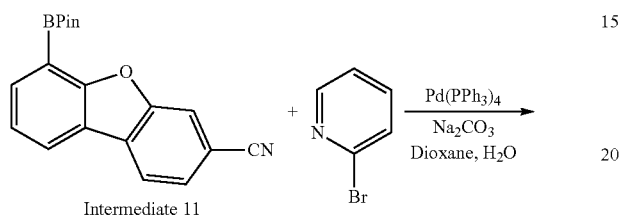

Intermediate 11

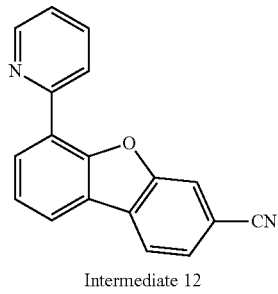

Intermediate 12

In a dried 500 mL round bottom flask, intermediate 11 (crude product), 2-bromopyridine (2.66 g, 16.85 mmol), Pd(PPh₃)₄ (0.88 g, 0.76 mmol), sodium carbonate (4.05 g, 38.25 mmol), dioxane (150 mL) and water (30 mL) were added successively. The reaction system was then replaced with N₂ three times and protected by N₂, heated at 100° C. and reacted for 12 h. After the reaction was completed, it was extracted with ethyl acetate, washed with saturated brine three times, dried over anhydrous magnesium sulfate, and concentrated under reduced pressure. The crude product was purified by column chromatography by eluting with a gradient of PE:EA=10:1 to 5:1 (v/v) to obtain 4.1 g of intermediate 12 as a white solid (90% yield). Intermediate 12 is compound 2 corresponding to ligand $L_a$, and the structure of the product was confirmed by NMR and GCMS.

Step 6:

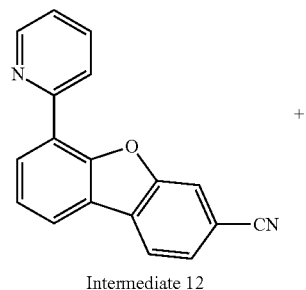

Intermediate 12

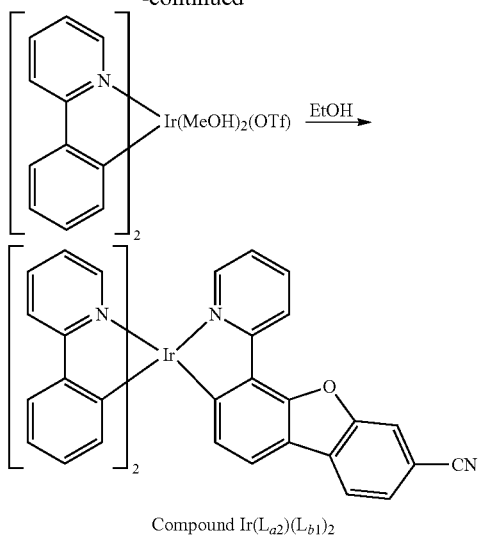

Compound Ir($L_{a2}$)($L_{b1}$)₂

In a dried 500 mL round bottom flask, intermediate 12 (3.52 g, 12.96 mmol), iridium complex (4.50 g, 6.31 mmol), and ethanol (250 mL) were added successively. The reaction system was then replaced with N₂ three times and protected by N₂, and then the reaction was heated to reflux for 24 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the IrL$_{a2}$(L$_{b1}$)₂ (Metal complex 2) as a yellow solid (1.3 g, 24.5% yield). The product structure was identified as the target product with a molecular weight of 770.

Synthesis Example 4: Synthesis of Compound IrL$_{a3}$(L$_{b1}$)₂ (Metal Complex 3)

Step 1:

In a dried 500 mL round bottom flask, 6-chloro-dibenzo-furan-2-nitrile (5 g, 22.0 mmol), bis(pinacolato)diboron (6.4 g, 25.3 mmol), X-Phos (0.6 g, 1.3 mmol), palladium acetate (0.15 g, 0.6 mmol), potassium acetate (3.2 g, 32.6 mmol) and dioxane (90 mL) were added successively. The reaction system was then replaced with N₂ three times and heated to reflux and stirred overnight under N₂ protection. After the reaction was completed, it was filtered through celite and anhydrous magnesium sulfate, and washed twice with ethyl acetate. The organic phase was collected and concentrated under reduced pressure to obtain intermediate 13, which was directly used in the next step.

Step 2:

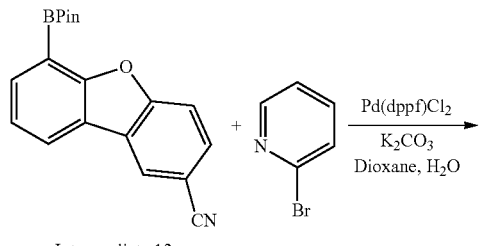

Intermediate 13

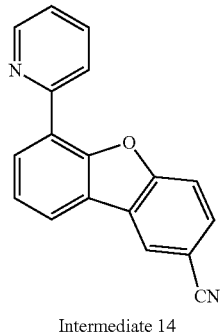

Intermediate 14

In a dried 500 mL round bottom flask, intermediate 13 (crude product), 2-bromopyridine (3.5 g, 22.2 mmol), Pd(dppf)Cl₂ (0.48 g, 0.66 mmol), potassium carbonate (3.5 g, 25.3 mmol), dioxane (90 mL) and water (30 mL) were added successively. Under N₂ protection, the reaction was heated to reflux and reacted for 12 h. After the reaction was completed, it was extracted with ethyl acetate, washed with saturated brine three times, dried over anhydrous magnesium sulfate, and concentrated under reduced pressure. The crude product was purified by column chromatography to obtain 3.9 g of intermediate 14 as a white solid (65.6% yield), and the structure of the product was confirmed by NMR and GCMS.

Step 3:

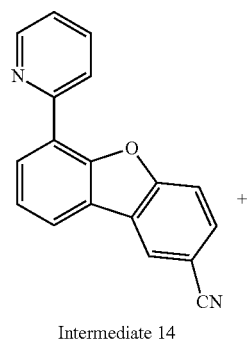

Intermediate 14

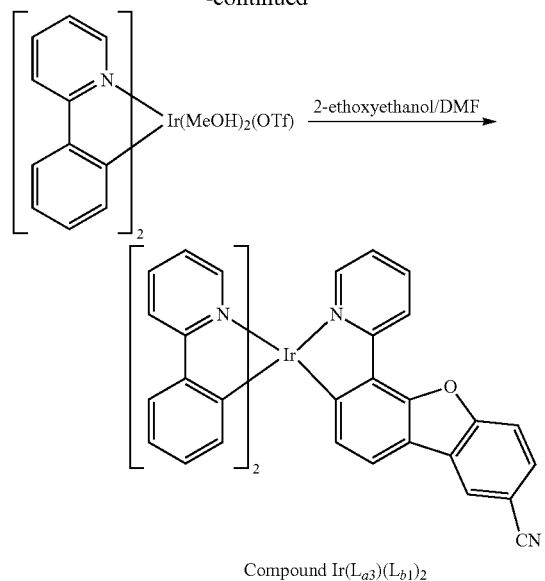

Compound Ir(L$_{a3}$)(L$_{b1}$)$_2$

In a dried 250 mL round bottom flask, intermediate 14 (3.5 g, 12.9 mmol), iridium complex (4.6 g, 6.3 mmol), 2-ethoxyethanol (50 mL) and DMF (50 mL) were added successively. Under N₂ protection, the mixture was heated to 85° C. and reacted for 96 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a3}$(L$_{b1}$)$_2$ (Metal complex 3) as a yellow solid (2.1 g, 43.3% yield). The product was identified as the target product with a molecular weight of 770.

Synthesis Example 5: Synthesis of Compound IrL$_{a1}$ (L$_{b3}$)$_2$ (Metal Complex 67)

Step 1:

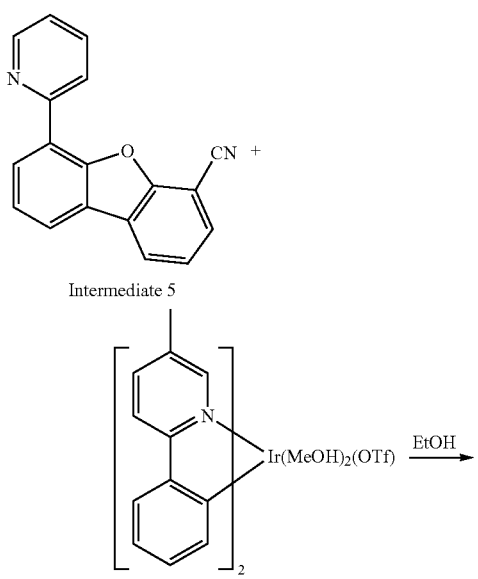

67

-continued

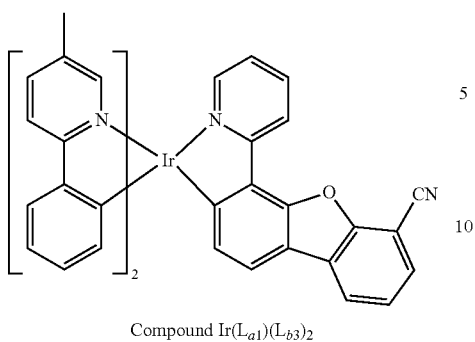

Compound Ir(L$_{a1}$)(L$_{b3}$)$_2$

In a dried 500 mL round bottom flask, intermediate 5 (2.4 g, 8.9 mmol), iridium complex (3.3 g, 4.4 mmol), and ethanol (250 mL) were added successively. The reaction system was then replaced with N$_2$ three times and protected by N$_2$, and then the reaction was heated to reflux for 24 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a1}$(L$_{b3}$)$_2$ (Metal complex 67) as a yellow solid (2.2 g, 63.7% yield). The product was identified as the target product with a molecular weight of 798.

Synthesis Example 6: Synthesis of Compound IrL$_{a1}$(L$_{b4}$)$_2$ (Metal Complex 107)

Step 1:

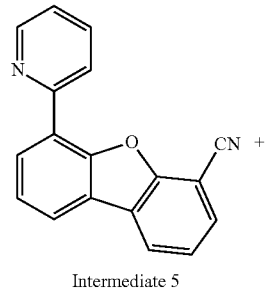

Intermediate 5

68

-continued

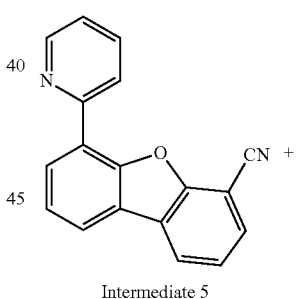

Compound Ir(L$_{a1}$)(L$_{b4}$)$_2$

In a dried 500 mL round bottom flask, intermediate 5 (2.2 g 8.1 mmol), iridium complex (4.0 g, 5.4 mmol), and ethanol (120 mL) were added successively. The reaction system was then replaced with N$_2$ three times and protected by N$_2$, and then the reaction was heated to reflux for 24 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a1}$(L$_{b4}$)$_2$ (Metal complex 107) as a yellow solid (0.8 g, 18.6% yield). The product was identified as the target product with a molecular weight of 798.

Synthesis Example 7: Synthesis of Compound IrL$_{a1}$(L$_{b8}$)$_2$ (Metal Complex 147)

Step 1:

Intermediate 5

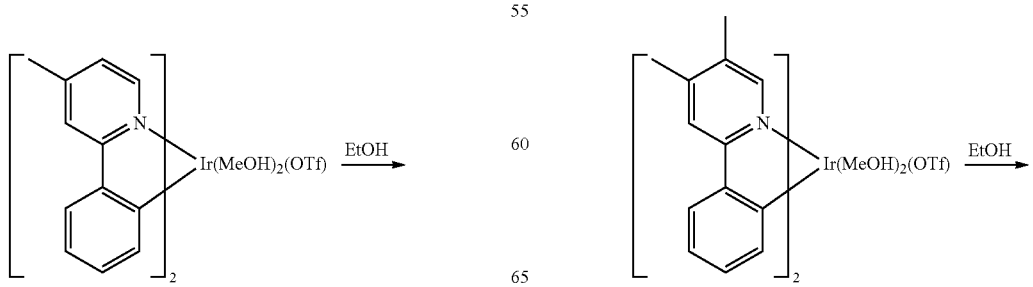

-continued

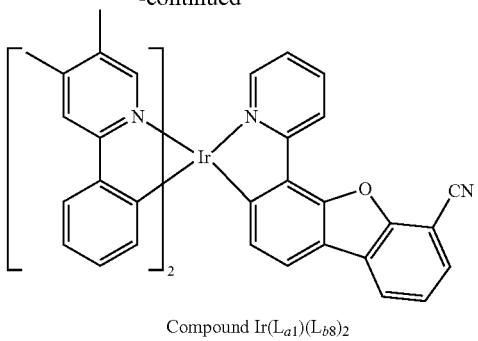

Compound Ir(L$_{a1}$)(L$_{b8}$)$_2$

In a dried 500 mL round bottom flask, intermediate 5 (2.4 g, 8.9 mmol), iridium complex (3.3 g, 4.4 mmol), and ethanol (250 mL) were added successively. The reaction system was then replaced with N$_2$ three times and protected by N$_2$, and then the reaction was heated to reflux for 24 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a1}$(L$_{b8}$)$_2$ (Metal complex 147) as a yellow solid (1.0 g, 27.5% yield). The product was identified as the target product with a molecular weight of 826.

Synthesis Example 8: Synthesis of Compound IrL$_{a221}$(L$_{b1}$)$_2$ (Metal Complex 17)

Step 1:

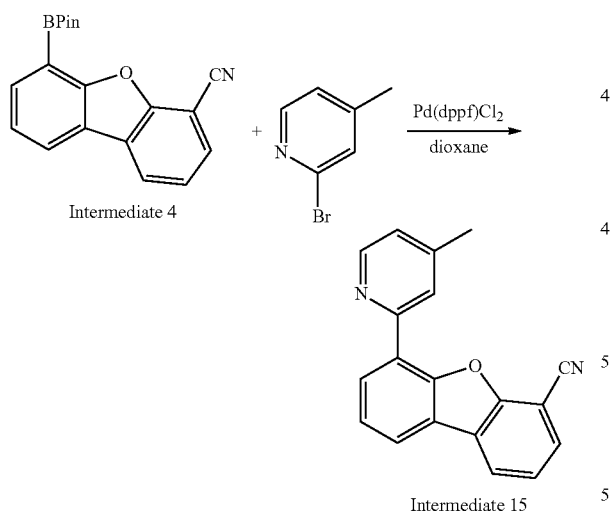

In a dried 500 mL round bottom flask, intermediate 4 (7.0 g, 22.0 mmol), 4-methyl-2-bromopyridine (4.2 g, 24.4 mmol), Pd(dppf)Cl$_2$ (0.67 g, 0.9 mmol), potassium carbonate (6.4 g, 46.3 mmol), dioxane (90 mL) and water (30 mL) were added successively. Under N$_2$ protection, the reaction was heated to reflux and reacted for 12 h. After the reaction was completed, it was extracted with ethyl acetate, washed with saturated brine three times, dried over anhydrous magnesium sulfate, and concentrated under reduced pressure. The crude product was purified by column chromatography to obtain 3 g of intermediate 15 as a white solid (48.0% yield), and the structure of the product was confirmed by NMR and LCMS.

Step 2:

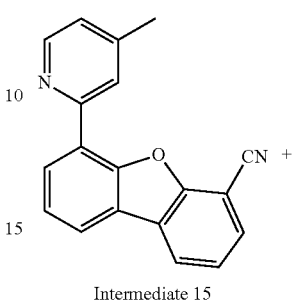

Intermediate 15

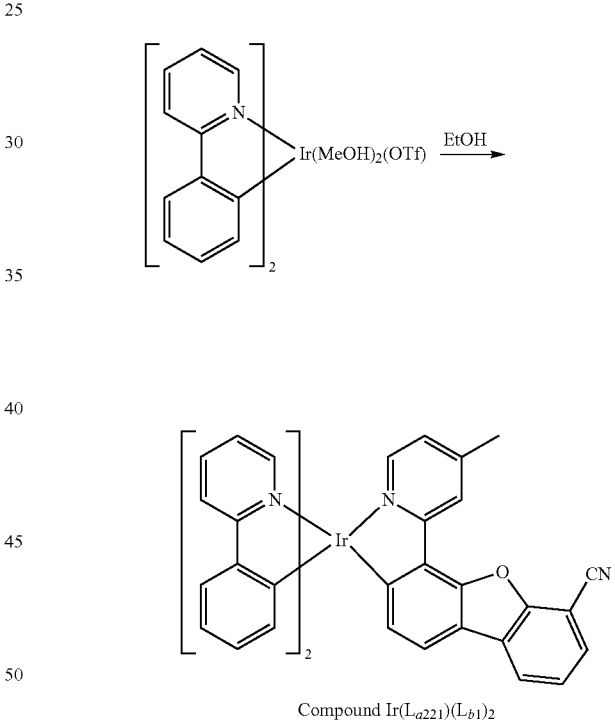

Compound Ir(L$_{a221}$)(L$_{b1}$)$_2$

In a dried 250 mL round bottom flask, intermediate 15 (3 g, 10.5 mmol), iridium complex (3.5 g, 5 mmol), and ethanol (100 mL) were added successively. Under N$_2$ protection, the mixture was heated to reflux and reacted for 36 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a221}$(L$_{b1}$)$_2$ (Metal complex 17) as a yellow solid (1.4 g, 33.6% yield). The product was identified as the target product with a molecular weight of 784.

Synthesis Example 9: Synthesis of Compound IrL$_{a962}$(L$_{b1}$)$_2$ (Metal Complex 53)

Step 1:

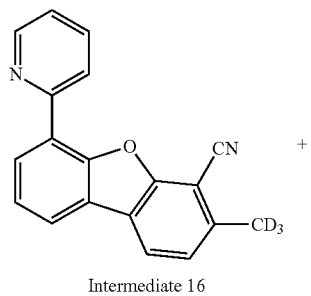

Intermediate 16

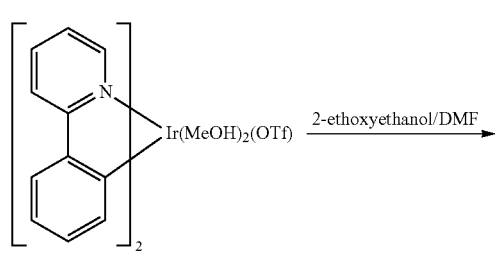 $\xrightarrow{\text{2-ethoxyethanol/DMF}}$

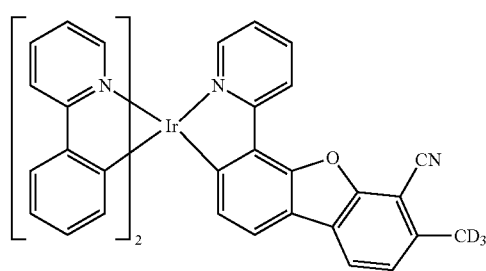

Compound Ir(L$_{a962}$)(L$_{b1}$)$_2$

Synthesis Example 10: Synthesis of Compound IrL$_{a962}$(L$_{b3}$)$_2$ (Metal Complex 93)

Step 1:

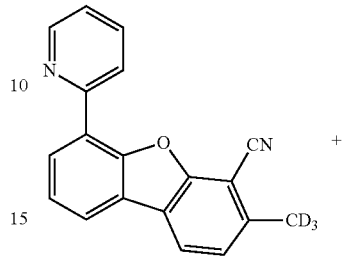

Intermediate 16

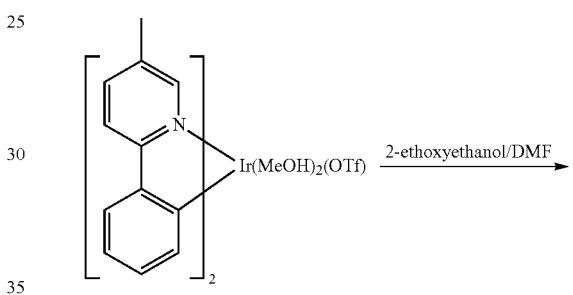 $\xrightarrow{\text{2-ethoxyethanol/DMF}}$

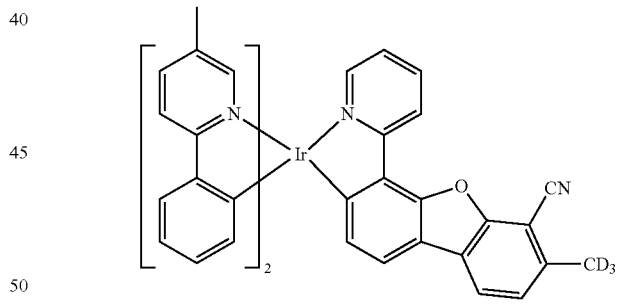

Compound Ir(L$_{a962}$)(L$_{b3}$)$_2$

In a dried 250 mL round bottom flask, intermediate 16 (2.6 g, 9 mmol), iridium complex (3.6 g, 5 mmol), 2-ethoxyethanol (50 mL) and DMF (50 mL) were added successively. Under N$_2$ protection, the mixture was heated to 85° C. and reacted for 96 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a962}$(L$_{b1}$)$_2$ (Metal complex 53) as a yellow solid (1.3 g, 33.3% yield). The product was identified as the target product with a molecular weight of 787.

In a dried 250 mL round bottom flask, intermediate 16 (2.8 g, 9.7 mmol), iridium complex (4.0 g, 5.4 mmol), 2-ethoxyethanol (50 mL) and DMF (50 mL) were added successively. Under N$_2$ protection, the mixture was heated to 85° C. and reacted for 96 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a962}$(L$_{b3}$)$_2$ (Metal complex 93) as a yellow solid (0.85 g, 19.3% yield). The product was identified as the target product with a molecular weight of 815.

Synthesis Example 11: Synthesis of Compound IrL$_{a293}$(L$_{b1}$)$_2$ (Metal Complex 19)

Step 1:

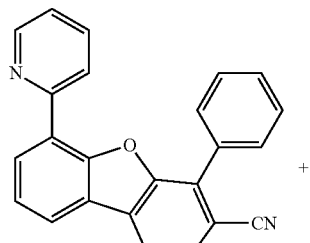

Intermediate 17

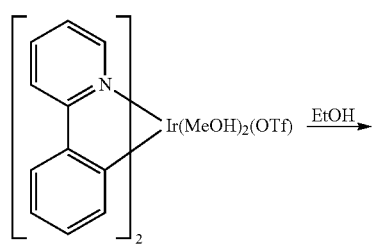

Compound Ir(L$_{a293}$)(L$_{b1}$)$_2$

In a dried 250 mL round bottom flask, intermediate 17 (2.6 g, 7.5 mmol), iridium complex (2.2 g, 6.0 mmol), and ethanol (150 mL) were added successively. Under N$_2$ protection, the mixture was heated to reflux and reacted for 24 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a293}$(L$_{b1}$)$_2$ (Metal complex 19) as a yellow solid (0.6 g, 12% yield). The product was identified as the target product with a molecular weight of 846.

Synthesis Example 12: Synthesis of Compound IrL$_{a293}$(L$_{b3}$)$_2$ (Metal Complex 77)

Step 1:

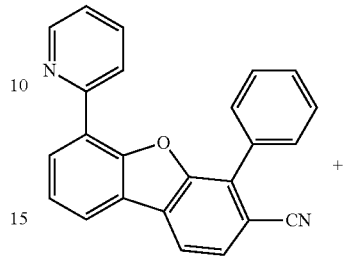

Intermediate 17

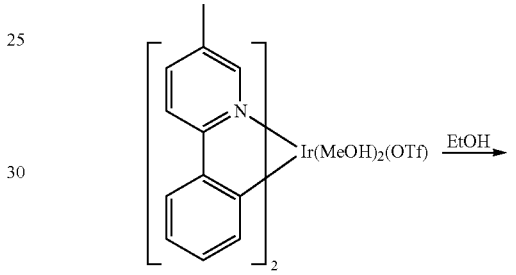

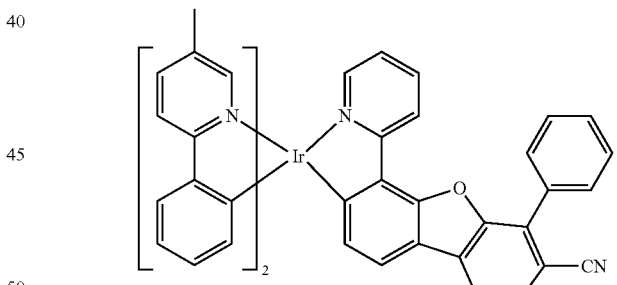

Compound Ir(L$_{a293}$)(L$_{b3}$)$_2$

In a dried 250 mL round bottom flask, intermediate 17 (2.6 g, 7.5 mmol), iridium complex (2.2 g, 6.0 mmol), and ethanol (150 mL) were added successively. Under N$_2$ protection, the mixture was heated to reflux and reacted for 24 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a293}$(L$_{b3}$)$_2$ (Metal complex 77) as a yellow solid (0.6 g, 12% yield). The product was identified as the target product with a molecular weight of 874.

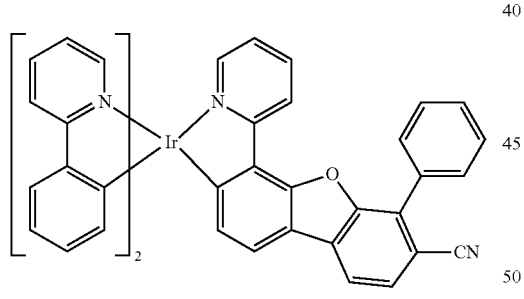

Synthesis Example 13: Synthesis of Compound IrL$_{a987}$(L$_{b3}$)$_2$ (Metal Complex 102)

Step 1:

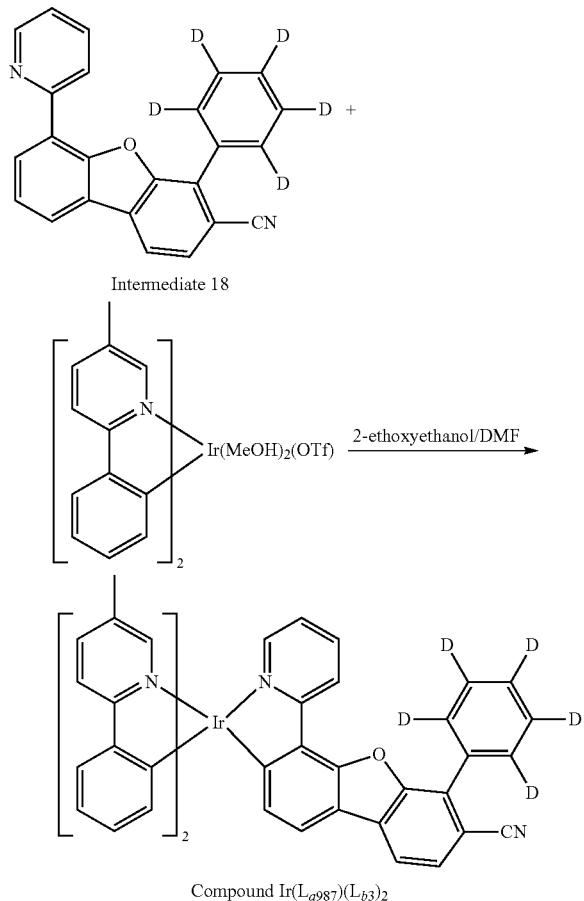

Intermediate 18

Compound Ir(L$_{a987}$)(L$_{b3}$)$_2$

In a dried 250 mL round bottom flask, intermediate 18 (3.0 g, 8.5 mmol), iridium complex (4.2 g, 5.7 mmol), 2-ethoxyethanol (100 mL) and DMF (100 mL) were added successively. Under N$_2$ protection, the mixture was heated to 85° C. and reacted for 96 h. After the reaction was cooled, it was filtered through celite. The mixture was washed twice with methanol and n-hexane. The yellow solid above the celite was dissolved in dichloromethane. The organic phase was collected, concentrated under reduced pressure, and purified by column chromatography to obtain the compound IrL$_{a987}$(L$_{b3}$)$_2$ (Metal complex 102) as a yellow solid (0.9 g, 18.0% yield). The product was identified as the target product with a molecular weight of 879.

Those skilled in the art should know that the above preparation method is only an exemplary example, and those skilled in the art can obtain other compound structures of the present disclosure by improving it.

DEVICE EXAMPLE

Example 1

Firstly, a glass substrate with a 120 nm-thick indium tin oxide (ITO) anode was cleaned, and then treated with oxygen plasma and UV ozone. After processing, the substrate was oven-dried in a glovebox to remove moisture. The substrate was then mounted on a substrate holder and loaded into a vacuum chamber. The organic layers specified below were deposited by thermal vacuum evaporation sequentially on the ITO anode at a rate of 0.2-2 angstroms per second under a vacuum degree of about $10^{-8}$ Torr. Compound HI (100 Å) was used as a hole injection layer (HIL). Compound HT (350 Å) was used as a hole transporting layer (HTL). Compound H1 (50 Å) was used as an electron blocking layer (EBL). Then, the compound IrL$_{a1}$(L$_{b1}$)$_2$ (Metal complex 1) of the present disclosure was doped in the host compounds H1 and H2 and used as a light-emitting layer (EML, 8:46:46, 400 Å). Compound H2 (100 Å) was used as a hole blocking layer (HBL). On the HBL, a mixture of Compound ET and 8-hydroxyquinolinolato-lithium (Liq) was deposited as an electron transporting layer (ETL, 40:60, 350 Å). Finally, 10 Å of Liq was deposited as an electron injection layer, and 1200 Å of Al was deposited as a cathode. The device was then transferred back to the glovebox and encapsulated with a glass lid and a moisture getter to complete the device.

Example 2

The implementation of Example 2 was the same as that of Example 1, except that the compound IrL$_{a2}$(L$_{b1}$)$_2$ (Metal complex 2) of the present disclosure was used in the light-emitting layer instead of the compound IrL$_{a1}$(L$_{b1}$)$_2$ (Metal complex 1) of the present disclosure in the Example 1.

Example 3

The implementation of Example 3 was the same as that of Example 1, except that the compound IrL$_{a1}$(L$_{b3}$)$_2$ (Metal complex 67) of the present disclosure was used in the light-emitting layer instead of the compound IrL$_{a1}$(L$_{b1}$)$_2$ (Metal complex 1) of the present disclosure in the Example 1, respectively.

Example 4

The implementation of Example 4 was the same as that of Example 1, except that the compound IrL$_{a1}$(L$_{b4}$)$_2$ (Metal complex 107) of the present disclosure was used in the light-emitting layer instead of the compound IrL$_{a1}$(L$_{b1}$)$_2$ (Metal complex 1) of the present disclosure in the Example 1, respectively.

Example 5

The implementation of Example 5 was the same as that of Example 1, except that the compound IrL$_{a1}$(L$_{b8}$)$_2$ (Metal complex 147) of the present disclosure was used in the light-emitting layer instead of the compound IrL$_{a1}$(L$_{b1}$)$_2$ (Metal complex 1) of the present disclosure in the Example 1, respectively.

Example 6

The implementation of Example 6 was the same as that of Example 1, except that the compound IrL$_{a962}$(L$_{b1}$)$_2$ (Metal complex 53) of the present disclosure was used in the light-emitting layer instead of the compound IrL$_{a1}$(L$_{b1}$)$_2$ (Metal complex 1) of the present disclosure in the Example 1, respectively.

Example 7

The implementation of Example 7 was the same as that of Example 1, except that the compound IrL$_{a2}$(L$_{b3}$)$_2$ (Metal complex 93) of the present disclosure was used in the light-emitting layer instead of the compound $IrL_{a1}(L_{b1})_2$ (Metal complex 1) of the present disclosure in the Example 1, respectively.

Example 8

The implementation of Example 8 was the same as that of Example 1, except that the compound $IrL_{a293}(L_{b3})_2$ (Metal complex 77) of the present disclosure was used in the light-emitting layer instead of the compound $IrL_{a1}(L_{b1})_2$ (Metal complex 1) of the present disclosure in the Example 1, respectively.

Example 9

The implementation of Example 9 was the same as that of Example 1, except that the compound $IrL_{a987}(L_{b3})_2$ (Metal complex 102) of the present disclosure was used in the light-emitting layer instead of the compound $IrL_{a1}(L_{b1})_2$ (Metal complex 1) of the present disclosure in the Example 1, respectively.

Comparative Example 1

The implementation of Comparative Example 1 was the same as that of Example 1, except that the comparative compound 1 was used in the light-emitting layer instead of the compound $IrL_{a1}(L_{b1})_2$ (Metal complex 1) of the present disclosure in the Example 1.

For a layer with more than one materials being used, it was obtained by doping different compounds at the recorded weight ratios.

Part detailed device layer structures and thicknesses are shown in Table 1.

TABLE 1

The device structure of the device examples

| Device ID | HIL | HTL | EBL | EML | HBL | ETL |
|---|---|---|---|---|---|---|
| Example 1 | Compound HI (100 Å) | Compound HT (350 Å) | Compound H1 (50 Å) | Compound H1:Compound H2:$IrL_{a1}(L_{b1})_2$ (Metal Complex 1) (46:46:8) (400 Å) | Compound H2 (100 Å) | Compound ET:Liq (40:60) (350 Å) |
| Example 2 | Compound HI (100 Å) | Compound HT (350 Å) | Compound H1 (50 Å) | Compound H1:Compound H2:$IrL_{a2}(L_{b1})_2$ (Metal Complex 2) (46:46:8) (400 Å) | Compound H2 (100 Å) | Compound ET:Liq (40:60) (350 Å) |
| Example 3 | Compound HI (100 Å) | Compound HT (350 Å) | Compound H1 (50 Å) | Compound H1:Compound H2:$IrL_{a1}(L_{b3})_2$ (Metal Complex 67) (46:46:8) (400 Å) | Compound H2 (100 Å) | Compound ET:Liq (40:60) (350 Å) |
| Example 4 | Compound HI (100 Å) | Compound HT (350 Å) | Compound H1 (50 Å) | Compound H1:Compound H2:$IrL_{a1}(L_{b4})_2$ (Metal Complex 107) (46:46:8) (400 Å) | Compound H2 (100 Å) | Compound ET:Liq (40:60) (350 Å) |
| Example 5 | Compound HI (100 Å) | Compound HT (350 Å) | Compound H1 (50 Å) | Compound H1:Compound H2:$IrL_{a1}(L_{b8})_2$ (Metal Complex 147) (46:46:8) (400 Å) | Compound H2 (100 Å) | Compound ET:Liq (40:60) (350 Å) |
| Example 6 | Compound HI (100 Å) | Compound HT (350 Å) | Compound H1 (50 Å) | Compound H1:Compound H2:$IrL_{a962}(L_{b1})_2$ (Metal Complex 53) (46:46:8) (400 Å) | Compound H2 (100 Å) | Compound ET:Liq (40:60) (350 Å) |
| Example 7 | Compound HI (100 Å) | Compound HT (350 Å) | Compound H1 (50 Å) | Compound H1:Compound H2:$IrL_{a962}(L_{b3})_2$ (Metal Complex 93) (46:46:8) (400 Å) | Compound H2 (100 Å) | Compound ET:Liq (40:60) (350 Å) |
| Example 8 | Compound HI (100 Å) | Compound HT (350 Å) | Compound H1 (50 Å) | Compound H1:Compound H2:$IrL_{a293}(L_{b3})_2$ (Metal Complex 77) (46:46:8) (400 Å) | Compound H2 (100 Å) | Compound ET:Liq (40:60) (350 Å) |
| Example 9 | Compound HI (100 Å) | Compound HT (350 Å) | Compound H1 (50 Å) | Compound H1:Compound H2:$IrL_{a987}(L_{b3})_2$ (Metal Complex 102) (46:46:8) (400 Å) | Compound H2 (100 Å) | Compound ET:Liq (40:60) (350 Å) |
| Comparative Example 1 | Compound HI (100 Å) | Compound HT (350 Å) | Compound H1 (50 Å) | Compound H1:Compound H2:Comparative compound 1 (46:46:8) (400 Å) | Compound H2 (100 Å) | Compound ET:Liq (40:60) (350 Å) |

The structures of the materials used in the device are as follows:
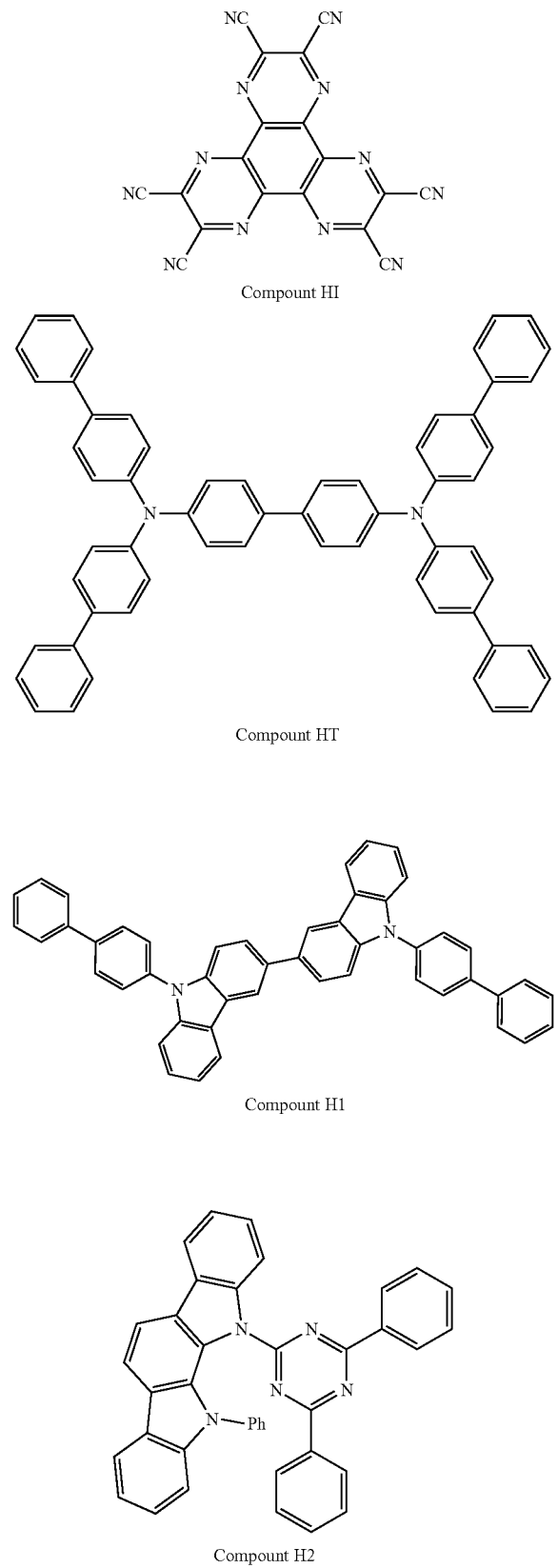
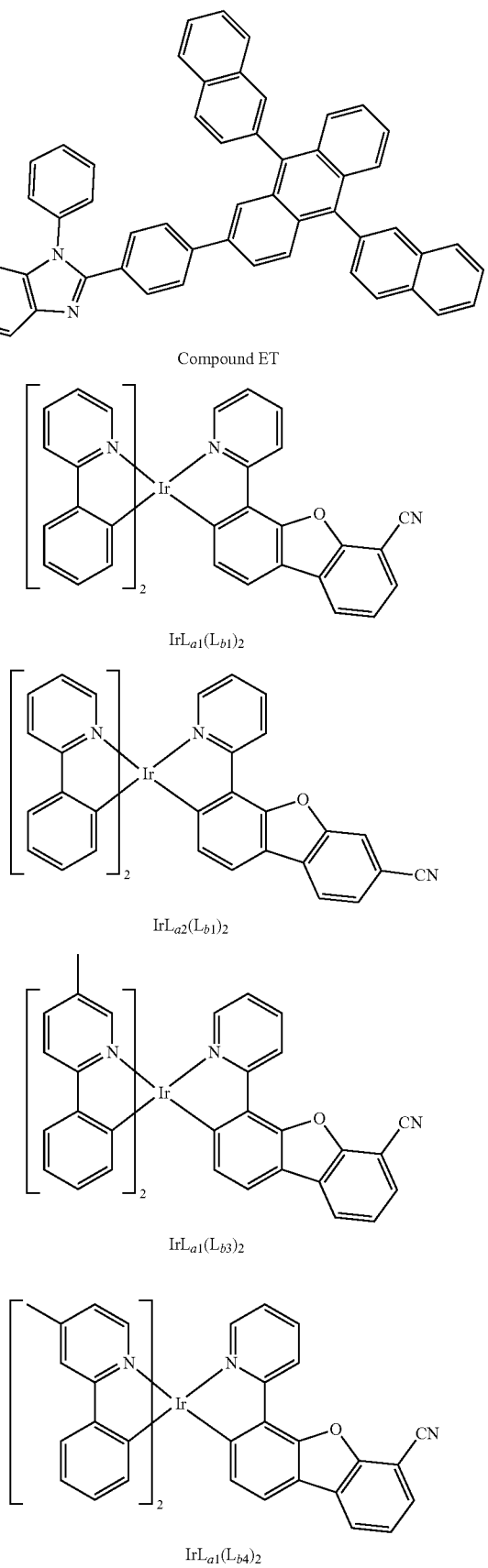

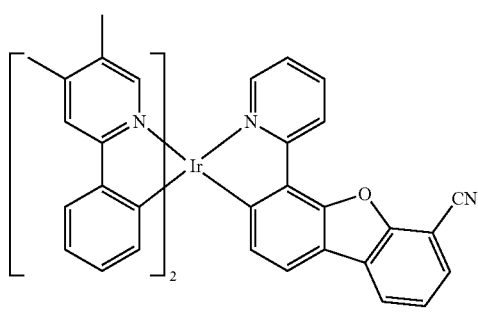

IrL$_{a1}$(L$_{b8}$)$_2$

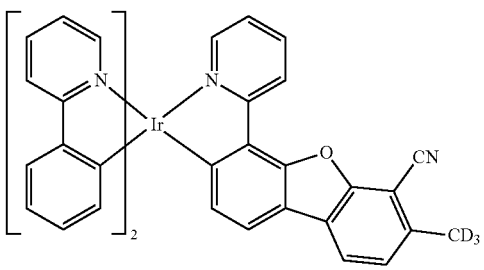

IrL$_{a962}$(L$_{b1}$)$_2$

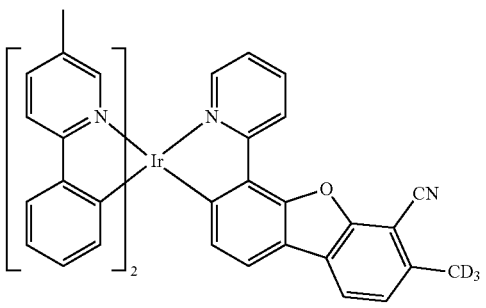

IrL$_{a962}$(L$_{b3}$)$_2$

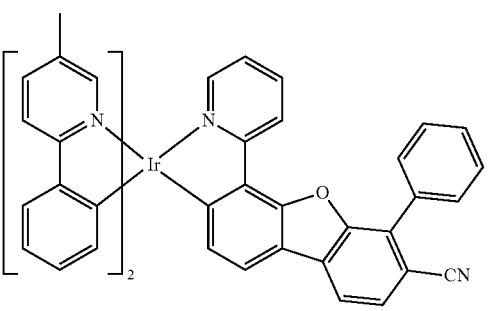

IrL$_{a293}$(L$_{b3}$)$_2$

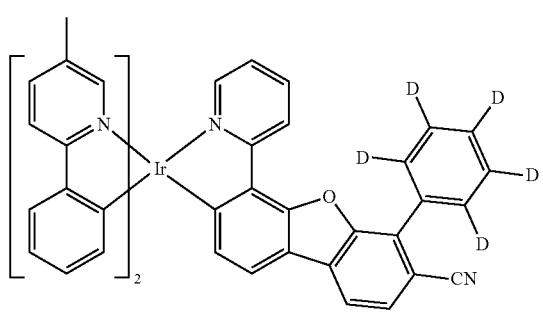

IrL$_{a987}$(L$_{b3}$)$_2$

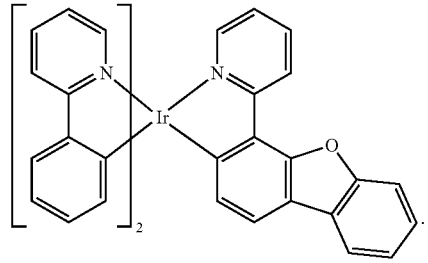

Comparative Compound 1

The IVL and lifetime characteristics of the device were measured at different current densities and voltages. Table 2 shows the data about the external quantum efficiency (EQE), λmax, full width at half maximum (FWHM), voltage (V), and CIE measured at 1000 nits.

TABLE 2

Device data

| Device number | CIE (x, y) | λmax (nm) | FWHM (nm) | Voltage (V) | EQE (%) |
|---|---|---|---|---|---|
| Example 1 | 0.316, 0.645 | 523 | 53.9 | 2.76 | 23.62 |
| Example 2 | 0.325, 0.644 | 526 | 42.5 | 2.76 | 24.81 |
| Comparative Example 1 | 0.341, 0.630 | 528 | 59.3 | 2.98 | 22.52 |

Table 3 shows the data about the external quantum efficiency (EQE), λmax, full width at half maximum (FWHM), voltage (V), and CIE of Examples 3 to 9 and Comparative Example 1 measured at 1000 nits. The lifetime (LT97) data of Examples 3 to 9 and Comparative Example 1 were tested at a constant current of 80 mA/cm$^2$.

TABLE 3

Device data

| Device number | CIE (x, y) | λmax (nm) | FWHM (nm) | Voltage (V) | EQE (%) | LT97 (h) |
|---|---|---|---|---|---|---|
| Example 3 | 0.341, 0.631 | 527 | 57.8 | 2.67 | 23.65 | 17.9 |
| Example 4 | 0.345, 0.628 | 528 | 58.5 | 2 | 23.26 | 21.9 |
| Example 5 | 0.339, 0.632 | 527 | 57.9 | 2.83 | 24.15 | 20.7 |
| Example 6 | 0.326, 0.639 | 525 | 55.0 | 2.70 | 23.52 | 23.7 |
| Example 7 | 0.345, 0.628 | 528 | 57.3 | 2.67 | 23.27 | 20.7 |
| Example 8 | 0.346, 0.632 | 531 | 37.8 | 2.64 | 26.23 | 15.0 |
| Example 9 | 0.346, 0.631 | 531 | 41.1 | 2.67 | 25.93 | 17.2 |
| Comparative Example 1 | 0.341, 0.630 | 528 | 59.3 | 2.98 | 22.52 | 15.0 |

Discussion:

As can be seen from Table 2, the device examples with the compounds of the present disclosure show several advantages over the comparative compound. Compared to Comparative Compound 1, the compounds of the present disclosure unexpectedly showed many characteristics, for example, in Examples 1 and 2, high efficiency of 23.62% and 24.81% EQE were achieved, respectively, and the voltage was more than 0.2 V lower than that of Comparative Compound 1 which contained no cyano substitution, and there was no noticeable blue-shifted or red-shifted light emission. The most unexpected is that they had a very narrow peak width of emitted light. In particular, the full width at half maximum of Example 2 was only 42.5 nm, which was unprecedented in green phosphorescent devices.

These advantages will greatly help to improve the level and color saturation of green light devices.

As can be seen from Table 3, the device examples with the compounds of the present disclosure show several advantages over the comparative compound. Compared to Comparative Example 1, Examples 3-7 showed a higher EQE (23.25%-24.15% vs. 22.52%), and the life time was significantly better than Comparative Example 1 (17.9 h-23.7 h vs. 15 h). The life time of Example 6 was nearly 60% higher than that of Comparative Example 1 (23.7 h vs. 15 h), and the voltage was more than 0.2 V-0.3 V lower than that of Comparative Example 1 which contained no cyano substitution.

Compared with Comparative Example 1, Example 8 and Example 9 showed much higher EQE (26.23%, 25.93% vs. 22.52%), and a voltage drop exceeding 0.3 V (2.64 V-2.67 V vs. 2.98 V). The life time of Example 9 was 14.67% higher than that of Comparative Example 1 (17.2 h vs. 15 h). The most unexpected is that they had a very narrow peak width of emitted light. In particular, the full width at half maximum of Example 8 was only 37.8 nm, which was unprecedented in green phosphorescent devices.

Example 8 and Example 9 are comparisons of hydrogen and deuterated compounds at corresponding substitution positions. Example 9 has a longer lifespan than Example 8 and proves the advantages of deuterated compounds in the present disclosure.

It should be understood that the various embodiments described herein are merely examples and are not intended to limit the scope of the present disclosure. Therefore, as will be apparent to those skilled in the art, the claimed disclosure may include variations from the specific and preferred embodiments described herein. Many of the materials and structures described herein may be replaced with other materials and structures without departing from the spirit of the disclosure. It should be understood that various theories as to why the present disclosure works are not intended to be limiting.

What is claimed is:

1. A metal complex comprising a ligand $L_a$ represented by Formula 1:

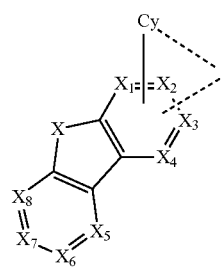

Formula 1 wherein,

Cy is any structure selected from the group consisting of:

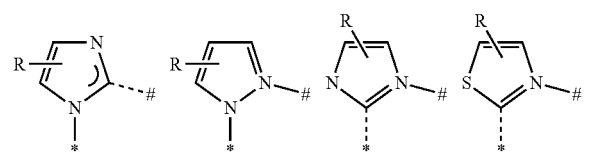

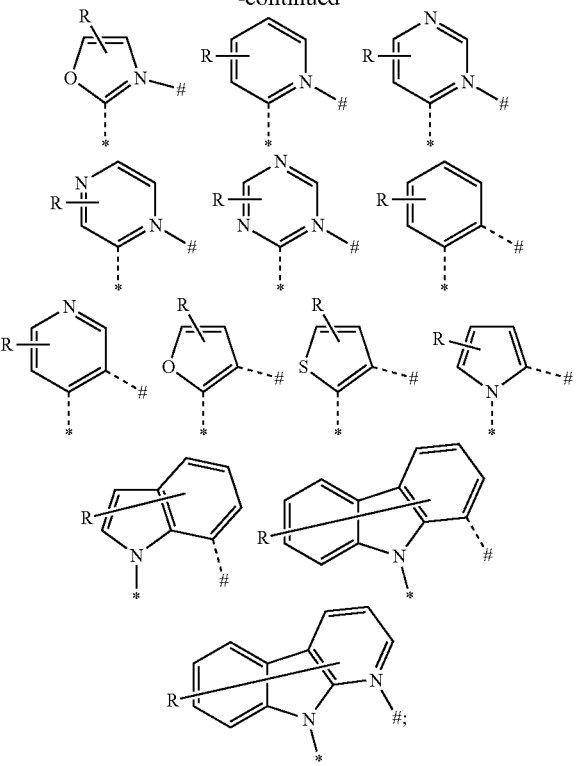

R may represent mono-substitution, up to the maximum available multi-substitution, or no substitution; when more than one R exists in any structure, the R may be the same or different;

$X_1$ to $X_4$ are each independently selected from C, $CR_{x1}$ or N, and at least one of $X_1$ to $X_4$ is C which is connected to the Cy; when more than one of $X_1$ to $X_4$ is $CR_{x1}$, the $R_{x1}$ may be the same or different;

$X_5$ to $X_8$ are each independently selected from $CR_{x2}$ or N; when more than one of $X_5$ to $X_8$ is $CR_{x2}$, the $R_{x2}$ may be the same or different;

X is selected from the group consisting of O, S, Se, $NR_{x3}$, $CR_{x4}R_{x5}$ and $SiR_{x6}R_{x7}$;

R, $R_{x1}$, $R_{x2}$, $R_{x3}$, $R_{x4}$, $R_{x5}$, $R_{x6}$ and $R_{x7}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof, wherein, at least one of $R_{x1}$ and $R_{x2}$ is present and is a cyano group;

wherein, "#" represents a position at which the metal is connected, and "*" represents a position at which $X_1$, $X_2$, $X_3$ or $X_4$ is connected;

any two adjacent substituents can optionally be joined to form a ring;

$X_1$, $X_2$, $X_3$ or $X_4$ is connected to the metal through a metal-carbon bond or a metal-nitrogen bond.

2. The metal complex according to claim 1, wherein Cy is any structure selected from the group consisting of:

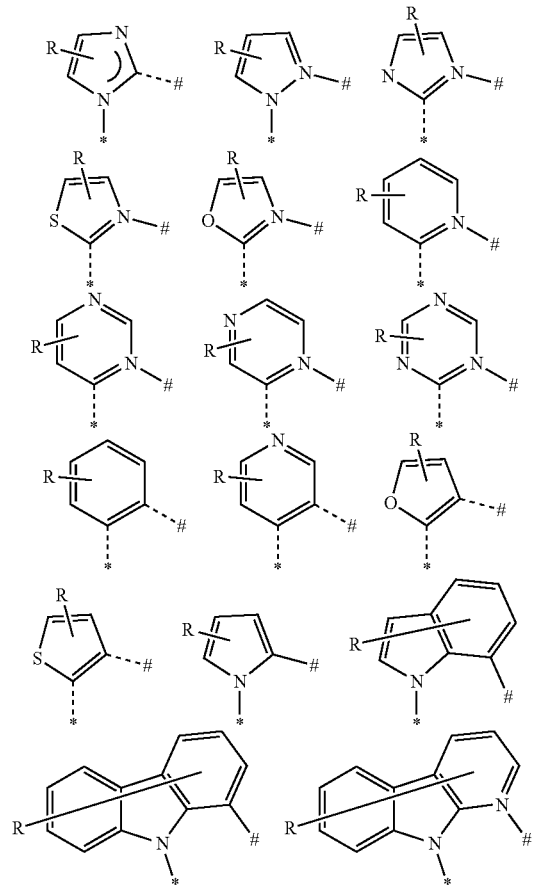

wherein,

R may represent mono-substitution, up to the maximum available multi-substitution, or no substitution; when more than one R exists in any structure, the R may be the same or different;

R is each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof, any two adjacent substituents can optionally be joined to form a ring;

wherein, "#" represents a position at which the metal is connected, and "*" represents a position at which $X_1$, $X_2$, $X_3$ or $X_4$ is connected.

3. The metal complex according to claim 1, wherein the metal complex has a general formula of $M(L_a)_m(L_b)_n(L_c)_q$, wherein $L_a$ is a first ligand coordinated to the metal M, and the $L_b$ and the $L_c$ are a second ligand and a third ligand coordinated to the metal M, respectively, the $L_b$ and the $L_c$ may be the same or different;

the $L_a$, $L_b$ and $L_c$ can optionally be linked to form a multidentate ligand;

wherein, m is 1, 2 or 3, n is 0, 1 or 2, q is 0, 1 or 2, and m+n+q is equal to the oxidation state of M;

wherein, the metal M is selected from the group consisting of Cu, Ag, Au, Ru, Rh, Pd, Os, Ir, and Pt;

wherein, $L_a$ is independently selected from the group consisting of:

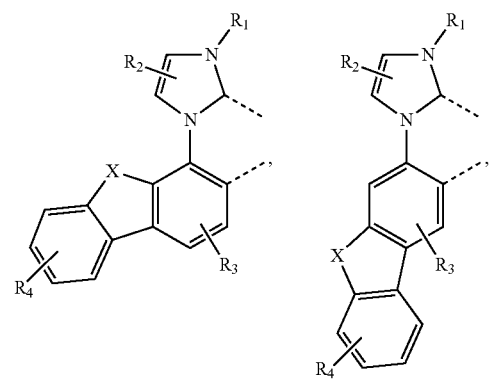

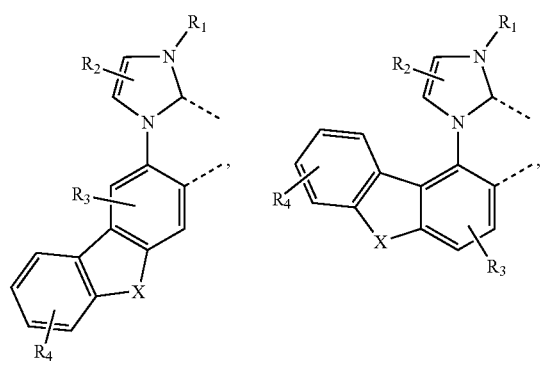

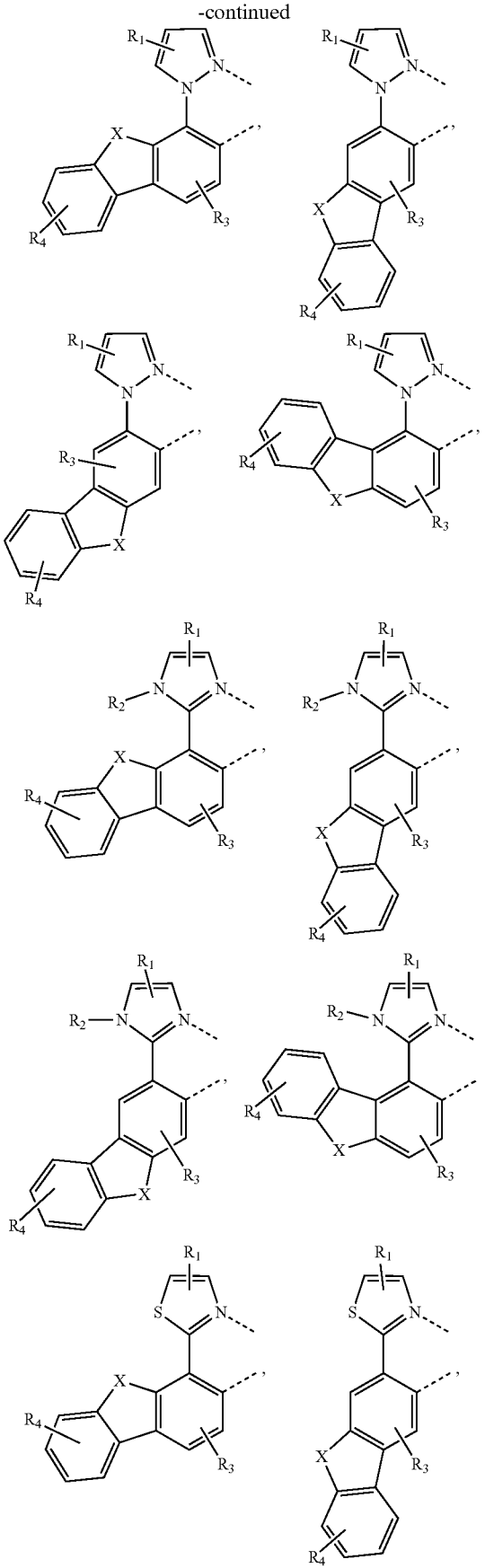
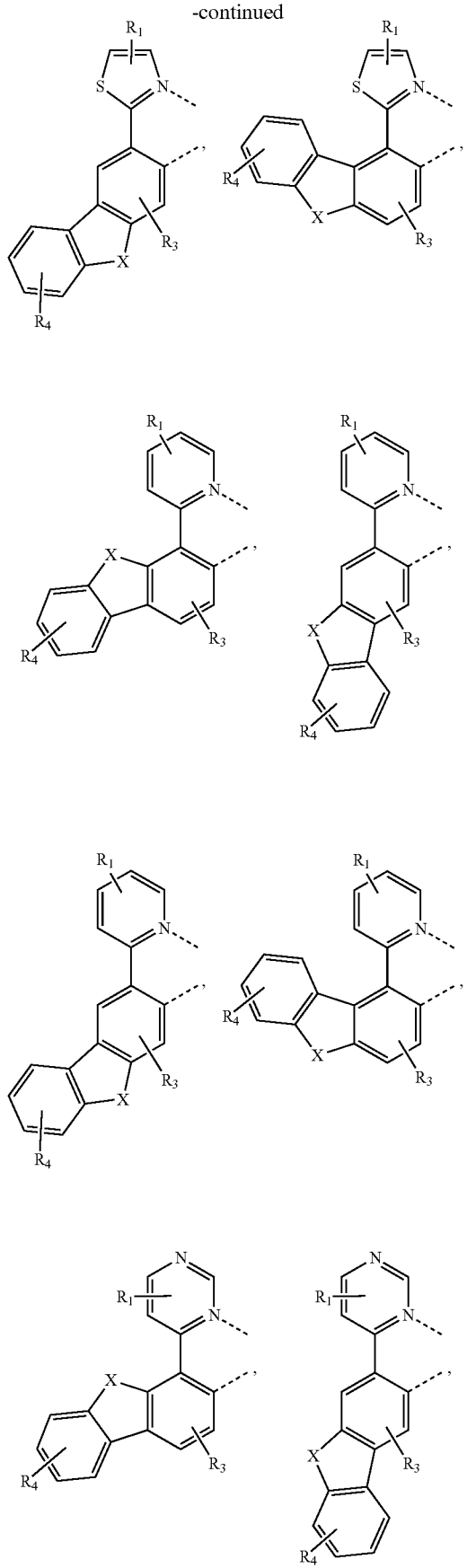

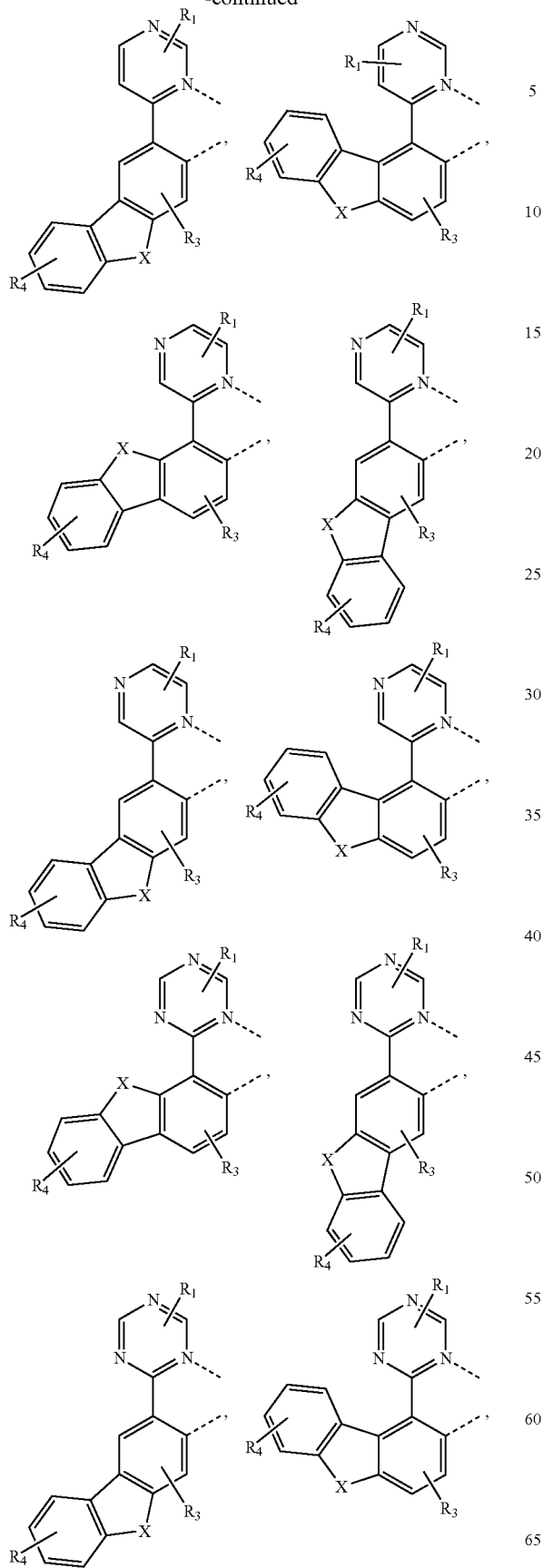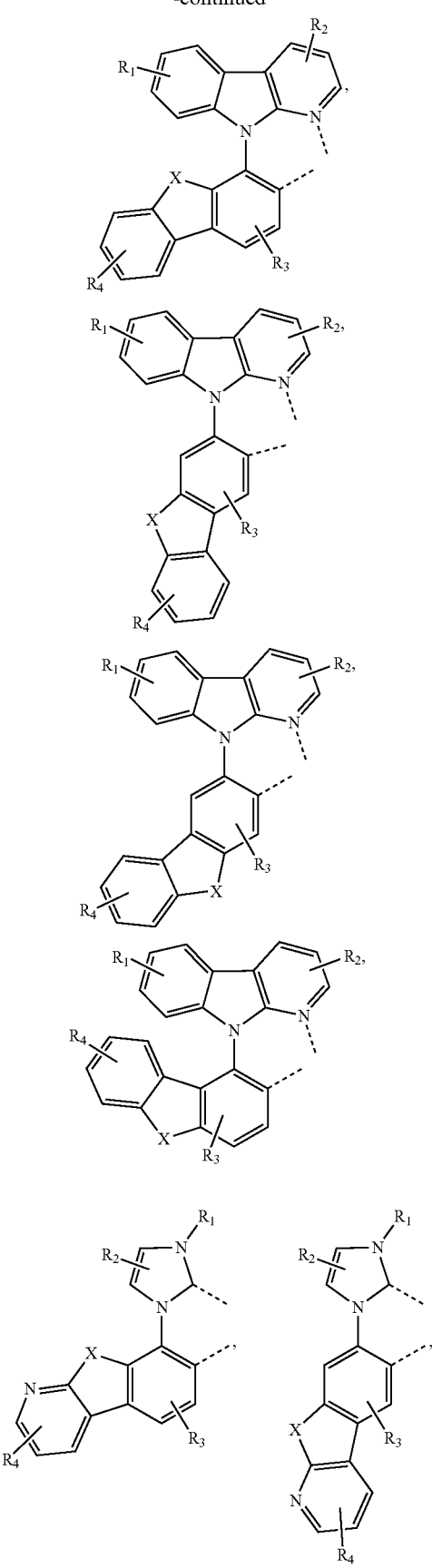

-continued
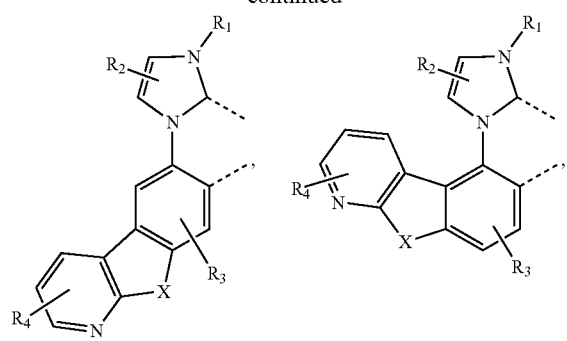
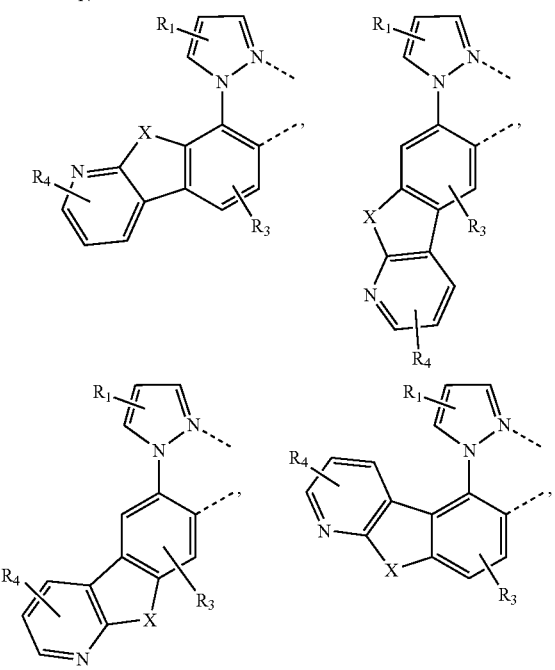
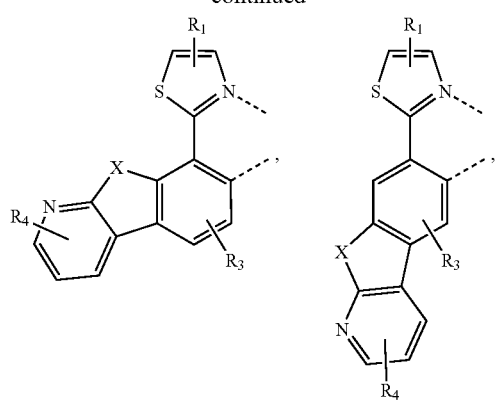
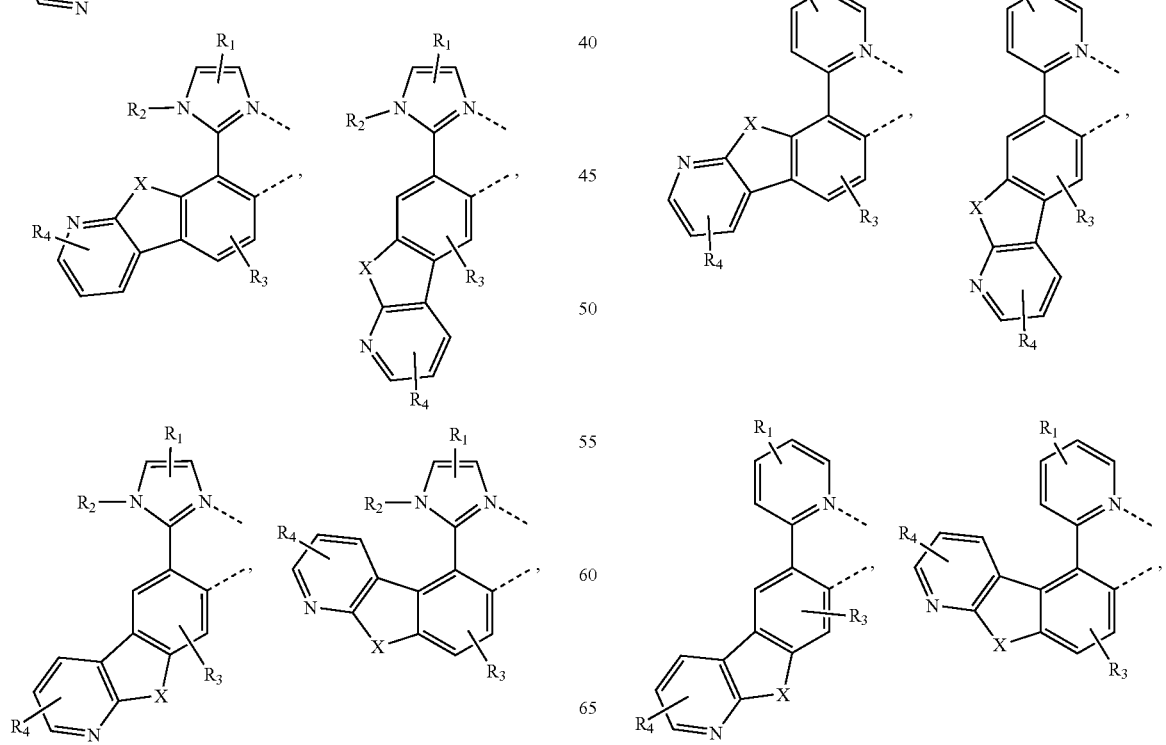

-continued
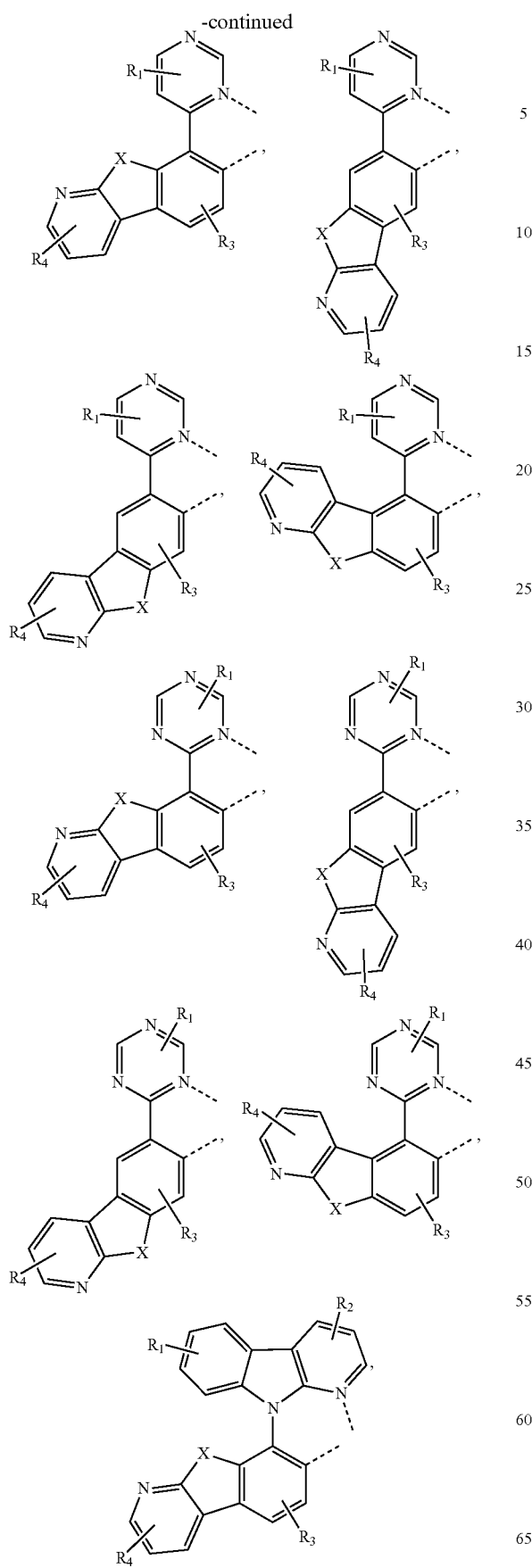
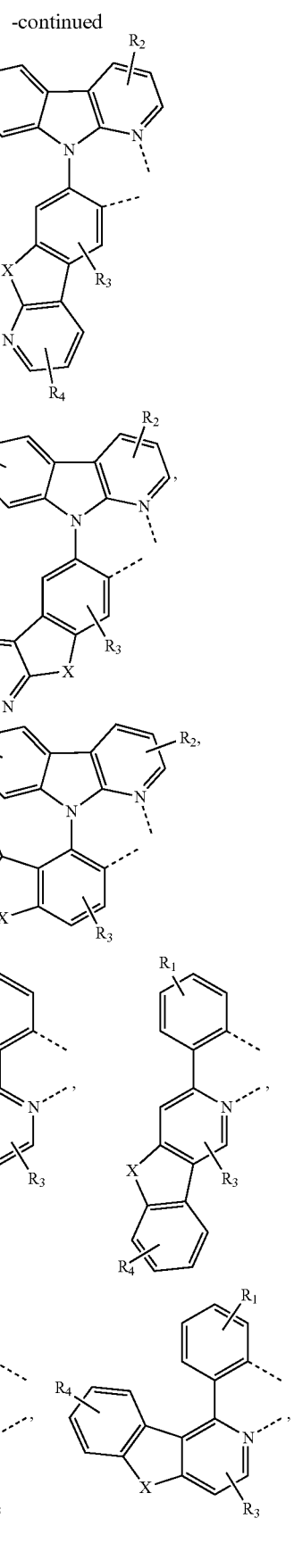

-continued

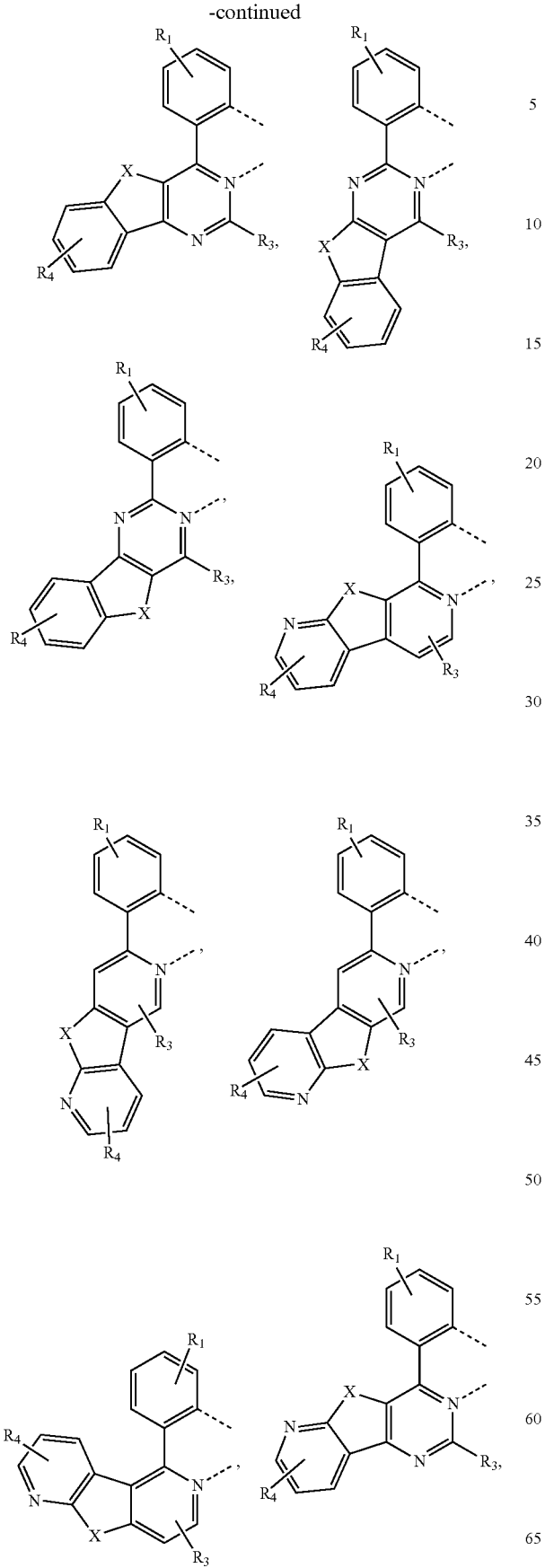
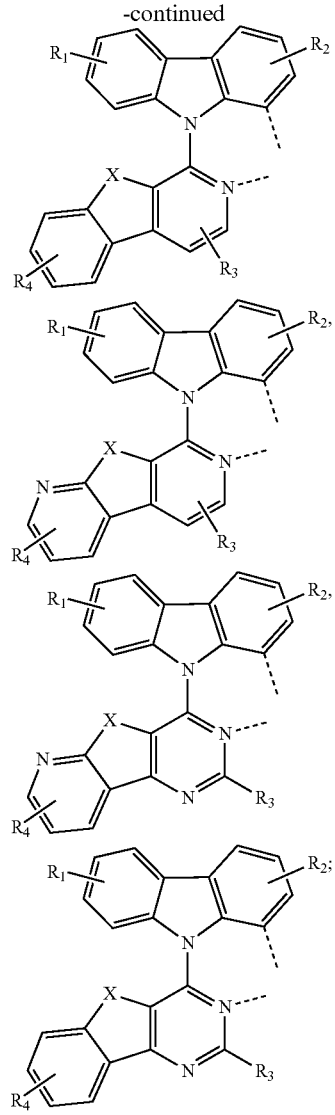

X is selected from the group consisting of O, S, Se, $NR_{x3}$, $CR_{x4}R_{x5}$ and $SiR_{x6}R_{x7}$;

$R_1$, $R_2$, $R_3$ and $R_4$ may represent mono-, di-, tri- or tetra-substitution, or no substitution;

$R_1$, $R_2$, $R_3$, $R_4$, $R_{x3}$, $R_{x4}$, $R_{x5}$, $R_{x6}$ and $R_{x7}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof, wherein, at least one of $R_3$ and $R_4$ is present and is a cyano group;

any two adjacent substituents can optionally be joined to form a ring;

wherein, the $L_b$ and $L_c$ are each independently selected from the group consisting of:

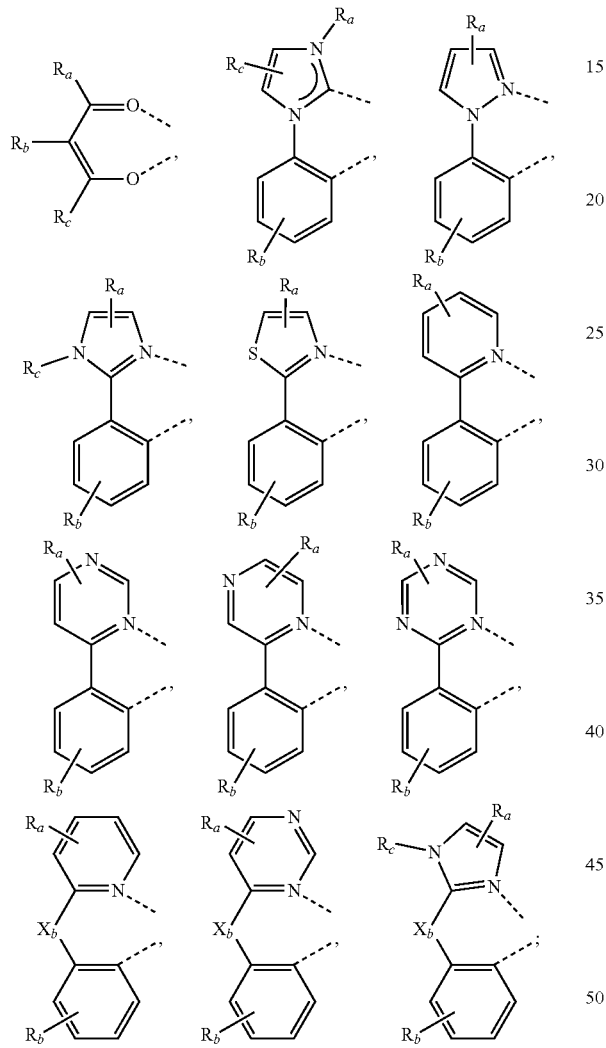

wherein, $R_a$, $R_b$, and $R_c$ may represent mono-, di-, tri- or tetra-substitution, or no substitution;

$X_b$ is selected from the group consisting of: O, S, Se, $NR_{N1}$, and $CR_{C1}R_{C2}$;

$R_a$, $R_b$, $R_c$, $R_{N1}$, $R_{C1}$ and $R_{C2}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof; and any two adjacent substituents can optionally be joined to form a ring.

4. The metal complex according to claim 3, wherein the metal complex has a structure represented by any one of Formulas 2 to 10:

Formula 2

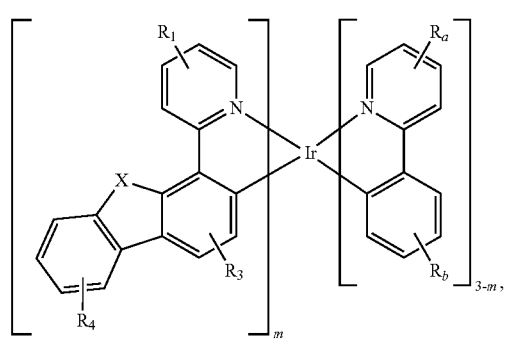

Formula 3

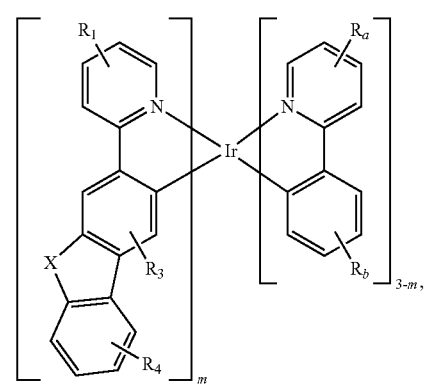

Formula 4

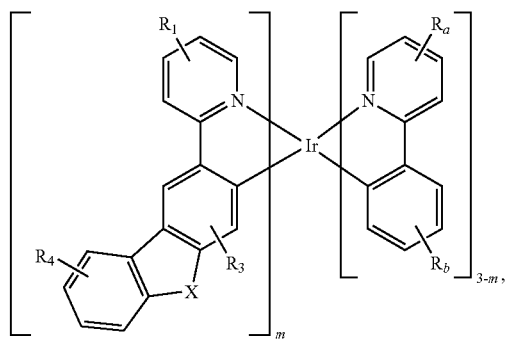

Formula 5

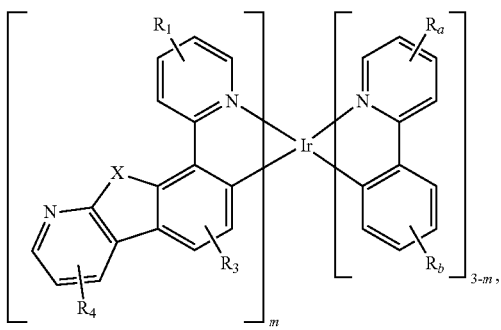

Formula 6

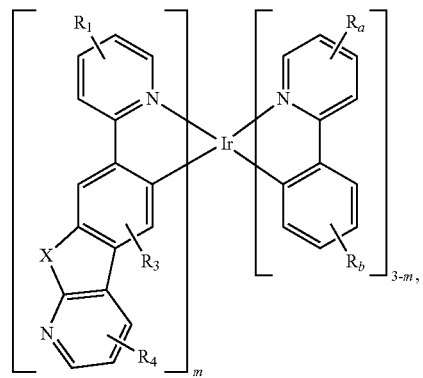

Formula 7

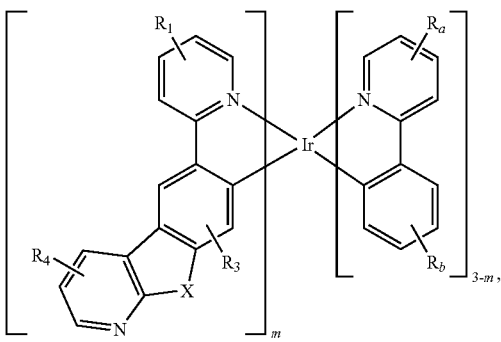

Formula 8

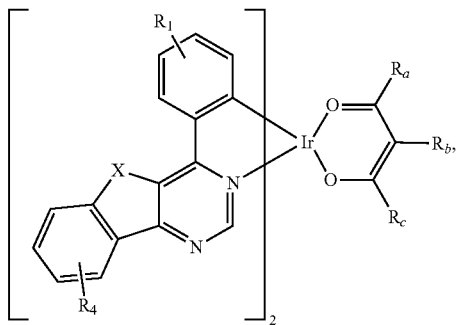

Formula 9

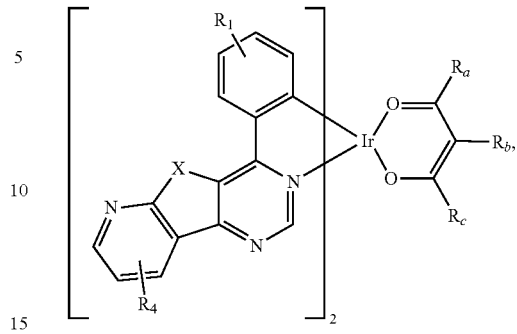

Formula 10

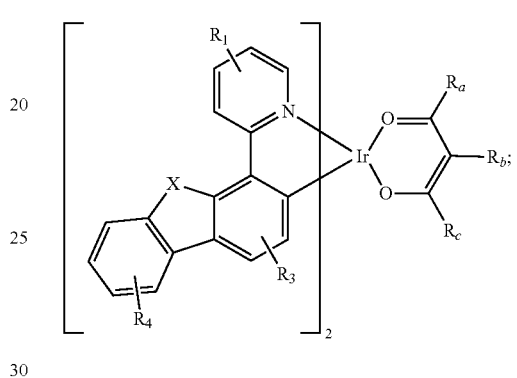

wherein, m is 1, 2 or 3;

X is selected from O, S or Se;

$R_1$, $R_3$, and $R_4$ may represent mono-, di-, tri- or tetra-substitution, or no substitution;

$R_a$, $R_b$, and $R_c$ may represent mono-, di-, tri- or tetr-substitution, or no substitution;

$R_1$, $R_3$, $R_4$, $R_a$, $R_b$ and $R_c$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof;

wherein, at least one of $R_3$ and $R_4$ is present and is a cyano group;

any two adjacent substituents can optionally be joined to form a ring.

5. The metal complex according to claim 4, wherein the metal complex has a structure of Formula 2-a:

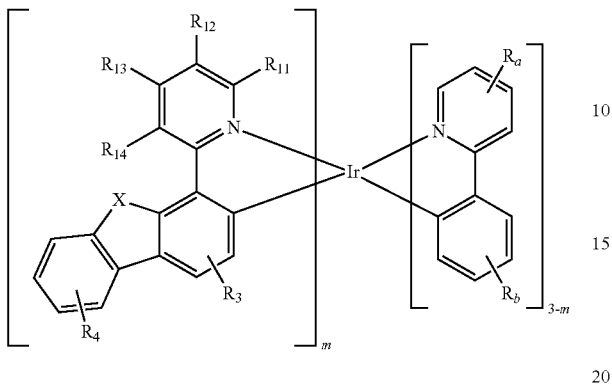

Formula 2-a wherein,
m is 1, 2 or 3;
X is selected from O, S or Se;
$R_3$, and $R_4$ may represent mono-, di-, tri- or tetra-substitution, or no substitution;
$R_a$, $R_b$, and $R_c$ may represent mono-, di-, tri- or tetra-substitution, or no substitution;
wherein, $R_{11}$, $R_{12}$, $R_{13}$, $R_{14}$, $R_3$, $R_4$, $R_a$, and $R_b$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof,
wherein, at least one of $R_3$ and $R_4$ is present and is a cyano group;
any two adjacent substituents can optionally be joined to form a ring.

6. The metal complex according to claim 1, wherein at least one of $X_5$ to $X_8$ in Formula 1 is $CR_{x2}$, and the $R_{x2}$ is a cyano group.

7. The metal complex according to claim 4, wherein $R_4$ may represent mono-, di-, tri- or tetra-substitution; when more than one $R_4$ exists, the $R_4$ may be the same or different; $R_4$ is selected from the group consisting of deuterium, halogen, a substituted or unsubstituted alkyl group having 1-20 carbon atoms, a substituted or unsubstituted cycloalkyl group having 3-20 ring carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a cyano group, and combinations thereof; and at least one $R_4$ is a cyano group.

8. The metal complex according to claim 3, wherein the ligand $L_a$ is selected from the group consisting of:

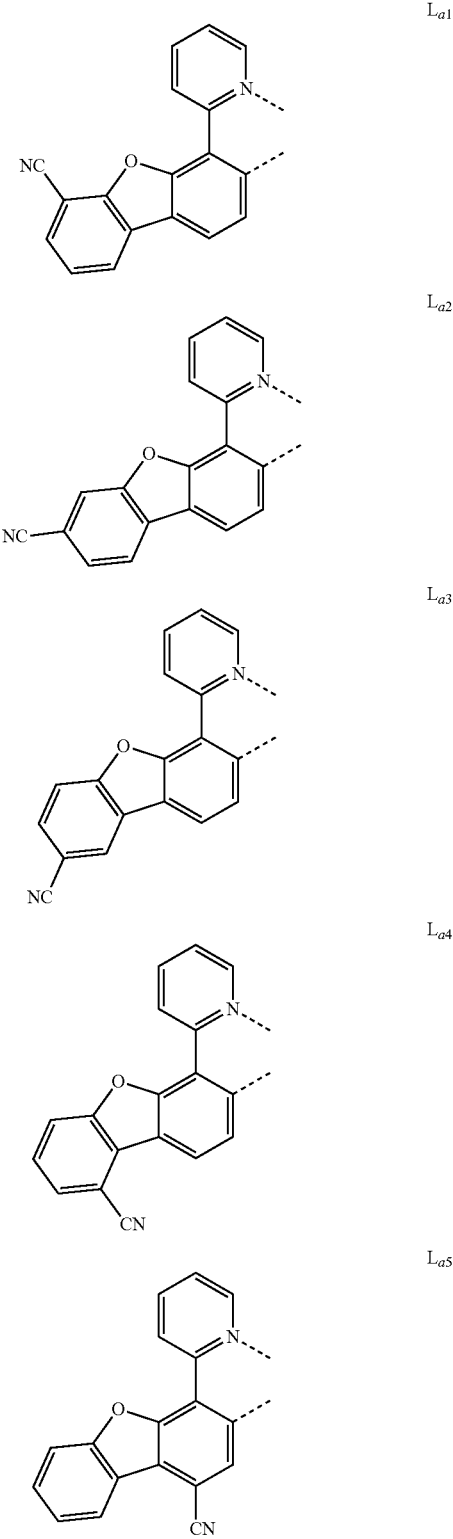

-continued
L_{a6} 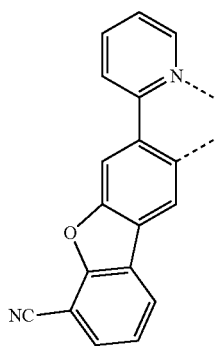
L_{a7} 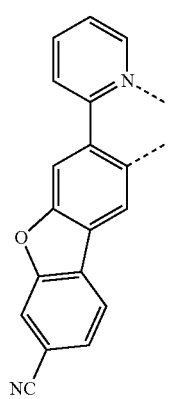
L_{a8} 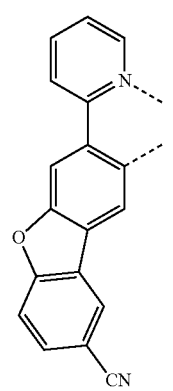
L_{a9} 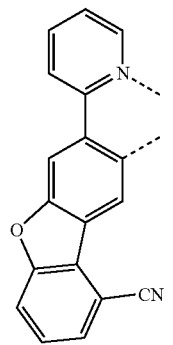
-continued
L_{a10} 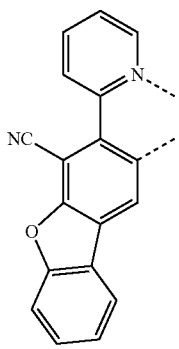
L_{a11} 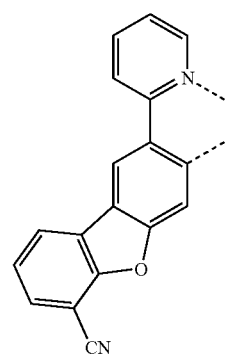
L_{a12} 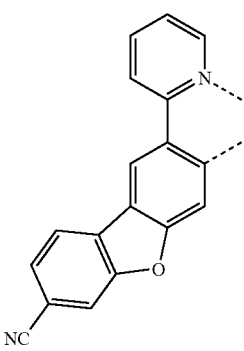
L_{a13} 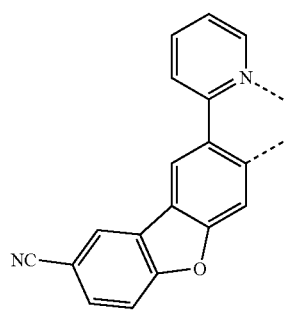

105
-continued
L_{a14}
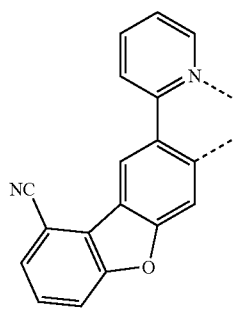
L_{a15}
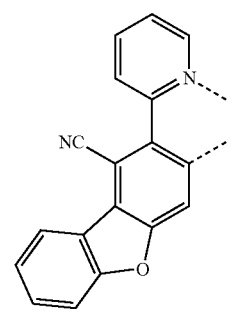
L_{a16}
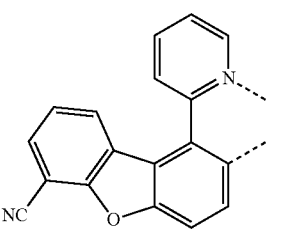
L_{a17}
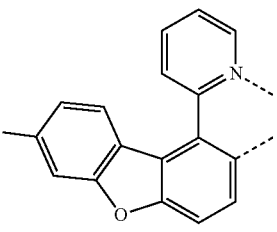
L_{a18}
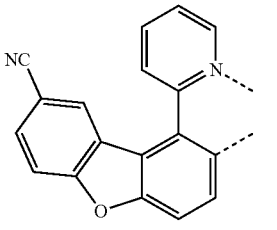
L_{a19}
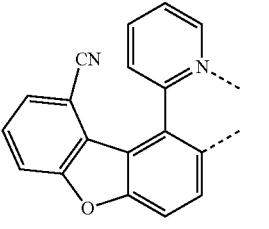
106
-continued
L_{a20}
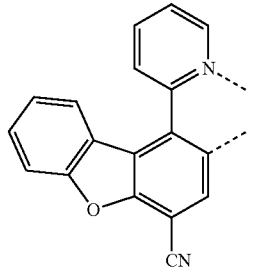
L_{a21}
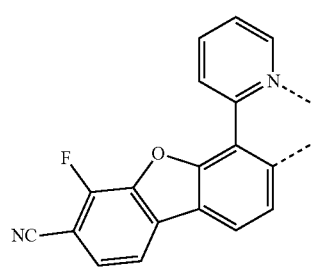
L_{a22}
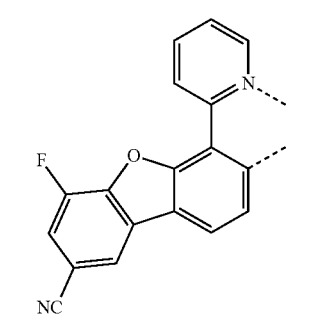
L_{a23}
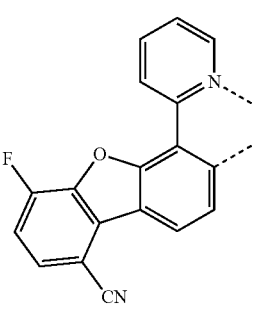
L_{a24}
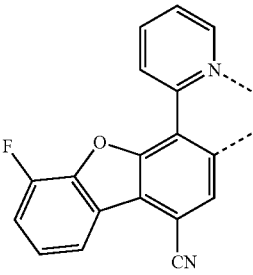

107
-continued
L<sub>a25</sub>
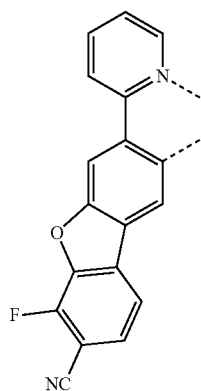
L<sub>a26</sub>
L<sub>a27</sub>
L<sub>a28</sub>
108
-continued
L<sub>a29</sub>
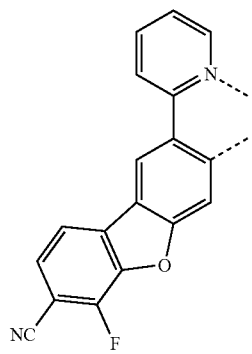
L<sub>a30</sub>
L<sub>a31</sub>
L<sub>a32</sub>

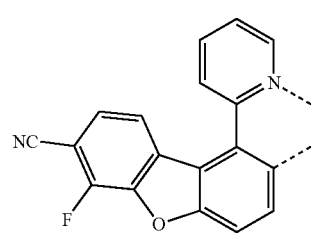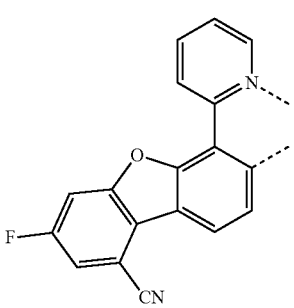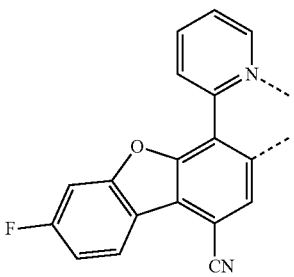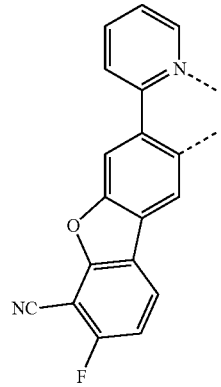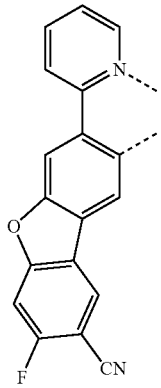

L_{a43} 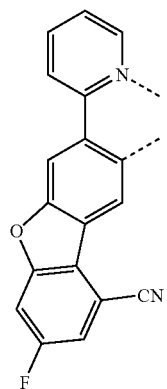
L_{a44} 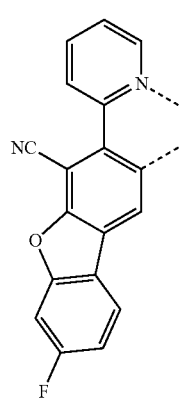
L_{a45} 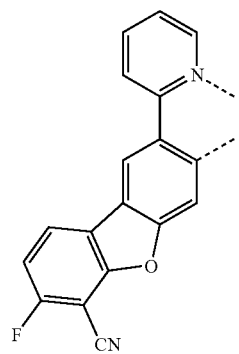
L_{a46} 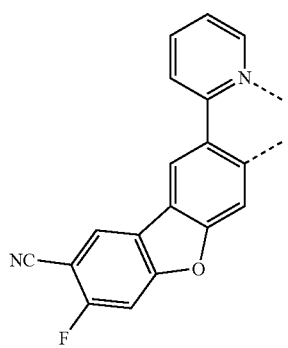
L_{a47} 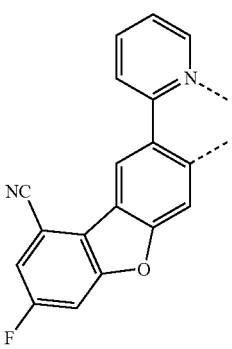
L_{a48} 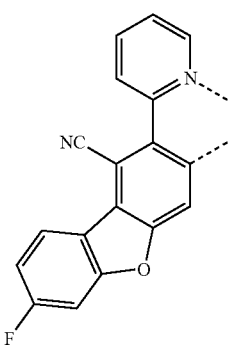
L_{a49} 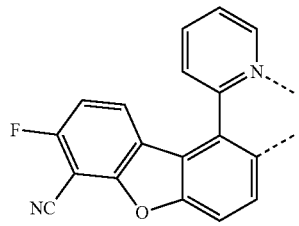
L_{a50} 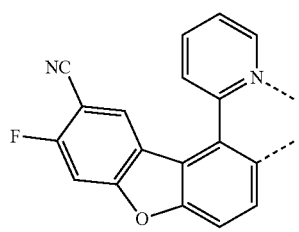
L_{a51} 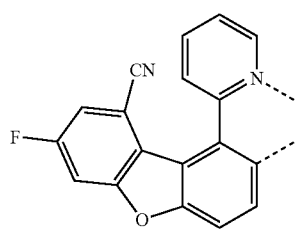

113
-continued
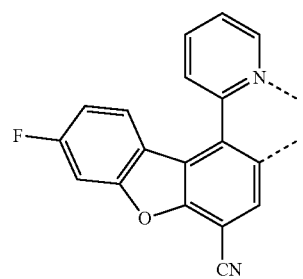
L_a52
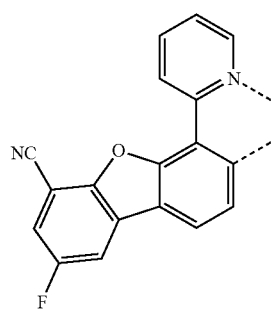
L_a53
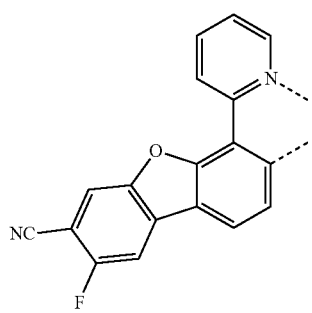
L_a54
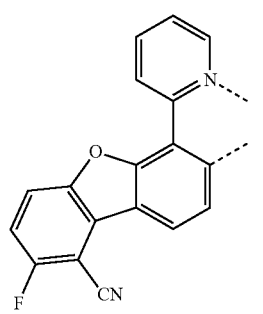
L_a55
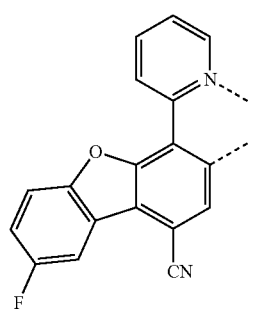
L_a56
114
-continued
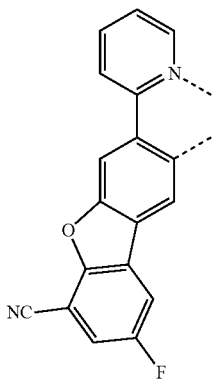
L_a57
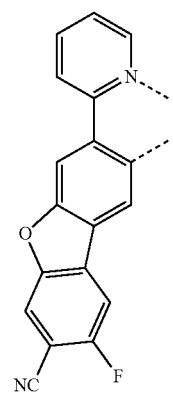
L_a58
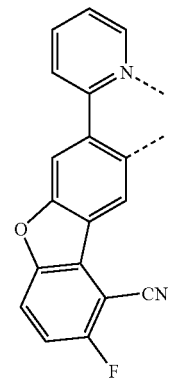
L_a59
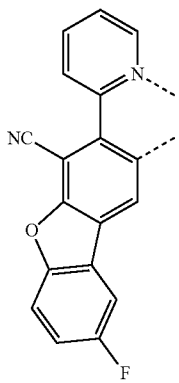
L_a60

| | |
|---|---|
| 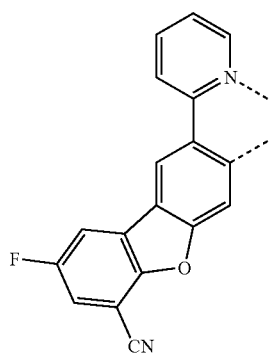 | L_{a61} |
| 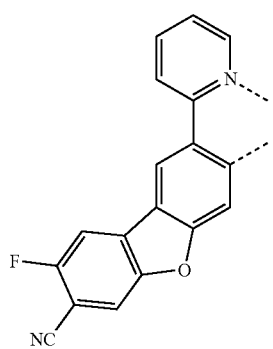 | L_{a62} |
| 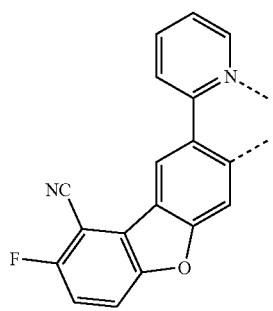 | L_{a63} |
| 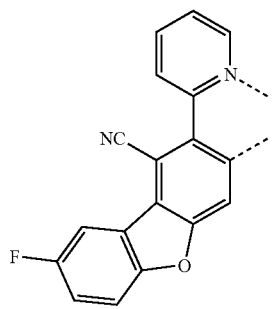 | L_{a64} |
| 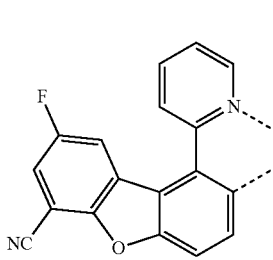 | L_{a65} |
| | |
|---|---|
| 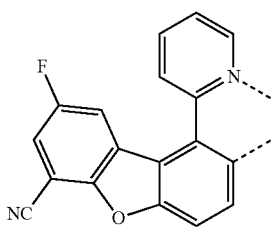 | L_{a66} |
| 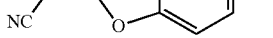 | L_{a67} |
| 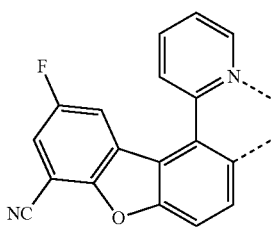 | L_{a68} |
|  | L_{a69} |
| 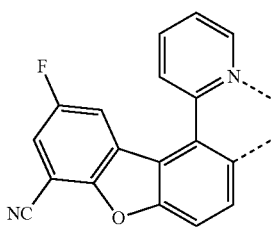 | L_{a70} |

-continued

L_a71

L_a72

L_a73

L_a74

L_a75

L_a76

L_a77

L_a78

119 -continued
L<sub>a79</sub>
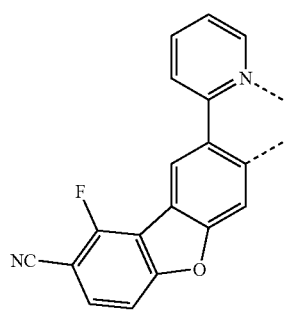
L<sub>a80</sub>
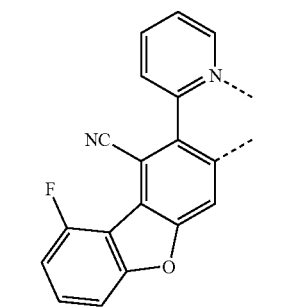
L<sub>a81</sub>
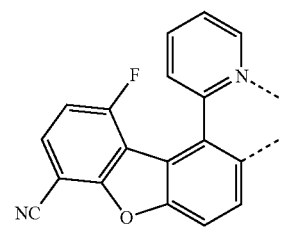
L<sub>a82</sub>
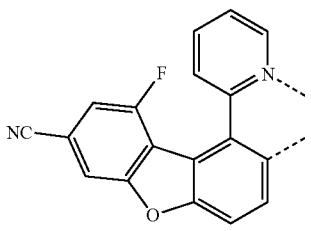
L<sub>a83</sub>
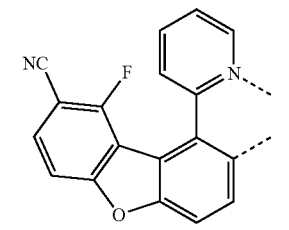
L<sub>a84</sub>
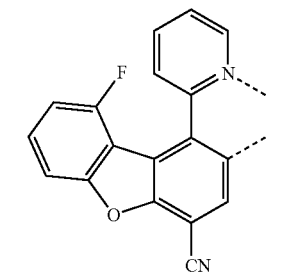
120 -continued
L<sub>a85</sub>
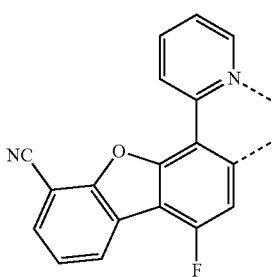
L<sub>a86</sub>
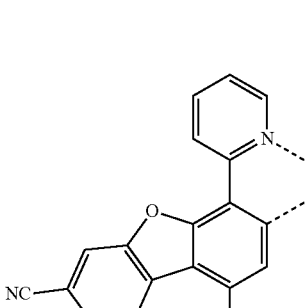
L<sub>a87</sub>
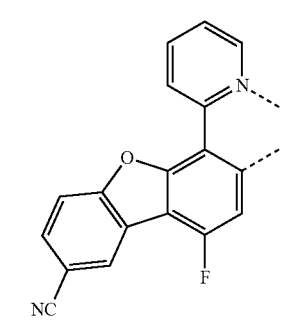
L<sub>a88</sub>
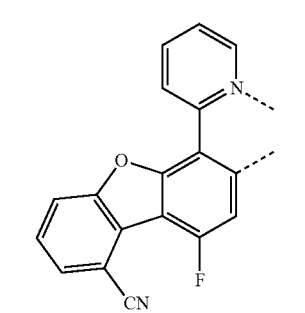
L<sub>a89</sub>
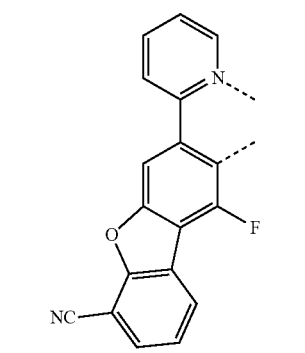

-continued
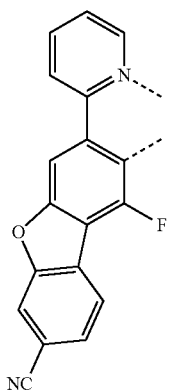 L_{a90}
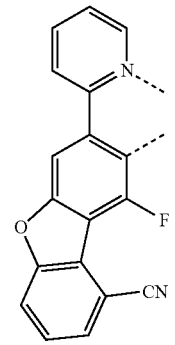 L_{a91}
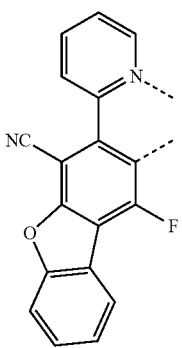 L_{a92}
L_{a93}
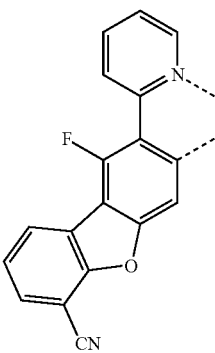 L_{a94}
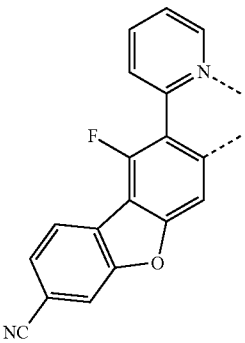 L_{a95}
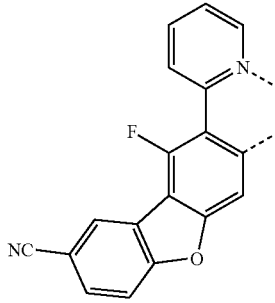 L_{a96}
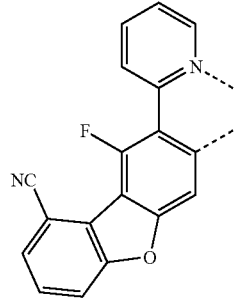 L_{a97}
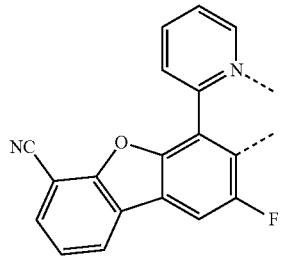 L_{a98}

-continued

| | |
|---|---|
| L_a99 | L_a104 |
| L_a100 | L_a105 |
| L_a101 | L_a106 |
| L_a102 | L_a107 |
| L_a103 | L_a108 |

-continued
L_{a109}
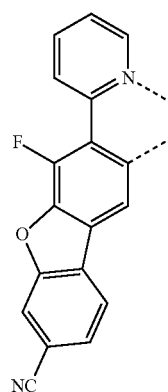
L_{a110}
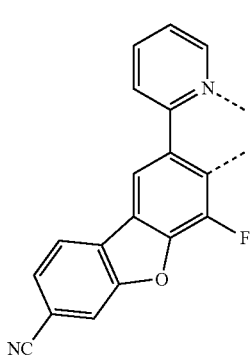 L_{a113}
L_{a111}
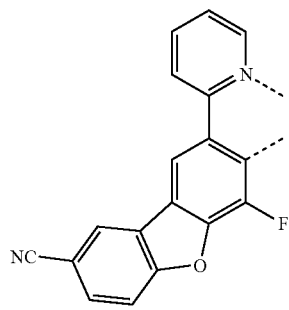 L_{a114}
L_{a112}
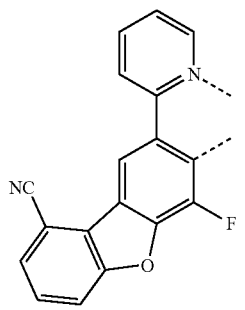 L_{a115}
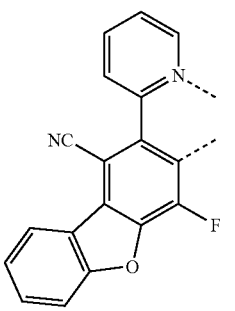 L_{a116}
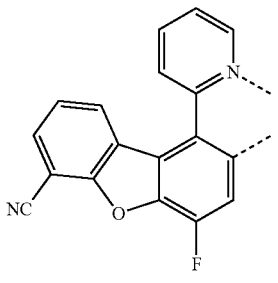 L_{a117}

-continued
L<sub>a118</sub>
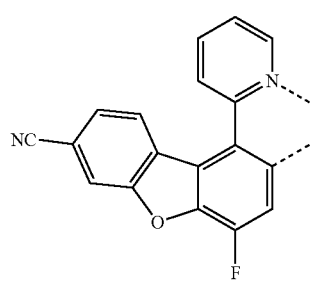
L<sub>a119</sub>
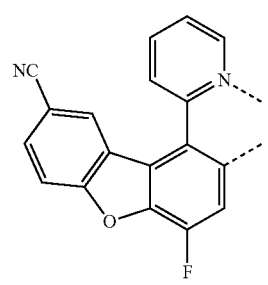
L<sub>a120</sub>
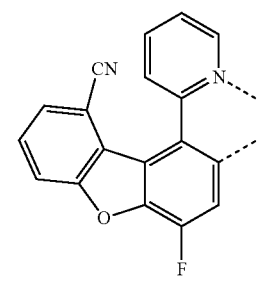
L<sub>a121</sub>
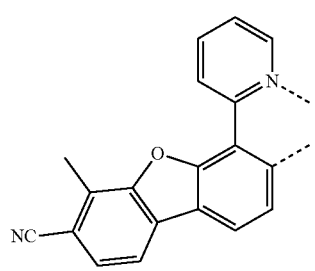
L<sub>a122</sub>
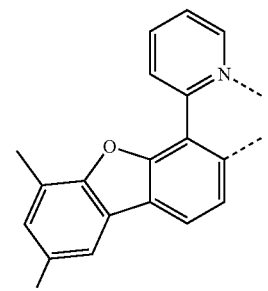
-continued
L<sub>a123</sub>
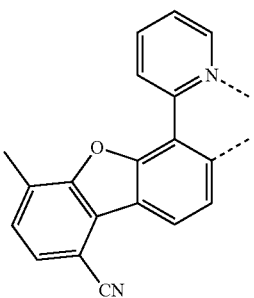
L<sub>a124</sub>
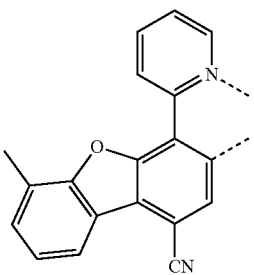
L<sub>a125</sub>
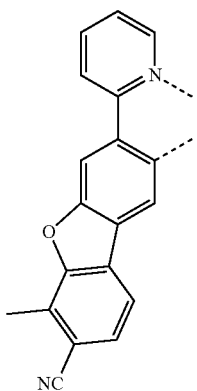
L<sub>a126</sub>
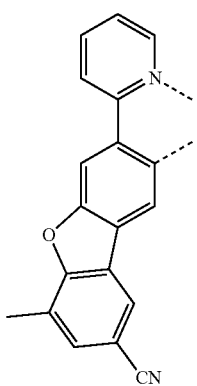

| | |
|---|---|
| 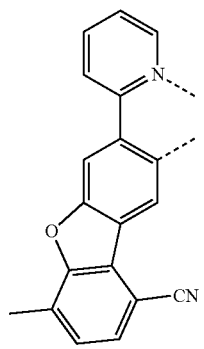 La127 | 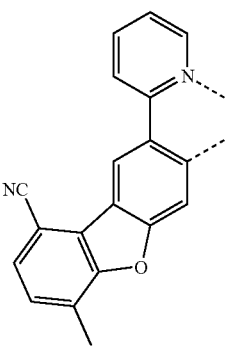 La131 |
| 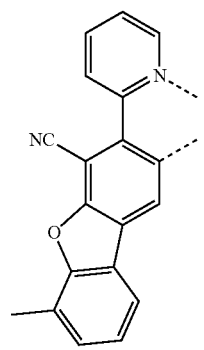 La128 | 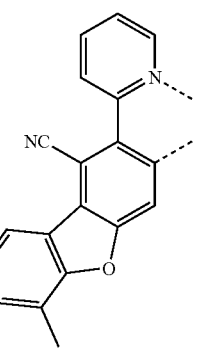 La132 |
| 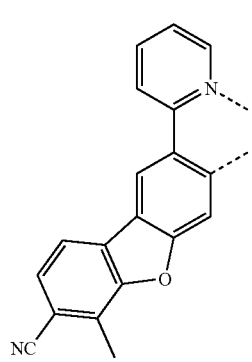 La129 | 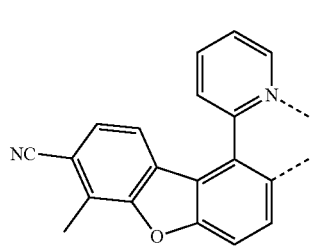 La133 |
| 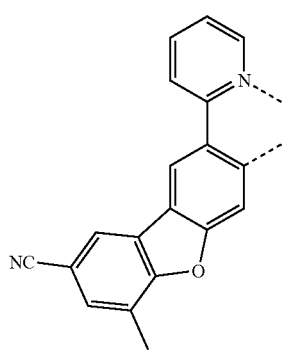 La130 | 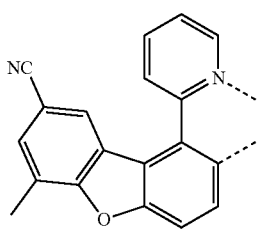 La134 |
|  | La135 |

L<sub>a</sub>136
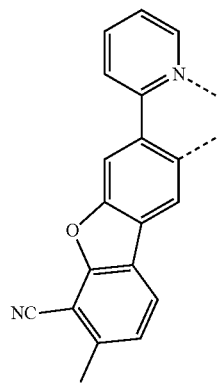
L<sub>a</sub>137
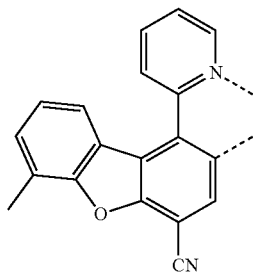
L<sub>a</sub>138
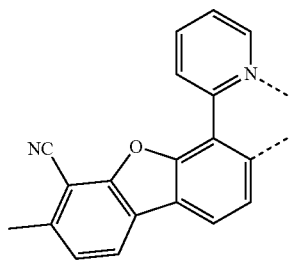
L<sub>a</sub>139
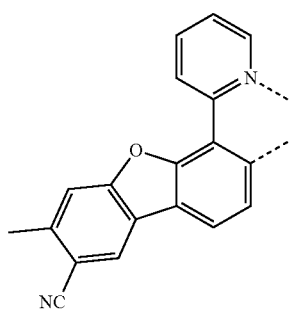
L<sub>a</sub>140
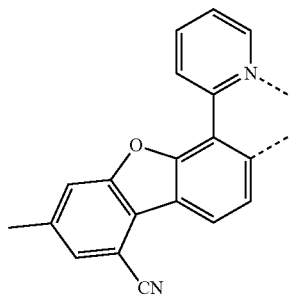
L<sub>a</sub>141
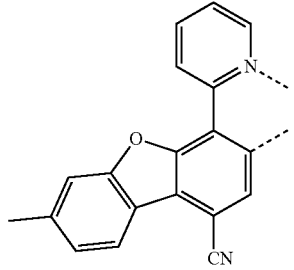
L<sub>a</sub>142
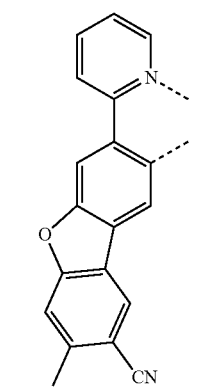
L<sub>a</sub>143
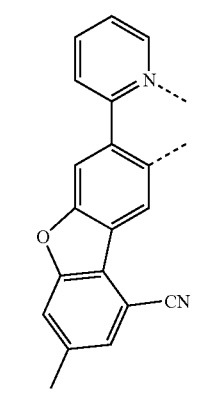
L<sub>a</sub>144
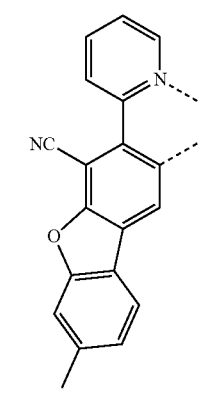

| | |
|---|---|
| L<sub>a</sub>145 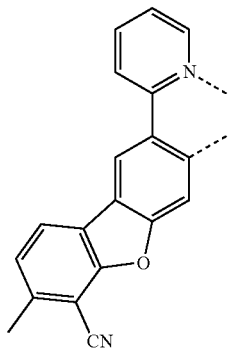 | L<sub>a</sub>150 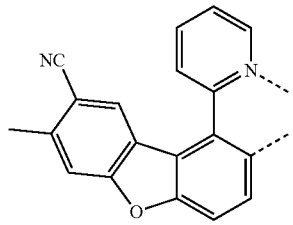 |
| L<sub>a</sub>146 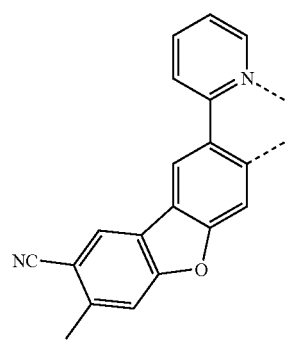 | L<sub>a</sub>151 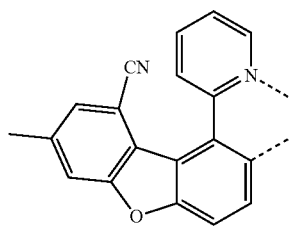 |
| L<sub>a</sub>147 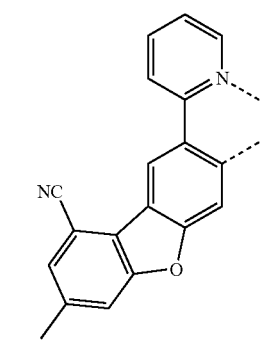 | L<sub>a</sub>152 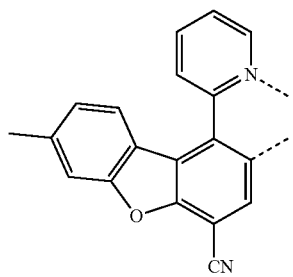 |
| L<sub>a</sub>148 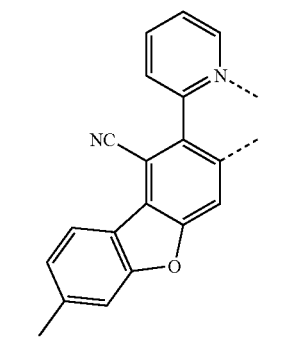 | L<sub>a</sub>153 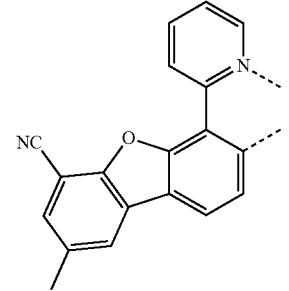 |
| L<sub>a</sub>149 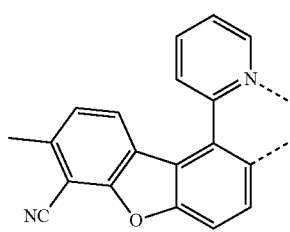 | L<sub>a</sub>154 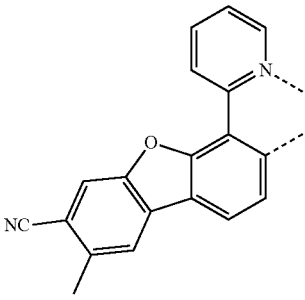 |

L<sub>a</sub>155
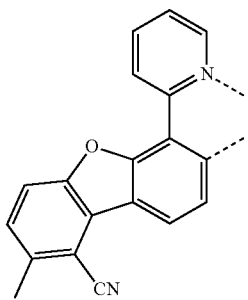
L<sub>a</sub>156
L<sub>a</sub>157
L<sub>a</sub>158
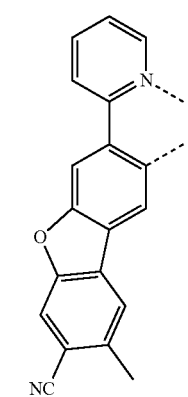
L<sub>a</sub>159
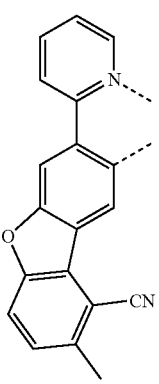
L<sub>a</sub>160
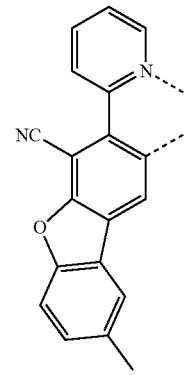
L<sub>a</sub>161
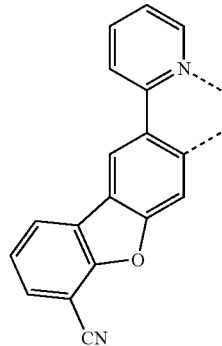
L<sub>a</sub>162
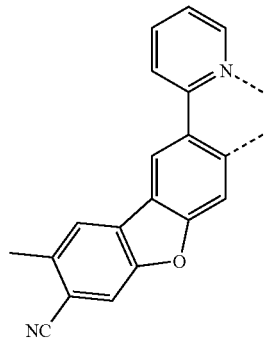

L<sub>a163</sub> 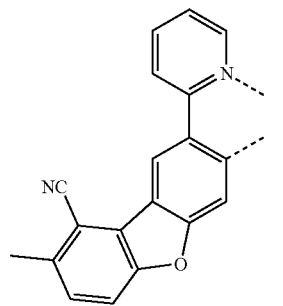
L<sub>a164</sub> 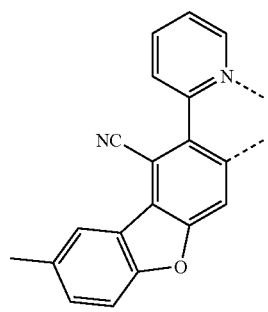
L<sub>a165</sub> 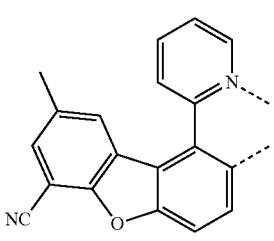
L<sub>a166</sub> 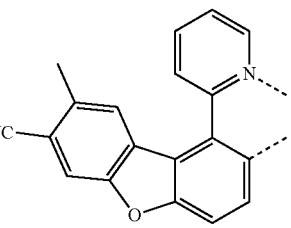
L<sub>a167</sub> 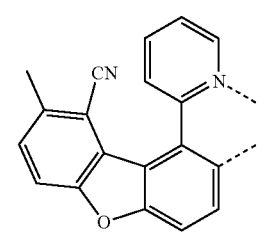
L<sub>a168</sub> 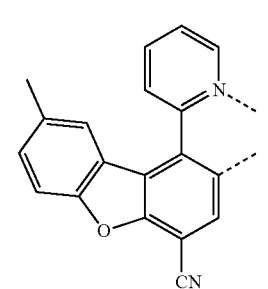
L<sub>a169</sub> 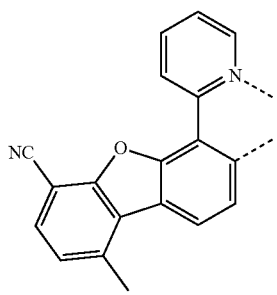
L<sub>a170</sub> 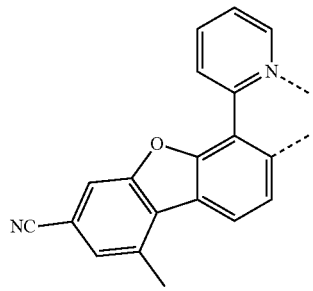
L<sub>a171</sub> 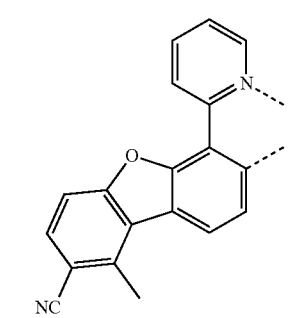
L<sub>a172</sub> 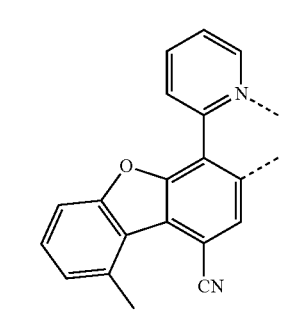
L<sub>a173</sub> 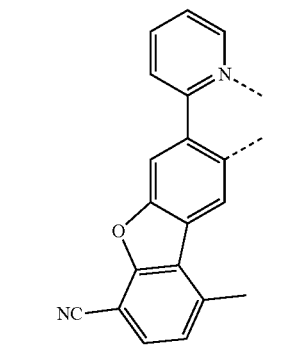

L*a*174

L*a*175

L*a*176

L*a*177

L*a*178

L*a*179

L*a*180

L*a*181

L*a*182

| | |
|---|---|
| 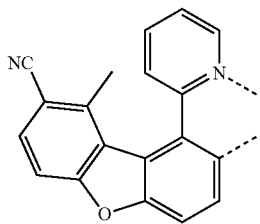 | $L_{a183}$ |
| 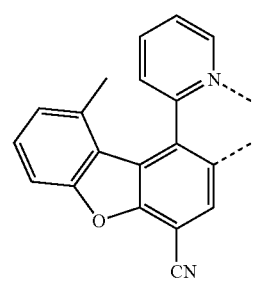 | $L_{a184}$ |
| 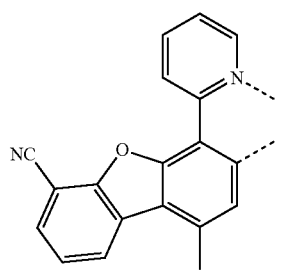 | $L_{a185}$ |
| 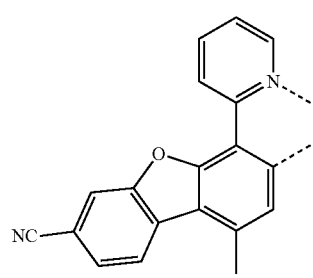 | $L_{a186}$ |
| 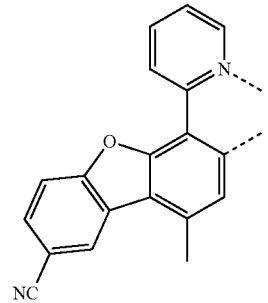 | $L_{a187}$ |
| 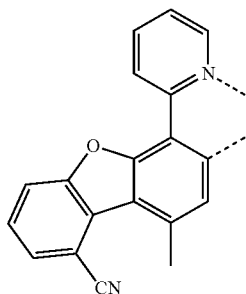 | $L_{a188}$ |
| 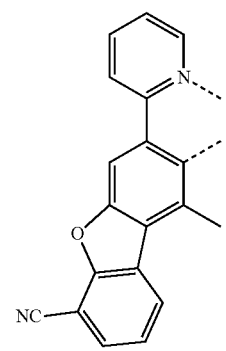 | $L_{a189}$ |
| 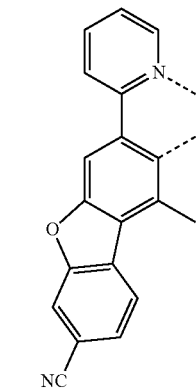 | $L_{a190}$ |
| 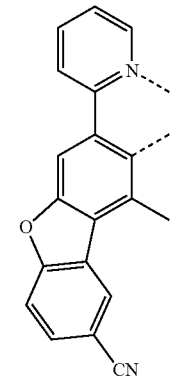 | $L_{a191}$ |

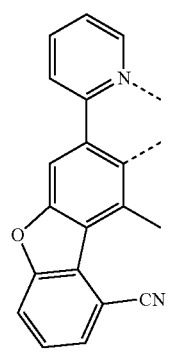 L<sub>a</sub>192
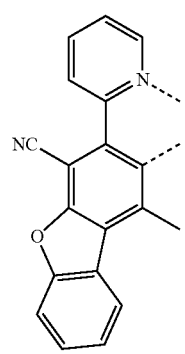 L<sub>a</sub>193
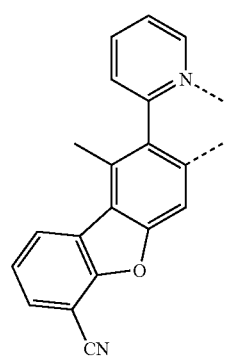 L<sub>a</sub>194
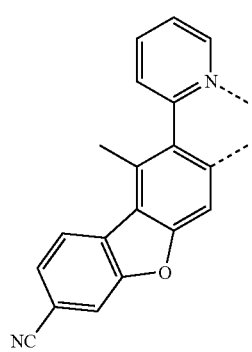 L<sub>a</sub>195
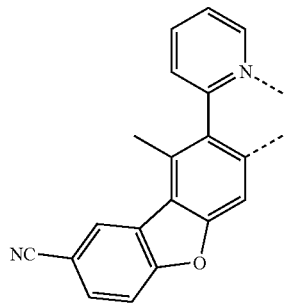 L<sub>a</sub>196
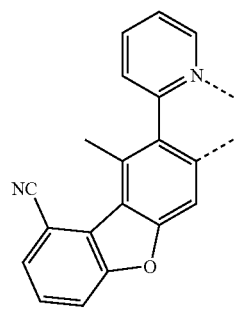 L<sub>a</sub>197
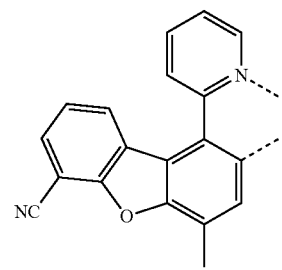 L<sub>a</sub>198
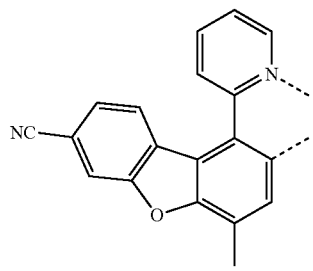 L<sub>a</sub>199
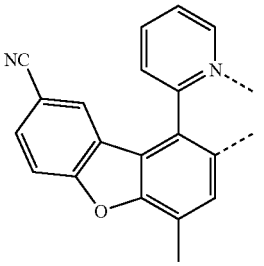 L<sub>a</sub>200

L_{a201}
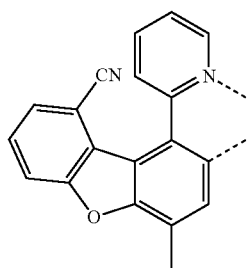
L_{a202}
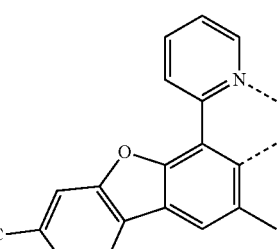
L_{a203}

L_{a204}
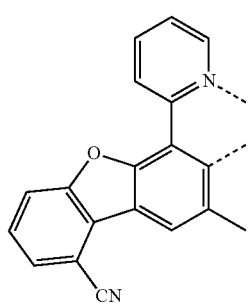
L_{a205}
L_{a206}
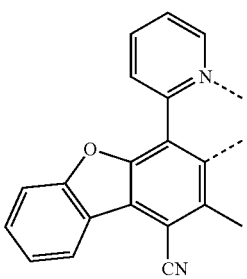
L_{a207}
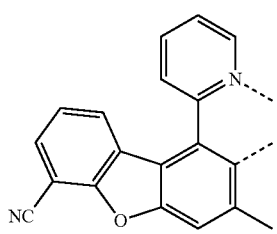
L_{a208}
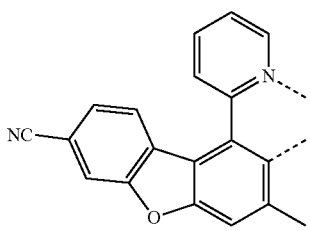
L_{a209}
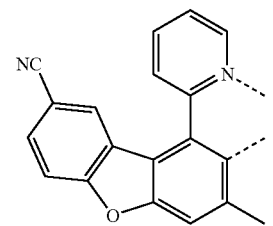
L_{a210}
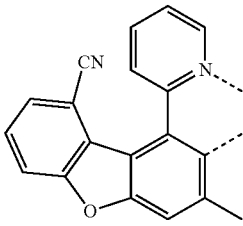
L_{a211}
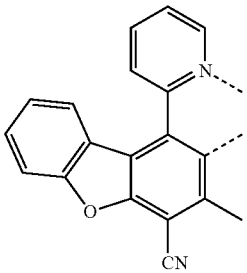

-continued
L<sub>a212</sub>
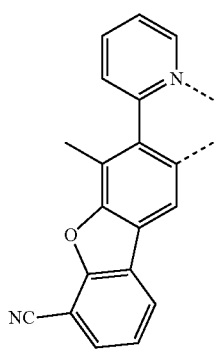
L<sub>a213</sub>
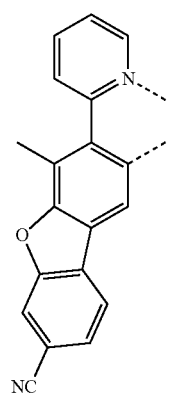
L<sub>a214</sub>
L<sub>a215</sub>
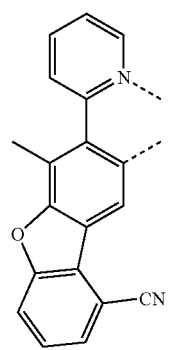
-continued
L<sub>a216</sub>
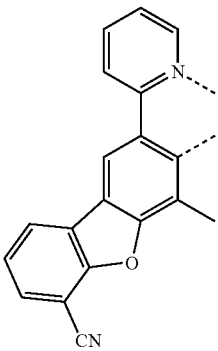
L<sub>a217</sub>
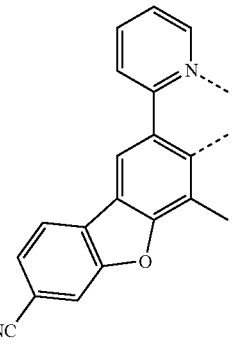
L<sub>a218</sub>
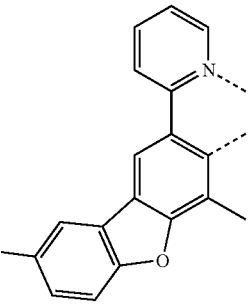
L<sub>a219</sub>
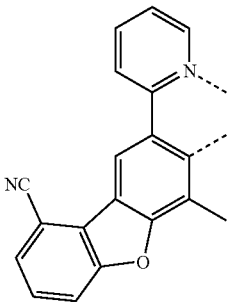
L<sub>a220</sub>
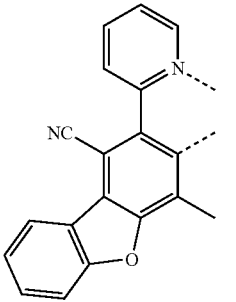

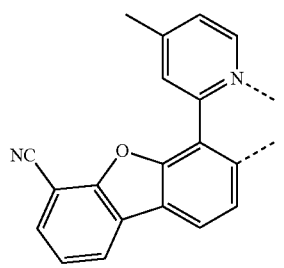 L<sub>a221</sub>
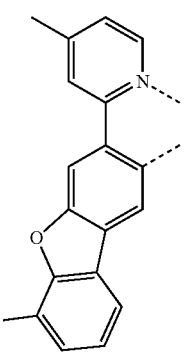 L<sub>a226</sub>
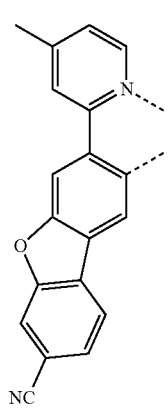 L<sub>a227</sub>
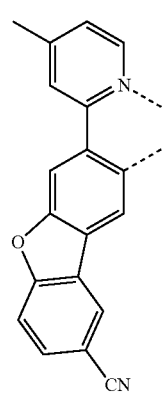 L<sub>a228</sub>
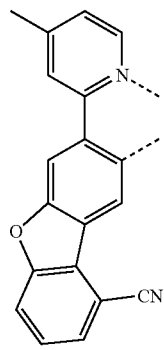 L<sub>a229</sub>

L<sub>a230</sub>
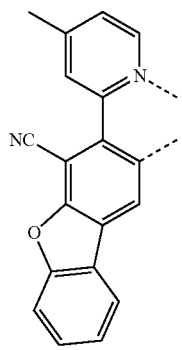
L<sub>a231</sub>
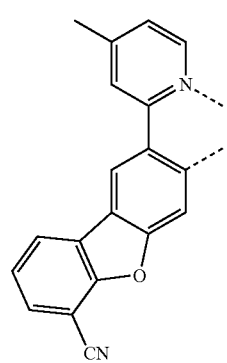
L<sub>a232</sub>
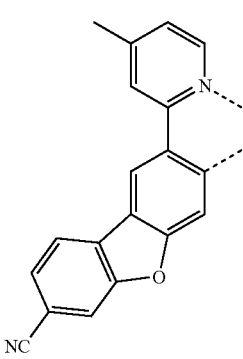
L<sub>a233</sub>
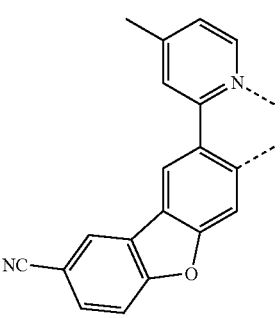
L<sub>a234</sub>
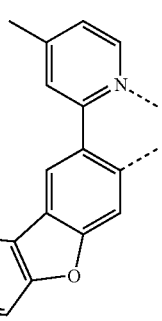
L<sub>a235</sub>
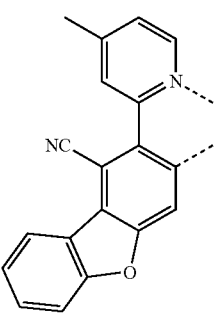
L<sub>a236</sub>
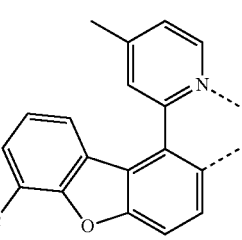
L<sub>a237</sub>
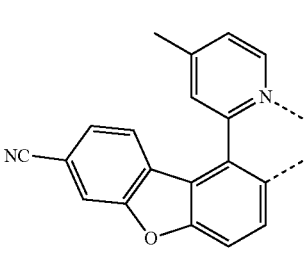
L<sub>a238</sub>
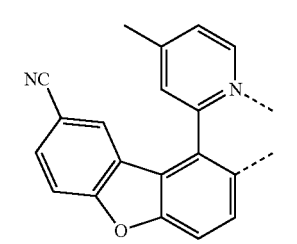
L<sub>a239</sub>
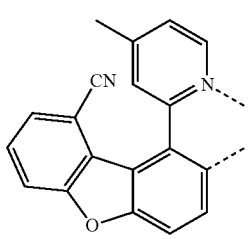

| | |
|---|---|
| L<sub>a240</sub> 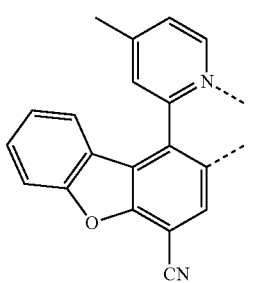 | L<sub>a245</sub> 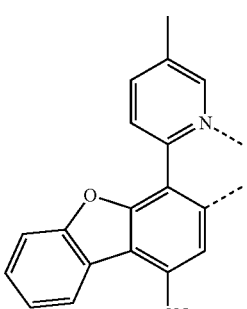 |
| L<sub>a241</sub> 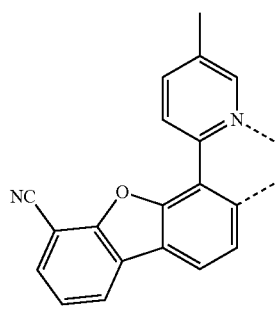 | L<sub>a246</sub> 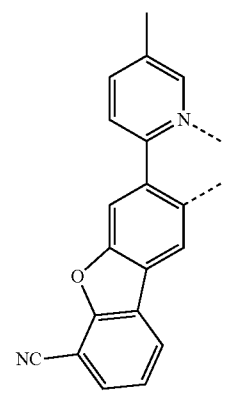 |
| L<sub>a242</sub> 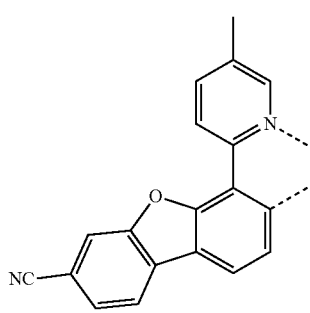 | L<sub>a247</sub> 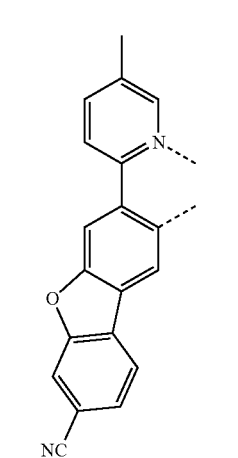 |
| L<sub>a243</sub> 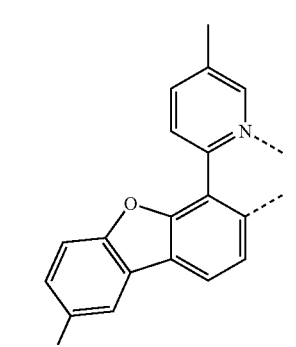 | L<sub>a248</sub> 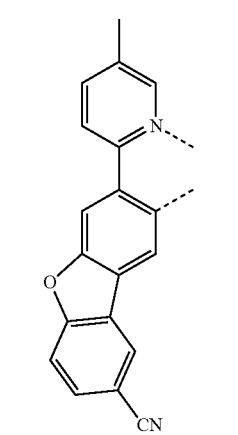 |
| L<sub>a244</sub> 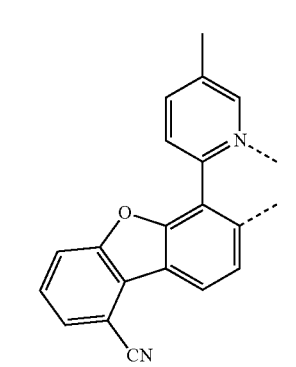 | |

L_{a249}
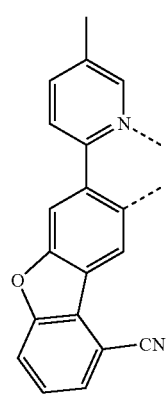
L_{a250}
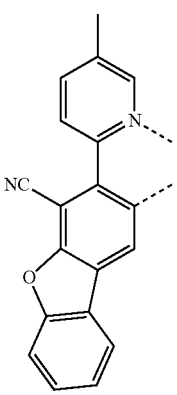
L_{a251}
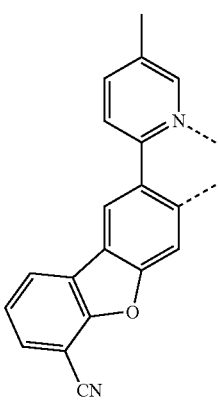
L_{a252}
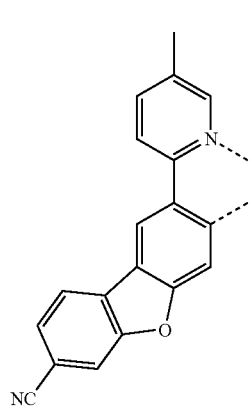
L_{a253}
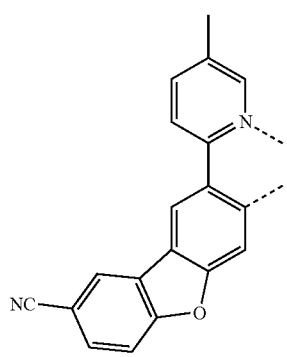
L_{a254}
L_{a255}
L_{a256}
L_{a257}

| L_{a258} | 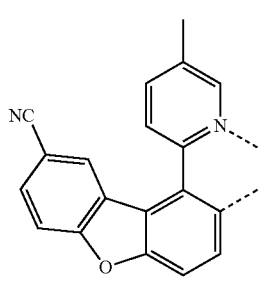 |
| L_{a259} | 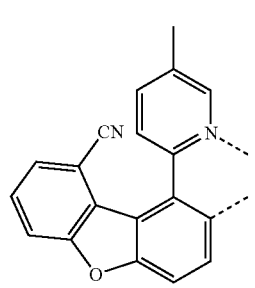 |
| L_{a260} | 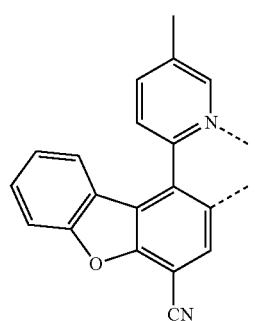 |
| L_{a261} | 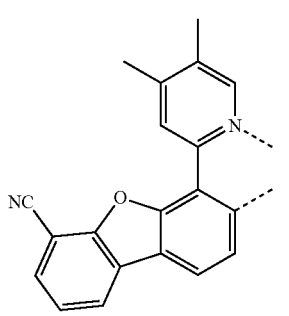 |
| L_{a262} | 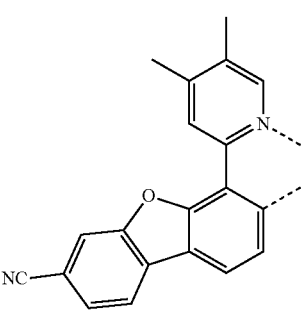 |
| L_{a263} | 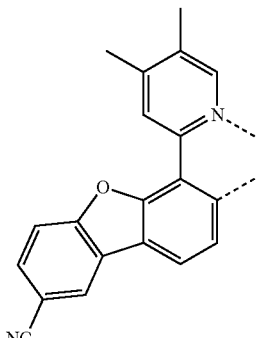 |
| L_{a264} | 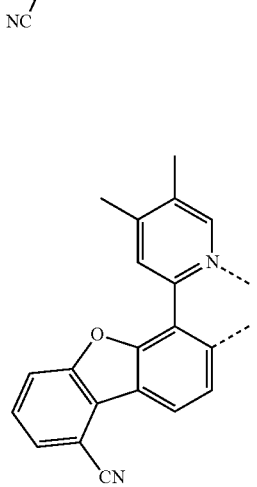 |
| L_{a265} | 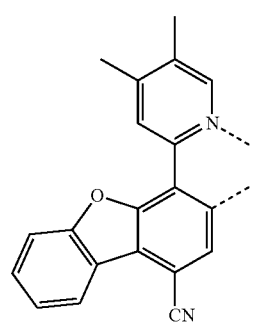 |
| L_{a266} | 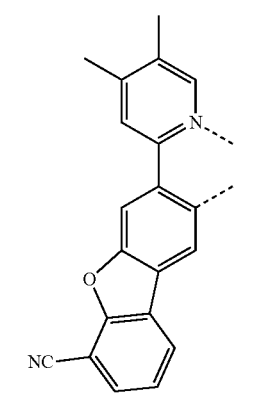 |

L_{a267}
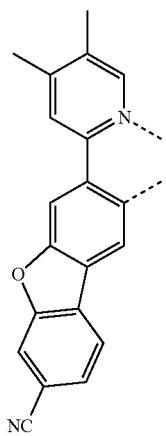
L_{a268}
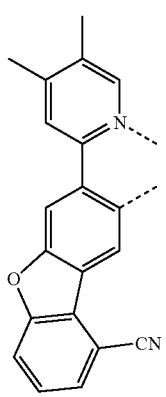
L_{a269}
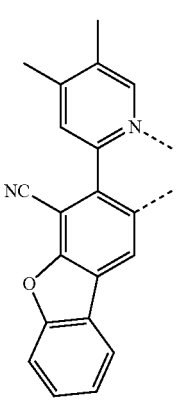
L_{a270}
L_{a271}
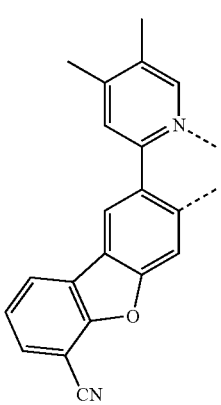
L_{a272}
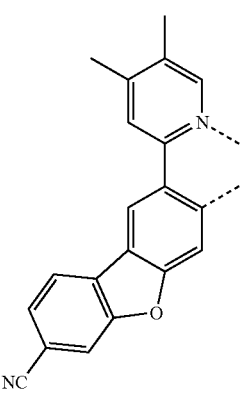
L_{a273}
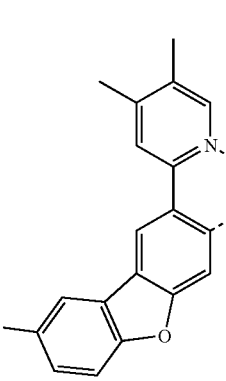
L_{a274}
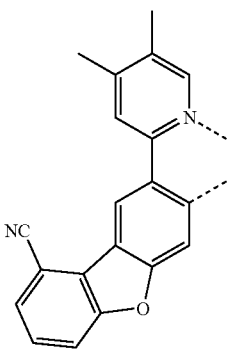

-continued
L<sub>a275</sub>
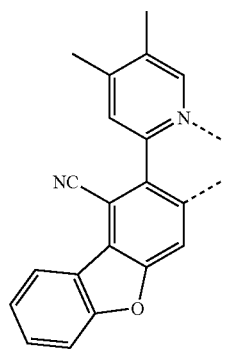
L<sub>a276</sub>
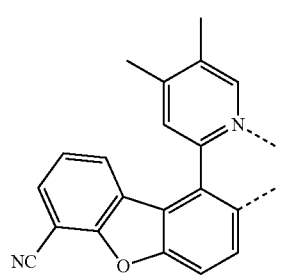
L<sub>a277</sub>
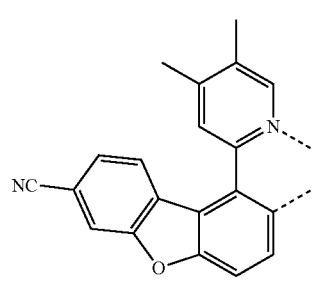
L<sub>a278</sub>
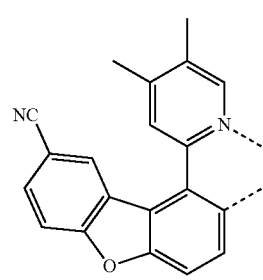
L<sub>a279</sub>
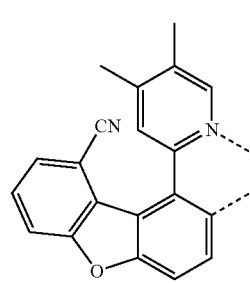
-continued
L<sub>a280</sub>
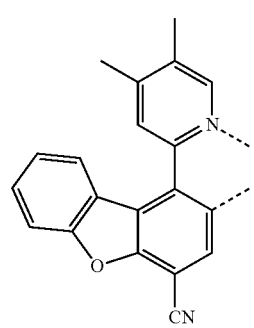
L<sub>a281</sub>
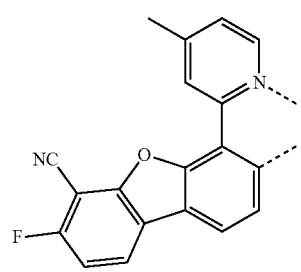
L<sub>a282</sub>
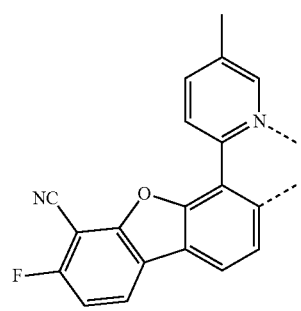
L<sub>a283</sub>
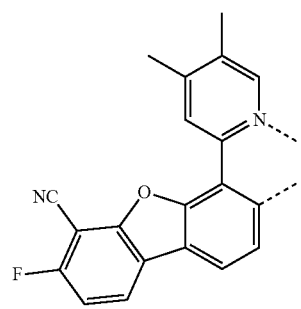
L<sub>a284</sub>
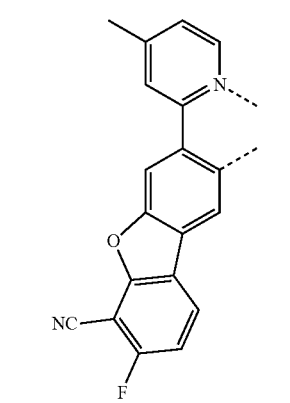

| | |
|---|---|
| L_{a285} 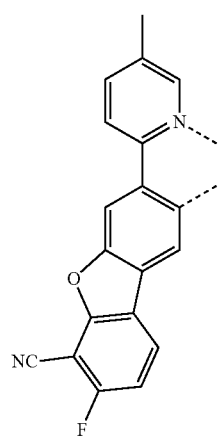 | L_{a289} 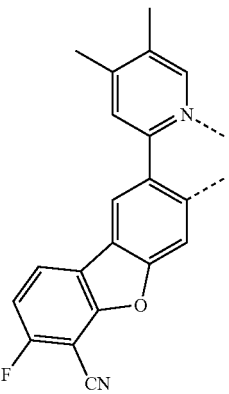 |
| L_{a286} 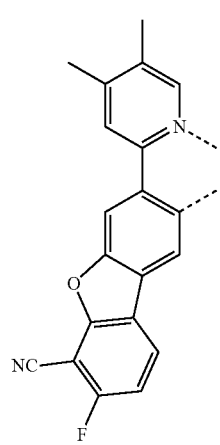 | L_{a290} 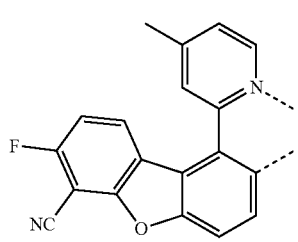 |
| L_{a287} 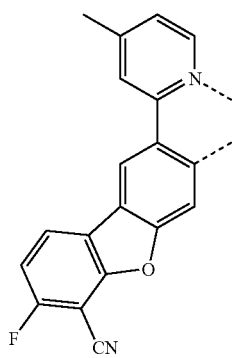 | L_{a291} 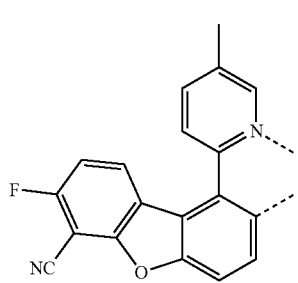 |
| | L_{a292} 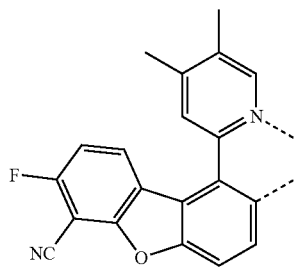 |
| L_{a288} 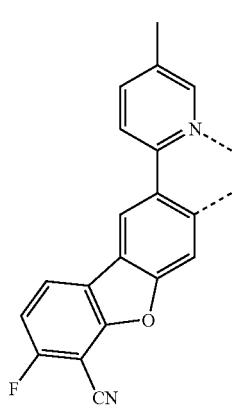 | L_{a293} 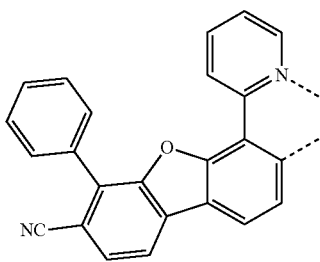 |

L_{a294}
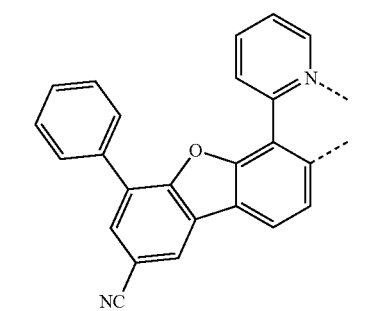
L_{a295}
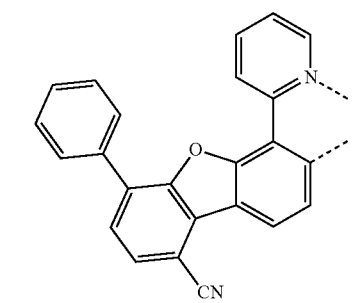
L_{a296}
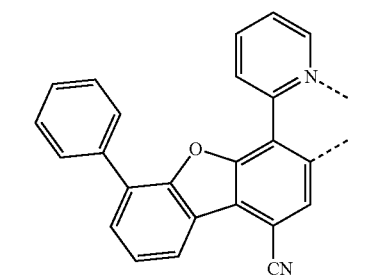
L_{a297}
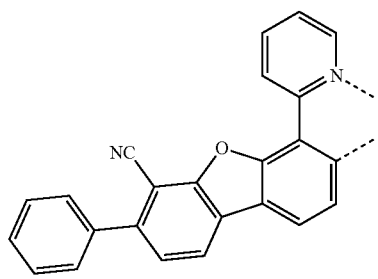
L_{a298}
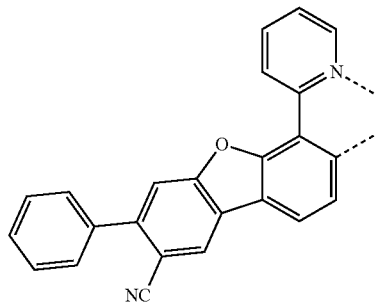
L_{a299}
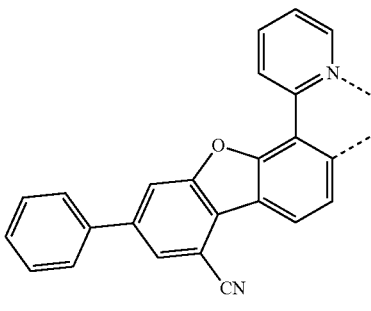
L_{a300}
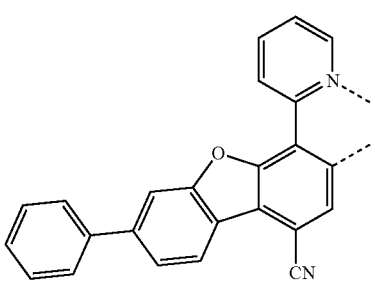
L_{a301}
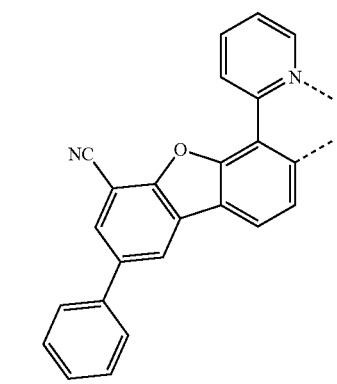
L_{a302}
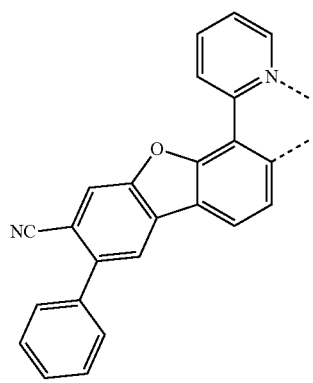

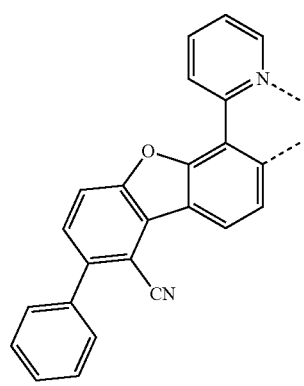
L_{a303}
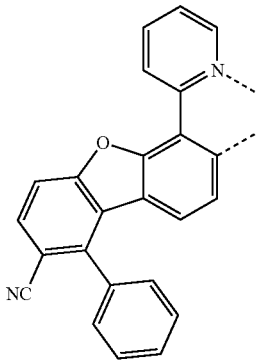
L_{a307}
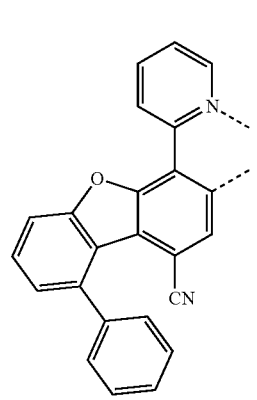
L_{a308}
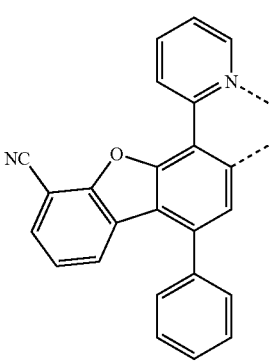
L_{a309}
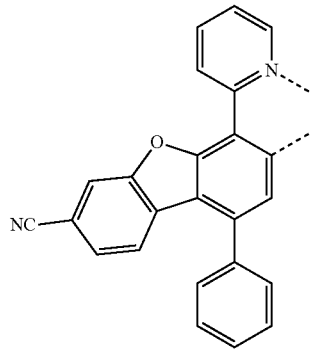
L_{a310}

L<sub>a311</sub> 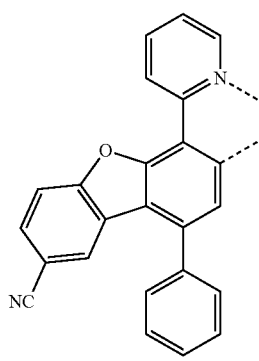
L<sub>a312</sub> 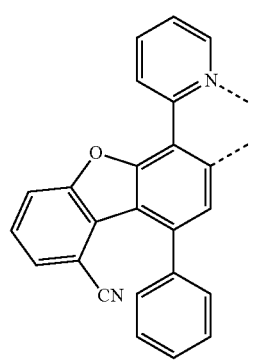
L<sub>a313</sub> 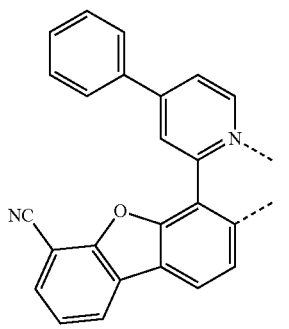
L<sub>a314</sub> 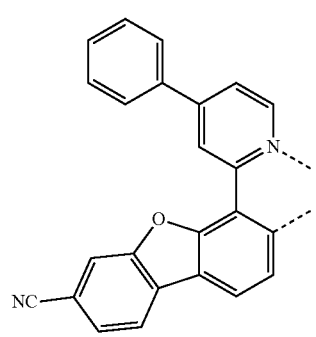
L<sub>a315</sub> 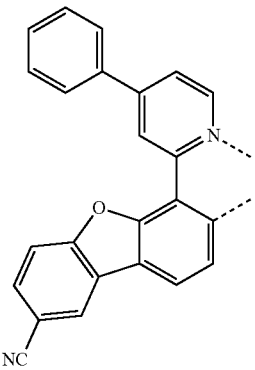
L<sub>a316</sub> 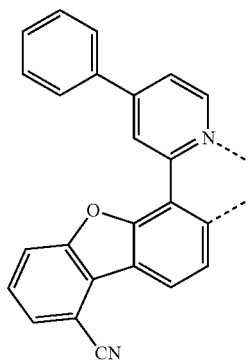
L<sub>a317</sub> 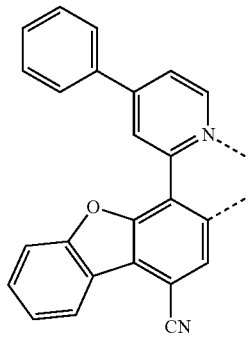
L<sub>a318</sub> 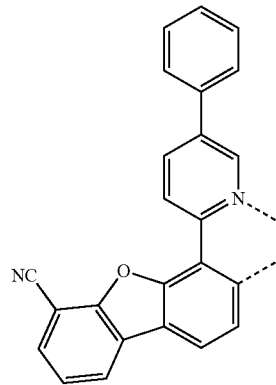

L_{a319}
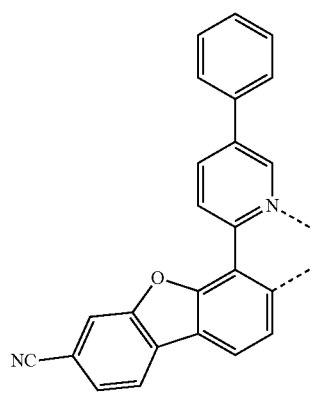
L_{a320}
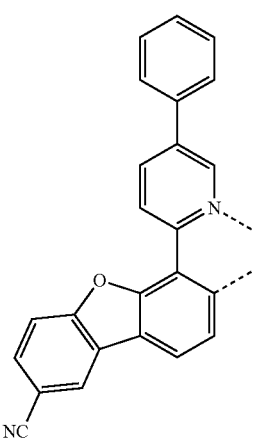
L_{a321}
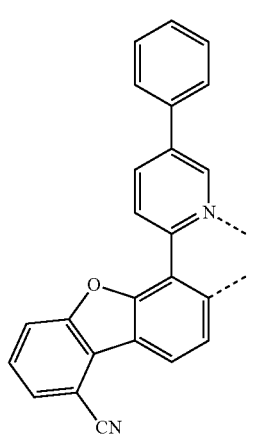
L_{a322}
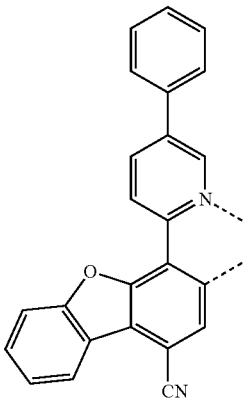
L_{a323}
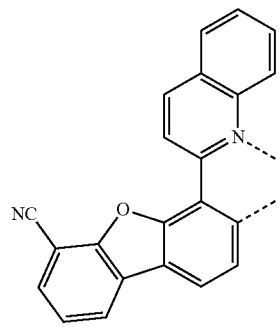
L_{a324}
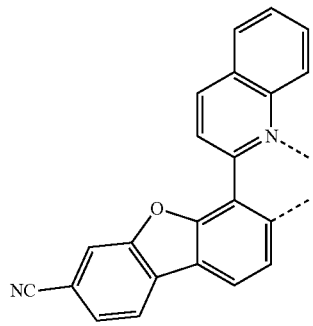
L_{a325}
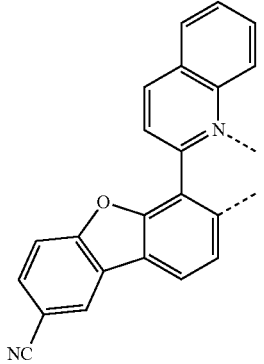

L<sub>a326</sub>
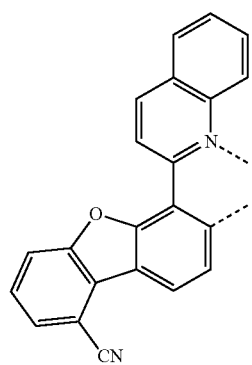
L<sub>a327</sub>
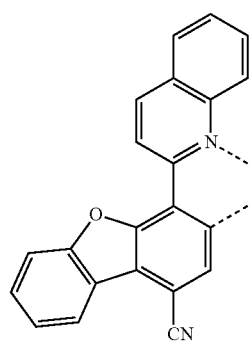
L<sub>a328</sub>
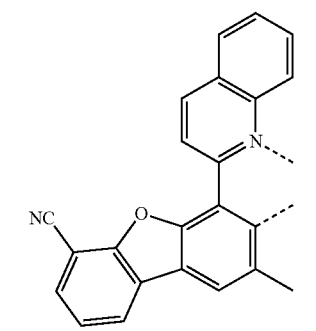
L<sub>a329</sub>
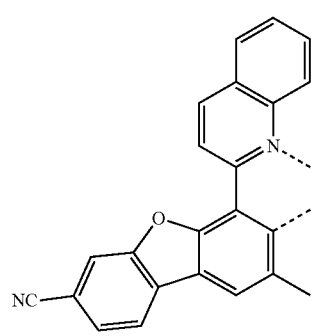
L<sub>a330</sub>
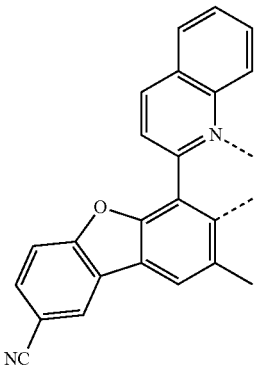
L<sub>a331</sub>
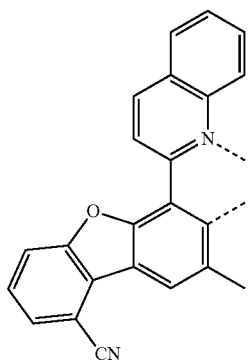
L<sub>a332</sub>
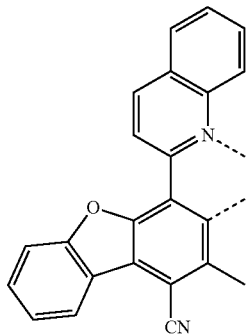
L<sub>a333</sub>
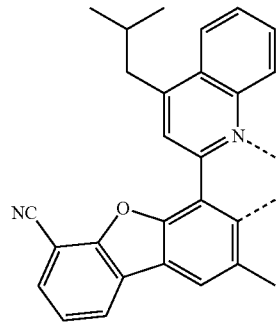

-continued
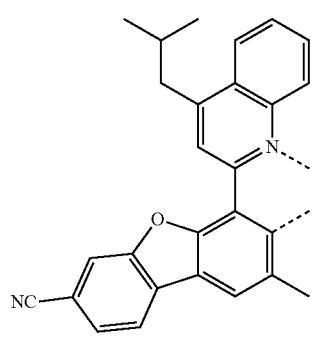
L<sub>a</sub>334
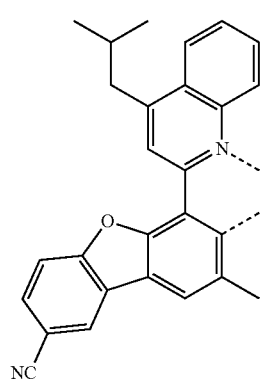
L<sub>a</sub>335
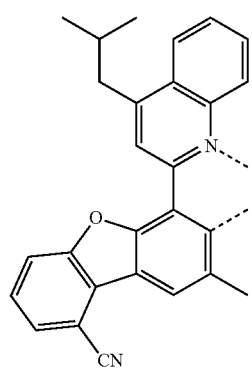
L<sub>a</sub>336
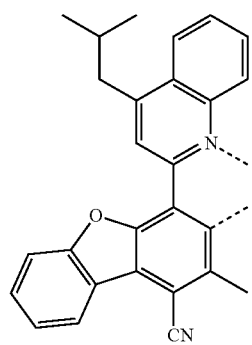
L<sub>a</sub>337
-continued
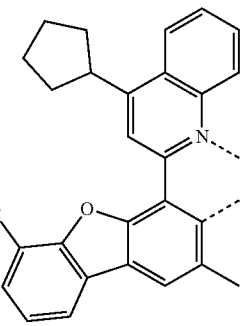
L<sub>a</sub>338
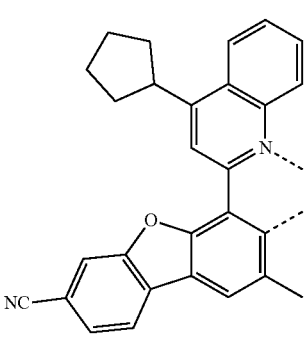
L<sub>a</sub>339
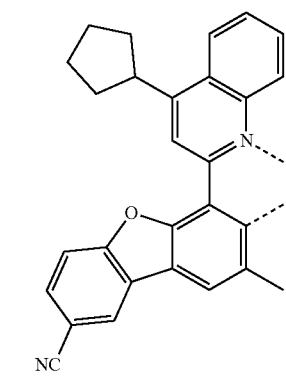
L<sub>a</sub>340
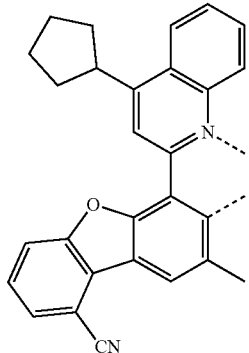
L<sub>a</sub>341

-continued
La342
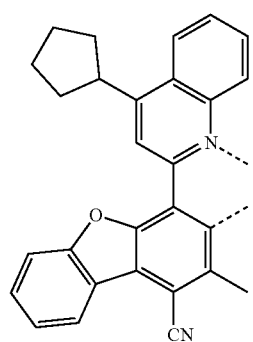
La343
La344
La345
La346
-continued
La347
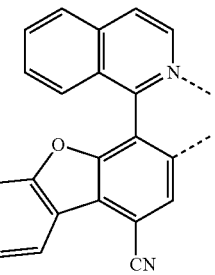
La348
La349
La350
La351

| | |
|---|---|
| 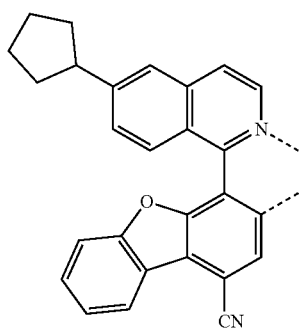 L<sub>a352</sub> | 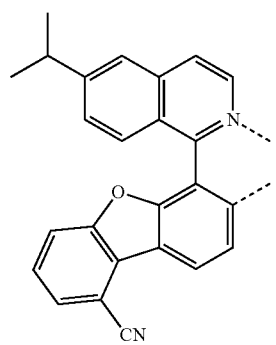 L<sub>a356</sub> |
| 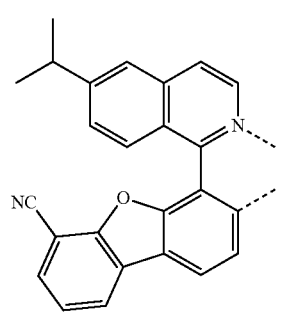 L<sub>a353</sub> | 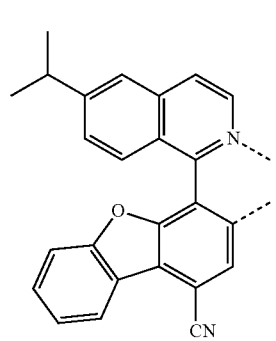 L<sub>a357</sub> |
| 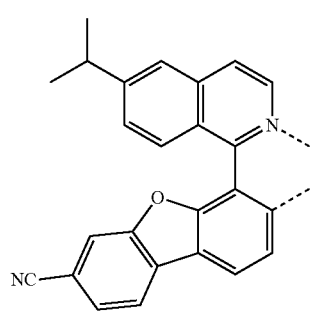 L<sub>a354</sub> | 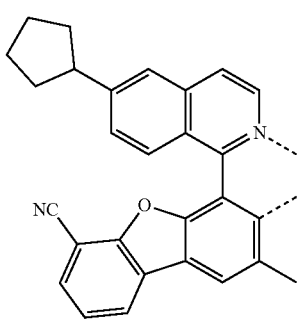 L<sub>a358</sub> |
| 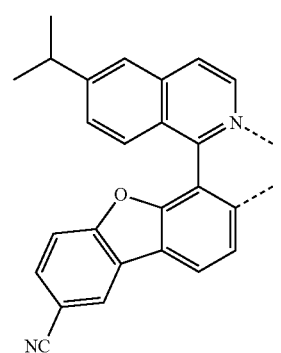 L<sub>a355</sub> | 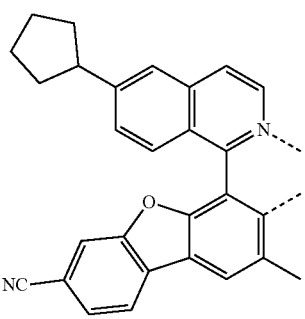 L<sub>a359</sub> |

L<sub>a</sub>360
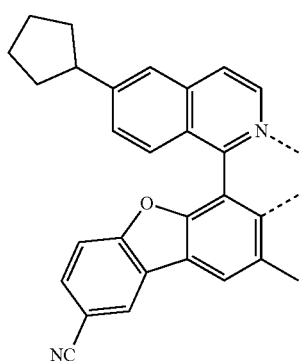
L<sub>a</sub>361
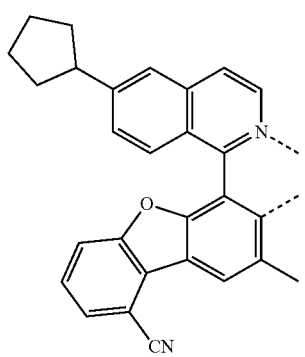
L<sub>a</sub>362
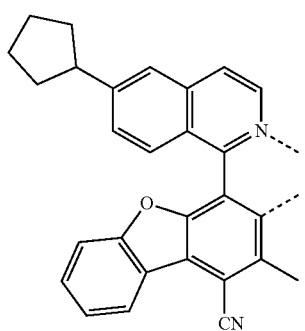
L<sub>a</sub>363
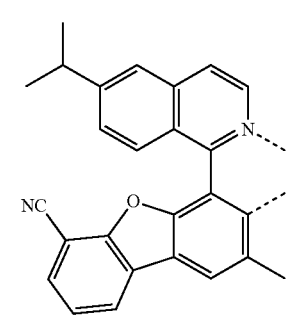
L<sub>a</sub>364
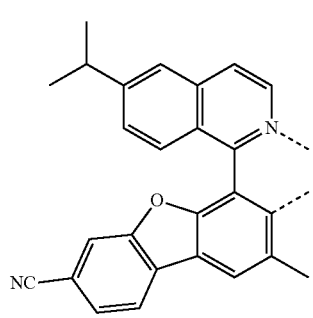
L<sub>a</sub>365
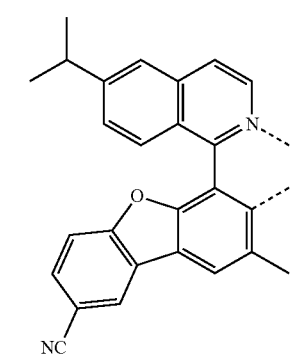
L<sub>a</sub>366
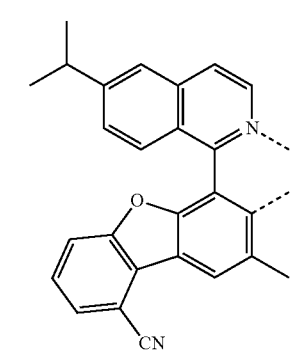
L<sub>a</sub>367
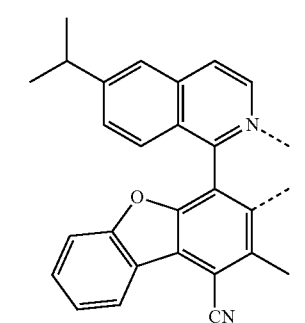

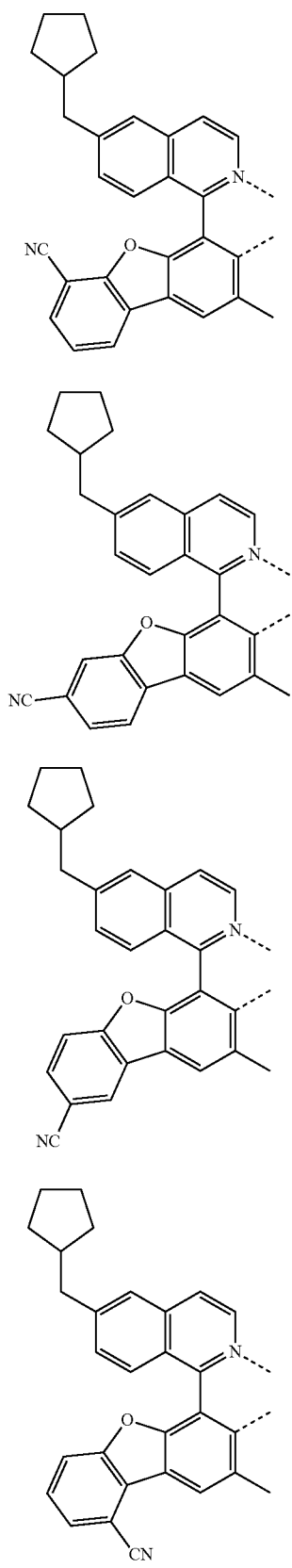
L<sub>a368</sub>
L<sub>a369</sub>
L<sub>a370</sub>
L<sub>a371</sub>
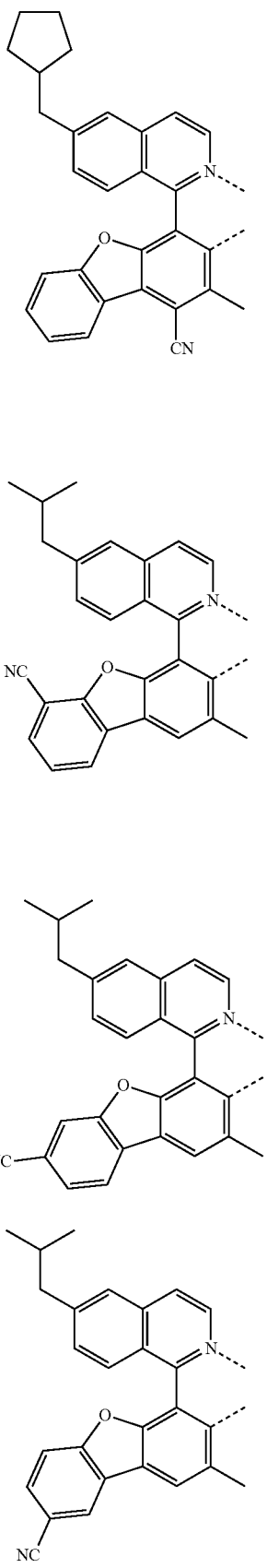
L<sub>a372</sub>
L<sub>a373</sub>
L<sub>a374</sub>
L<sub>a375</sub>

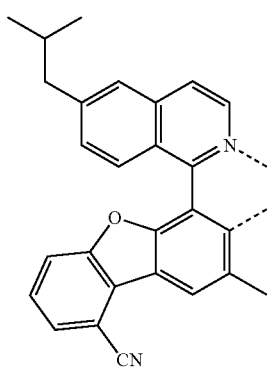 L<sub>a376</sub>
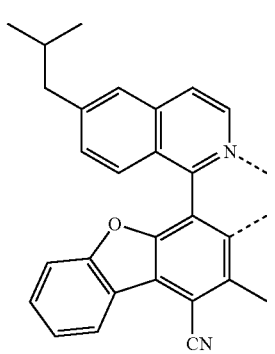 L<sub>a377</sub>
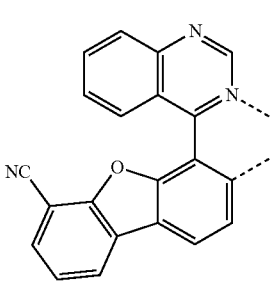 L<sub>a378</sub>
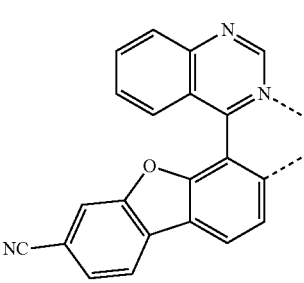 L<sub>a379</sub>
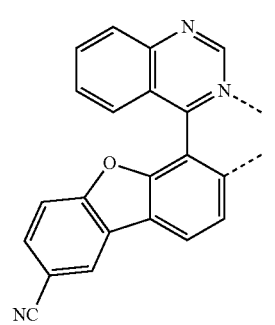 L<sub>a380</sub>
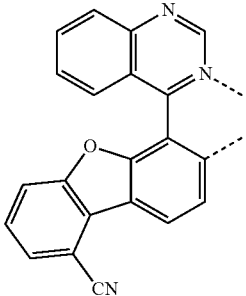 L<sub>a381</sub>
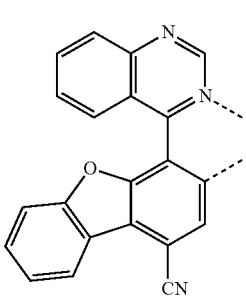 L<sub>a382</sub>
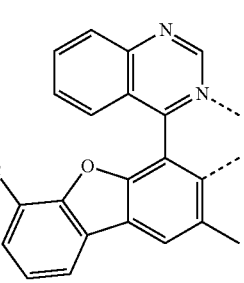 L<sub>a383</sub>
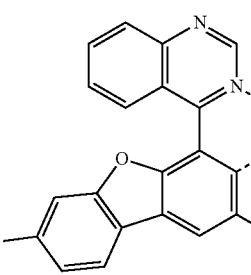 L<sub>a384</sub>
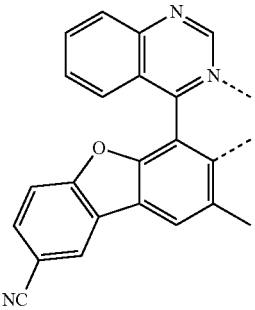 L<sub>a385</sub>

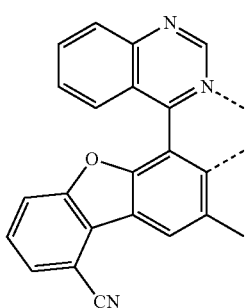 L<sub>a386</sub>
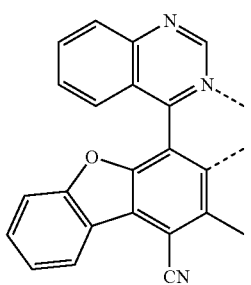 L<sub>a387</sub>
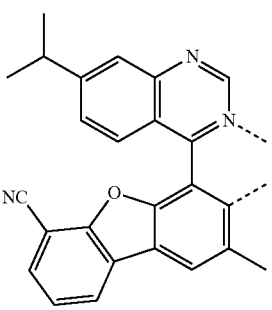 L<sub>a388</sub>
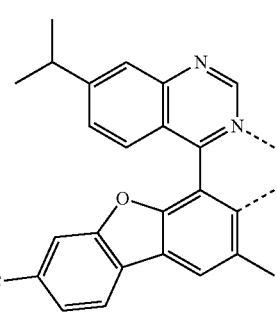 L<sub>a389</sub>
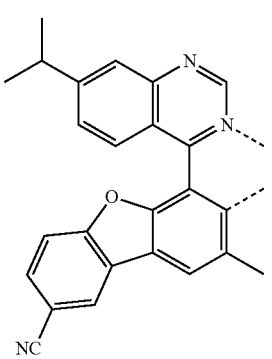 L<sub>a390</sub>
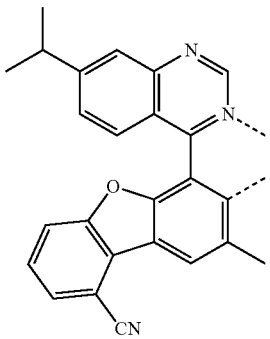 L<sub>a391</sub>
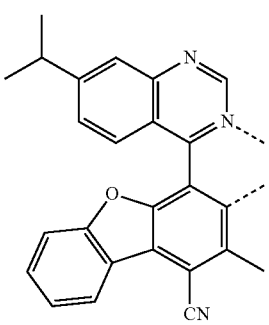 L<sub>a392</sub>
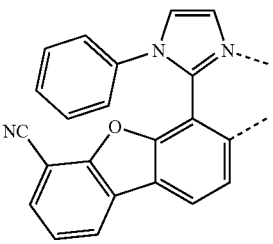 L<sub>a393</sub>
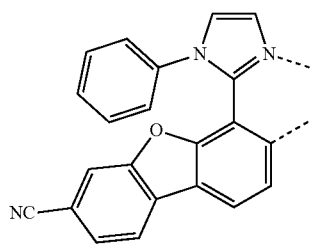 L<sub>a394</sub>
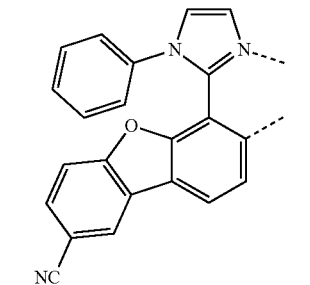 L<sub>a395</sub>

189
-continued
L_{a396}
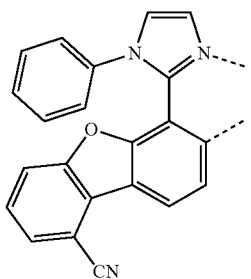
L_{a397}
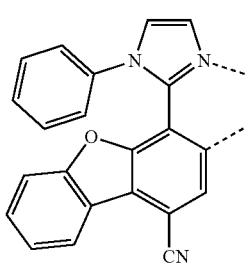
L_{a398}
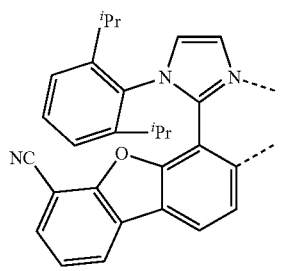
L_{a399}
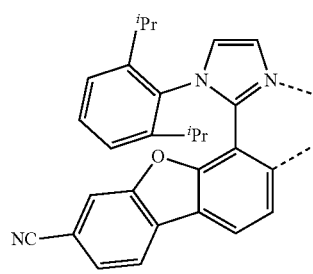
L_{a400}
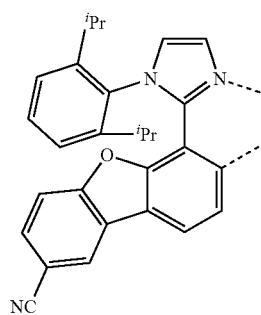
190
-continued
L_{a401}
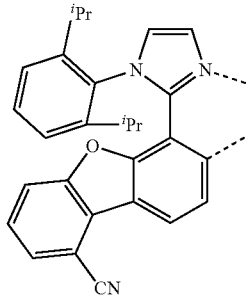
L_{a402}
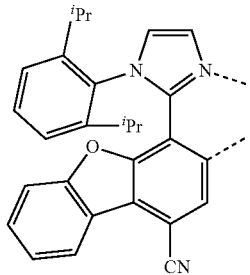
L_{a403}
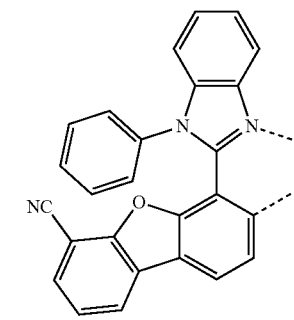
L_{a404}
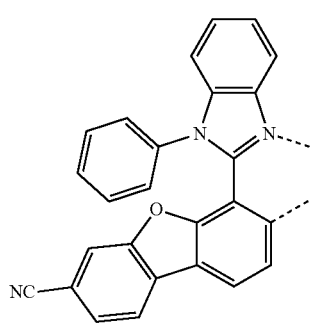
L_{a405}
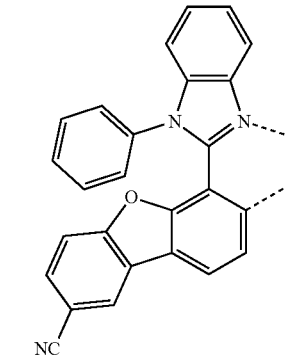

| L_{a406} | 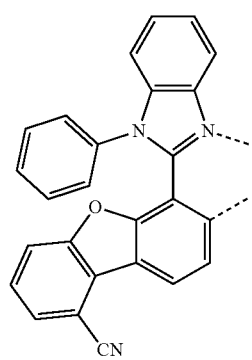 | L_{a411} | 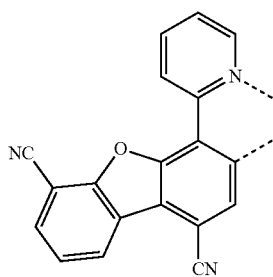 |
| L_{a407} | | L_{a412} | 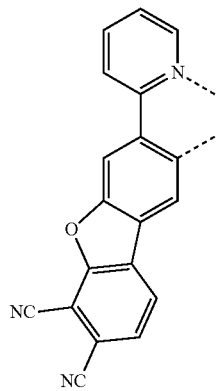 |
| L_{a408} | | L_{a413} | 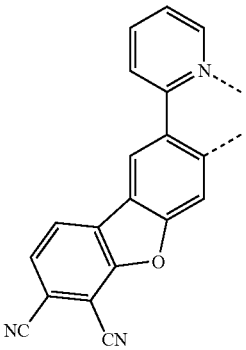 |
| L_{a409} | | L_{a414} | 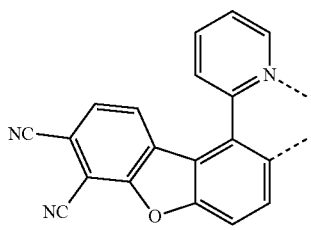 |
| L_{a410} | | L_{a415} | 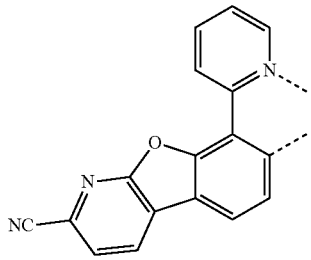 |

-continued
L<sub>a416</sub>
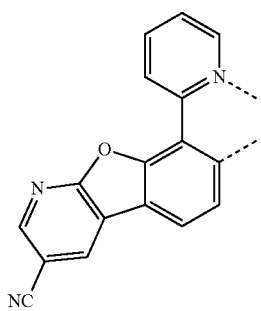
L<sub>a417</sub>
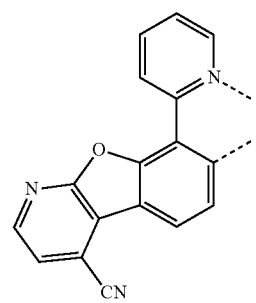
L<sub>a418</sub>
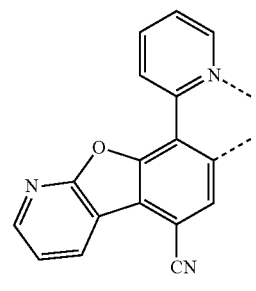
L<sub>a419</sub>
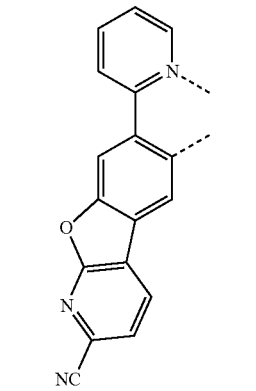
-continued
L<sub>a420</sub>
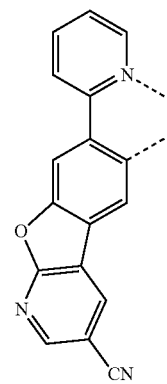
L<sub>a421</sub>
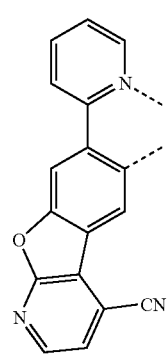
L<sub>a422</sub>
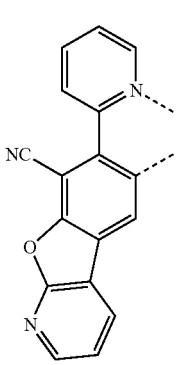
L<sub>a423</sub>
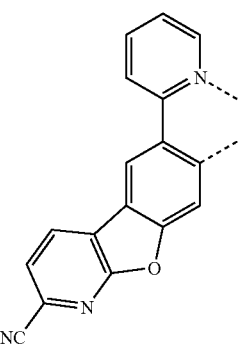

L<sub>a424</sub>
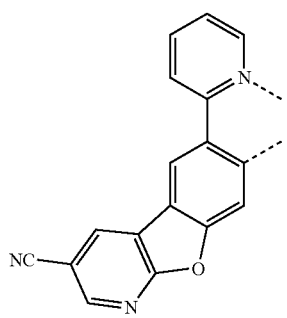
L<sub>a425</sub>
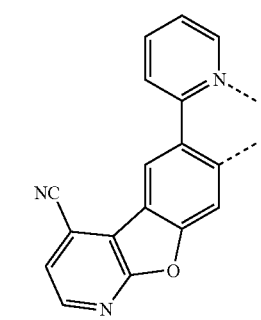
L<sub>a426</sub>
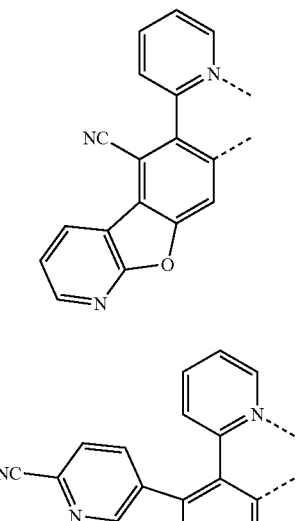
L<sub>a427</sub>
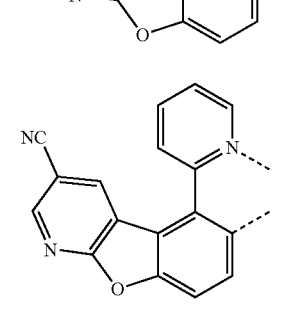
L<sub>a428</sub>
L<sub>a429</sub>
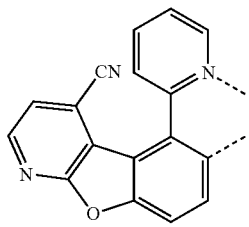
L<sub>a430</sub>
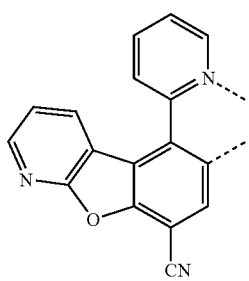
L<sub>a431</sub>
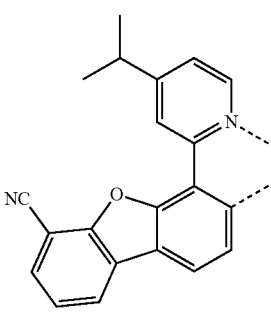
L<sub>a432</sub>
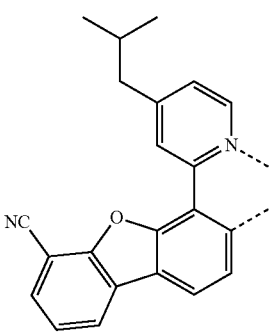
L<sub>a433</sub>
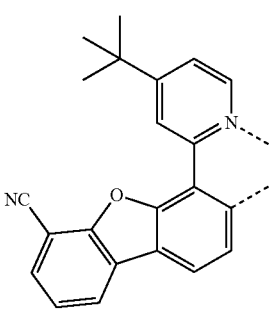

197
-continued
L<sub>a434</sub>
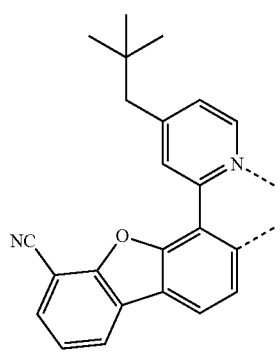
L<sub>a435</sub>
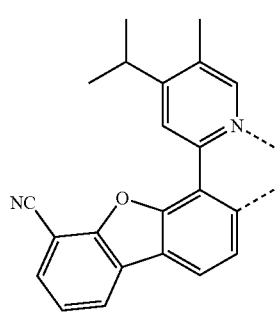
L<sub>a436</sub>
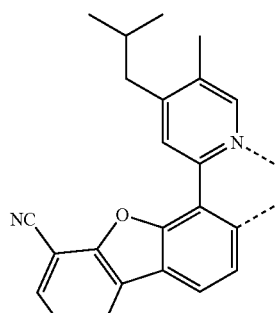
L<sub>a437</sub>
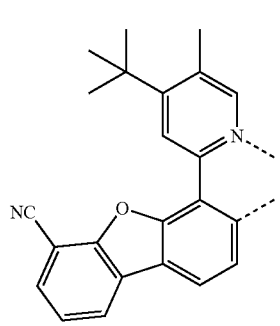
L<sub>a438</sub>
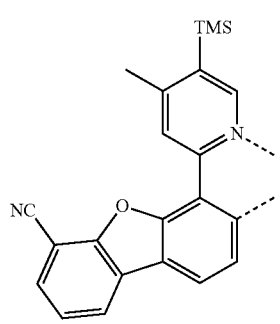
198
-continued
L<sub>a439</sub>
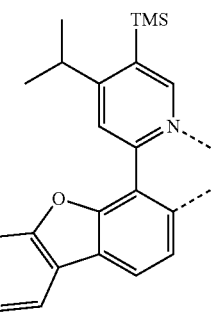
L<sub>a440</sub>
L<sub>a441</sub>
L<sub>a442</sub>
L<sub>a443</sub>

L_a444 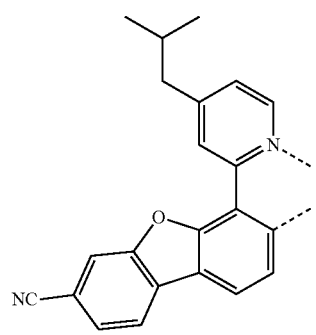
L_a445 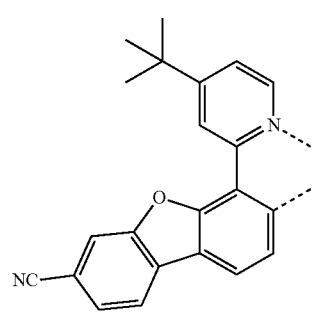
L_a446 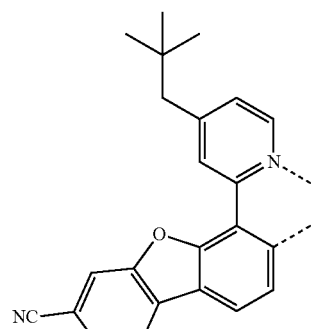
L_a447 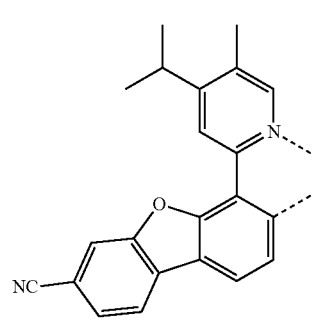
L_a448 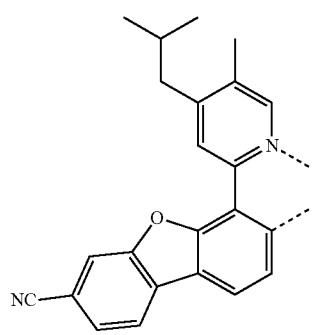
L_a449 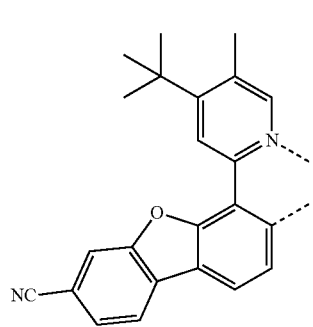
L_a450 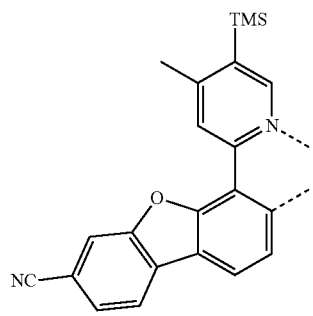
L_a451 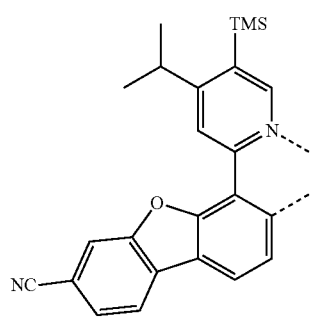
L_a452 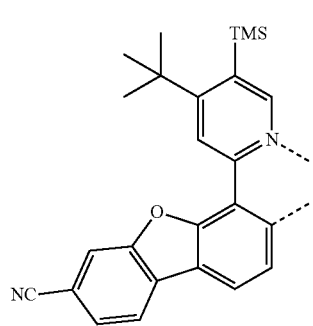

| 201 | 202 |
|---|---|
| 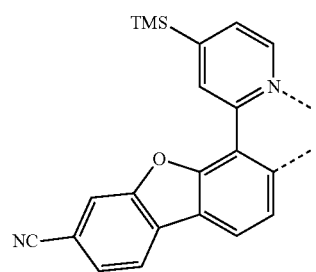 L<sub>a453</sub> | 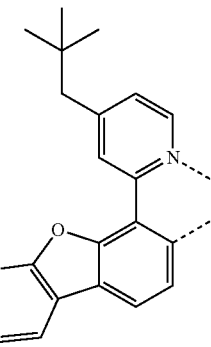 L<sub>a458</sub> |
| 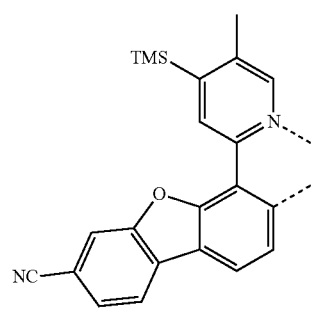 L<sub>a454</sub> | 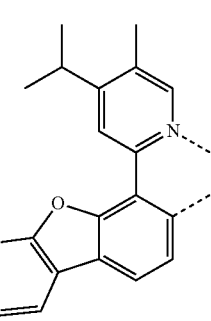 L<sub>a459</sub> |
| 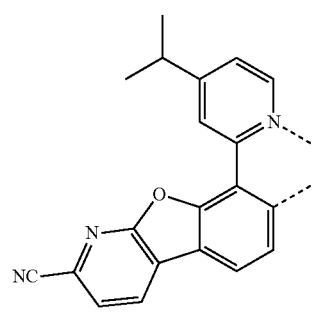 L<sub>a455</sub> | 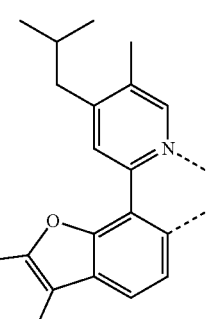 L<sub>a460</sub> |
| 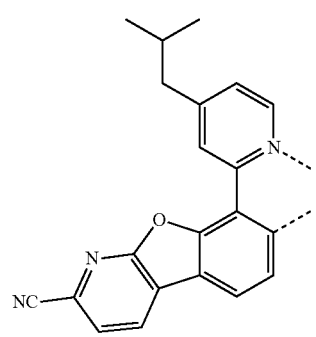 L<sub>a456</sub> | 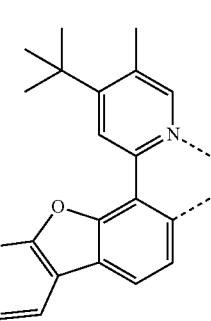 L<sub>a461</sub> |
| 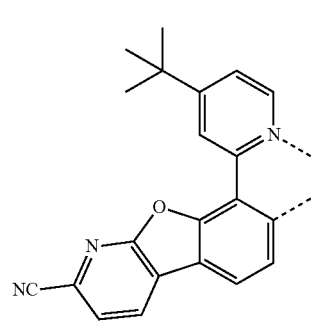 L<sub>a457</sub> | 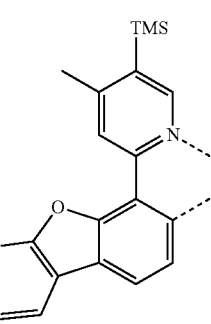 L<sub>a462</sub> |

203
-continued
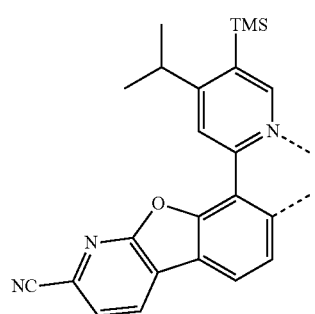
L<sub>a463</sub>
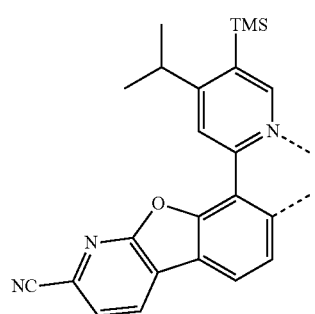
L<sub>a464</sub>
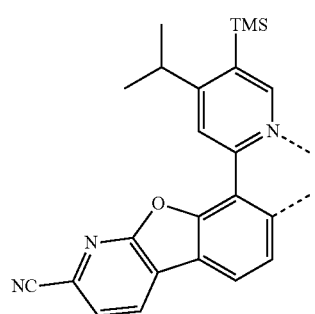
L<sub>a465</sub>
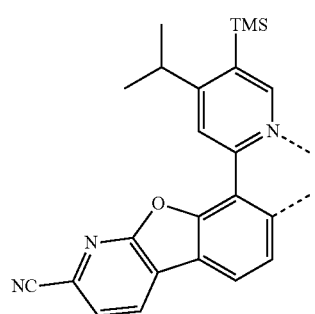
L<sub>a466</sub>
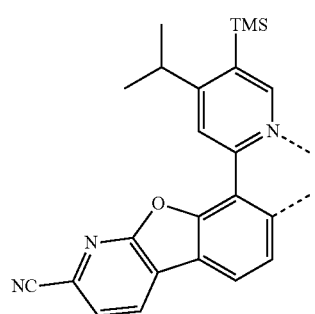
L<sub>a467</sub>
204
-continued
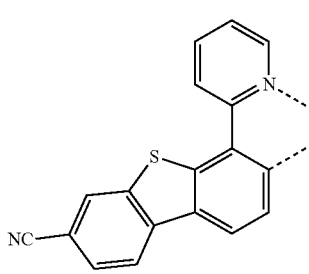
L<sub>a468</sub>
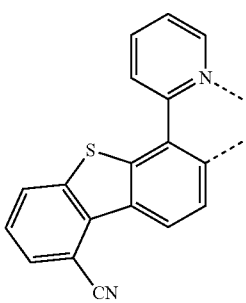
L<sub>a469</sub>
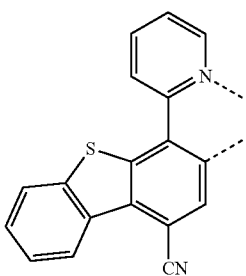
L<sub>a470</sub>
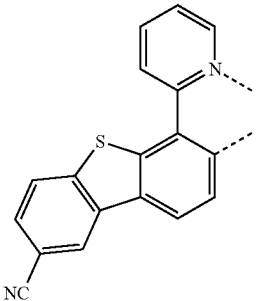
L<sub>a471</sub>
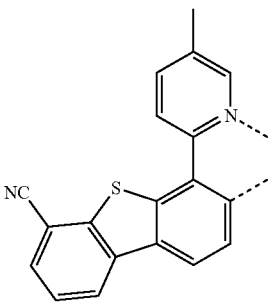
L<sub>a472</sub>

L_{a473} 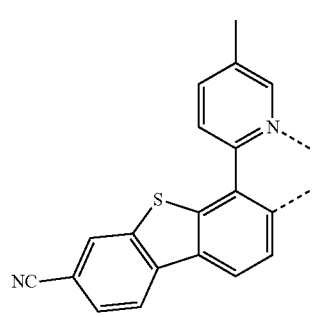
L_{a474} 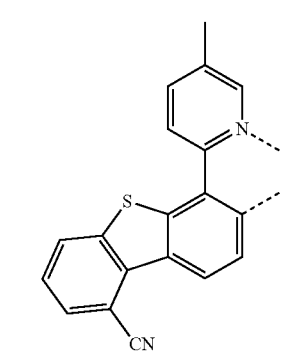
L_{a475} 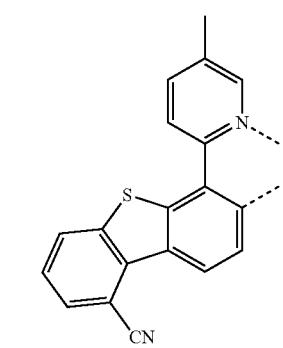
L_{a476} 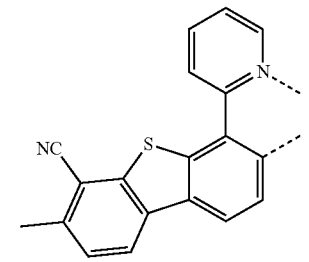
L_{a477} 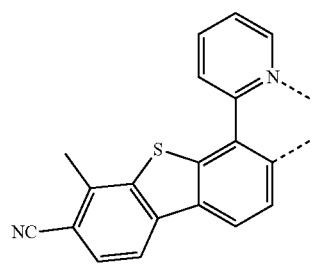
L_{a478} 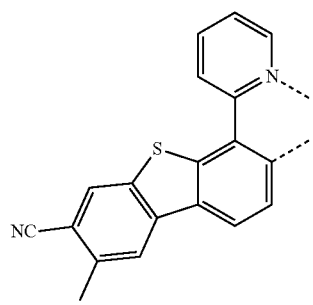
L_{a479} 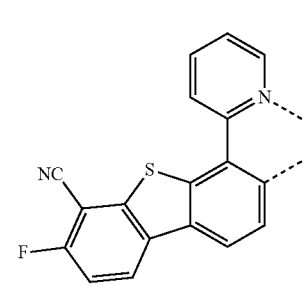
L_{a480} 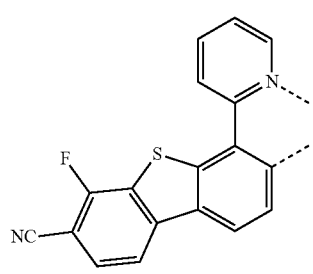
L_{a481} 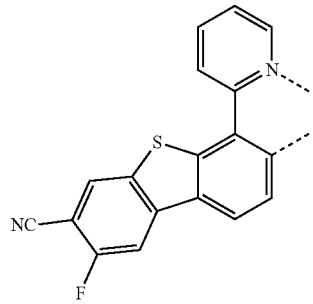
L_{a482} 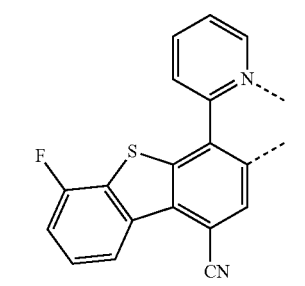

L_a483 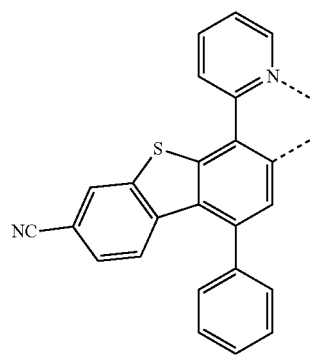
L_a484 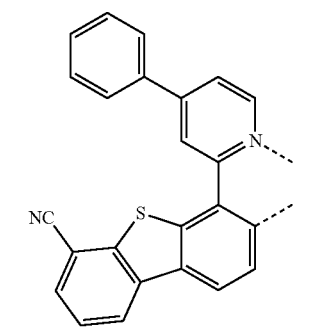
L_a485 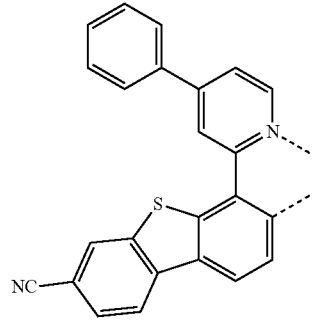
L_a486 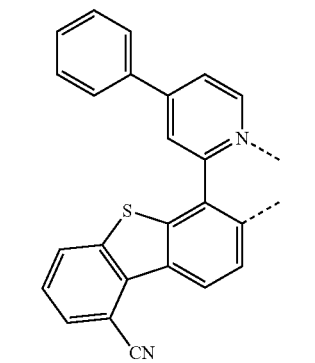
L_a487 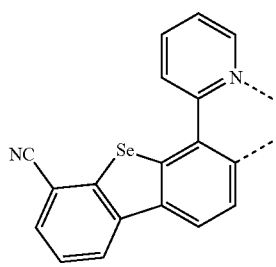
L_a488 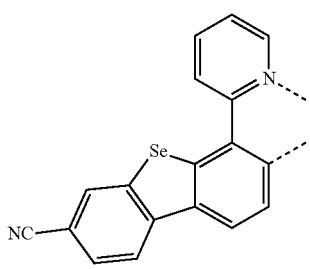
L_a489 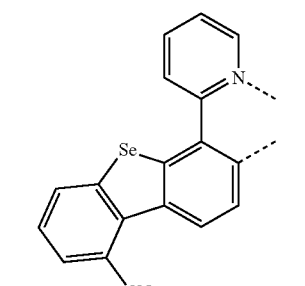
L_a490 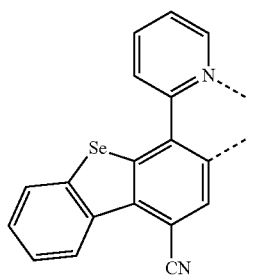
L_a491 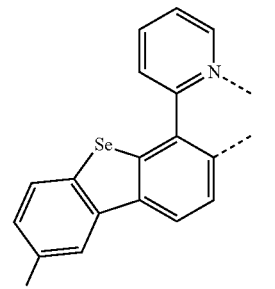

-continued
L_{a492}
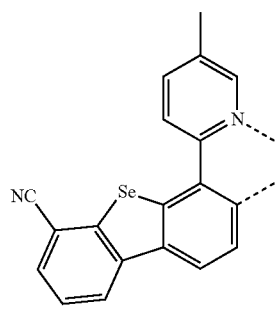
L_{a493}
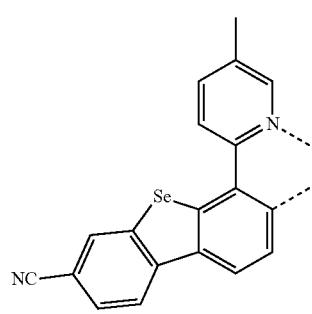
L_{a494}
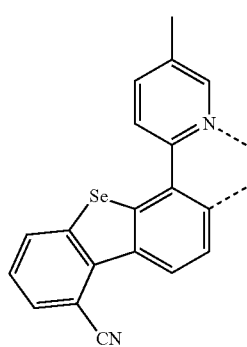
L_{a495}
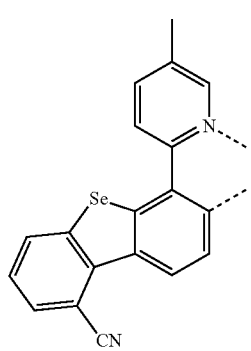
L_{a496}
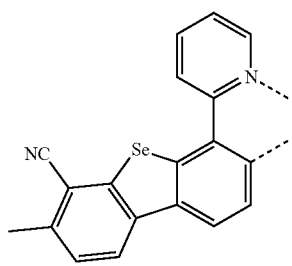
-continued
L_{a497}
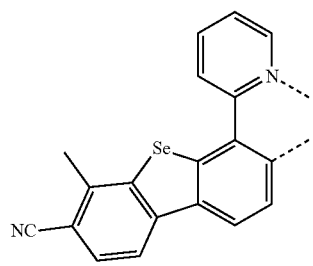
L_{a498}
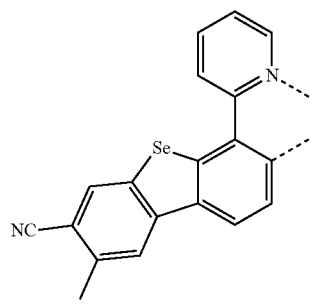
L_{a499}
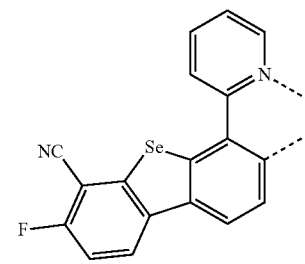
L_{a500}
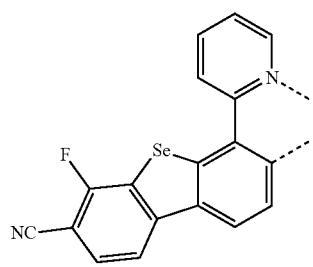
L_{a501}
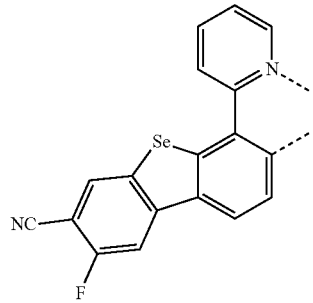

211
-continued
L_a502
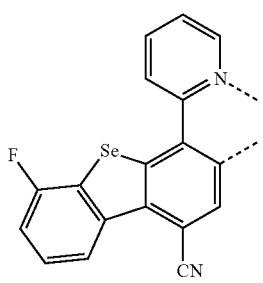
L_a503
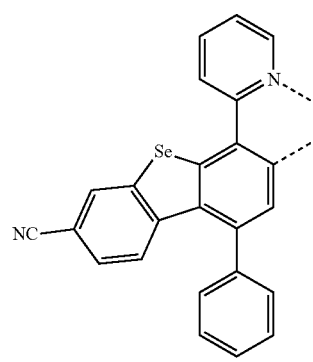
L_a504
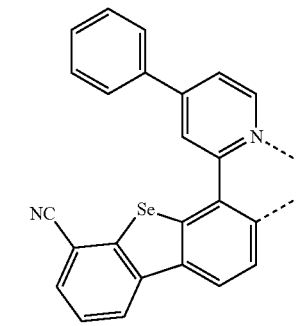
L_a505
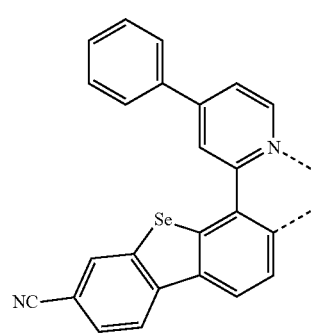
212
-continued
L_a506
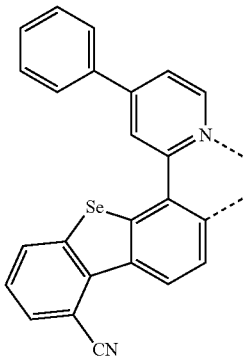
L_a507
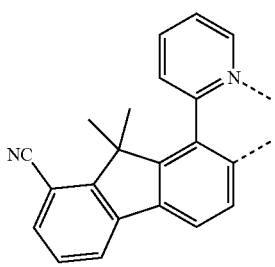
L_a508
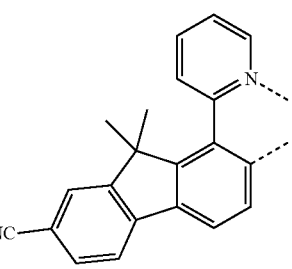
L_a509
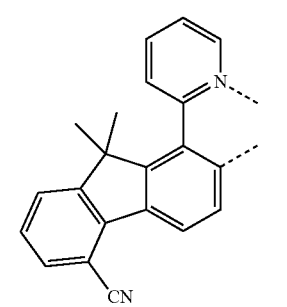
L_a510
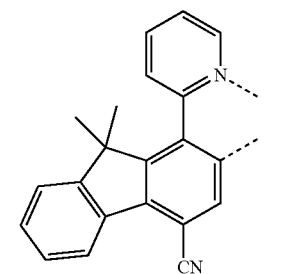

-continued
L_a511
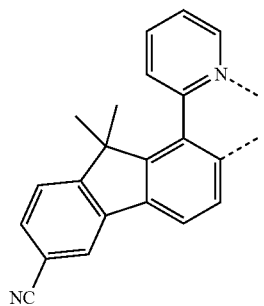
L_a512
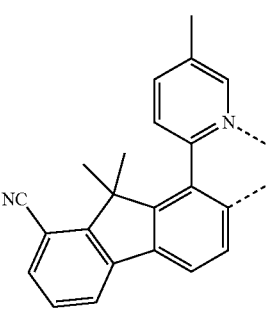
L_a513
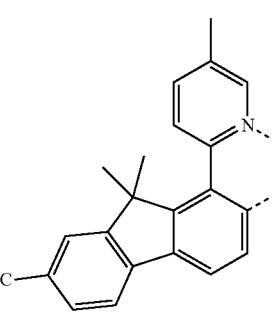
L_a514
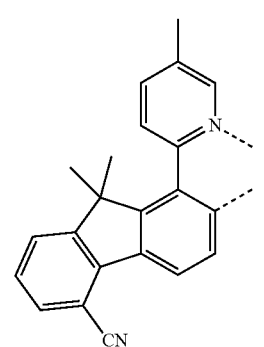
L_a515
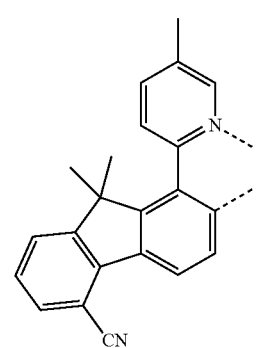
-continued
L_a516
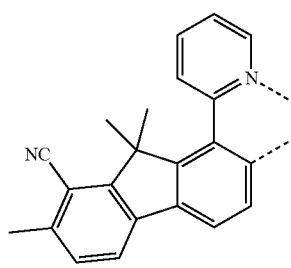
L_a517
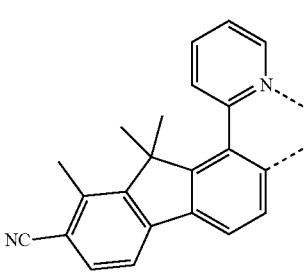
L_a518
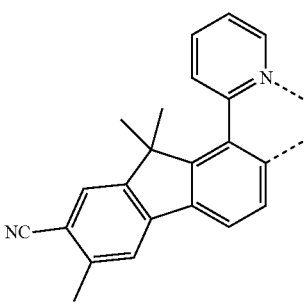
L_a519
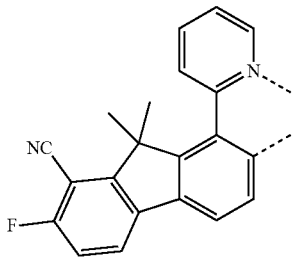
L_a520
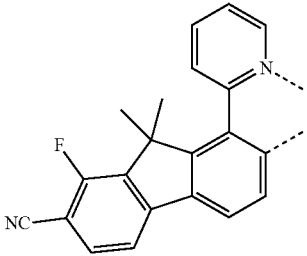

| | |
|---|---|
| 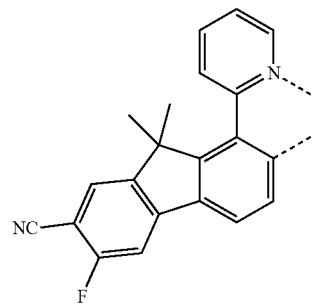 | $L_{a521}$ |
| 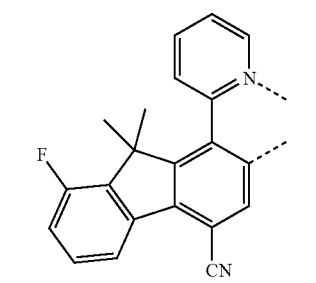 | $L_{a522}$ |
| 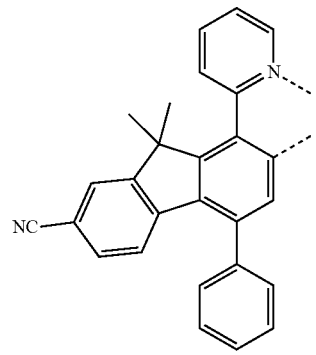 | $L_{a523}$ |
| 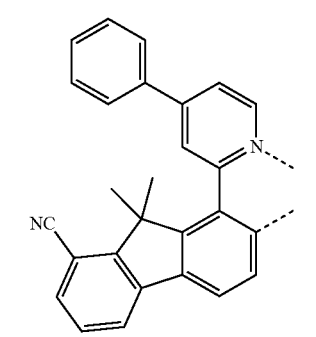 | $L_{a524}$ |
| 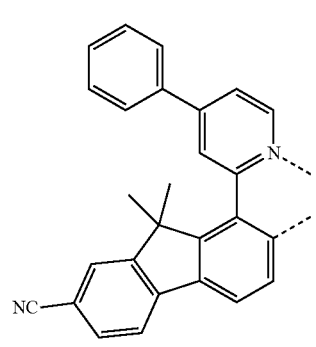 | $L_{a525}$ |
| 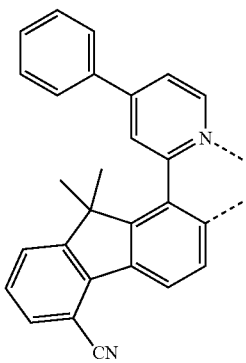 | $L_{a526}$ |
| 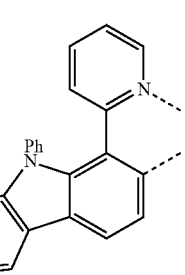 | $L_{a527}$ |
| 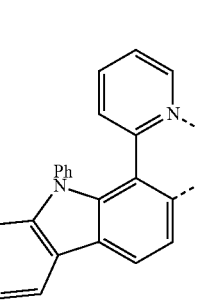 | $L_{a528}$ |
| 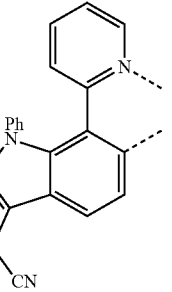 | $L_{a529}$ |
| 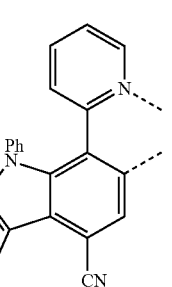 | $L_{a530}$ |

| | |
|---|---|
| L<sub>a531</sub> 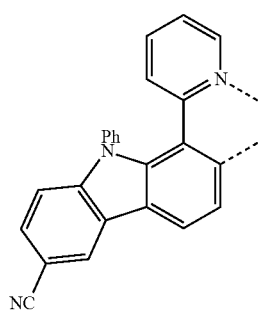 | L<sub>a536</sub> 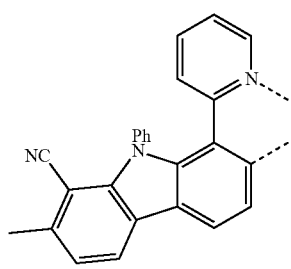 |
| L<sub>a532</sub> 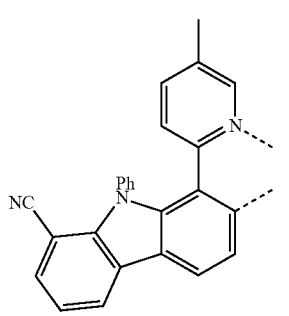 | L<sub>a537</sub> 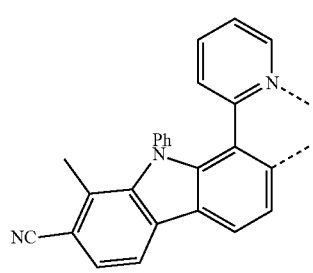 |
| L<sub>a533</sub> 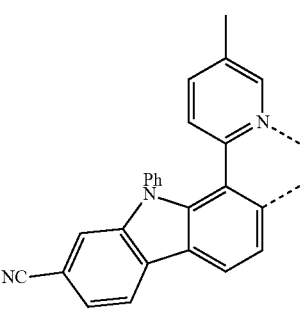 | L<sub>a538</sub> 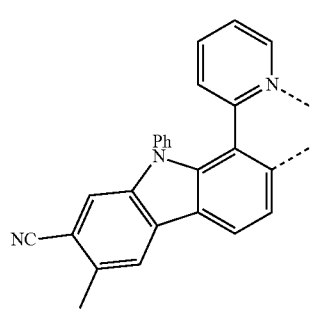 |
| L<sub>a534</sub> 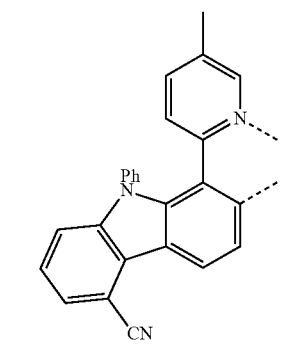 | L<sub>a539</sub> 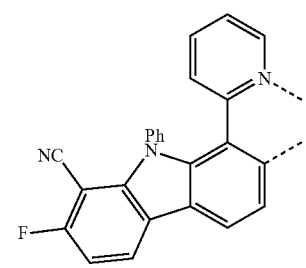 |
| L<sub>a535</sub> 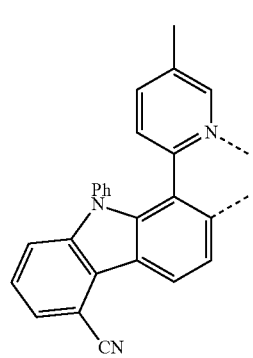 | L<sub>a540</sub> 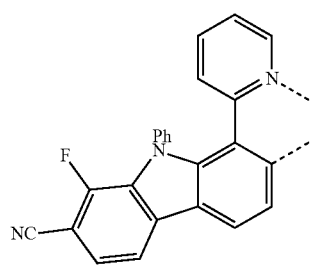 |

L_a541
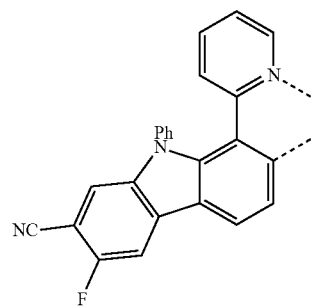
L_a542
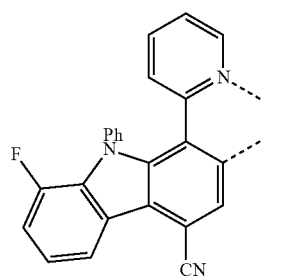
L_a543
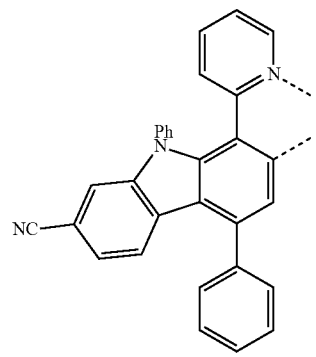
L_a544
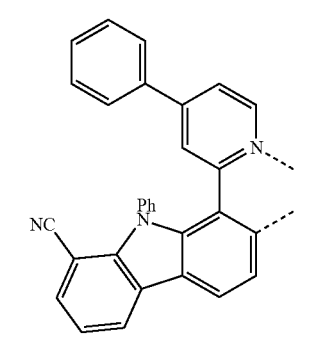
L_a545
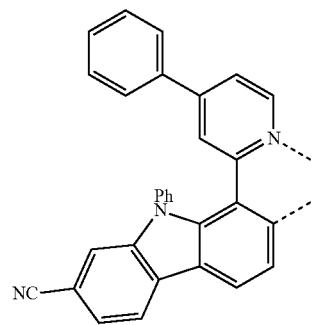
L_a546
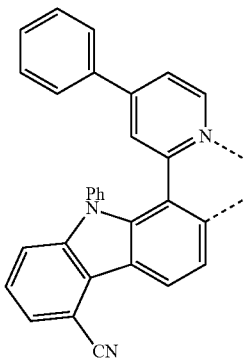
L_a547
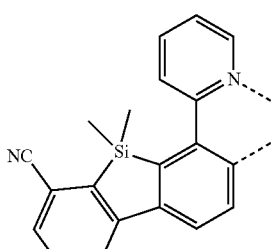
L_a548
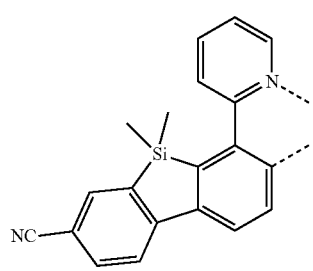
L_a549
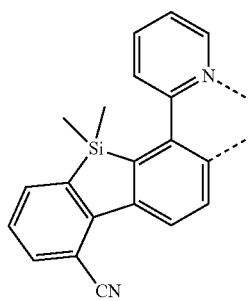
L_a550
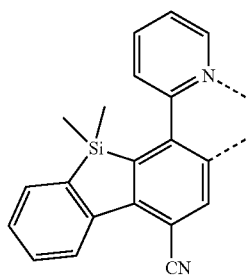

-continued
L<sub>a551</sub>
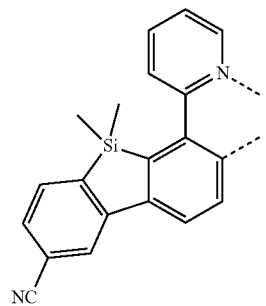
L<sub>a552</sub>
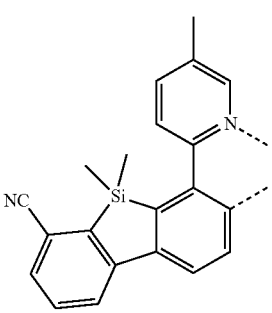
L<sub>a553</sub>
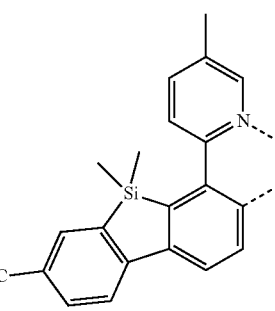
L<sub>a554</sub>
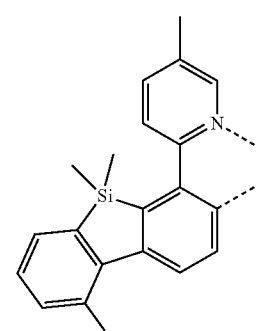
L<sub>a555</sub>
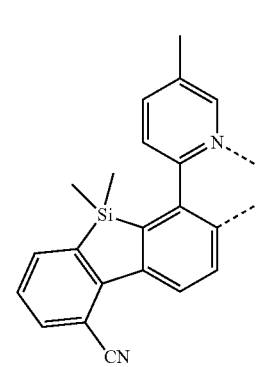
-continued
L<sub>a556</sub>
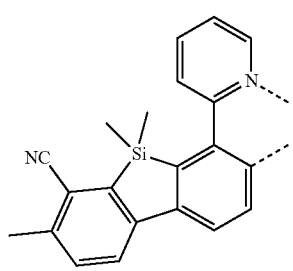
L<sub>a557</sub>
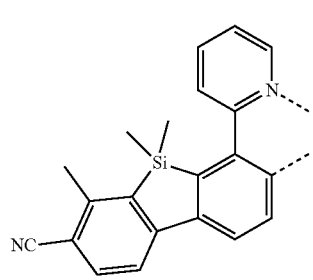
L<sub>a558</sub>
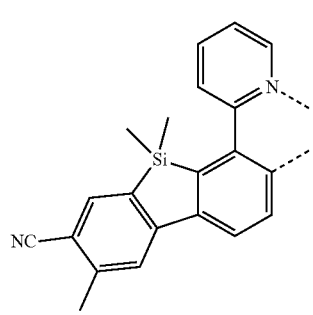
L<sub>a559</sub>
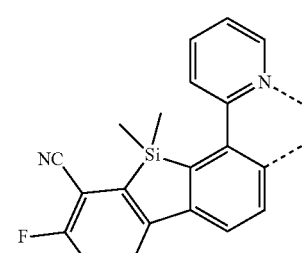
L<sub>a560</sub>
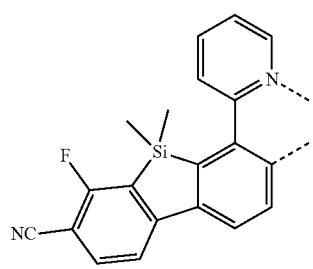

-continued
L<sub>a561</sub>
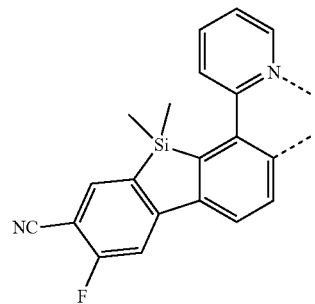
L<sub>a562</sub>
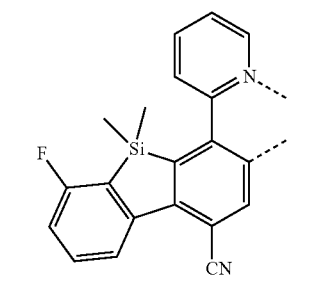
L<sub>a563</sub>
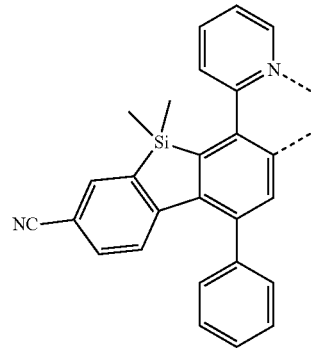
L<sub>a564</sub>
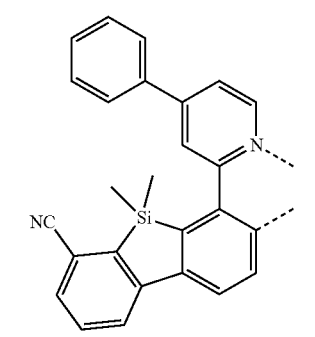
L<sub>a565</sub>

-continued
L<sub>a566</sub>
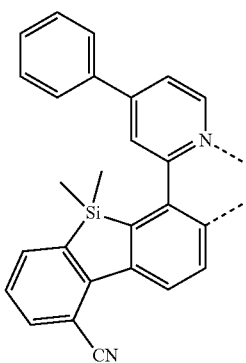
L<sub>a567</sub>
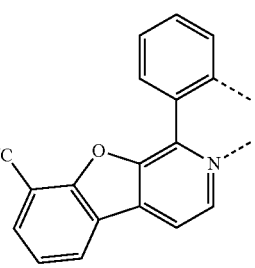
L<sub>a568</sub>
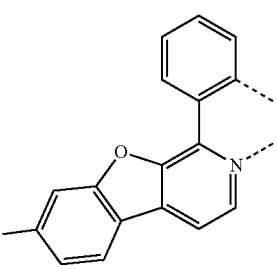
L<sub>a569</sub>
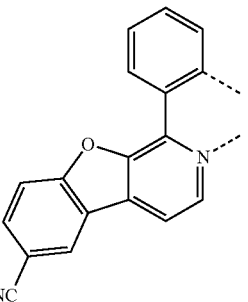
L<sub>a570</sub>
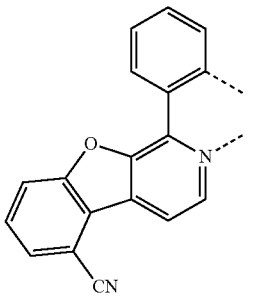

225
-continued
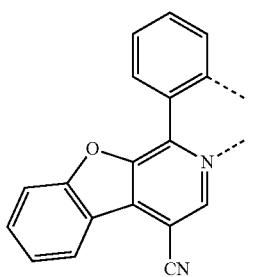
L<sub>a571</sub>
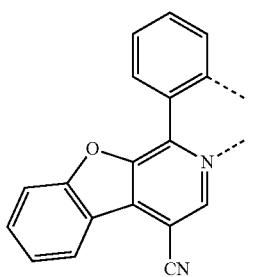
L<sub>a572</sub>
L<sub>a573</sub>
L<sub>a574</sub>
L<sub>a575</sub>
226
-continued
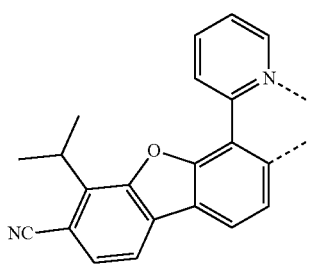 L<sub>a576</sub>
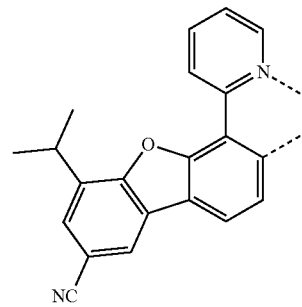 L<sub>a577</sub>
L<sub>a578</sub>
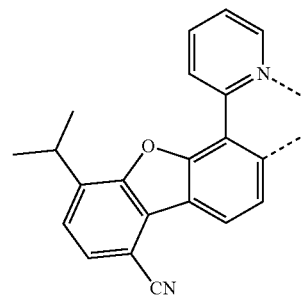 L<sub>a579</sub>
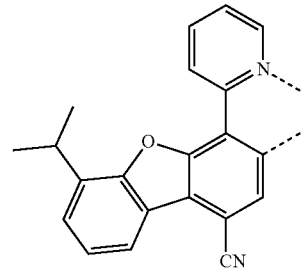 L<sub>a580</sub>
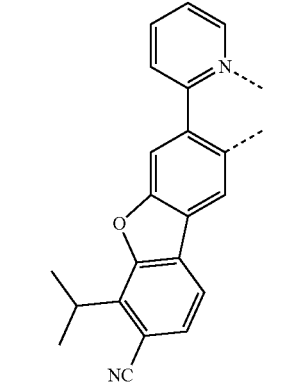

L_a581 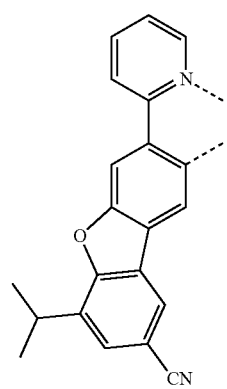
L_a583 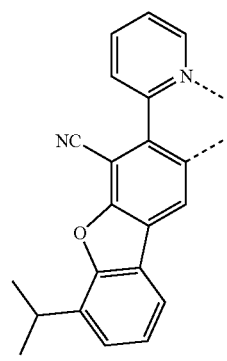
L_a584 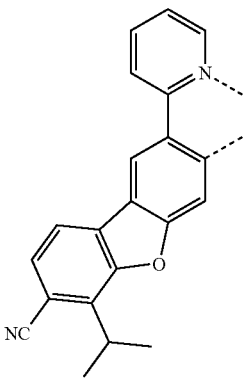
L_a585 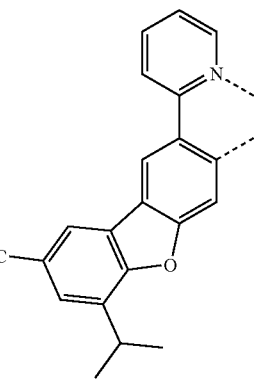
L_a586 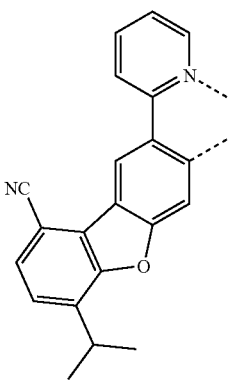
L_a587 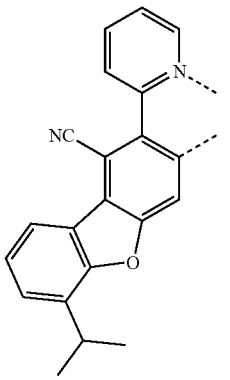
L_a588 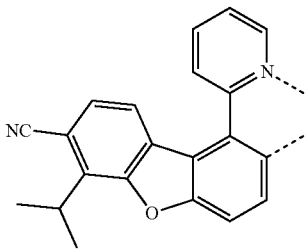
L_a589 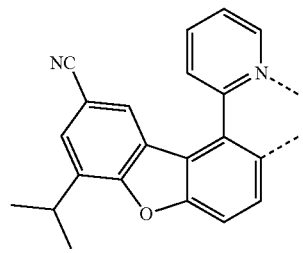
L_a590 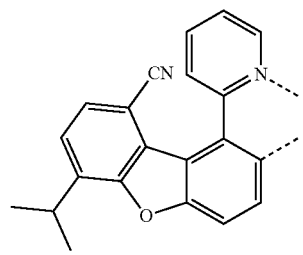

229
-continued
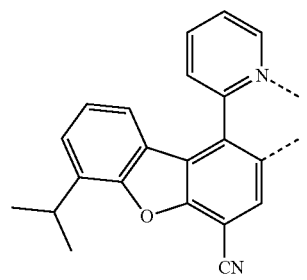 L_a591
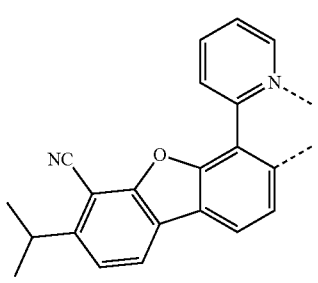 L_a592
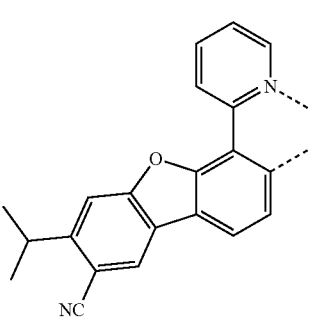 L_a593
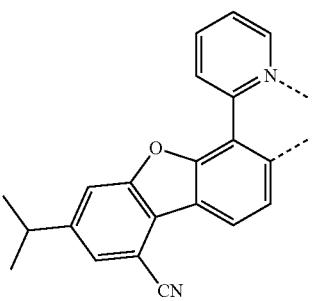 L_a594
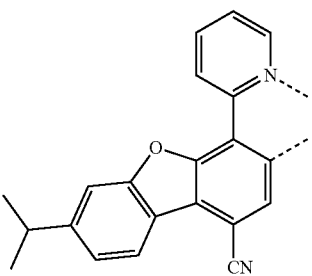 L_a595
230
-continued
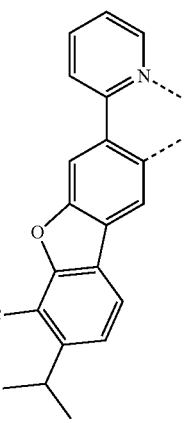 L_a596
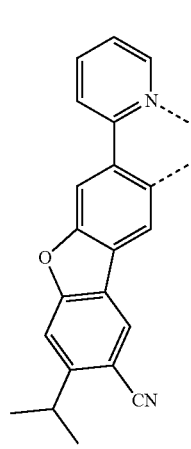 L_a597
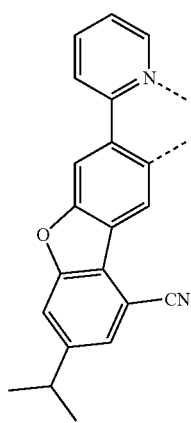 L_a598

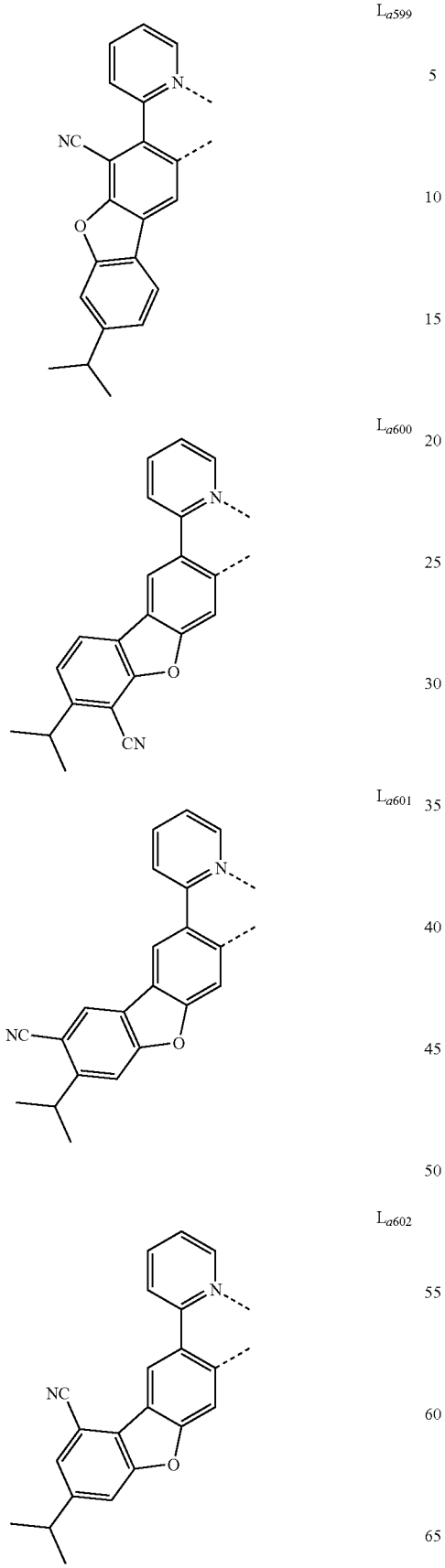
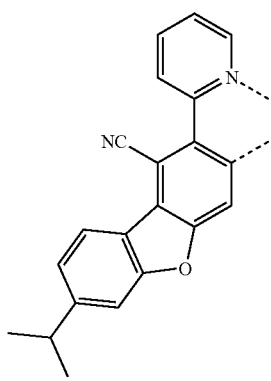
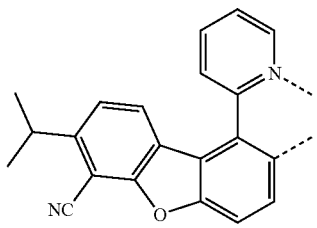
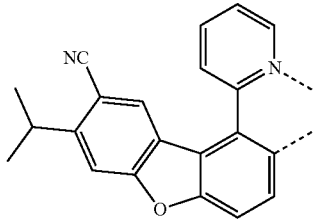
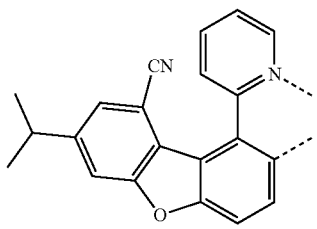
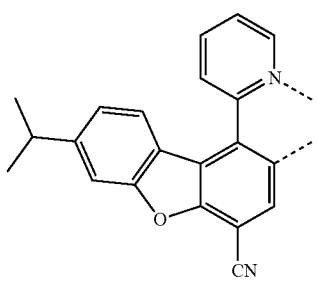
L<sub>a599</sub>
L<sub>a600</sub>
L<sub>a601</sub>
L<sub>a602</sub>
L<sub>a603</sub>
L<sub>a604</sub>
L<sub>a605</sub>
L<sub>a606</sub>
L<sub>a607</sub>

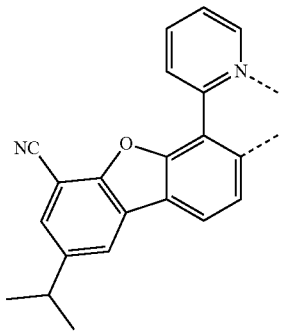
L_a608
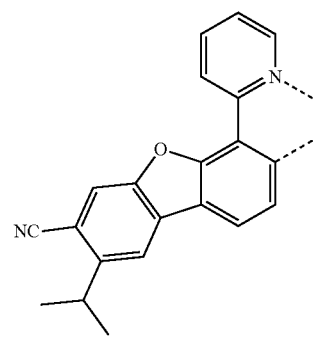
L_a609
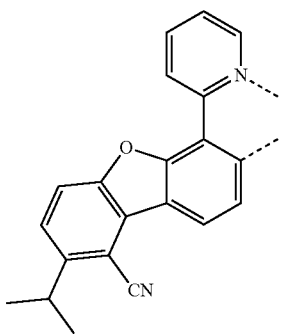
L_a610
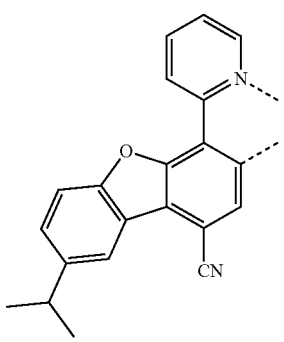
L_a611
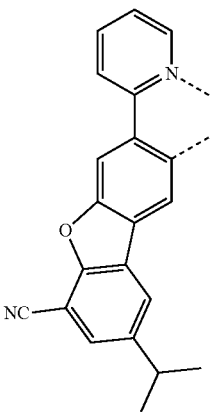
L_a612
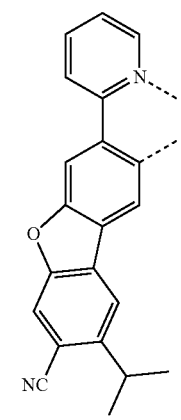
L_a613
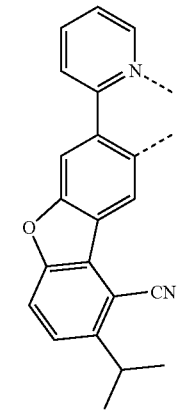
L_a614

L<sub>a</sub>615
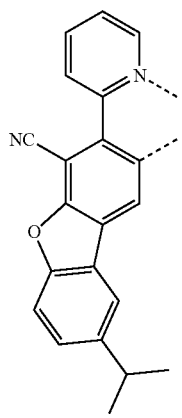
L<sub>a</sub>616
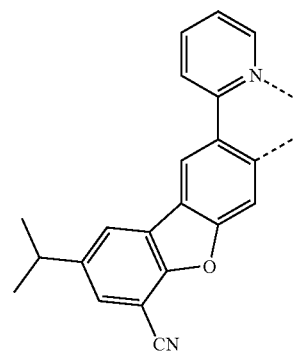
L<sub>a</sub>617
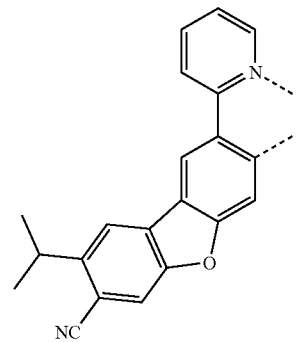
L<sub>a</sub>618
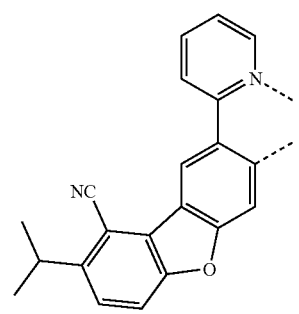
L<sub>a</sub>619
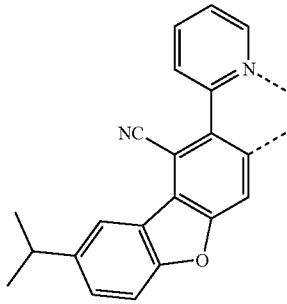
L<sub>a</sub>620
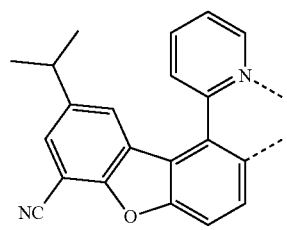
L<sub>a</sub>621
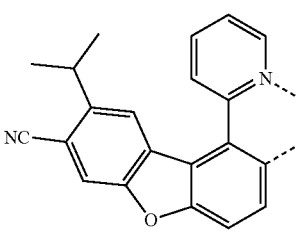
L<sub>a</sub>622
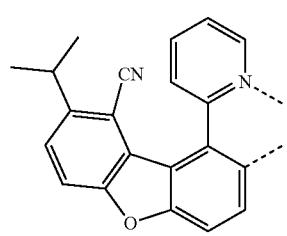
L<sub>a</sub>623
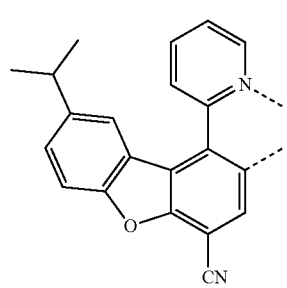
L<sub>a</sub>624
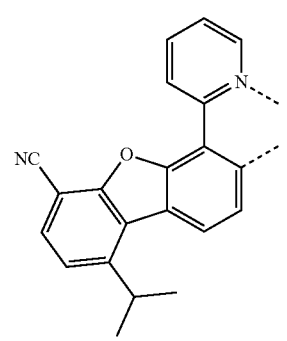

| | |
|---|---|
| L_{a625} 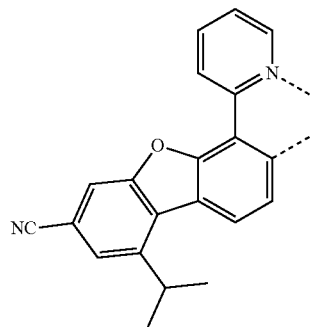 | L_{a629} 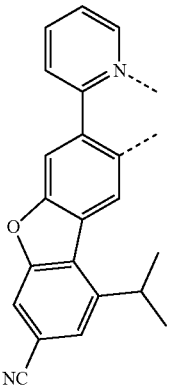 |
| L_{a626} 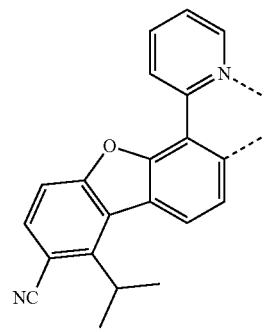 | L_{a630} 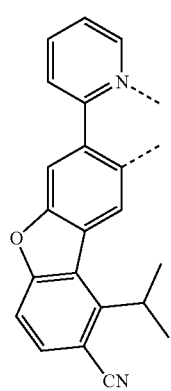 |
| L_{a627} 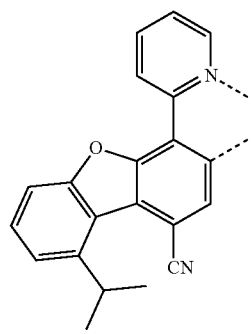 | L_{a631} 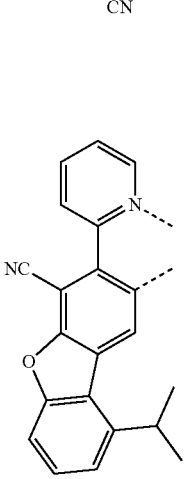 |
| L_{a628} 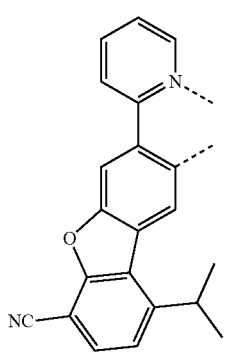 | L_{a632} 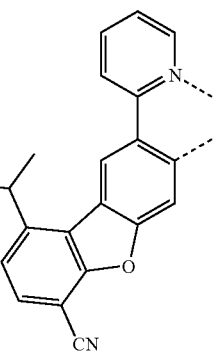 |

L_a633 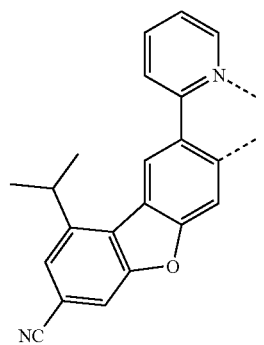
L_a634 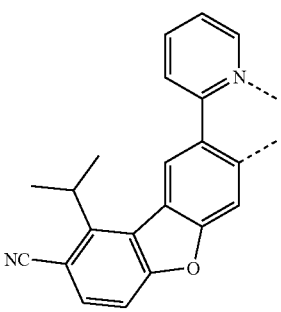
L_a635 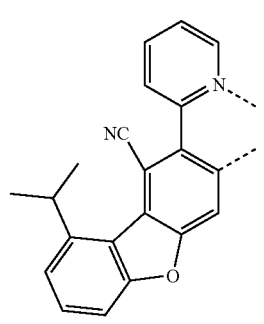
L_a636 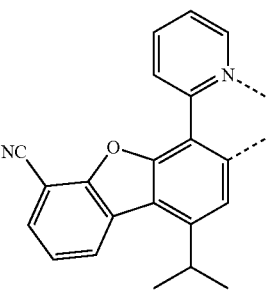
L_a637 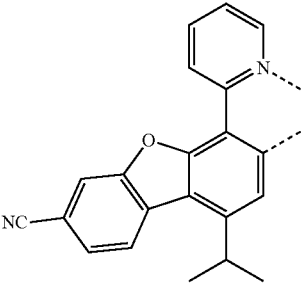
L_a638 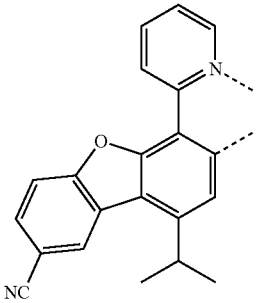
L_a639 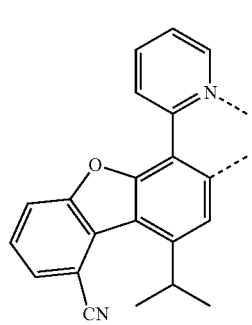
L_a640 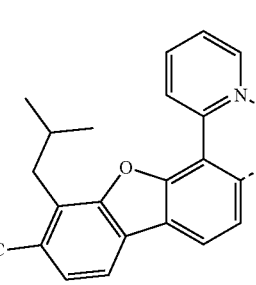
L_a641 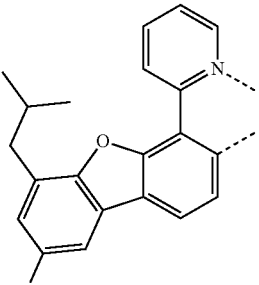
L_a642 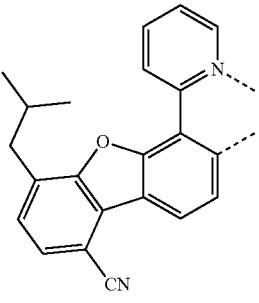

L_{a643}
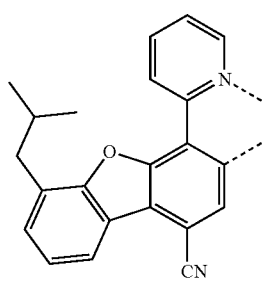
L_{a644}
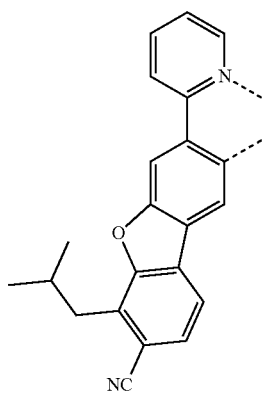
L_{a645}
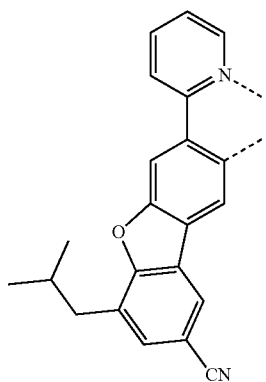
L_{a646}
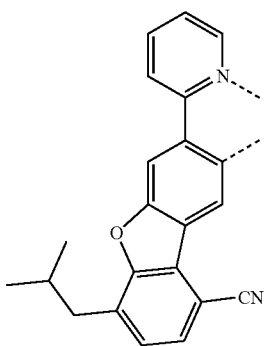
L_{a647}
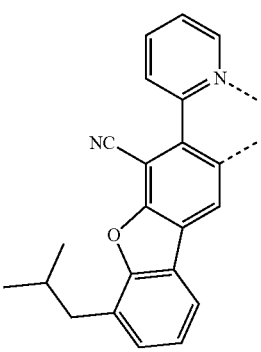
L_{a648}
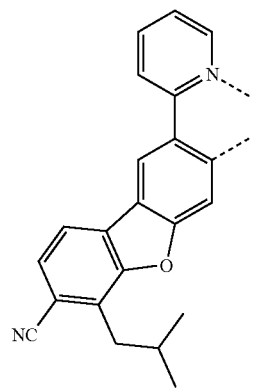
L_{a649}
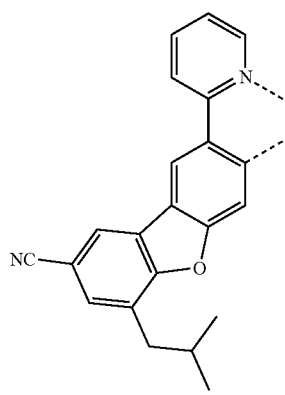
L_{a650}
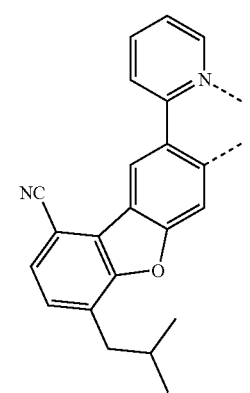

-continued
L<sub>a651</sub>
L<sub>a652</sub>
L<sub>a653</sub>
L<sub>a654</sub>
L<sub>a655</sub>
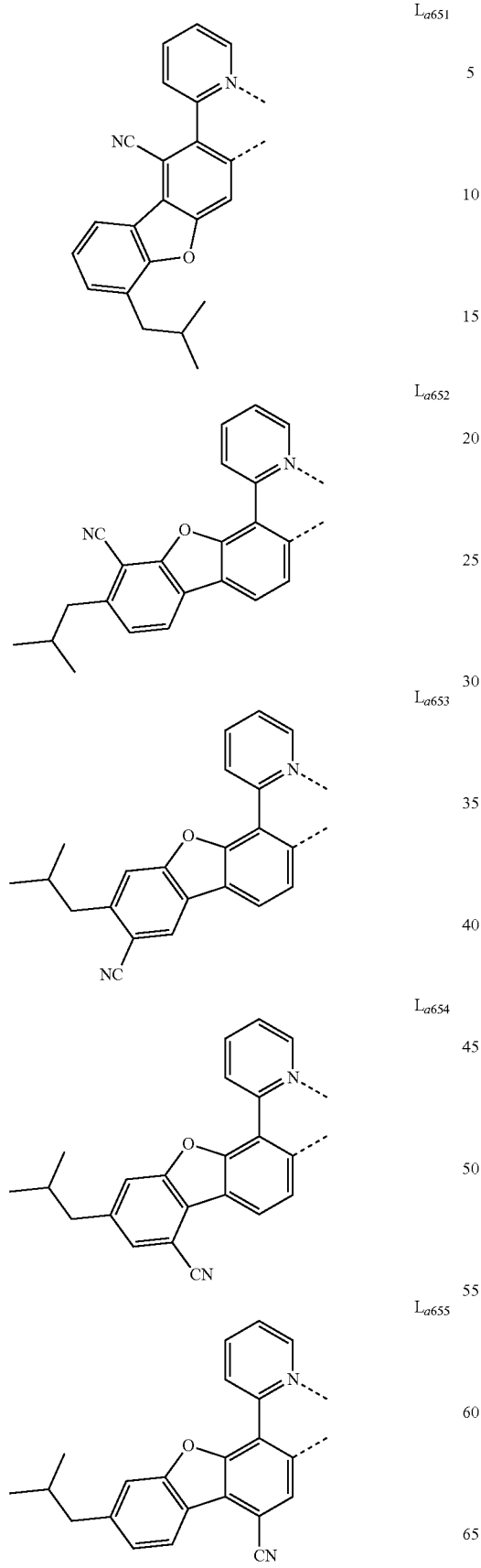
-continued
L<sub>a656</sub>
L<sub>a657</sub>
L<sub>a658</sub>
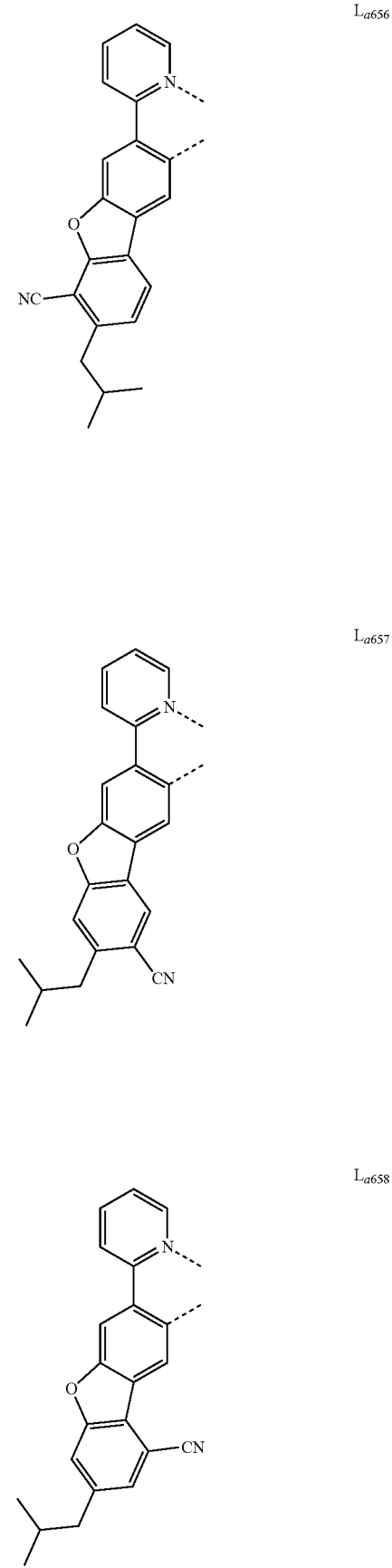

-continued
L<sub>a659</sub>
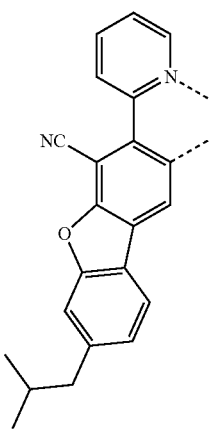
L<sub>a660</sub>
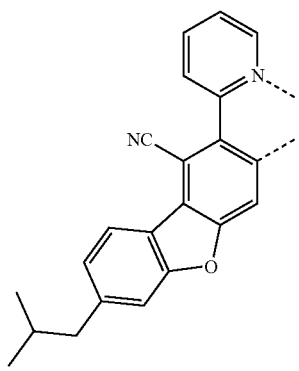
L<sub>a661</sub>
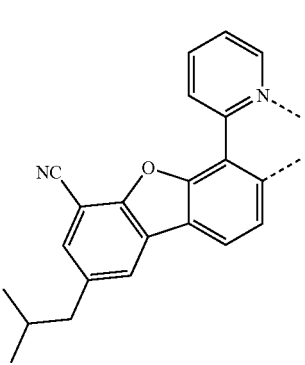
L<sub>a662</sub>
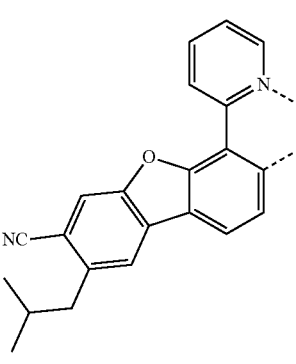
L<sub>a663</sub>
L<sub>a664</sub>
L<sub>a665</sub>
L<sub>a666</sub>
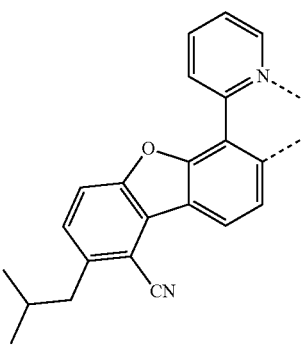

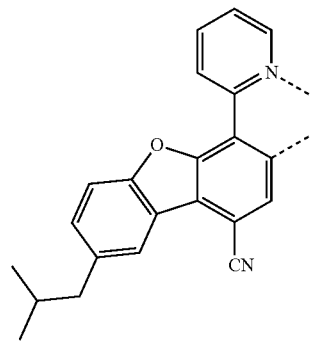 L<sub>a667</sub>
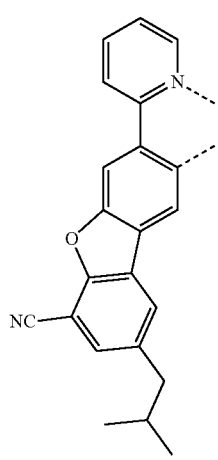 L<sub>a668</sub>
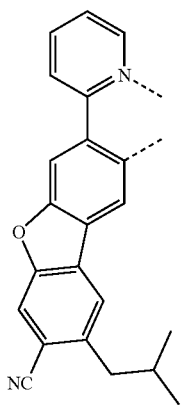 L<sub>a669</sub>
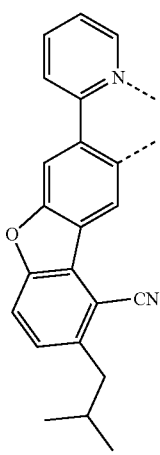 L<sub>a670</sub>
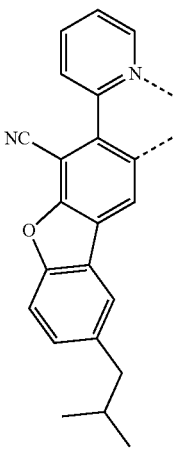 L<sub>a671</sub>
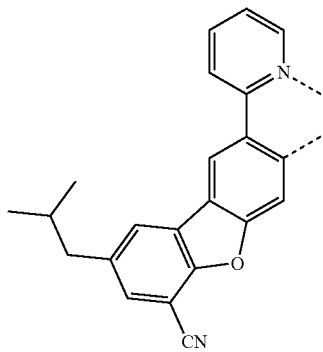 L<sub>a672</sub>
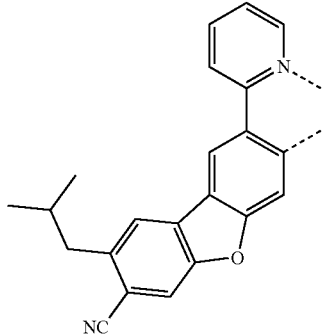 L<sub>a673</sub>

249
-continued
L_a674 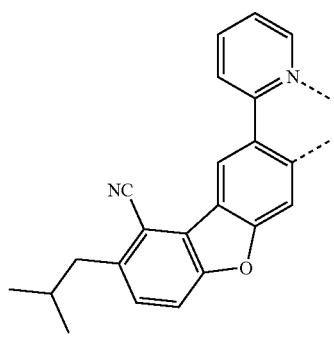
L_a675 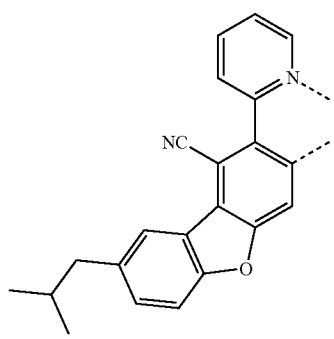
L_a676 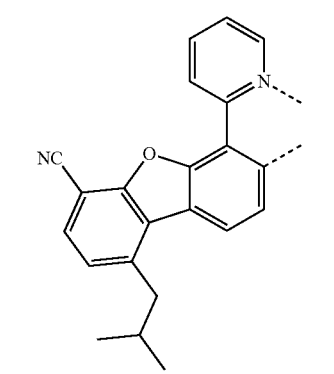
L_a677 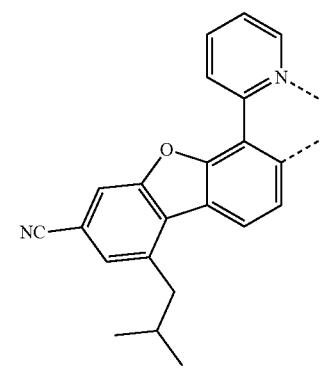
250
-continued
L_a678 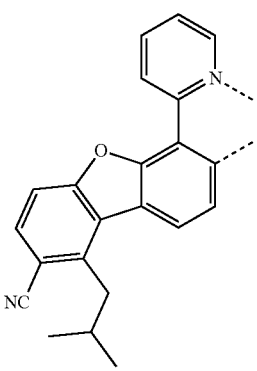
L_a679 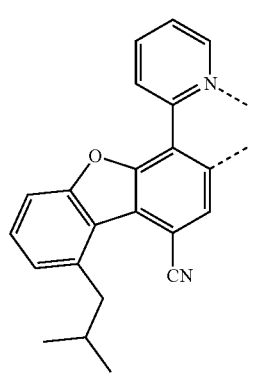
L_a680 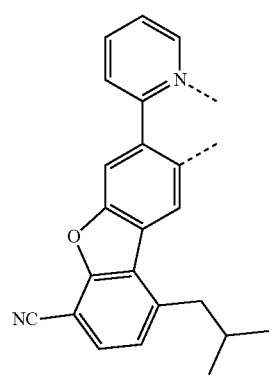
L_a681 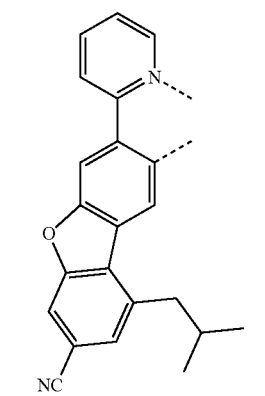

L_a682
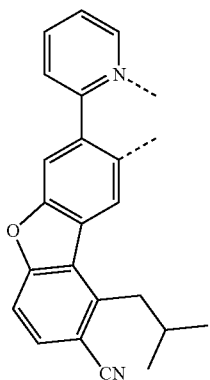
L_a683
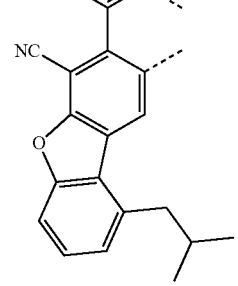
L_a684
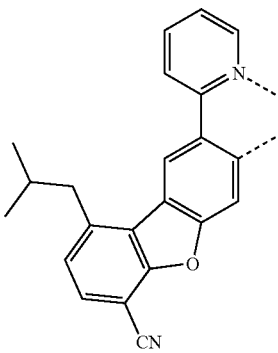
L_a685
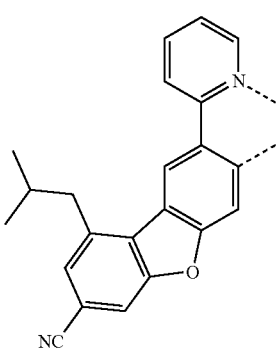
L_a686
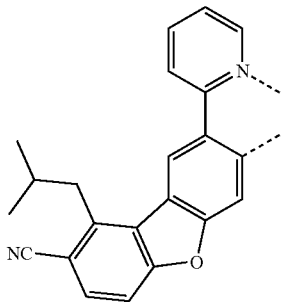
L_a687
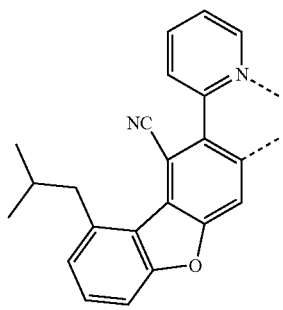
L_a688
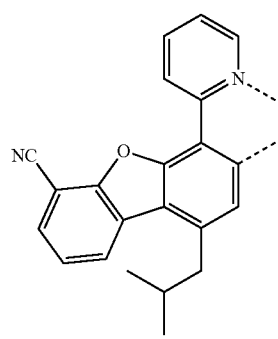
L_a689
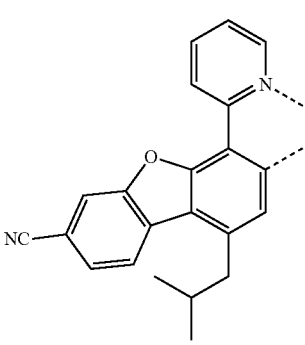
L_a690

253
-continued
L_{a691}
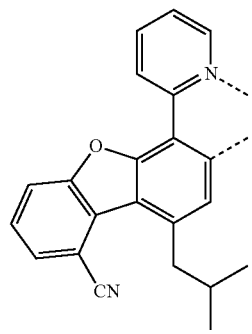
L_{a692}
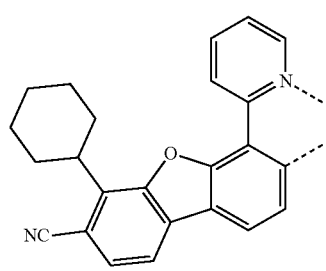
L_{a693}
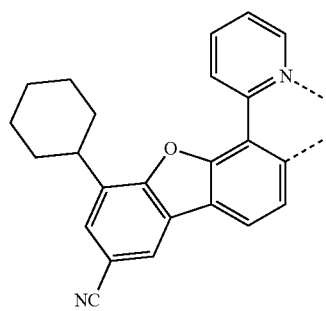
L_{a694}
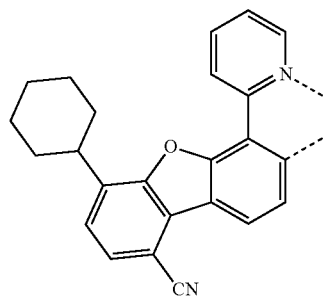
L_{a695}
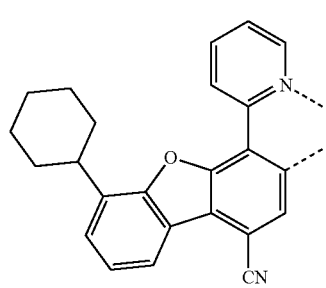
254
-continued
L_{a696}
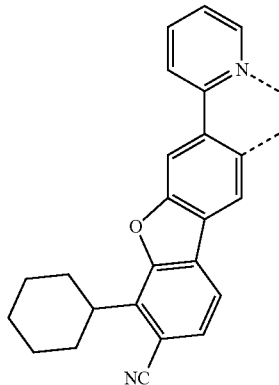
L_{a697}
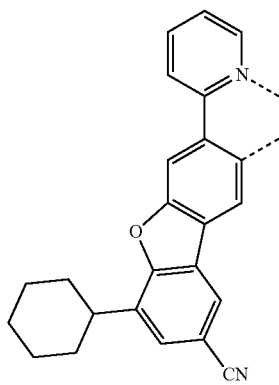
L_{a698}
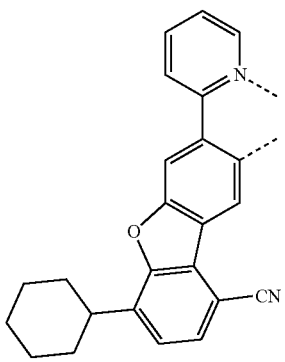
L_{a699}
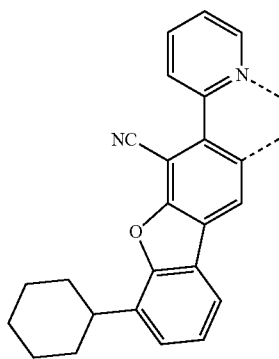

L_{a700}
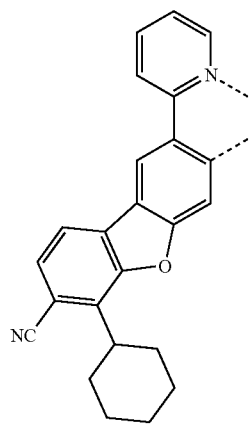
L_{a701}
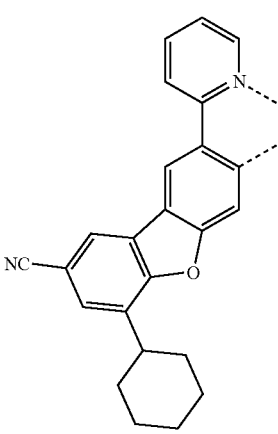
L_{a702}
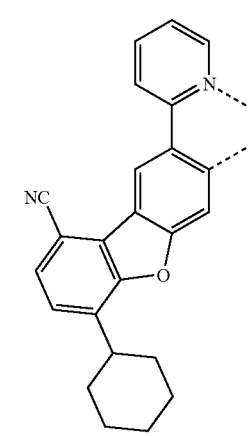
L_{a703}
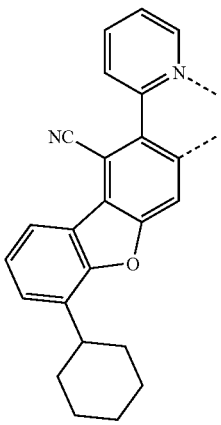
L_{a704}
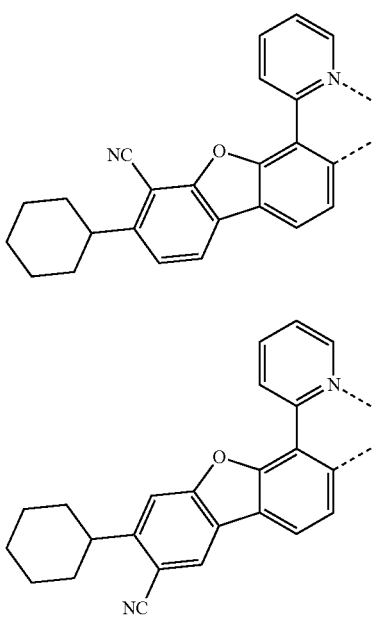
L_{a705}
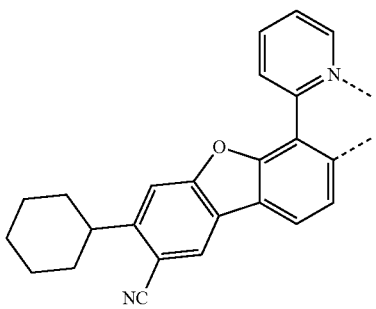
L_{a706}
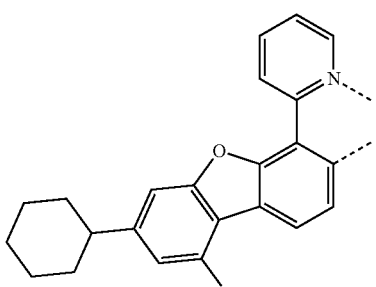
L_{a707}
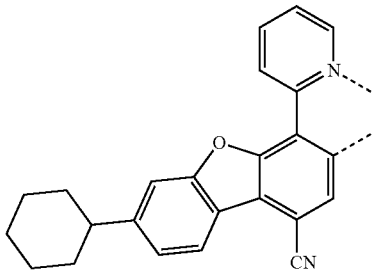

L<sub>a708</sub>
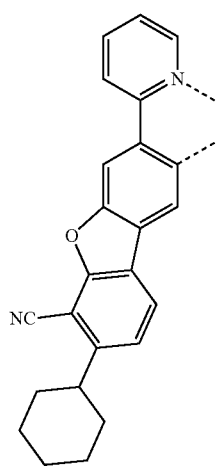
L<sub>a711</sub>
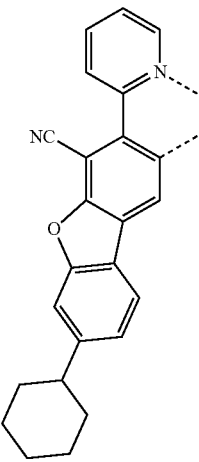
L<sub>a709</sub>
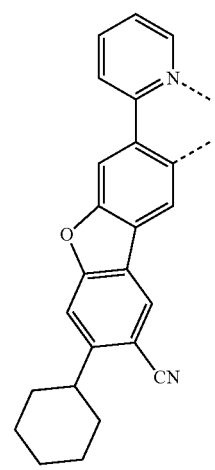
L<sub>a712</sub>
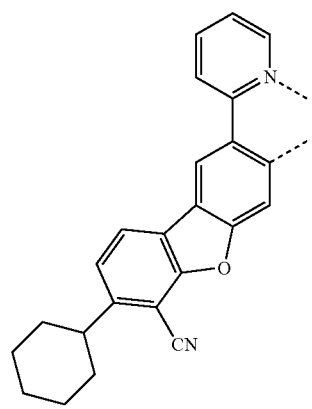
L<sub>a710</sub>
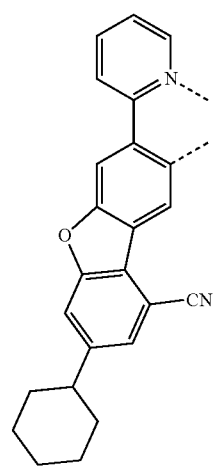
L<sub>a713</sub>
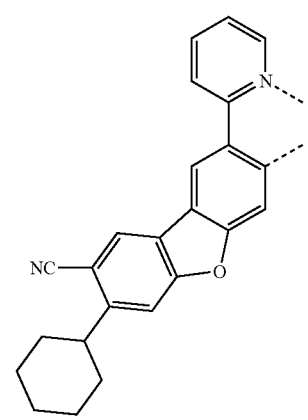

-continued
L<sub>a714</sub>
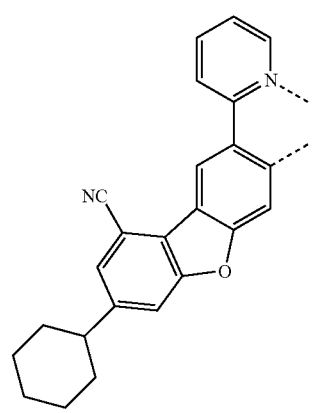
L<sub>a715</sub>
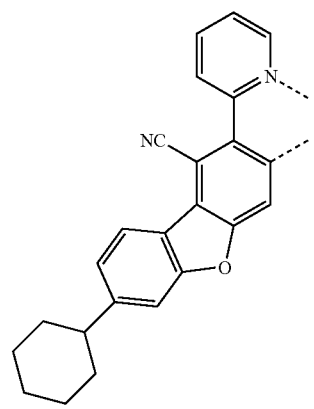
L<sub>a716</sub>
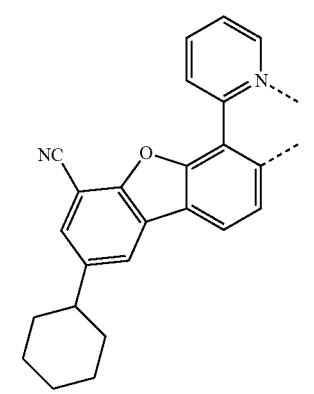
L<sub>a717</sub>
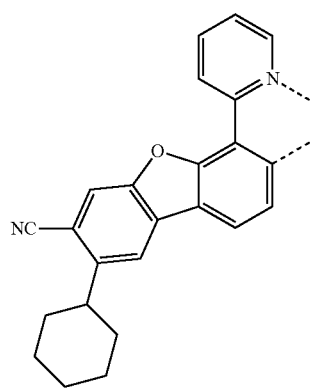
-continued
L<sub>a718</sub>
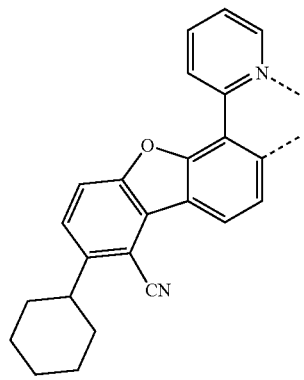
L<sub>a719</sub>
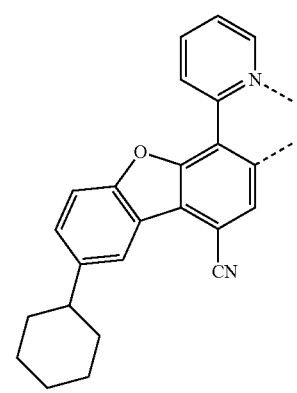
L<sub>a720</sub>
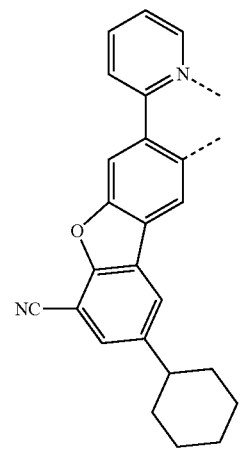

-continued
L<sub>a721</sub> 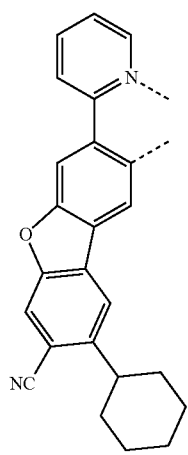
L<sub>a722</sub> 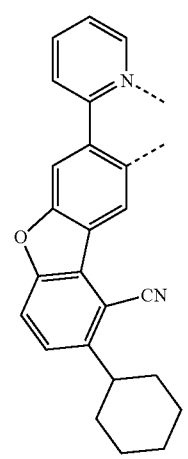
L<sub>a723</sub> 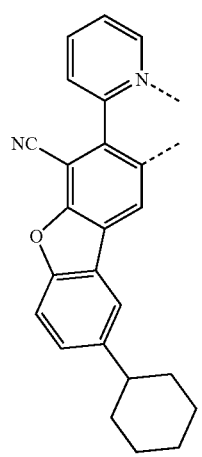
-continued
L<sub>a724</sub> 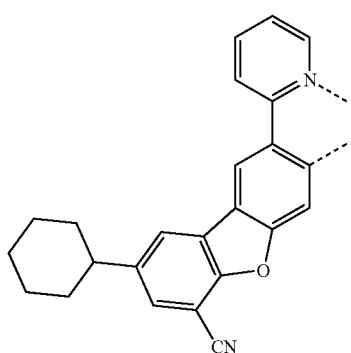
L<sub>a725</sub> 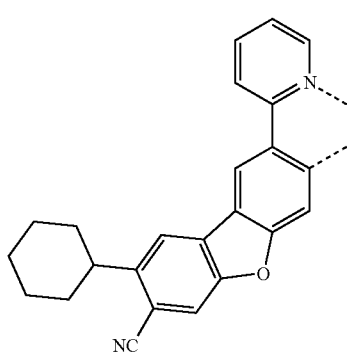
L<sub>a726</sub> 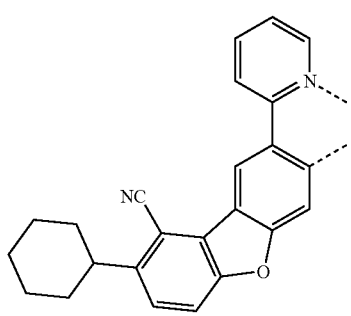
L<sub>a727</sub> 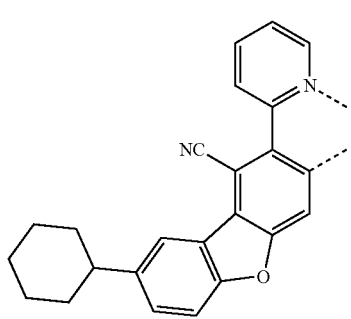

L_{a728} 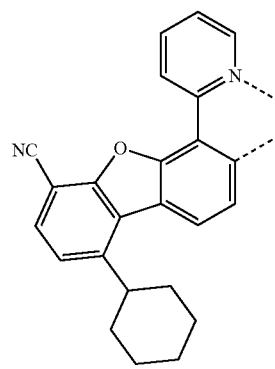
L_{a729} 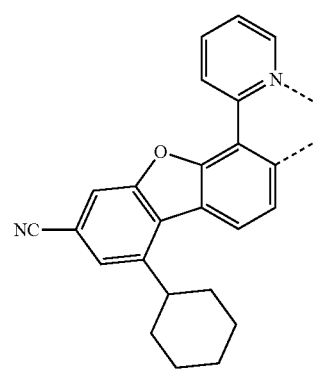
L_{a730} 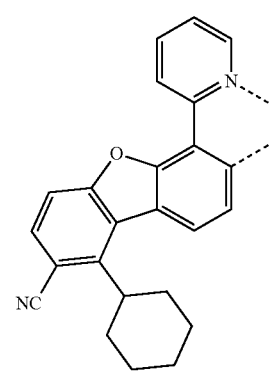
L_{a731} 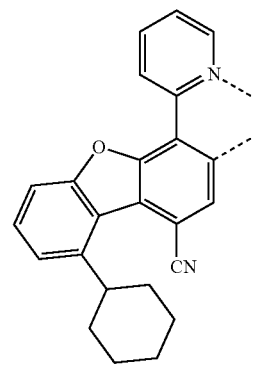
L_{a732} 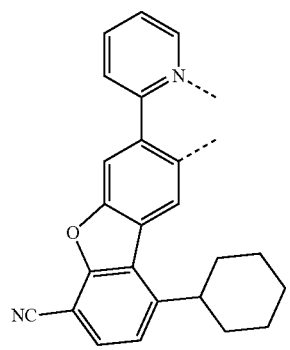
L_{a733} 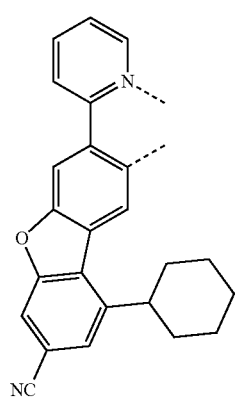
L_{a734} 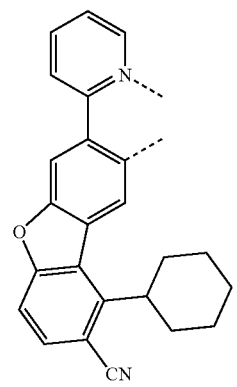
L_{a735} 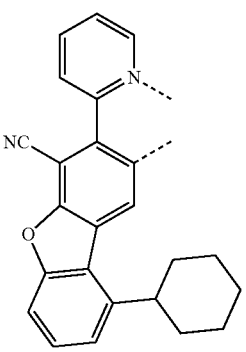

L$_{a736}$ 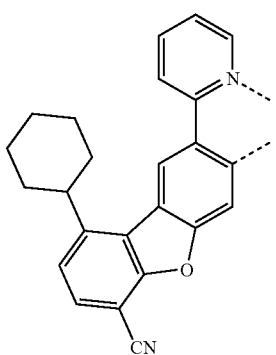
L$_{a737}$ 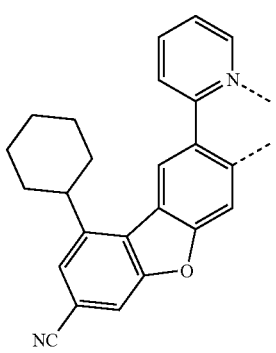
L$_{a738}$ 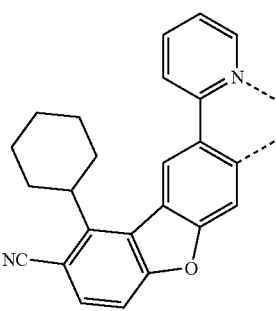
L$_{a739}$ 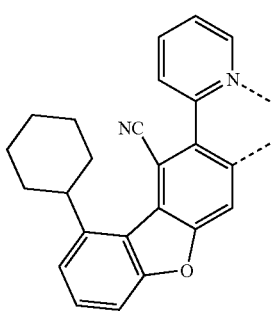
L$_{a740}$ 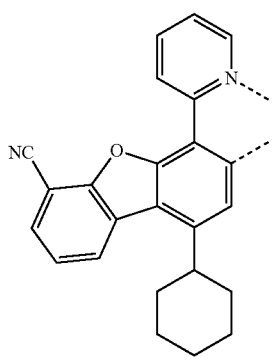
L$_{a741}$ 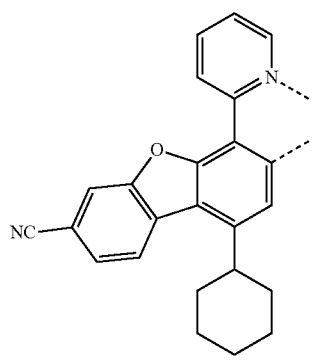
L$_{a742}$ 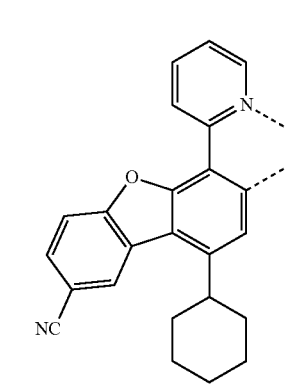
L$_{a743}$ 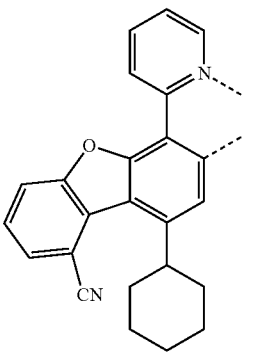

-continued
L_a744 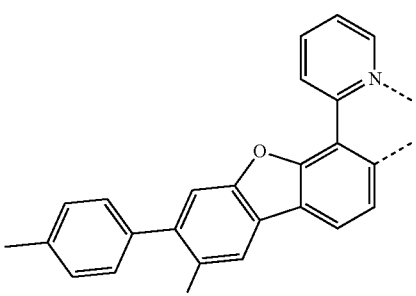
L_a745 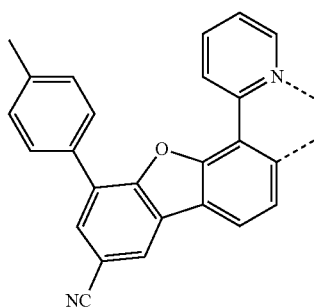
L_a746 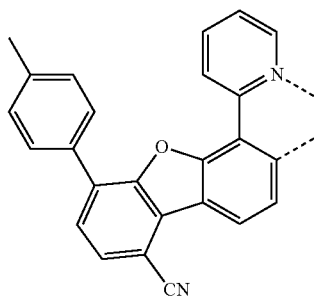
L_a747 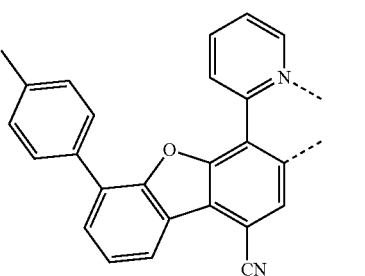
L_a748 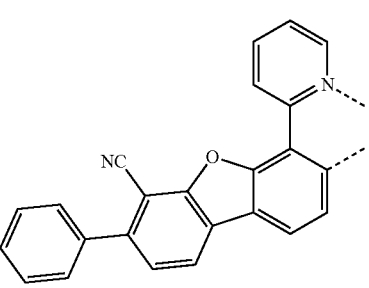
-continued
L_a749 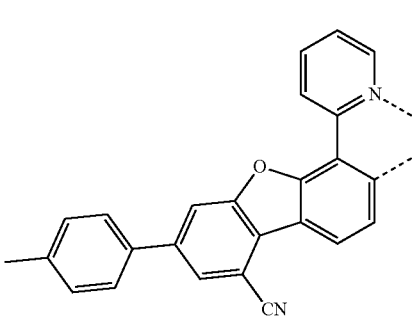
L_a750 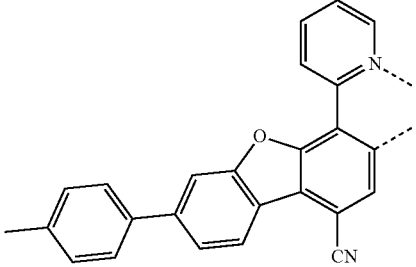
L_a751 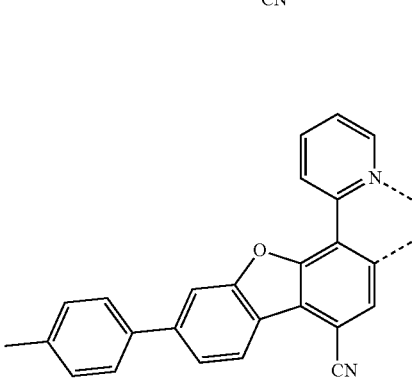
L_a752 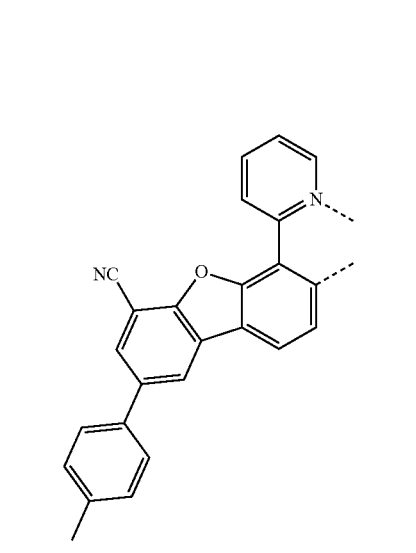

L<sub>a753</sub>
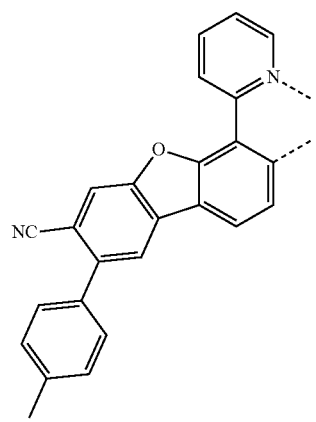
L<sub>a754</sub>
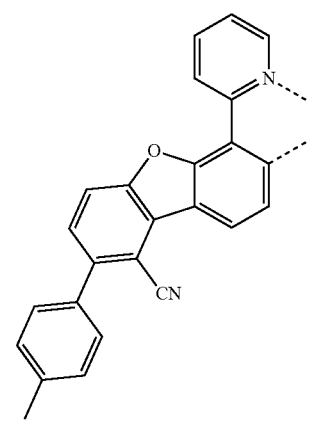
L<sub>a755</sub>
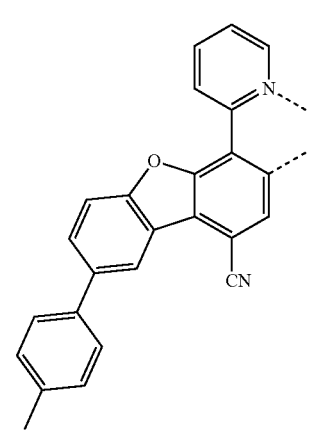
L<sub>a756</sub>
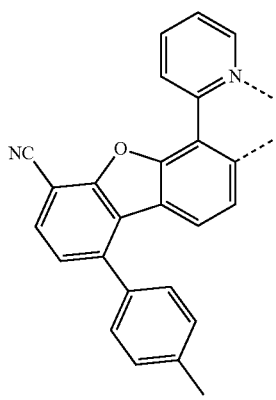
L<sub>a757</sub>
L<sub>a758</sub>
L<sub>a759</sub>

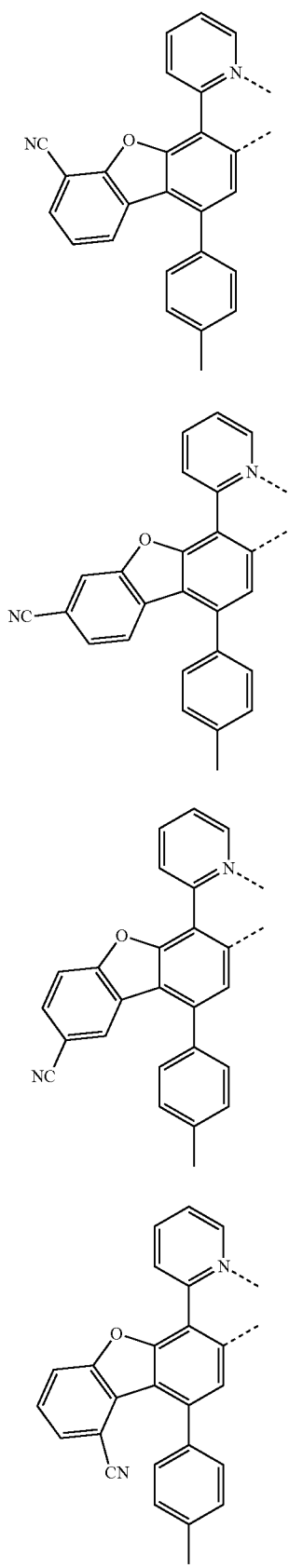
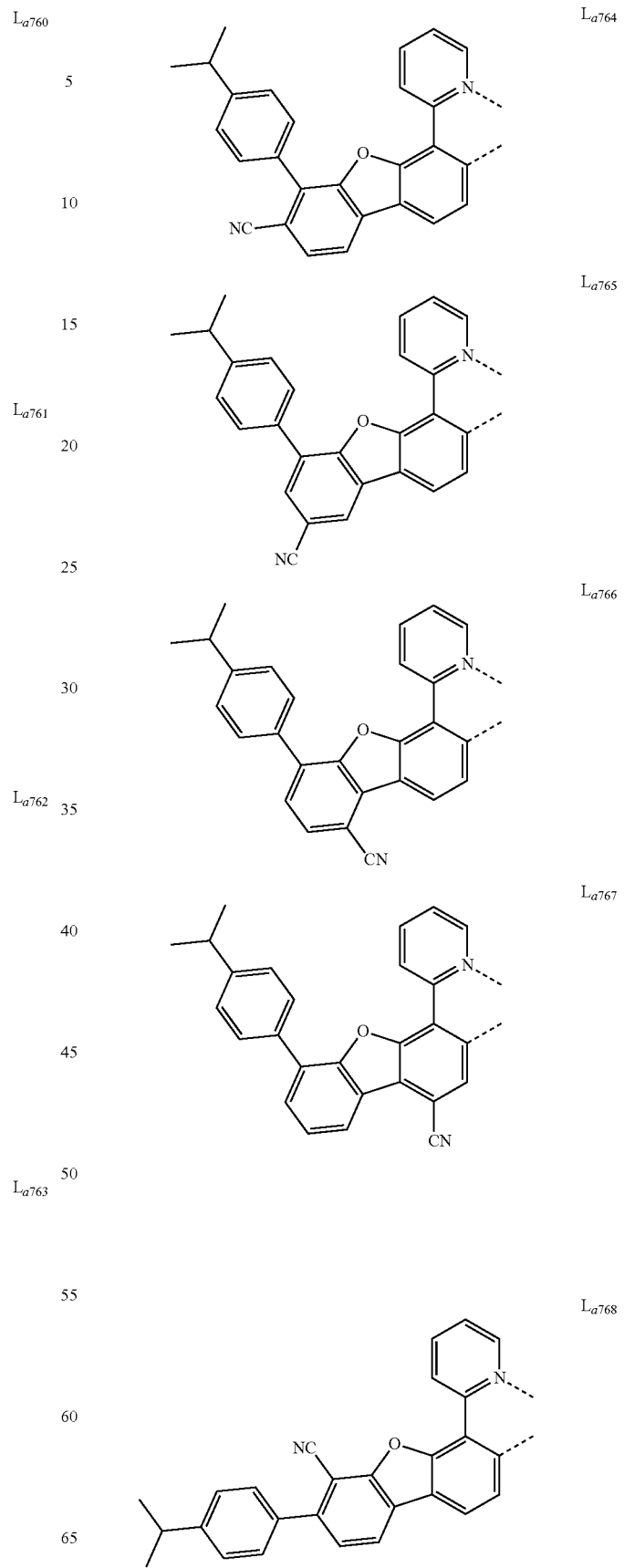

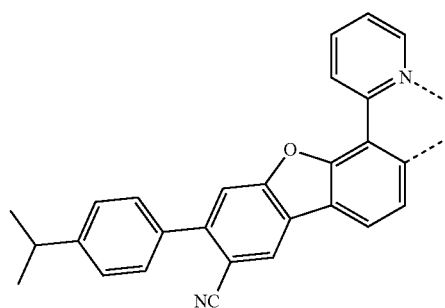
L<sub>a769</sub>
L<sub>a770</sub>
L<sub>a771</sub>
L<sub>a772</sub>
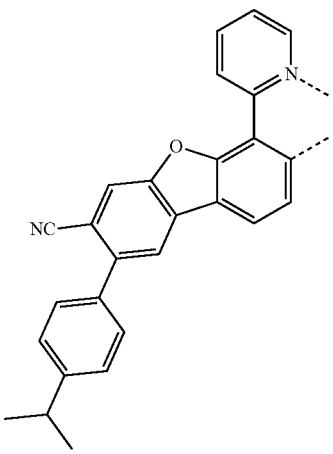
L<sub>a773</sub>
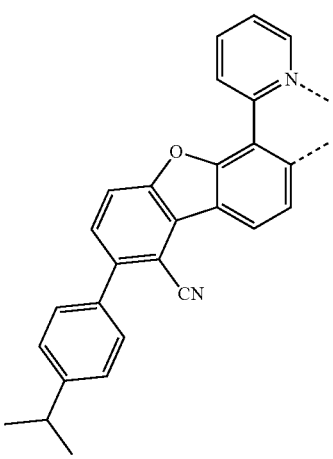
L<sub>a774</sub>
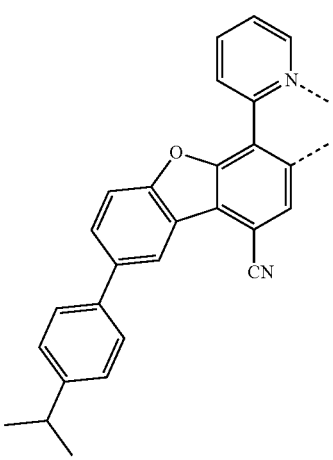
L<sub>a775</sub>

L<sub>a776</sub>
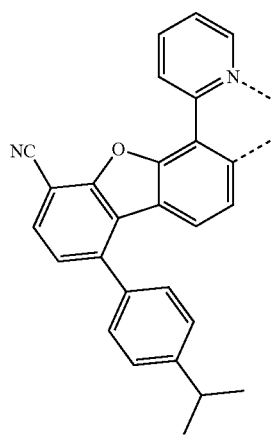
L<sub>a777</sub>
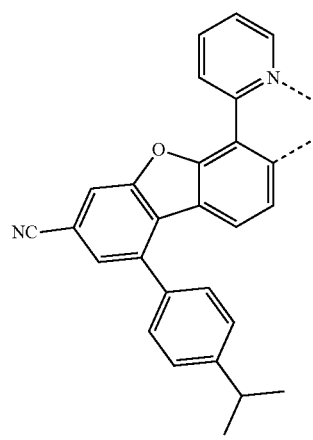
L<sub>a778</sub>
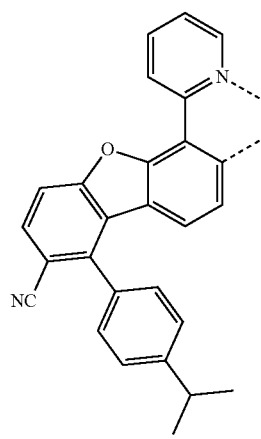
L<sub>a779</sub>
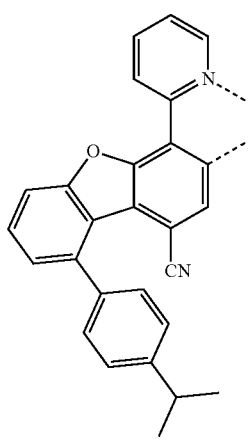
L<sub>a780</sub>
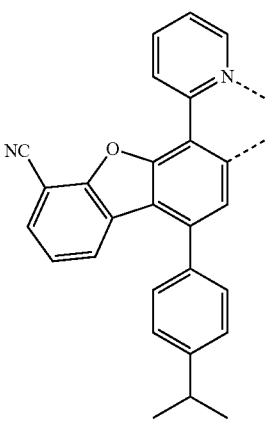
L<sub>a781</sub>
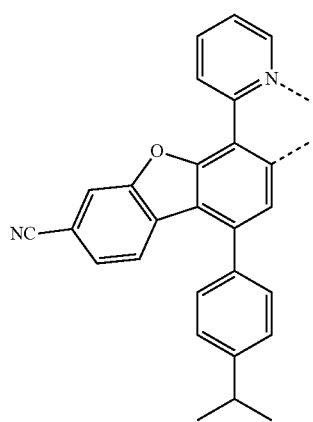

277
-continued
278
-continued
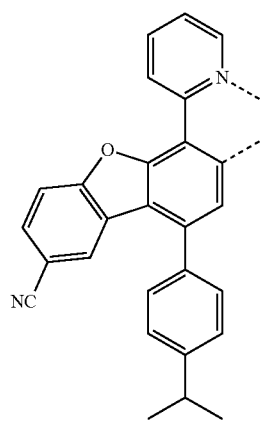
L_a782
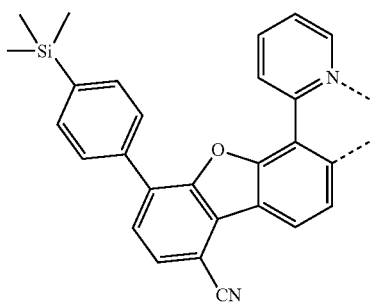
L_a786
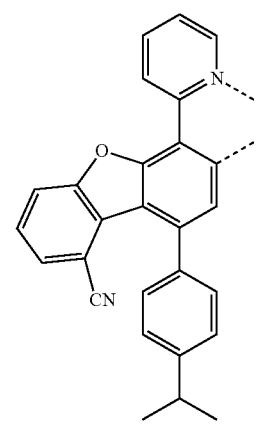
L_a783
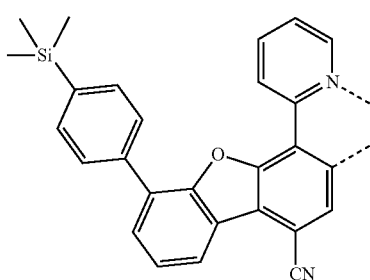
L_a787
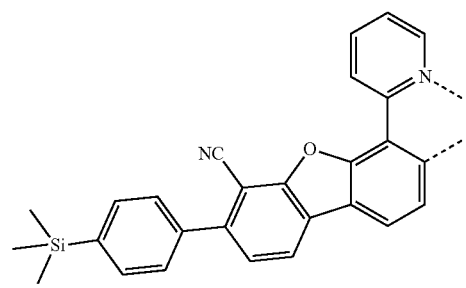
L_a788
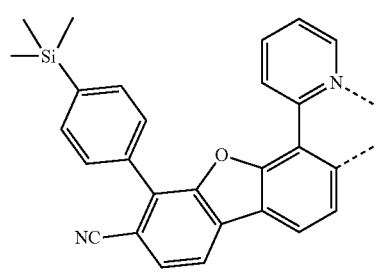
L_a784
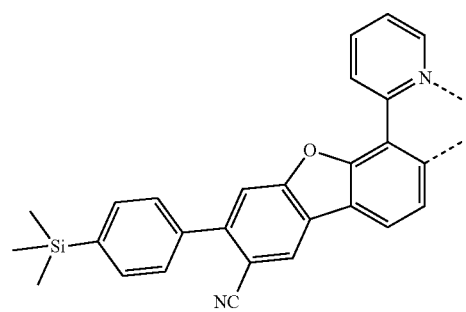
L_a789
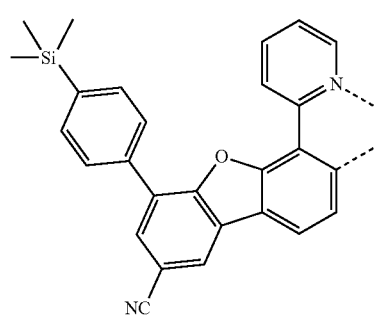
L_a785
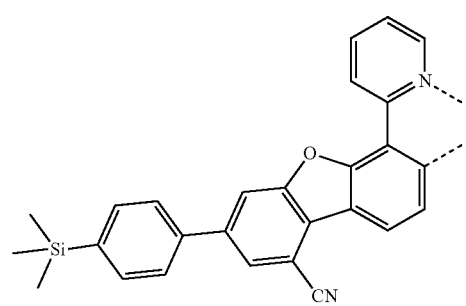
L_a790

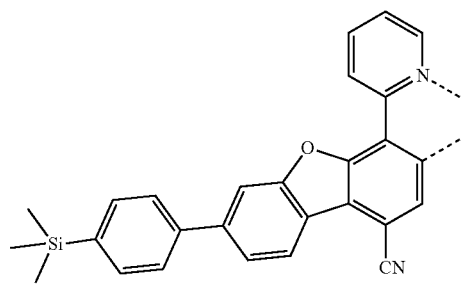
$L_{a791}$
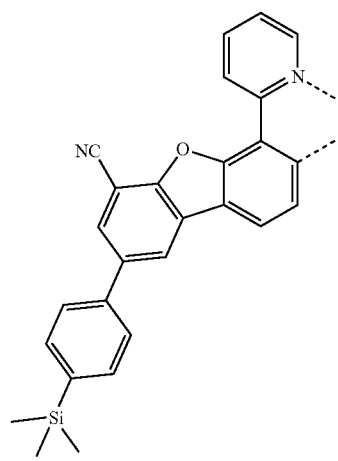
$L_{a792}$
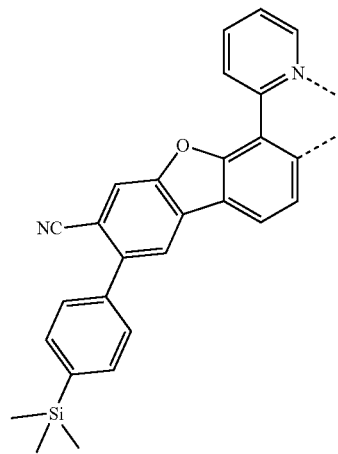
$L_{a793}$
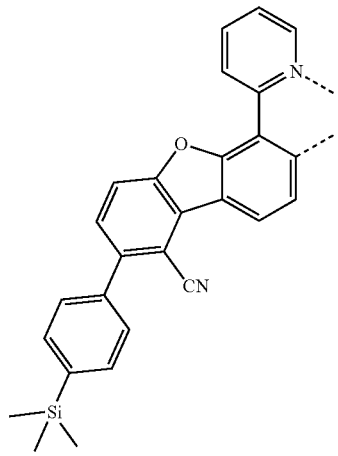
$L_{a794}$
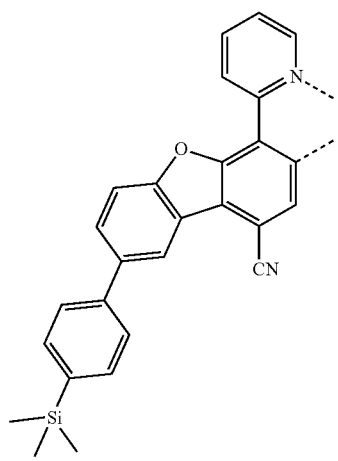
$L_{a795}$
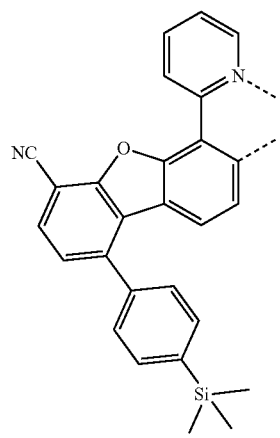
$L_{a796}$ -continued
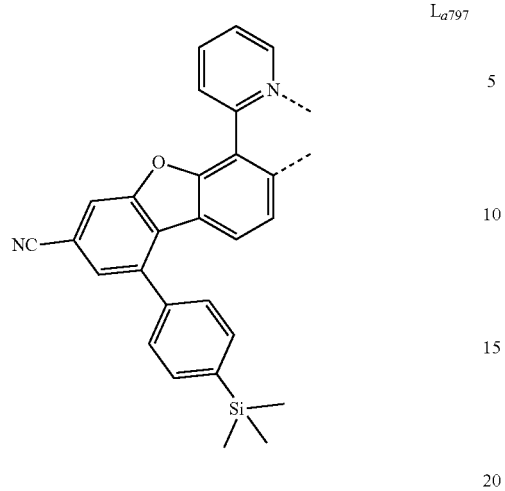
L<sub>a797</sub>
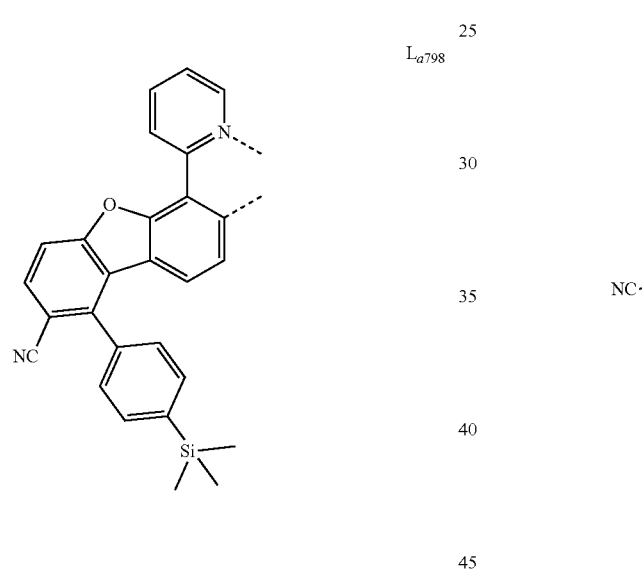
L<sub>a798</sub>
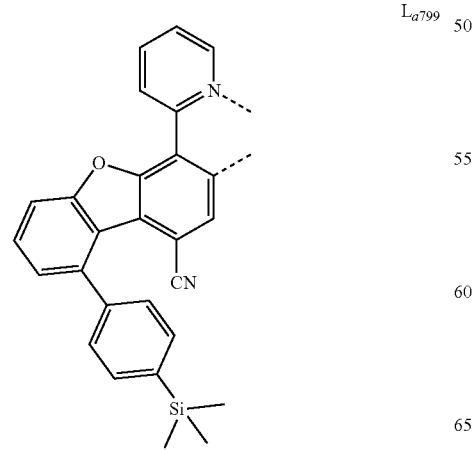
L<sub>a799</sub>
-continued
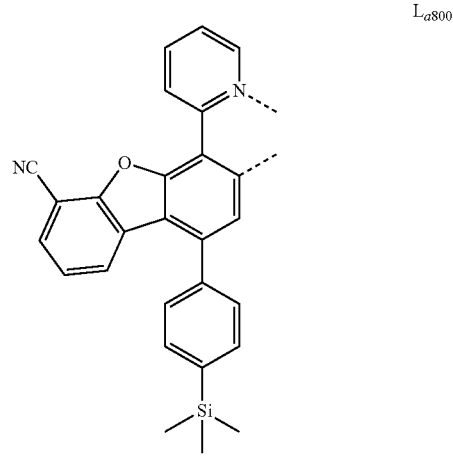
L<sub>a800</sub>
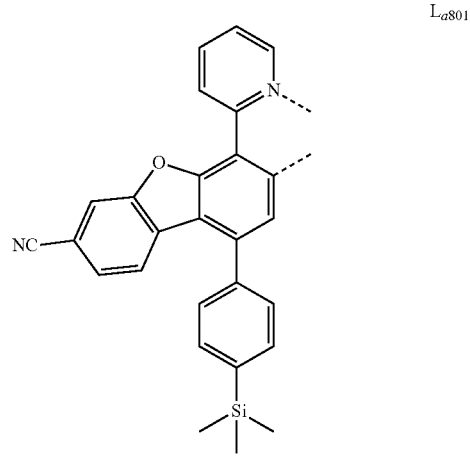
L<sub>a801</sub>
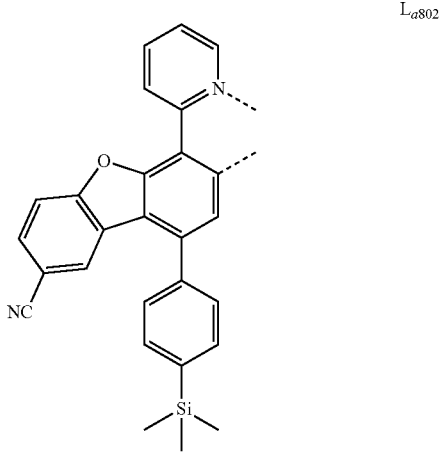
L<sub>a802</sub>

L{a803}
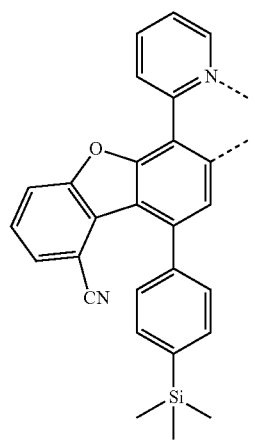
L{a804}
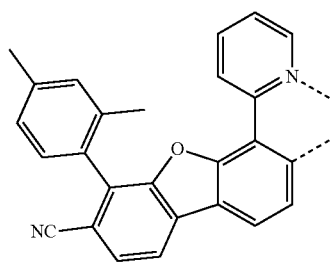
L{a805}
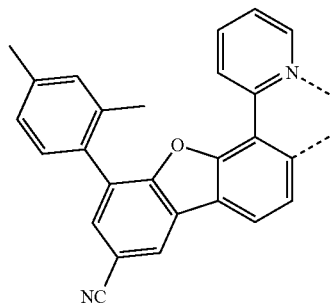
L{a806}
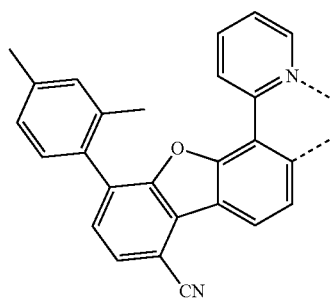
L{a807}
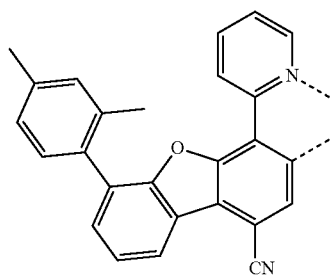
L{a808}
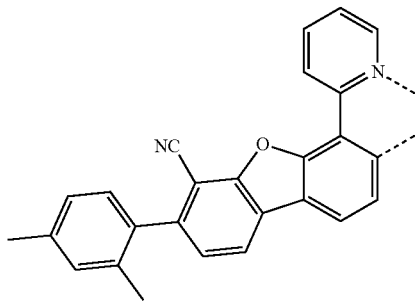
L{a809}
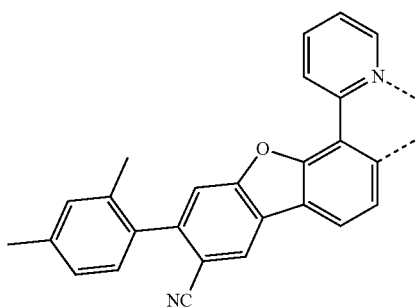
L{a810}
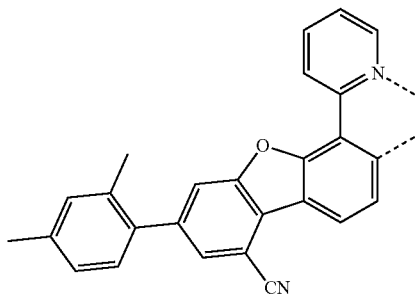
L{a811}
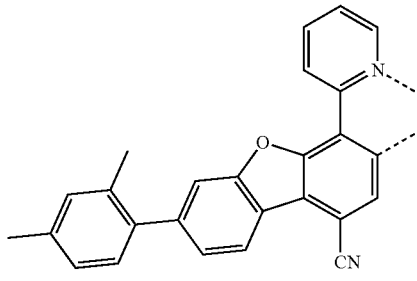
L{a812}
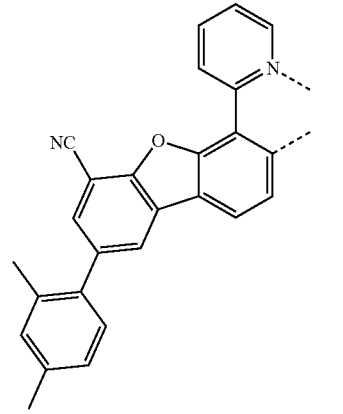

L<sub>a813</sub>
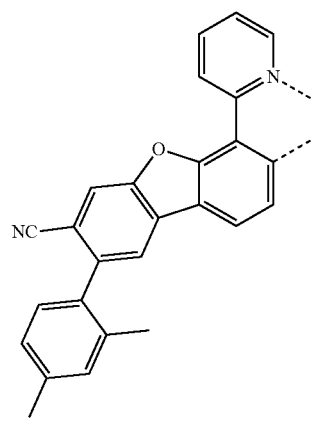
L<sub>a814</sub>
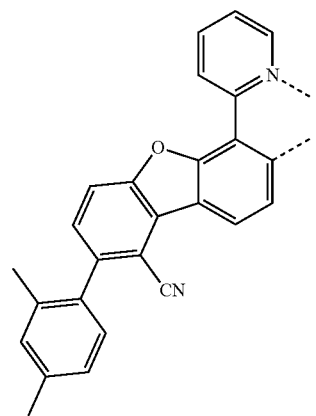
L<sub>a815</sub>
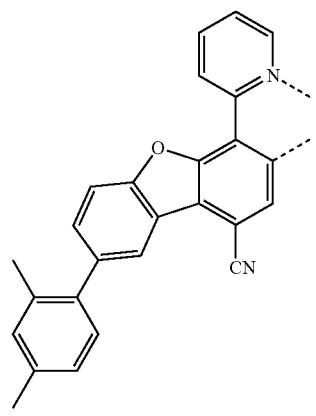
L<sub>a816</sub>
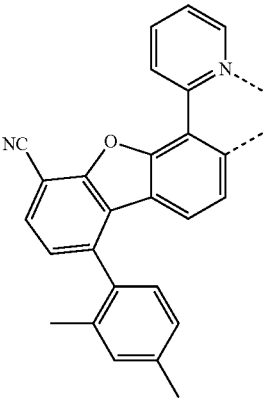
L<sub>a817</sub>
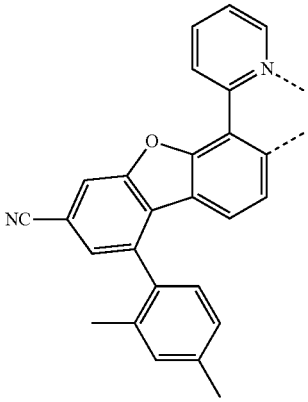
L<sub>a818</sub>
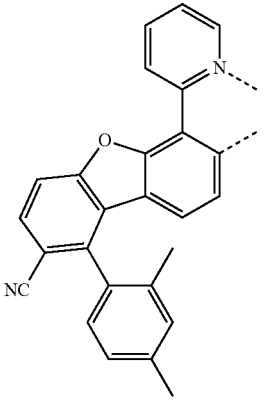
L<sub>a819</sub>

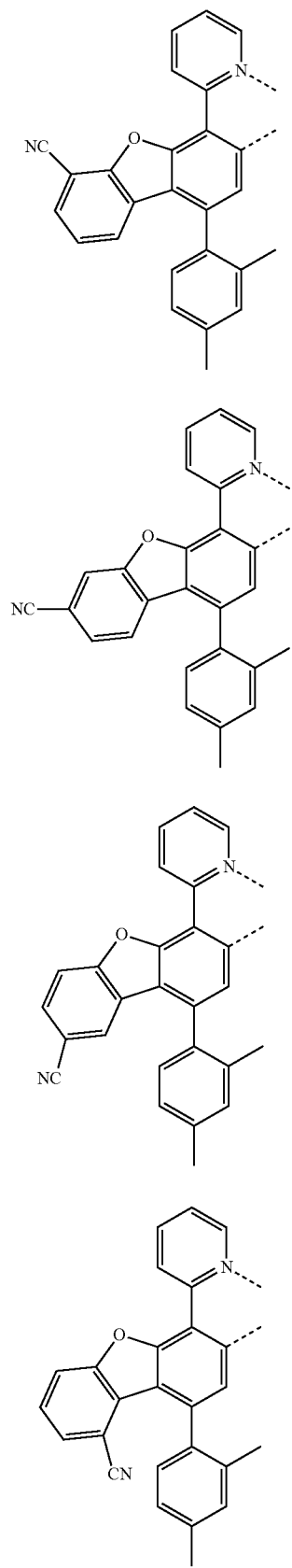
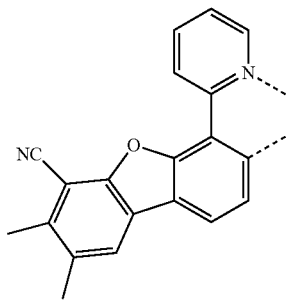
L_a824
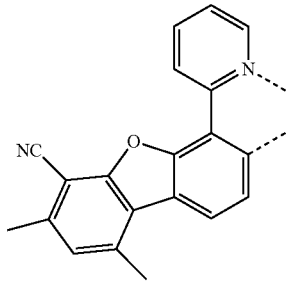
L_a825
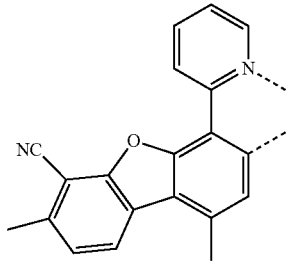
L_a826
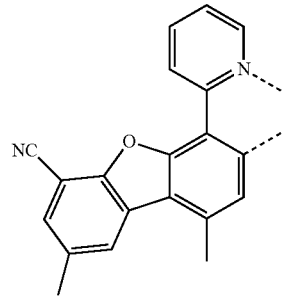
L_a827
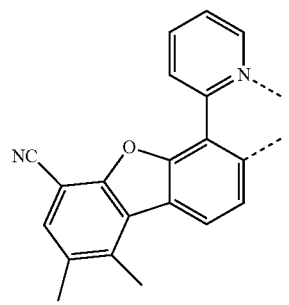
L_a828

L_a829 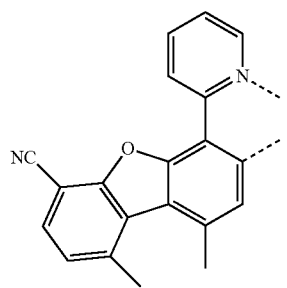
L_a830 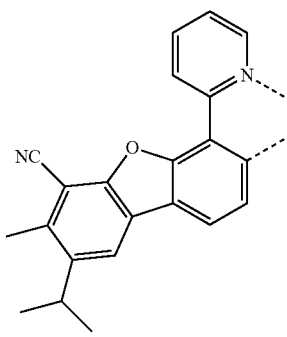
L_a831 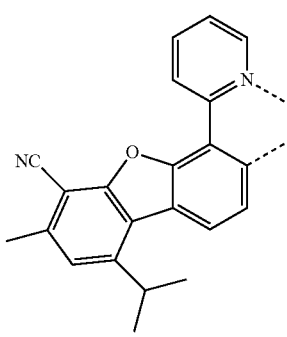
L_a832 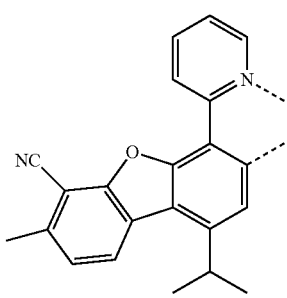
L_a833 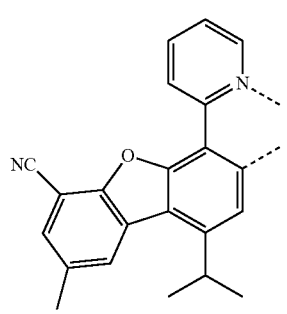
L_a834 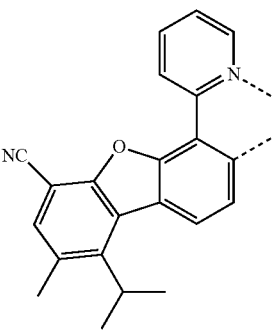
L_a835 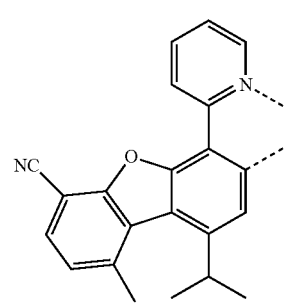
L_a836 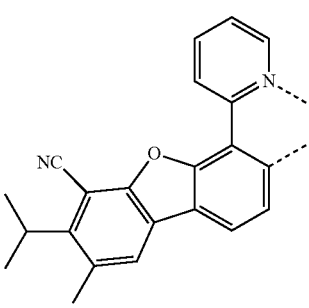
L_a837 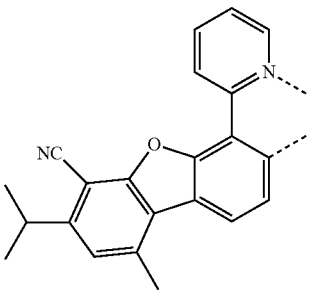
L_a838 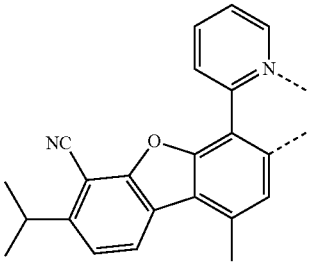

L_a839 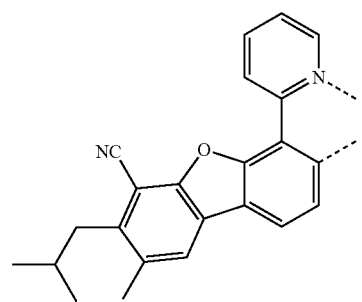
L_a840 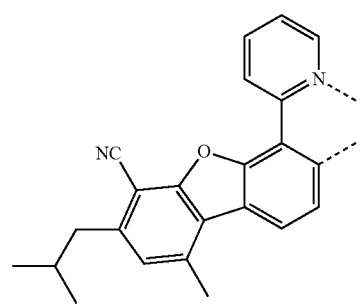
L_a841 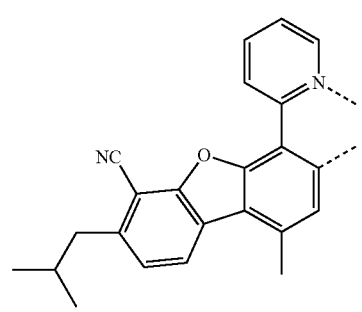
L_a842 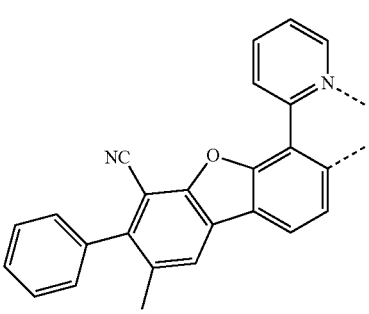
L_a843 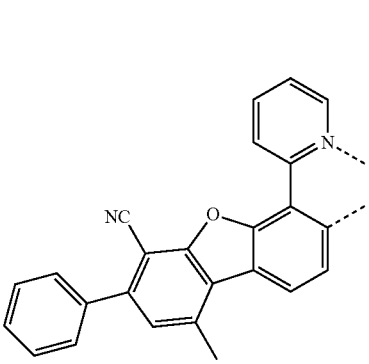
L_a844 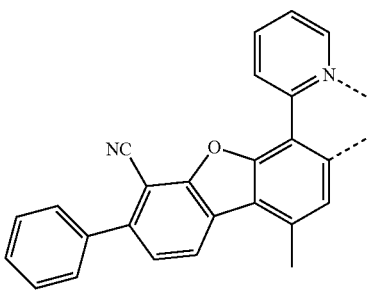
L_a845 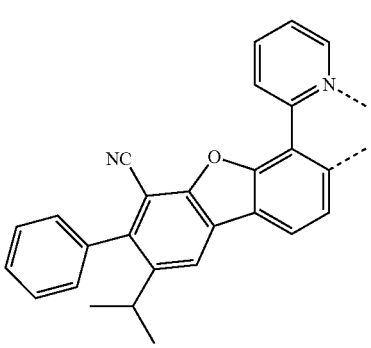
L_a846 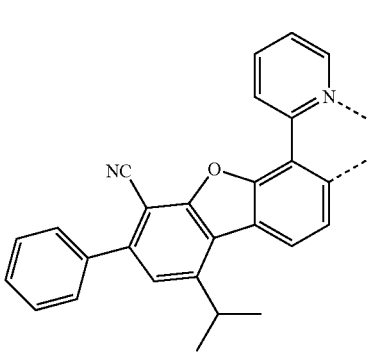
L_a847 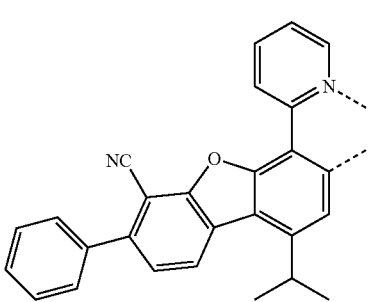
L_a848 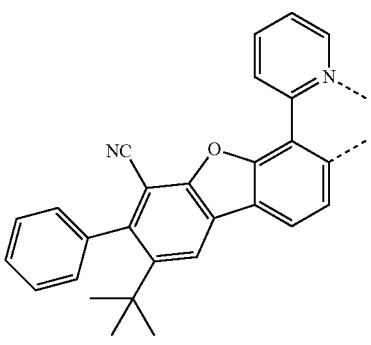

293
-continued
L*a*849
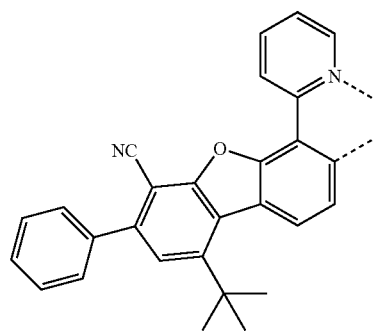
L*a*850
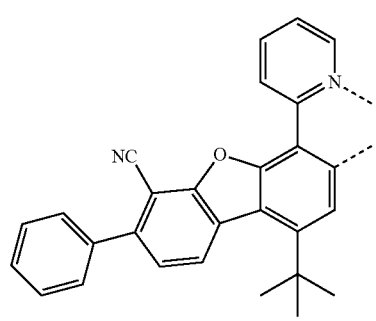
L*a*851
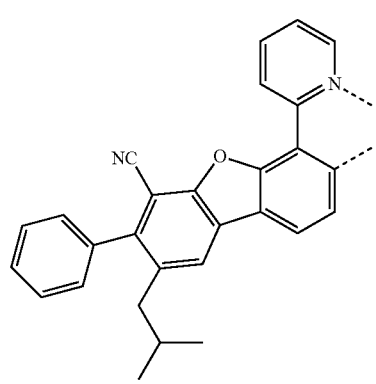
L*a*852
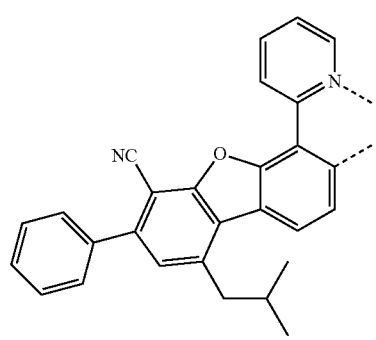
294
-continued
L*a*853
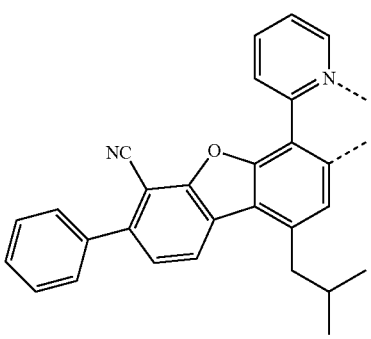
L*a*854
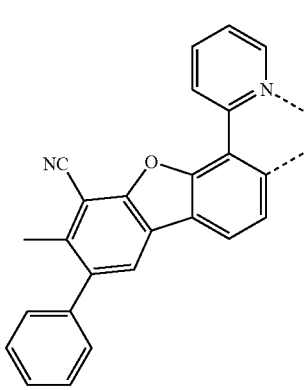
L*a*855
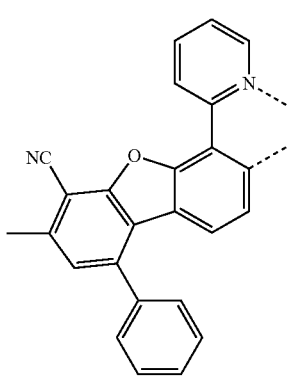
L*a*856
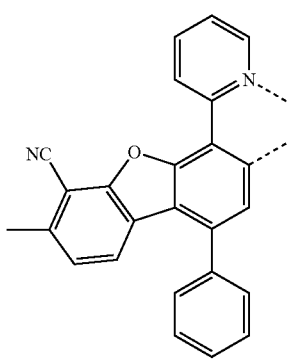

295
-continued
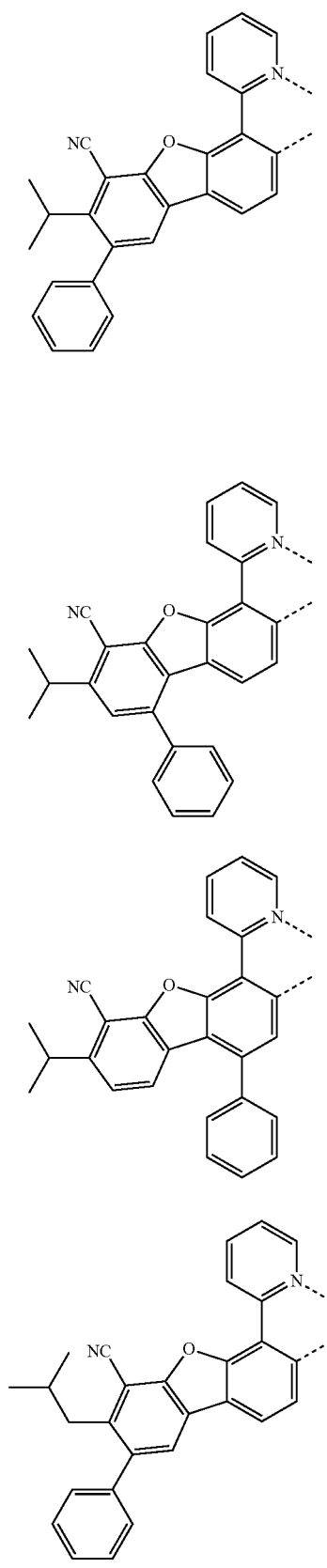
L_a857
L_a858
L_a859
L_a860
296
-continued
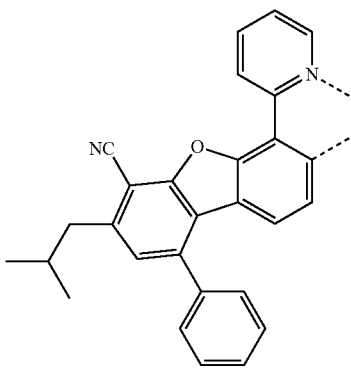
L_a861
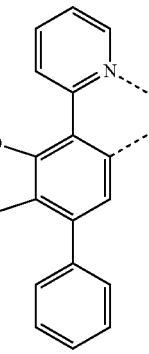
L_a862
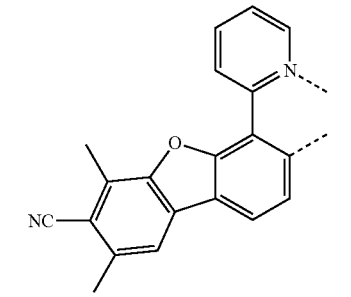
L_a863
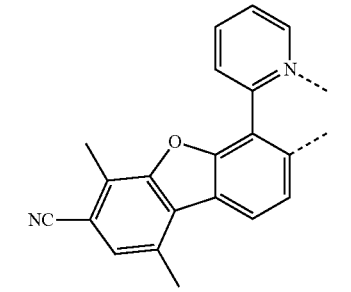
L_a864
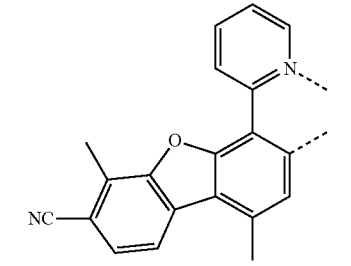
L_a865

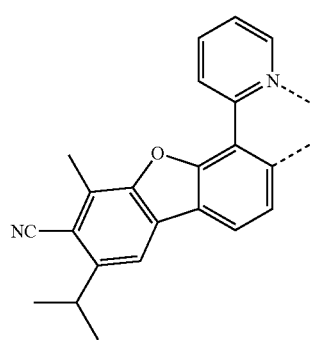 L<sub>a866</sub>
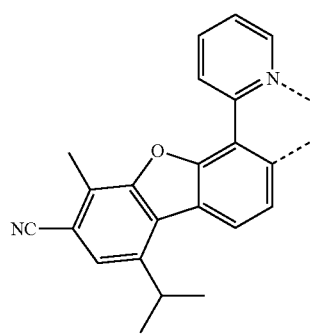 L<sub>a867</sub>
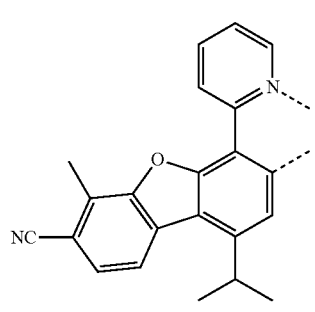 L<sub>a868</sub>
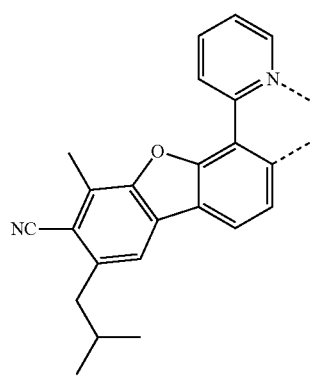 L<sub>a869</sub>
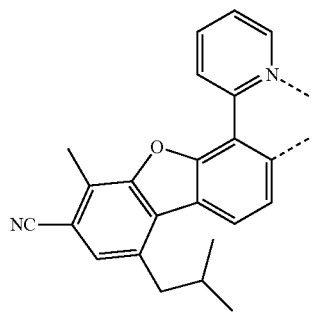 L<sub>a870</sub>
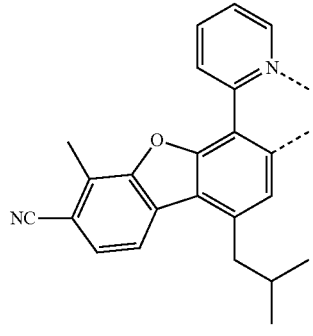 L<sub>a871</sub>
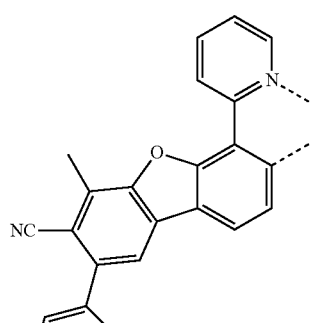 L<sub>a872</sub>
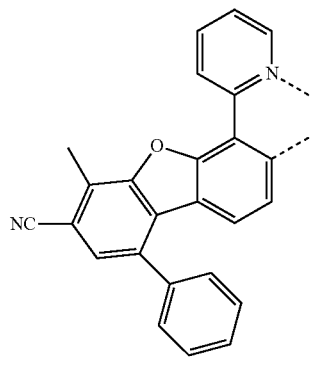 L<sub>a873</sub>

L<sub>a874</sub>
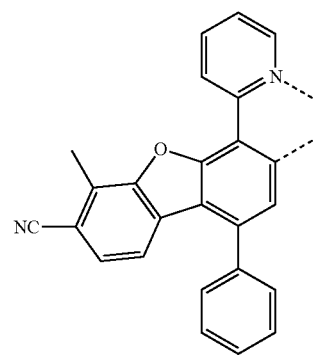
L<sub>a875</sub>
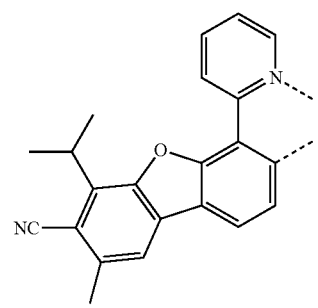
L<sub>a876</sub>
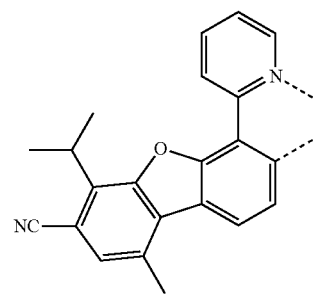
L<sub>a877</sub>
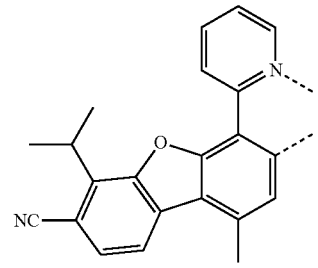
L<sub>a878</sub>
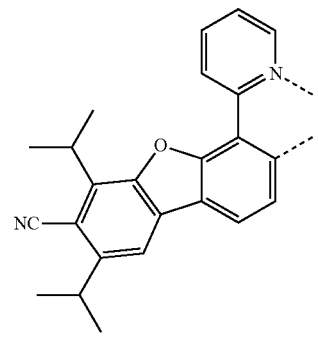
L<sub>a879</sub>
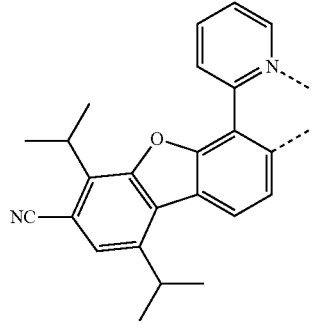
L<sub>a880</sub>
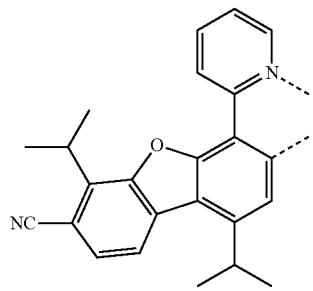
L<sub>a881</sub>
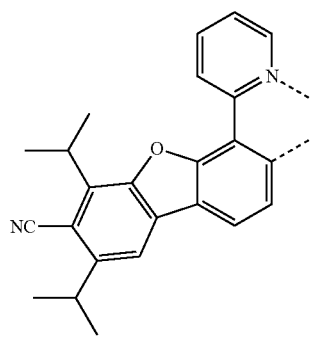
L<sub>a882</sub>
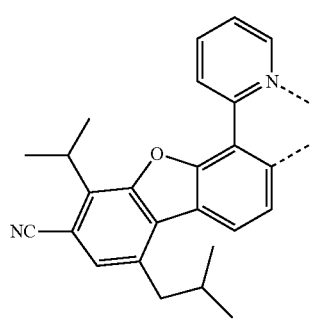
L<sub>a883</sub>
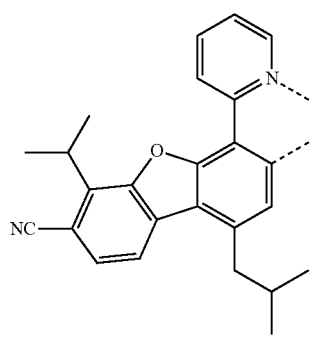

| | |
|---|---|
| 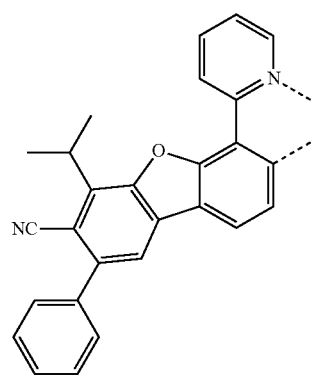 | L$_{a}$884 |
| 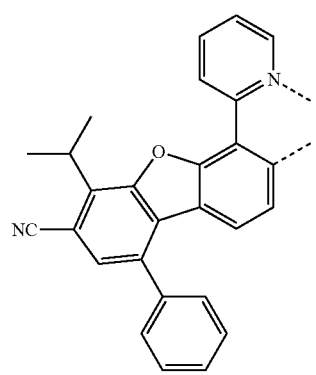 | L$_{a}$885 |
| 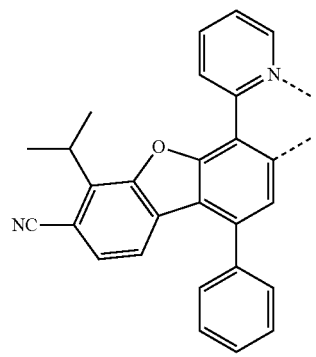 | L$_{a}$886 |
| 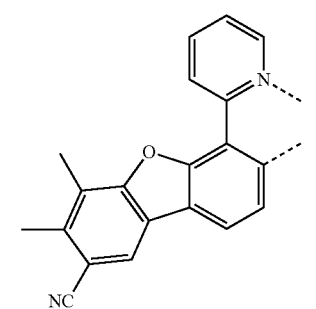 | L$_{a}$887 |
| 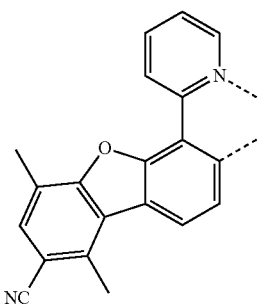 | L$_{a}$888 |
| 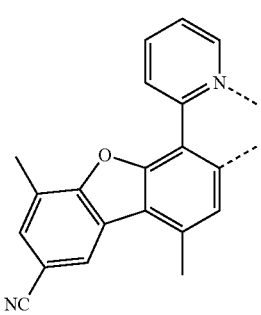 | L$_{a}$889 |
| 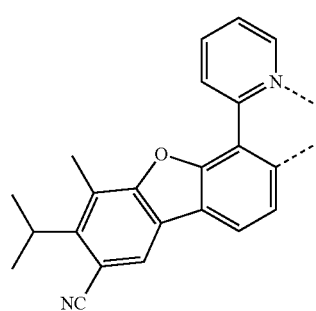 | L$_{a}$890 |
| 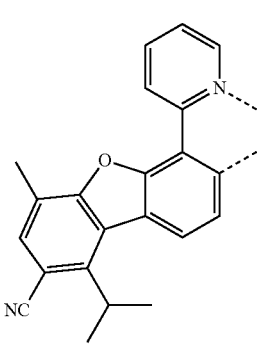 | L$_{a}$891 |
| 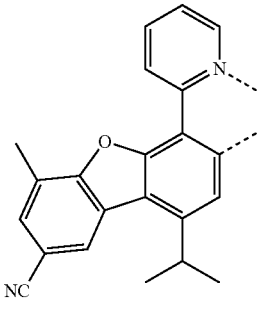 | L$_{a}$892 |

-continued
L$_{a893}$
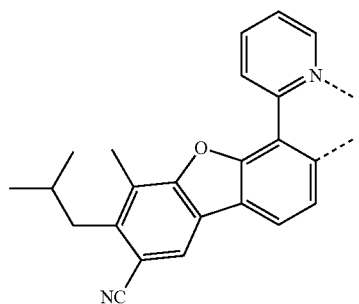
L$_{a894}$
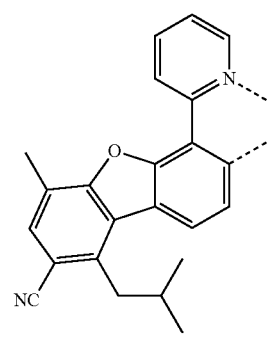
L$_{a895}$
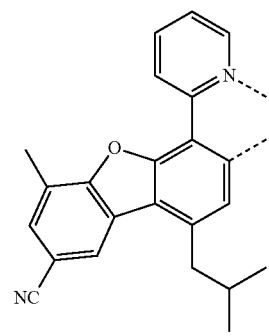
L$_{a896}$
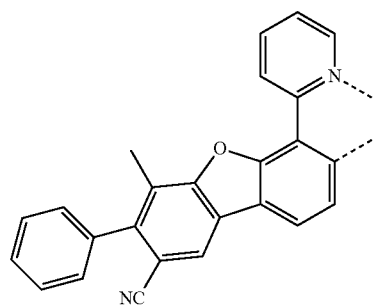
-continued
L$_{a897}$
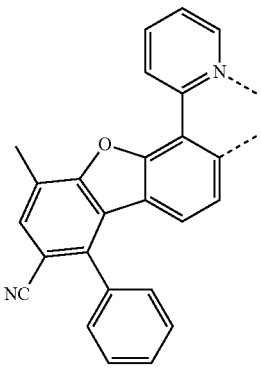
L$_{a898}$
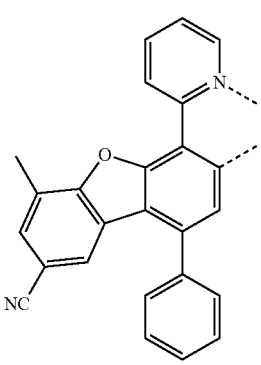
L$_{a899}$
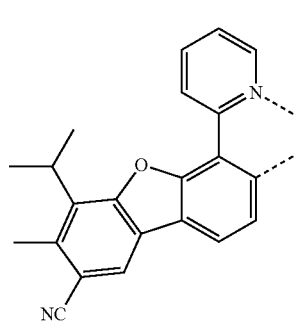
L$_{a900}$
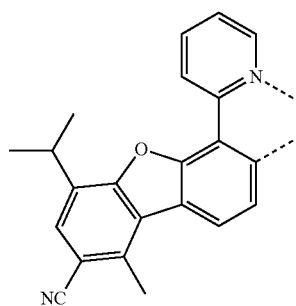

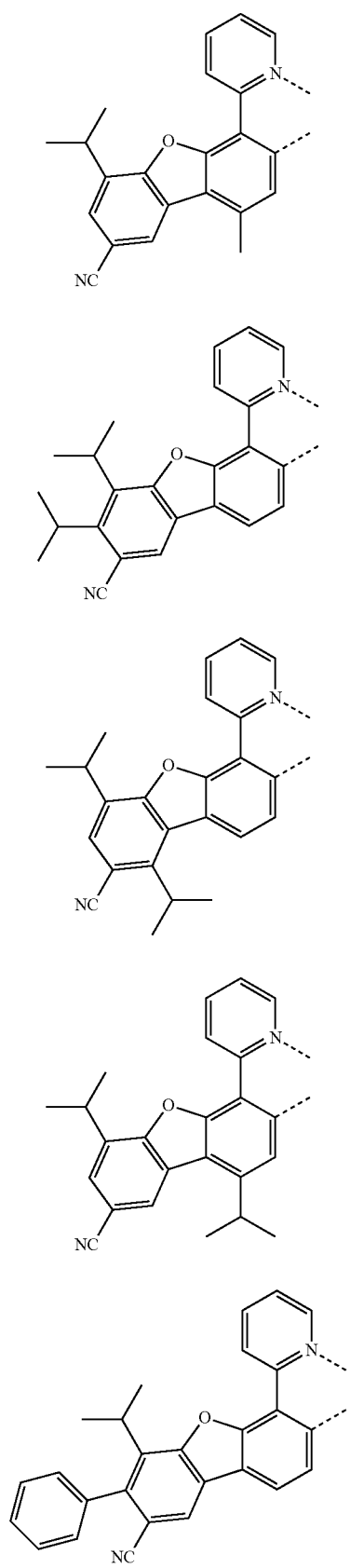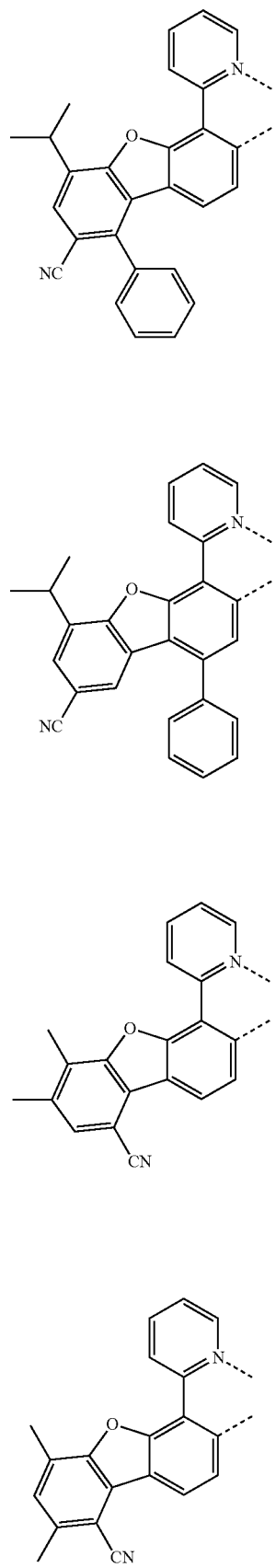

-continued
L_a910 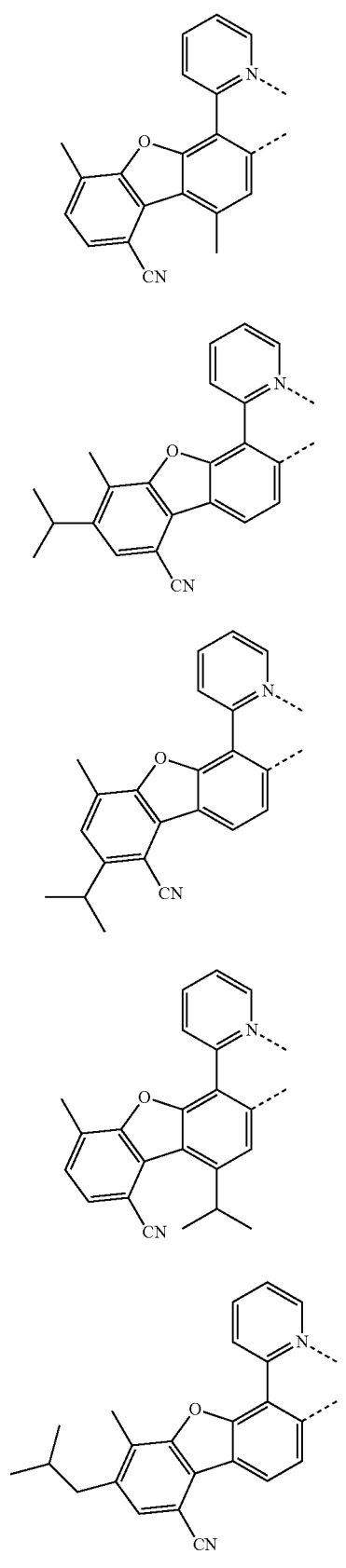
L_a911
L_a912
L_a913
L_a914
-continued
L_a915 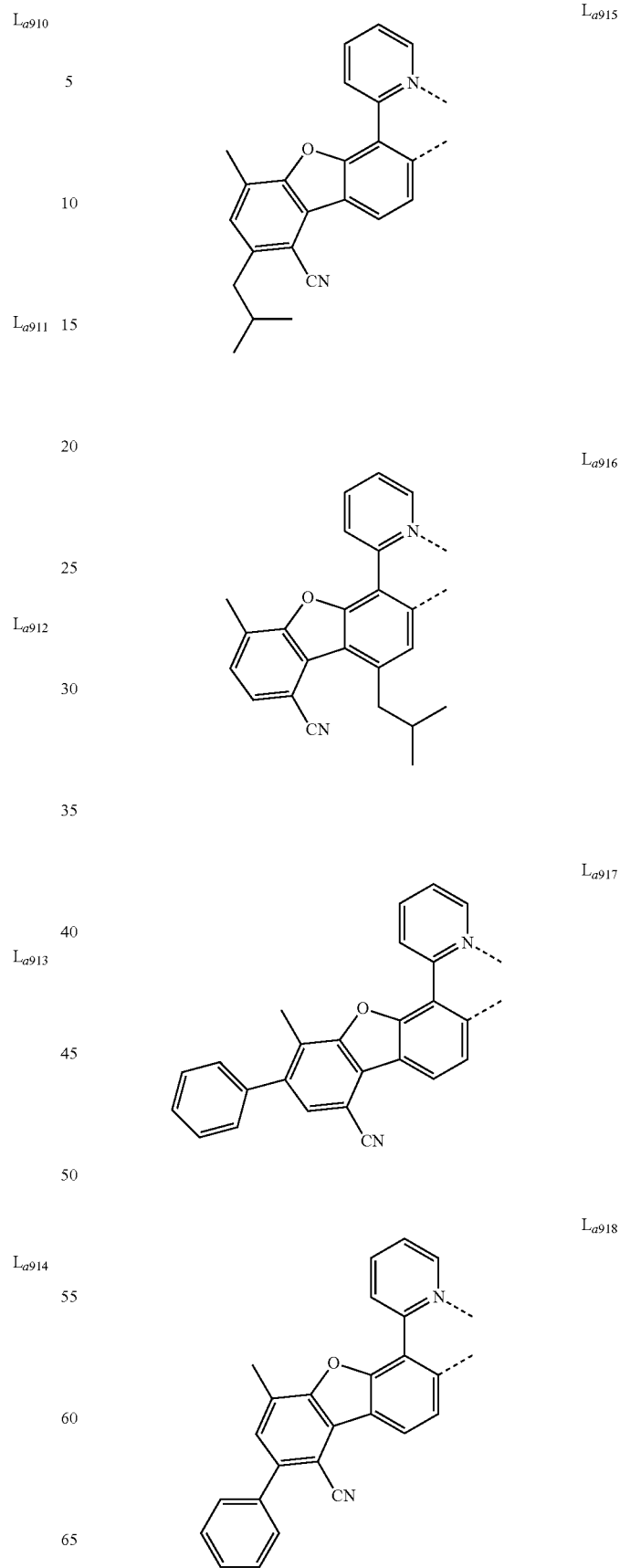
L_a916
L_a917
L_a918

309
-continued
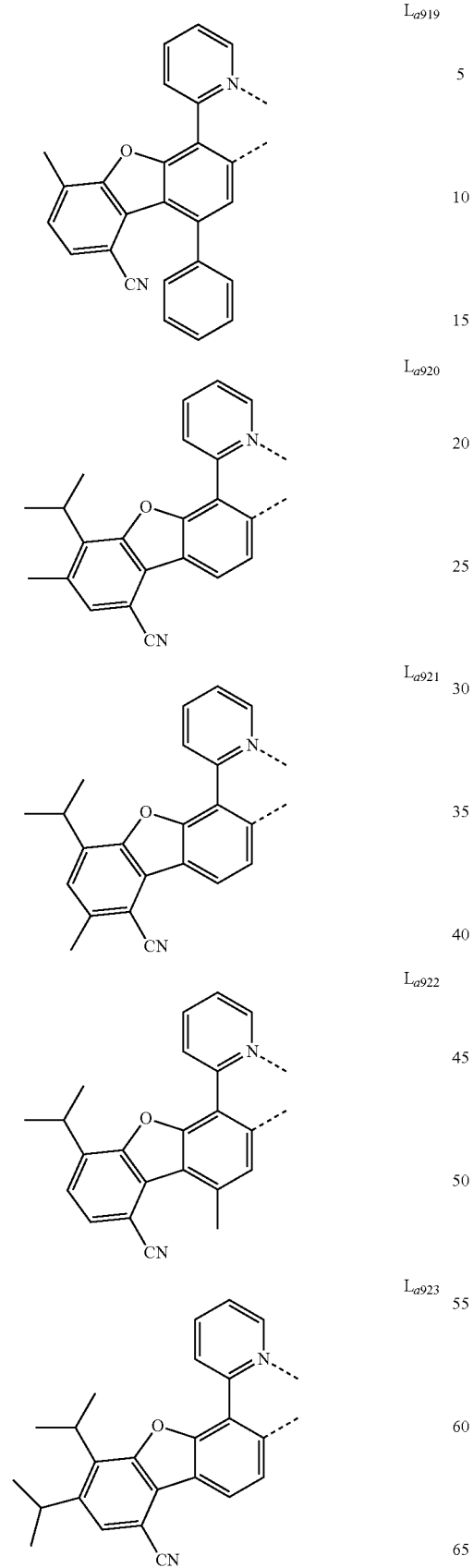
310
-continued
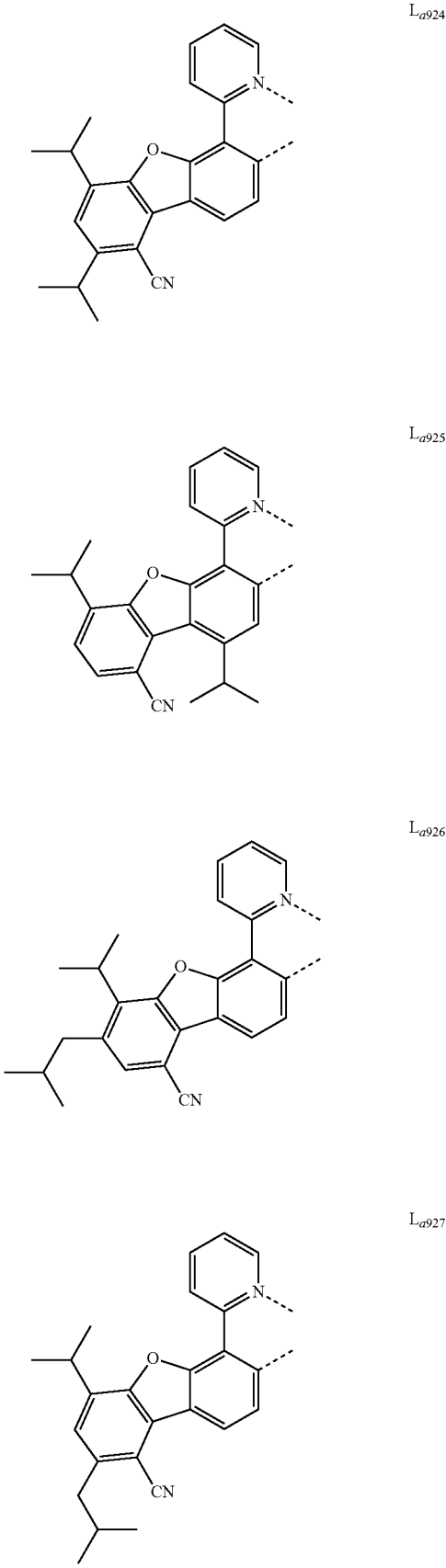

| | |
|---|---|
| 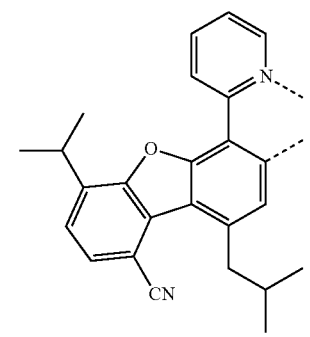 L$_{a928}$ | 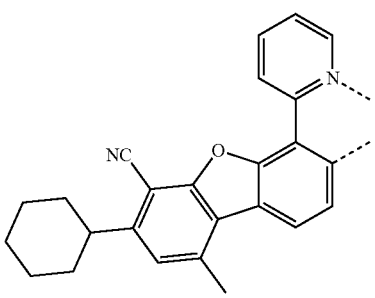 L$_{a932}$ |
| 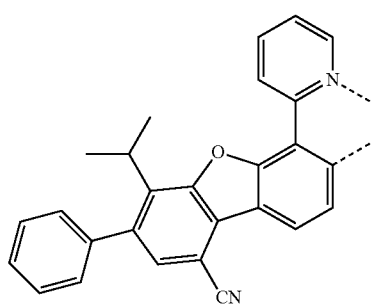 L$_{a929}$ | 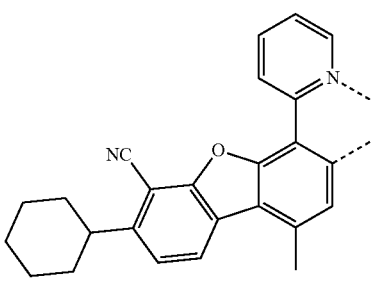 L$_{a933}$ |
| | 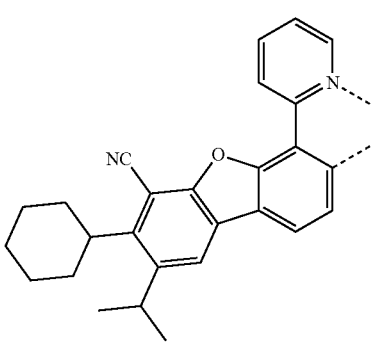 L$_{a934}$ |
| 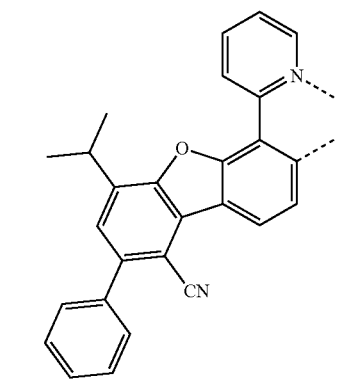 L$_{a930}$ | 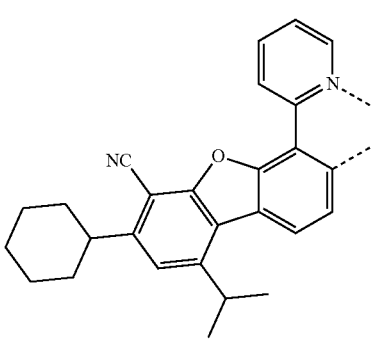 L$_{a935}$ |
| L$_{a931}$ | 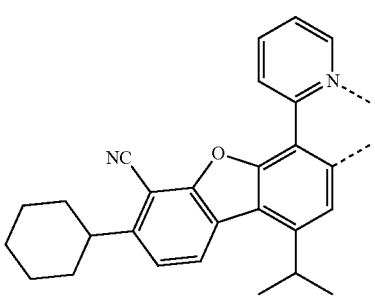 L$_{a936}$ |

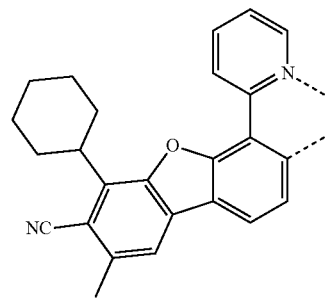
L_{a937}
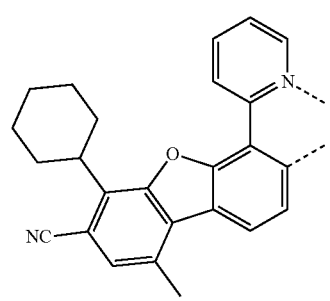
L_{a938}
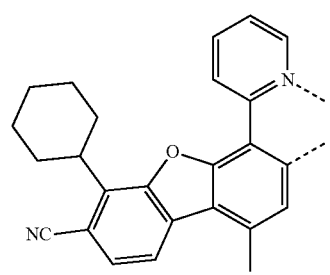
L_{a939}
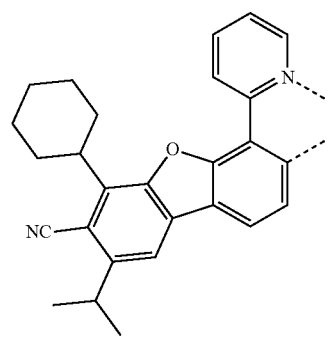
L_{a940}
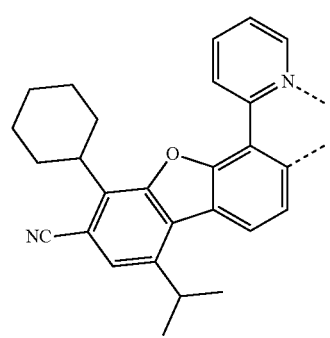
L_{a941}
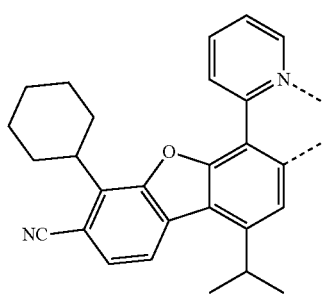
L_{a942}
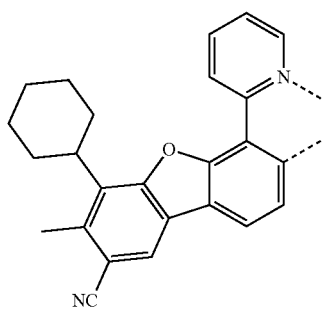
L_{a943}
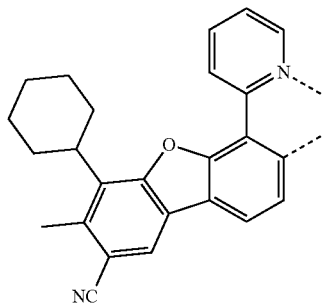
L_{a944}
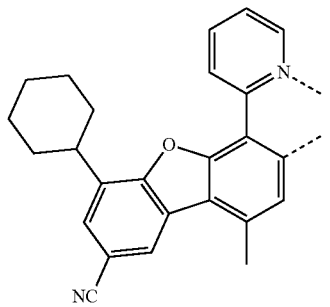
L_{a945}
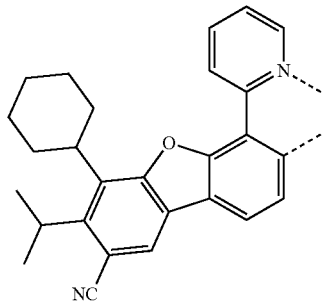
L_{a946}

| | |
|---|---|
| 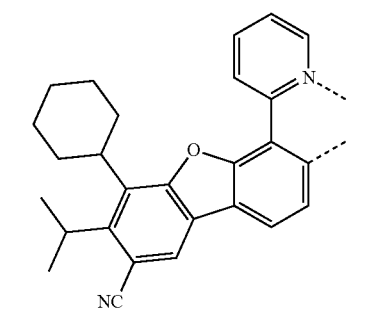 La947 | 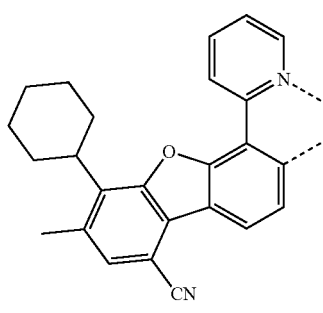 La952 |
| 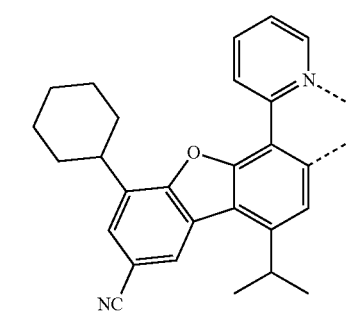 La948 | 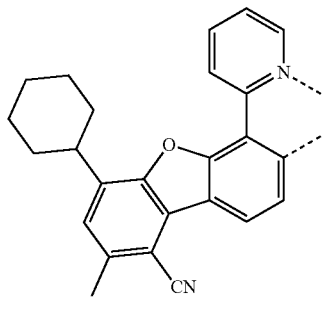 La953 |
| 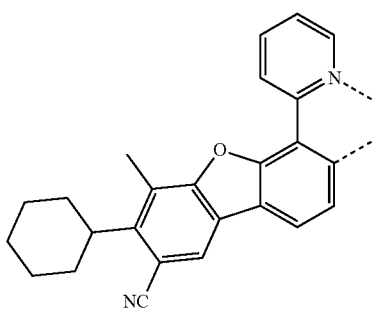 La949 | 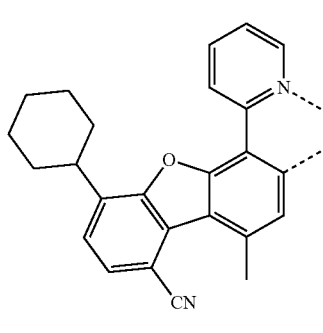 La954 |
| 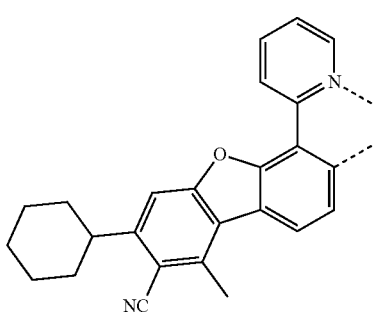 La950 | 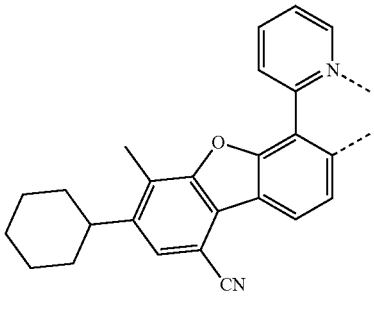 La955 |
| 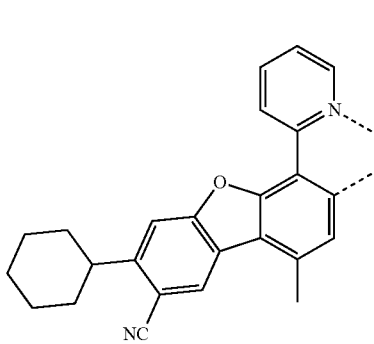 La951 | 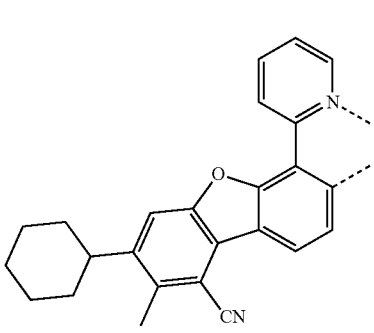 La956 |

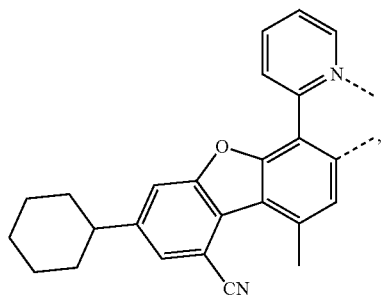
L_a957
9. The metal complex according to claim 8, wherein the $L_a$ can be partially or fully deuterated.
10. The metal complex according to claim 9, wherein the ligand $L_a$ is selected from the group consisting of:
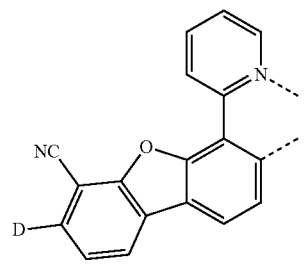
L_a958
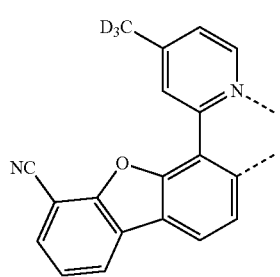
L_a959
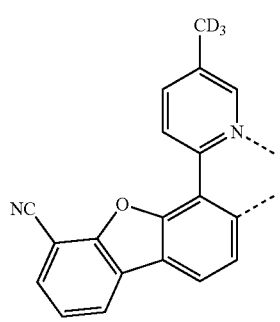
L_a960
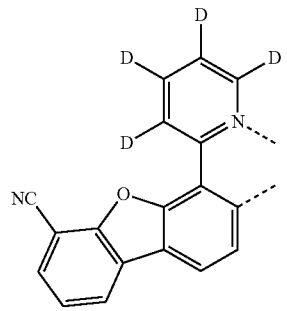
L_a961
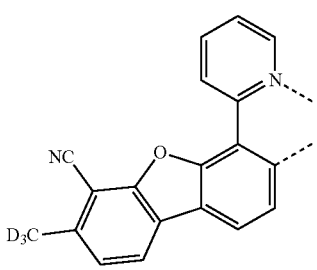
L_a962
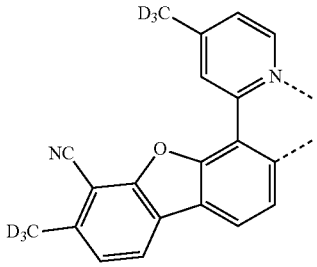
L_a963
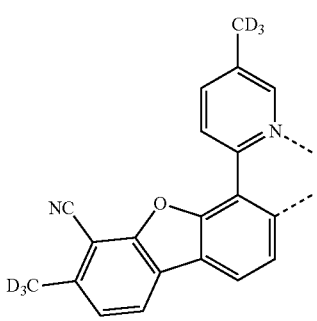
L_a964
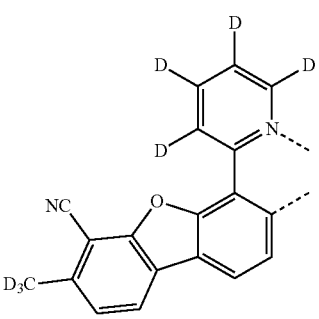
L_a965

L*a*966 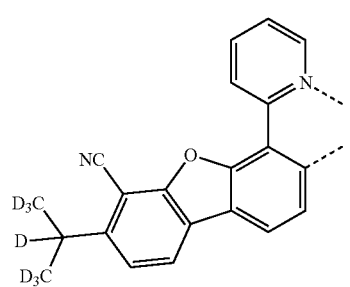
L*a*967 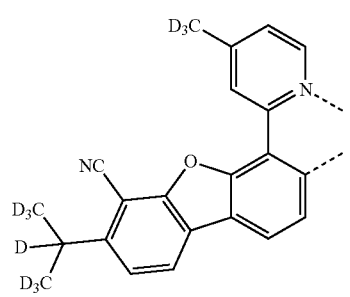
L*a*968 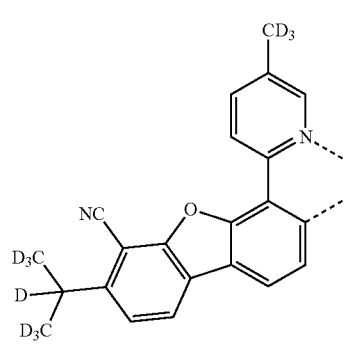
L*a*969 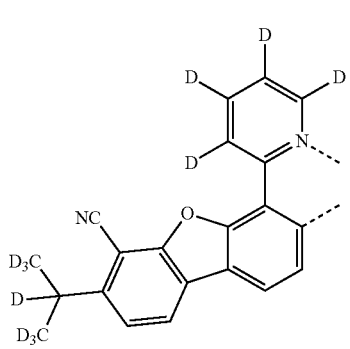
L*a*970 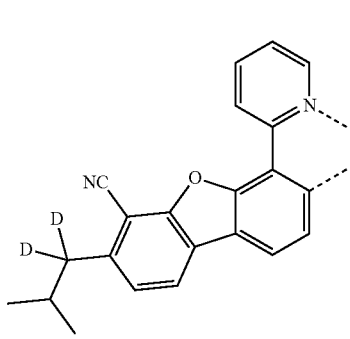
L*a*971 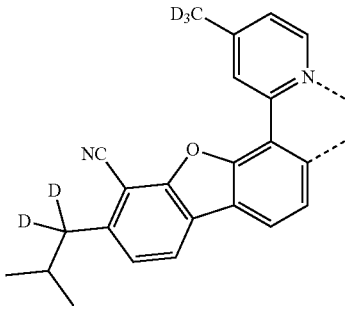
L*a*972 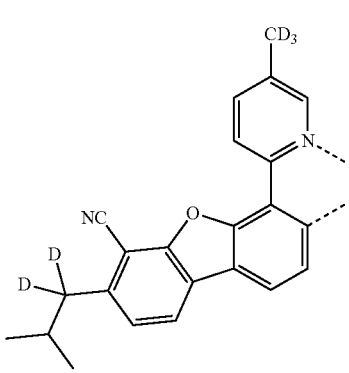
L*a*973 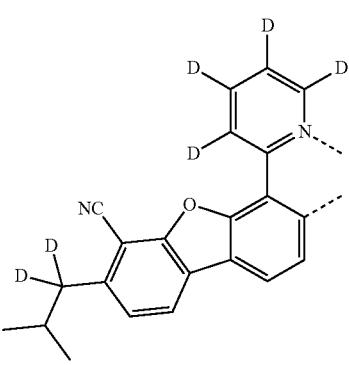
L*a*974 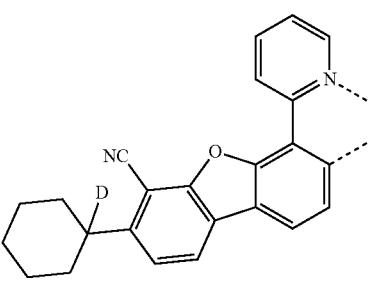
L*a*975 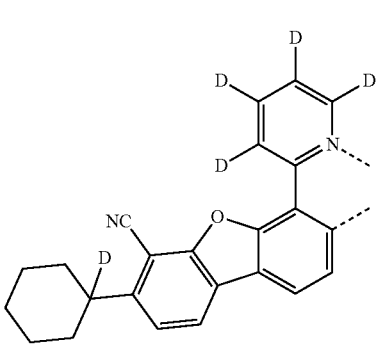

321
-continued
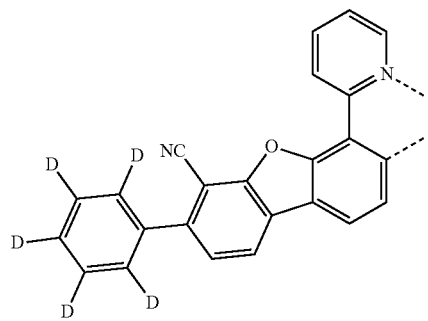 L$_{a976}$
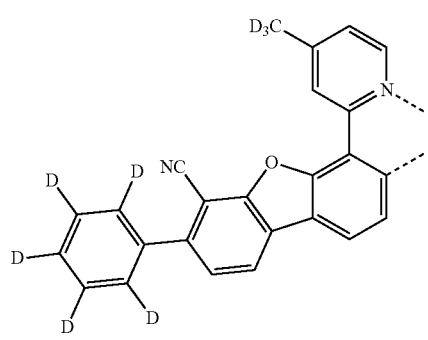 L$_{a977}$
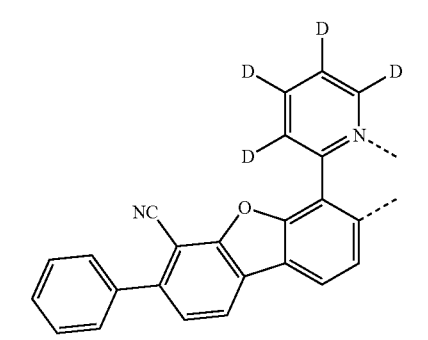 L$_{a978}$
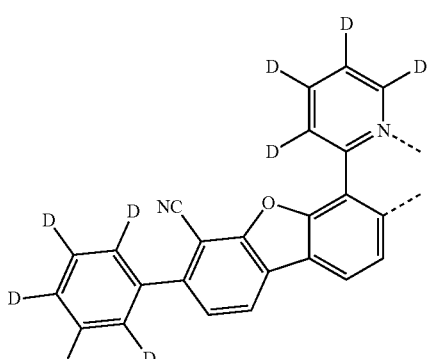 L$_{a979}$
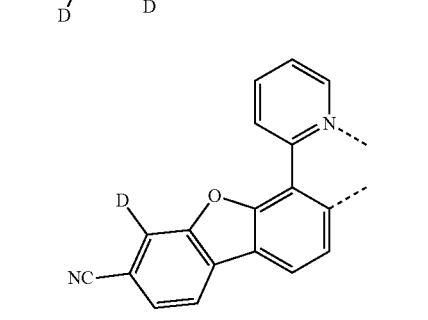 L$_{a980}$
322
-continued
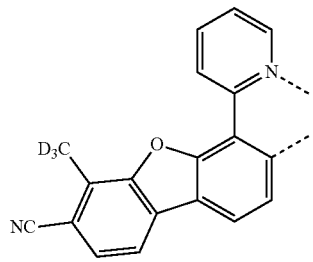 L$_{a981}$
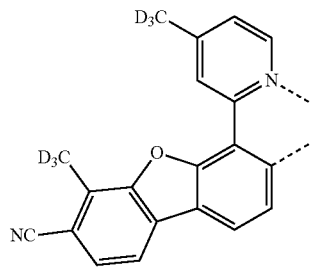 L$_{a982}$
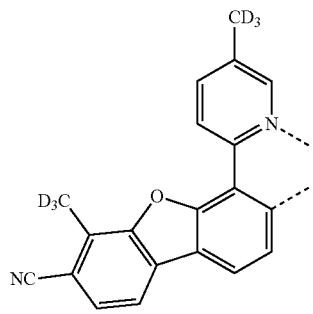 L$_{a983}$
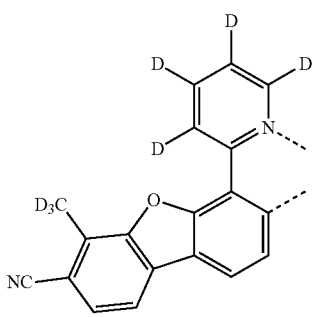 L$_{a984}$
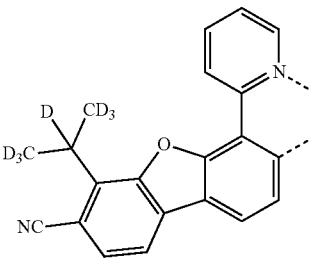 L$_{a985}$

| | |
|---|---|
| 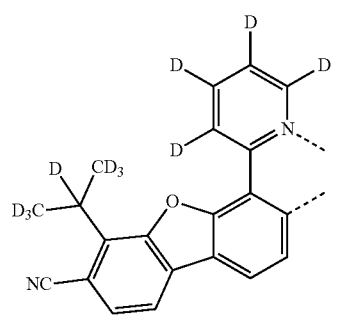 L_a986 | 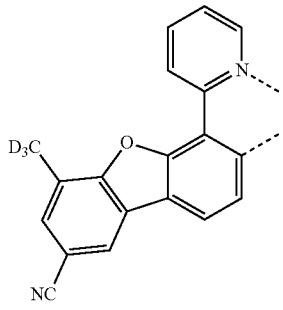 L_a991 |
| 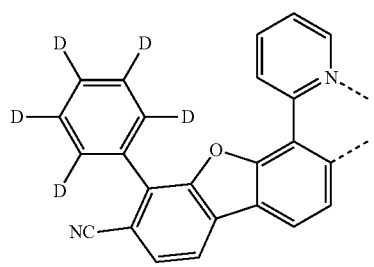 L_a987 | 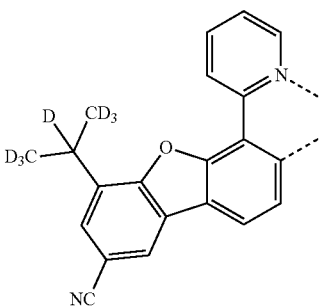 L_a992 |
| 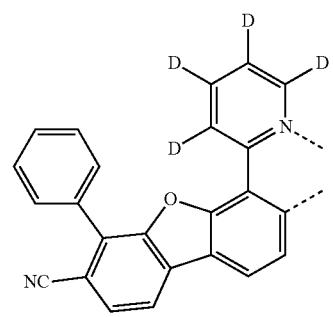 L_a988 | 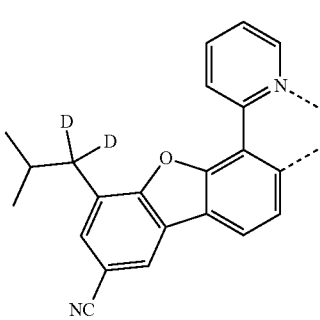 L_a993 |
| 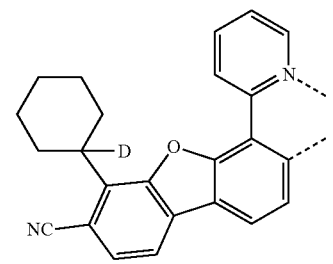 L_a989 | 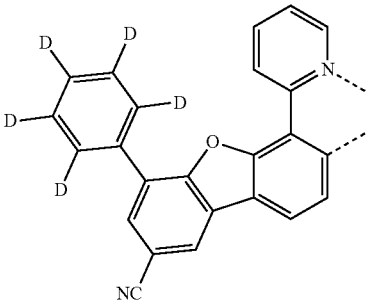 L_a994 |
| 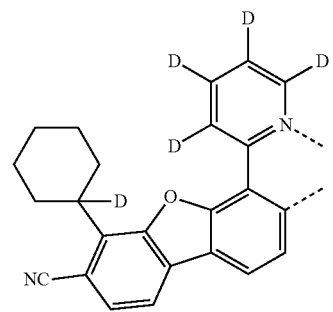 L_a990 | 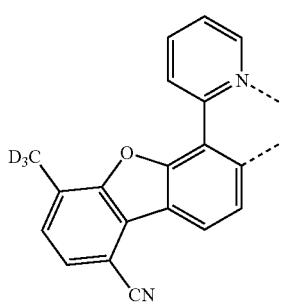 L_a995 |

La996 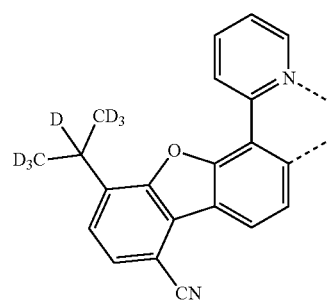
La997 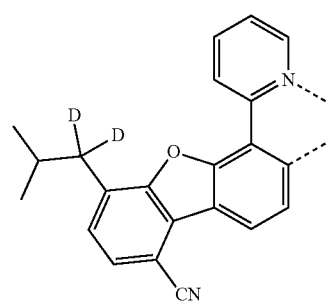
La998 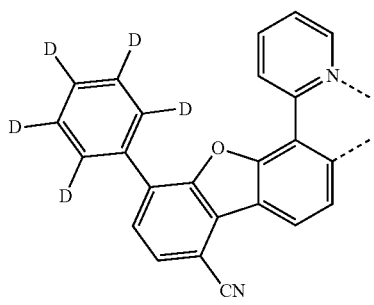
La999 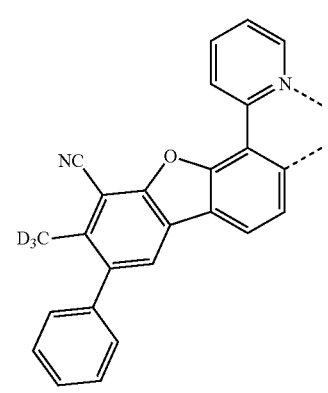
La1000 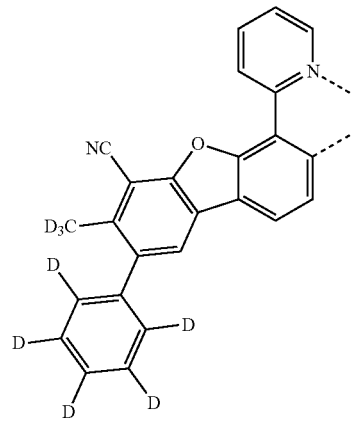
La1001 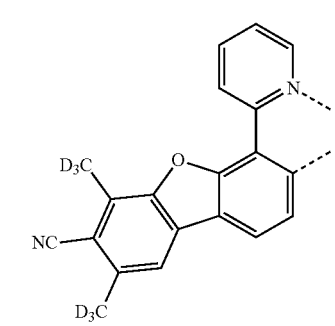
La1002 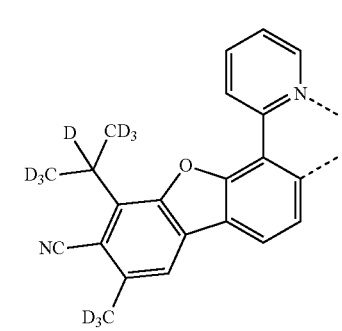
La1003 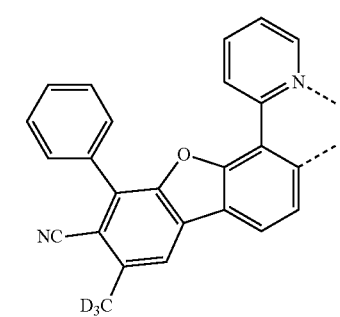

327
-continued
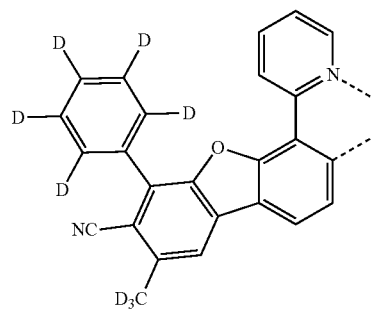
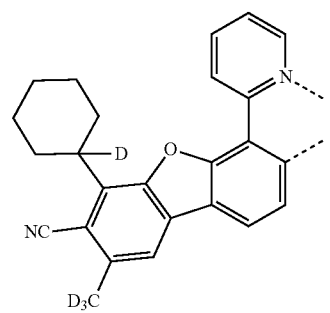
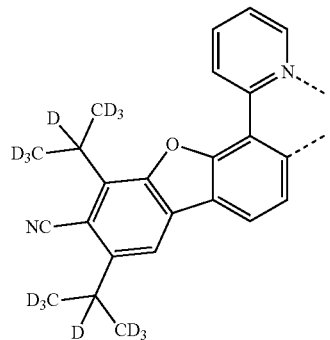
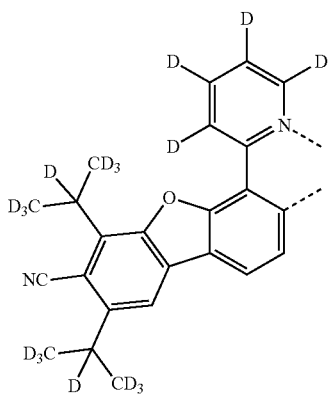
328
-continued
L_{a1004}
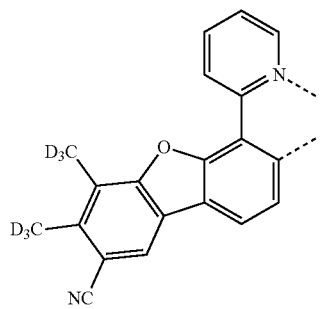
L_{a1005}
L_{a1006}
L_{a1007}
L_{a1008}
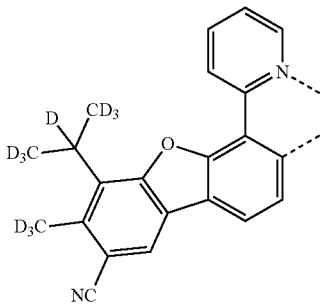
L_{a1009}
L_{a1010}
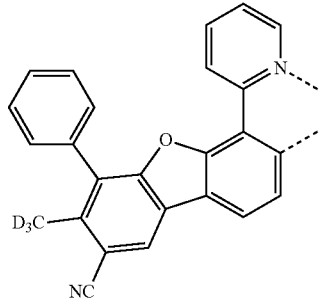
L_{a1011}
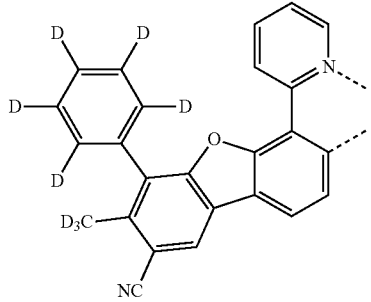
L_{a1012}
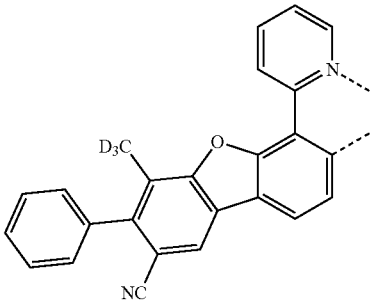

L<sub>a1013</sub> 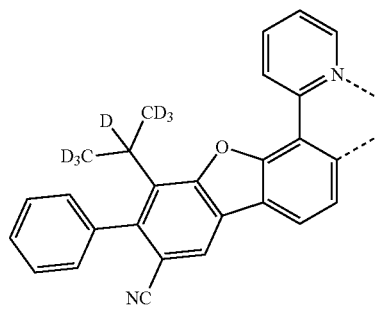
L<sub>a1014</sub> 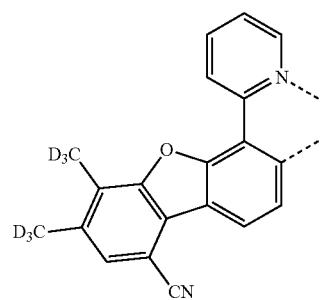
L<sub>a1015</sub> 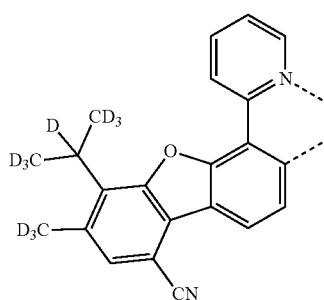
L<sub>a1016</sub> 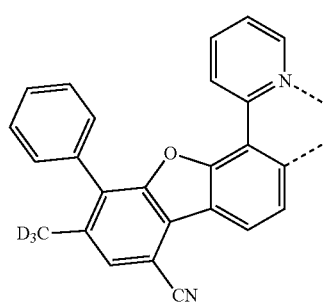
L<sub>a1017</sub> 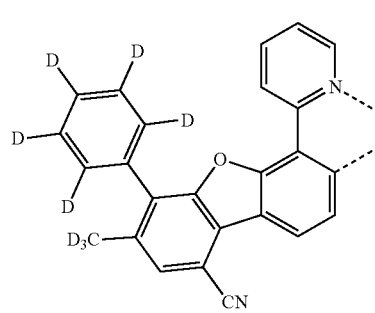
L<sub>a1018</sub> 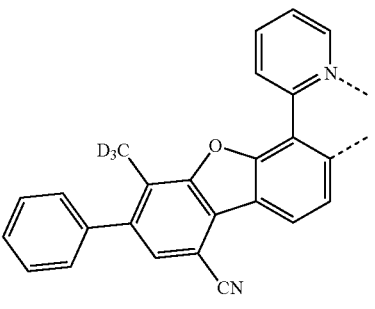
L<sub>a1019</sub> 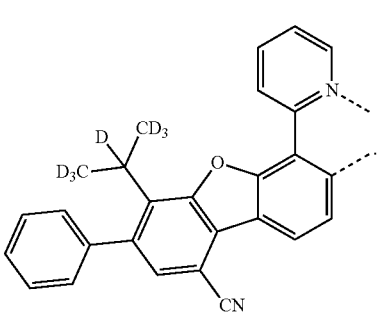
11. The metal complex according to claim 3, wherein the metal complex has the Formula IrL$_a$(L$_b$)$_2$ or Ir(L$_a$)$_2$L$_b$, wherein L$_a$ is one or two selected from L$_{a1}$ to L$_{a109}$, and L$_b$ is one or two selected from the group consisting of:
L<sub>b1</sub> 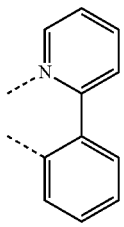
L<sub>b2</sub> 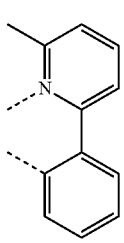
L<sub>b3</sub> 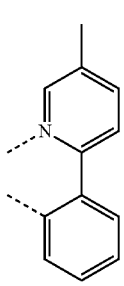

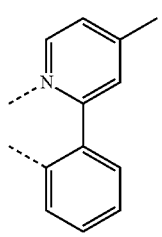 L<sub>b4</sub>
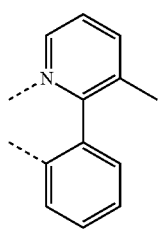 L<sub>b5</sub>
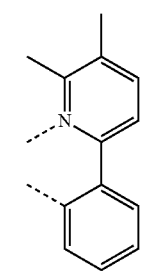 L<sub>b6</sub>
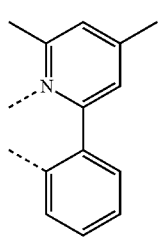 L<sub>b7</sub>
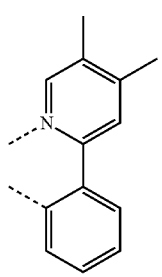 L<sub>b8</sub>
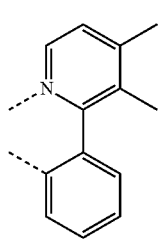 L<sub>b9</sub>
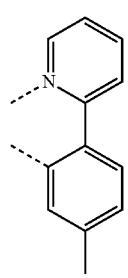 L<sub>b10</sub>
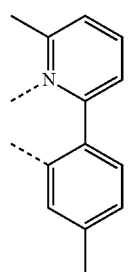 L<sub>b11</sub>
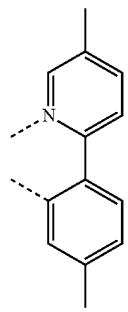 L<sub>b12</sub>
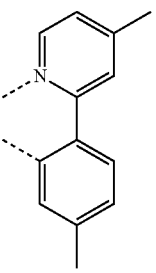 L<sub>b13</sub>
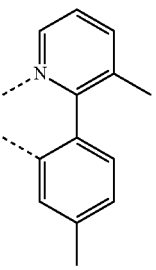 L<sub>b14</sub>

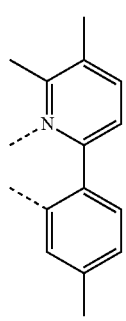 L_{b15}
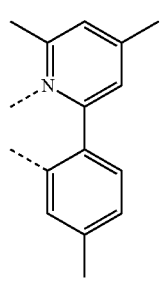 L_{b16}
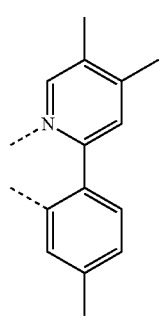 L_{b17}
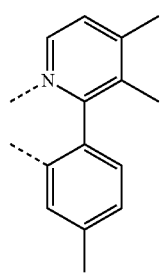 L_{b18}
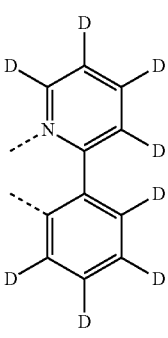 L_{b19}
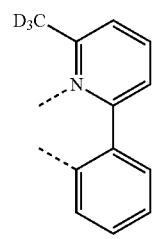 L_{b20}
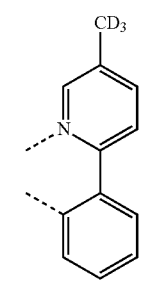 L_{b21}
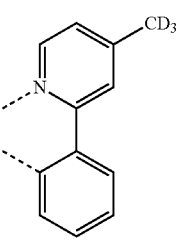 L_{b22}
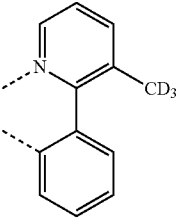 L_{b23}
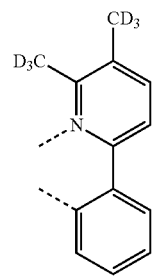 L_{b24}
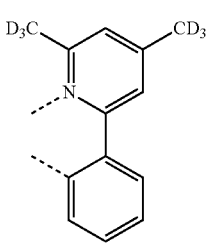 L_{b25}

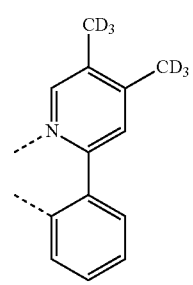 L_{b26}
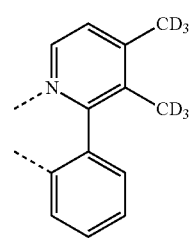 L_{b27}
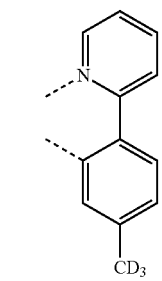 L_{b28}
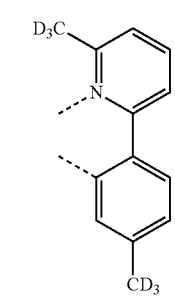 L_{b29}
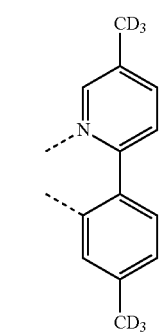 L_{b30}
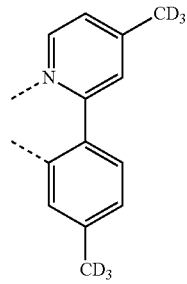 L_{b31}
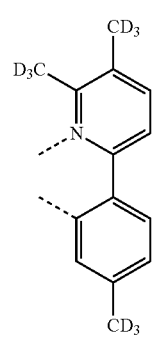 L_{b32}
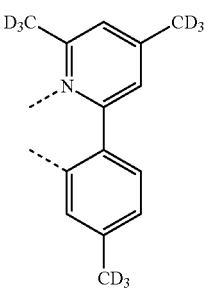 L_{b33}
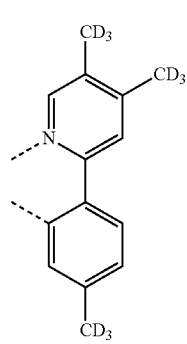 L_{b34}
L_{b35}

| | |
|---|---|
| 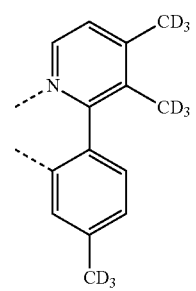 L_{b36} | 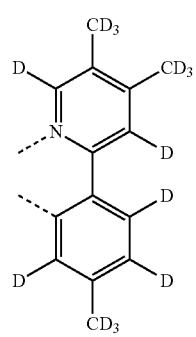 L_{b41} |
| 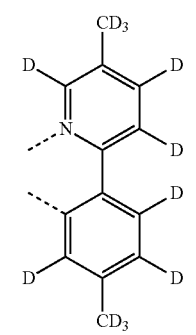 L_{b37} | 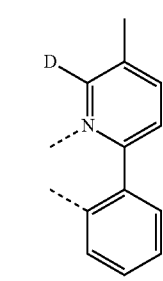 L_{b42} |
| 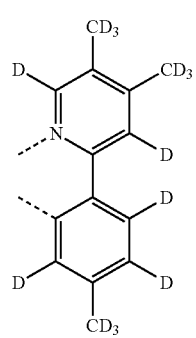 L_{b38} | 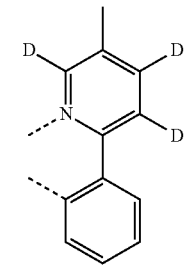 L_{b43} |
| 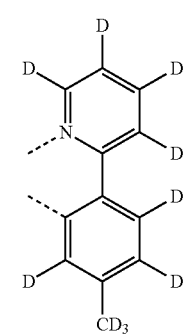 L_{b39} | 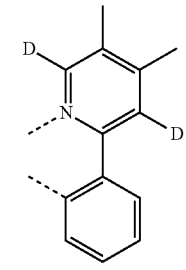 L_{b44} |
| 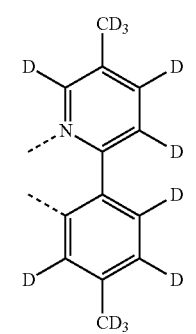 L_{b40} | 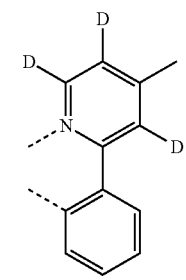 L_{b45} |

L<sub>b46</sub>
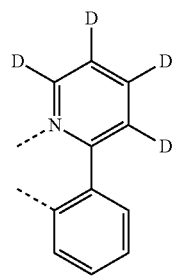
L<sub>b47</sub>
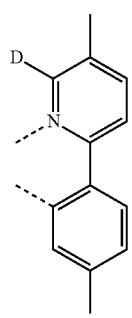
L<sub>b48</sub>
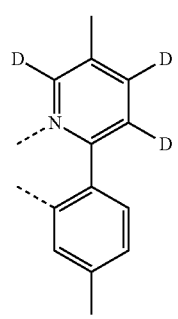
L<sub>b49</sub>
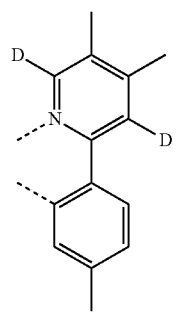
L<sub>b50</sub>
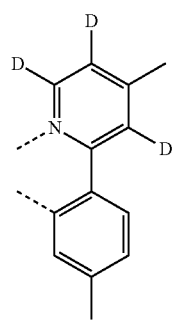
L<sub>b51</sub>
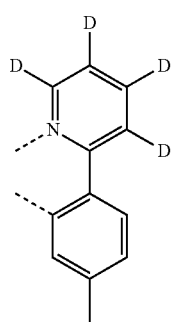
L<sub>b52</sub>
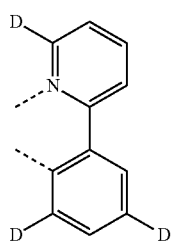
L<sub>b53</sub>
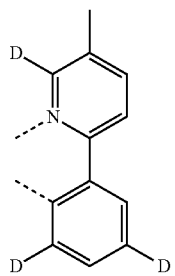
L<sub>b54</sub>
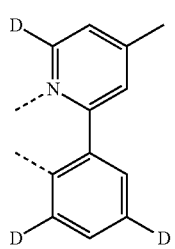
L<sub>b55</sub>
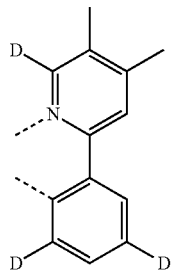

-continued
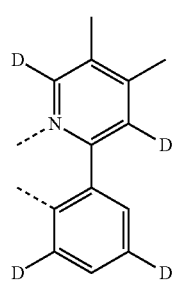 L$_{b56}$
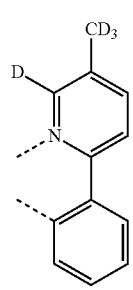 L$_{b57}$
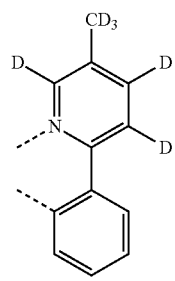 L$_{b58}$
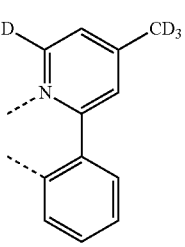 L$_{b59}$
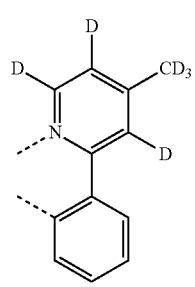 L$_{b60}$
-continued
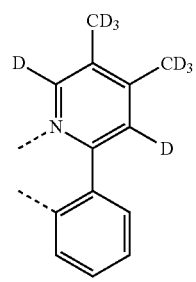 L$_{b61}$
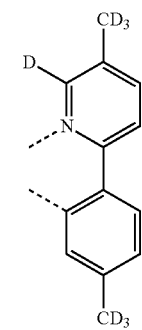 L$_{b62}$
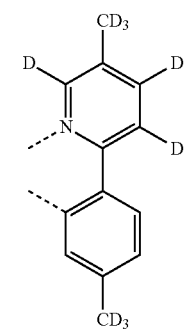 L$_{b63}$
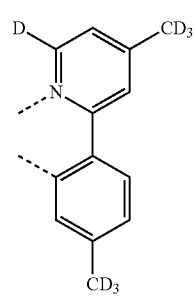 L$_{b64}$
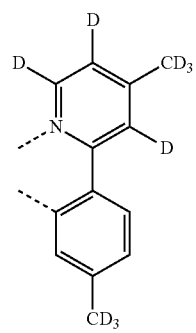 L$_{b65}$

| | |
|---|---|
| 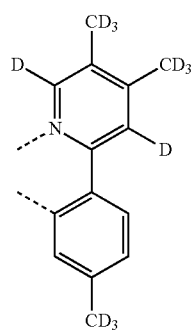 | L$_{b66}$ |
| 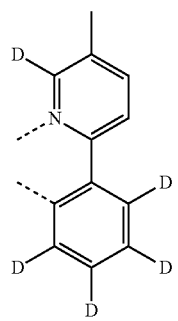 | L$_{b67}$ |
| 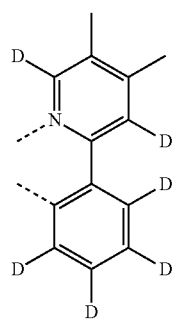 L$_{b68}$ | |
| 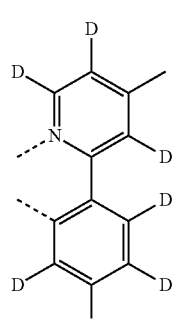 L$_{b69}$ | |
| L$_{b70}$ | |
| | |
|---|---|
| 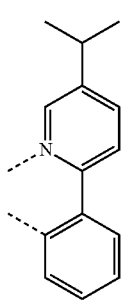 | L$_{b71}$ |
| 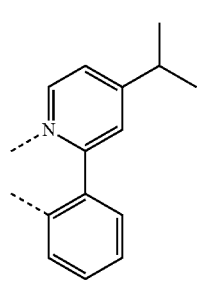 | L$_{b72}$ |
| 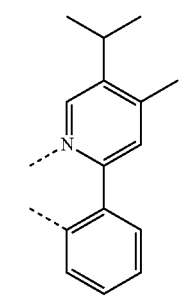 | L$_{b73}$ |
| 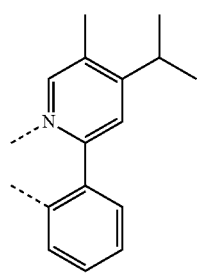 | L$_{b74}$ |
| 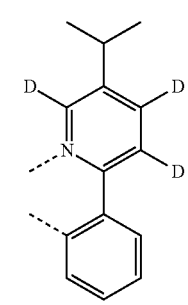 | L$_{b75}$ |

-continued
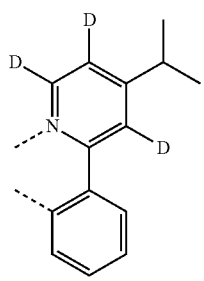
$L_{b76}$
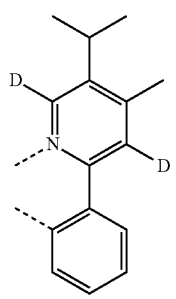
$L_{b77}$
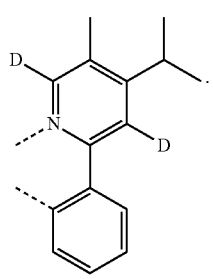
$L_{b78}$
12. The metal complex according to claim 3, wherein the metal complex has the Formula $Ir(L_a)_2L_c$ or $IrL_a(L_c)_2$, wherein $L_a$ is one or two selected from $L_{a1}$ to $L_{a109}$, and $L_c$ is one or two selected from the group consisting of:
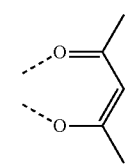
$L_{c1}$
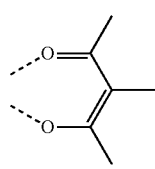
$L_{c2}$
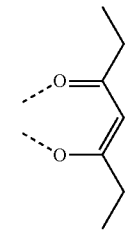
$L_{c3}$
-continued
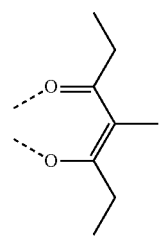
$L_{c4}$
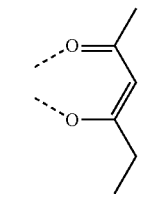
$L_{c5}$
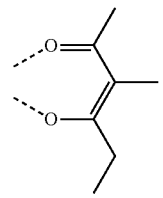
$L_{c6}$
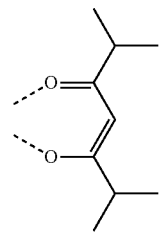
$L_{c7}$
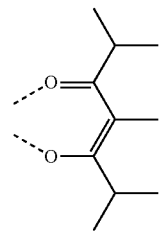
$L_{c8}$
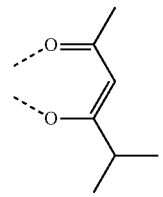
$L_{c9}$
$L_{c10}$ -continued
L<sub>c11</sub>
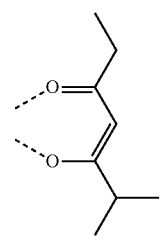
L<sub>c12</sub>
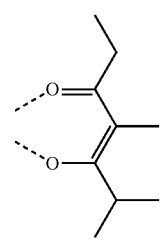
L<sub>c13</sub>
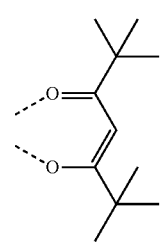
L<sub>c14</sub>
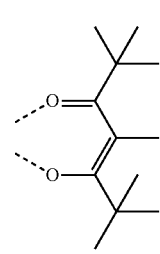
L<sub>c15</sub>
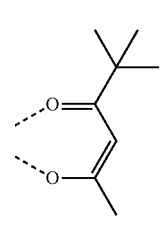
L<sub>c16</sub>
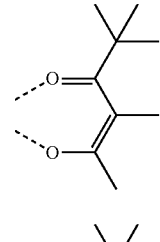
L<sub>c17</sub>
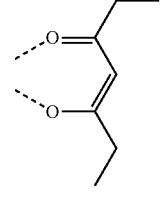
-continued
L<sub>c18</sub>
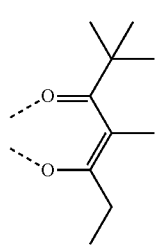
L<sub>c19</sub>
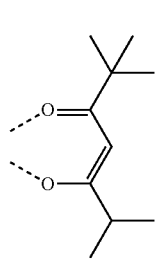
L<sub>c20</sub>
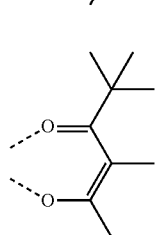
L<sub>c21</sub>
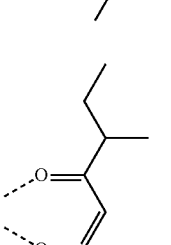
L<sub>c22</sub>
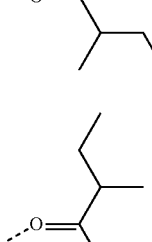
L<sub>c23</sub>
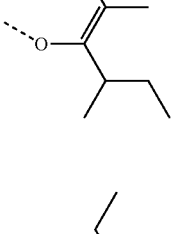

-continued
L_{c24}
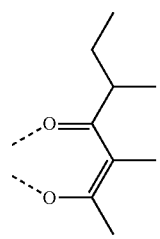
L_{c25}
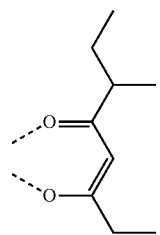
L_{c26}
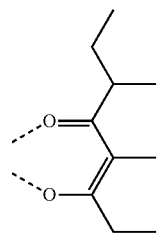
L_{c27}
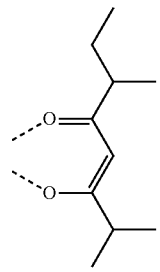
L_{c28}
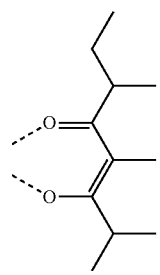
L_{c29}
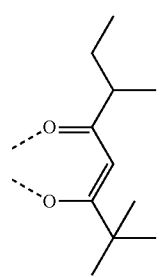
-continued
L_{c30}
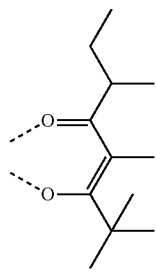
L_{c31}
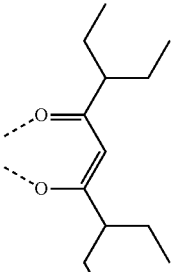
L_{c32}
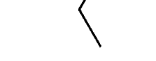
L_{c33}
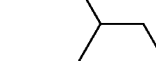
L_{c34}
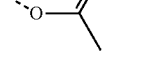
L_{c35}
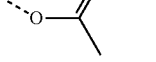

L_{c36}
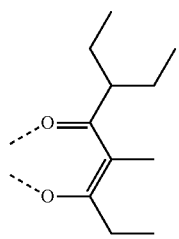
L_{c37}
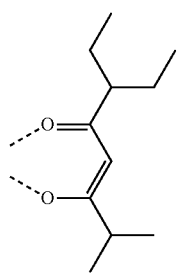
L_{c38}
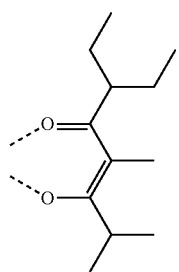
L_{c39}
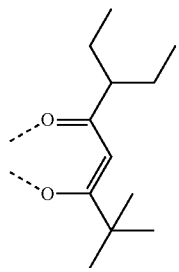
L_{c40}
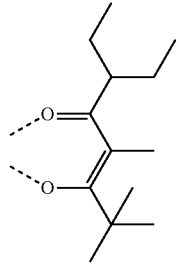
L_{c41}
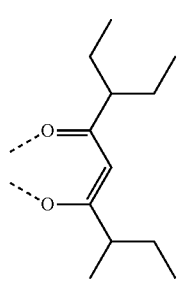
L_{c42}
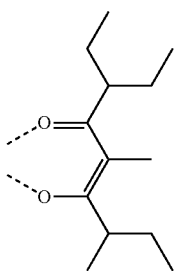
L_{c43}
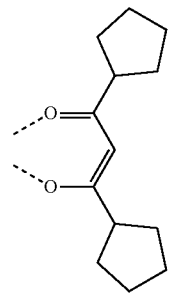
L_{c44}
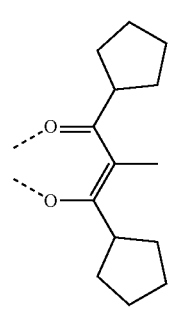
L_{c45}
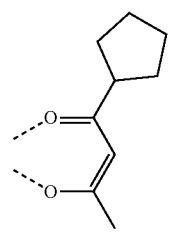
L_{c46}
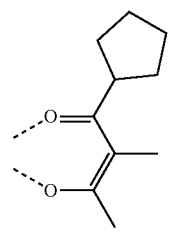
L_{c47}
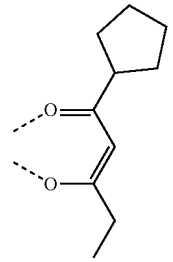

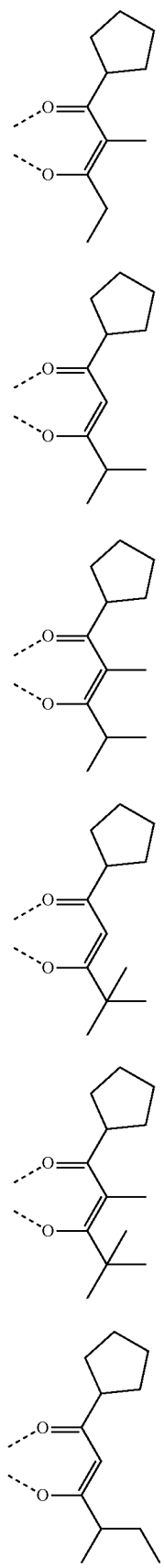
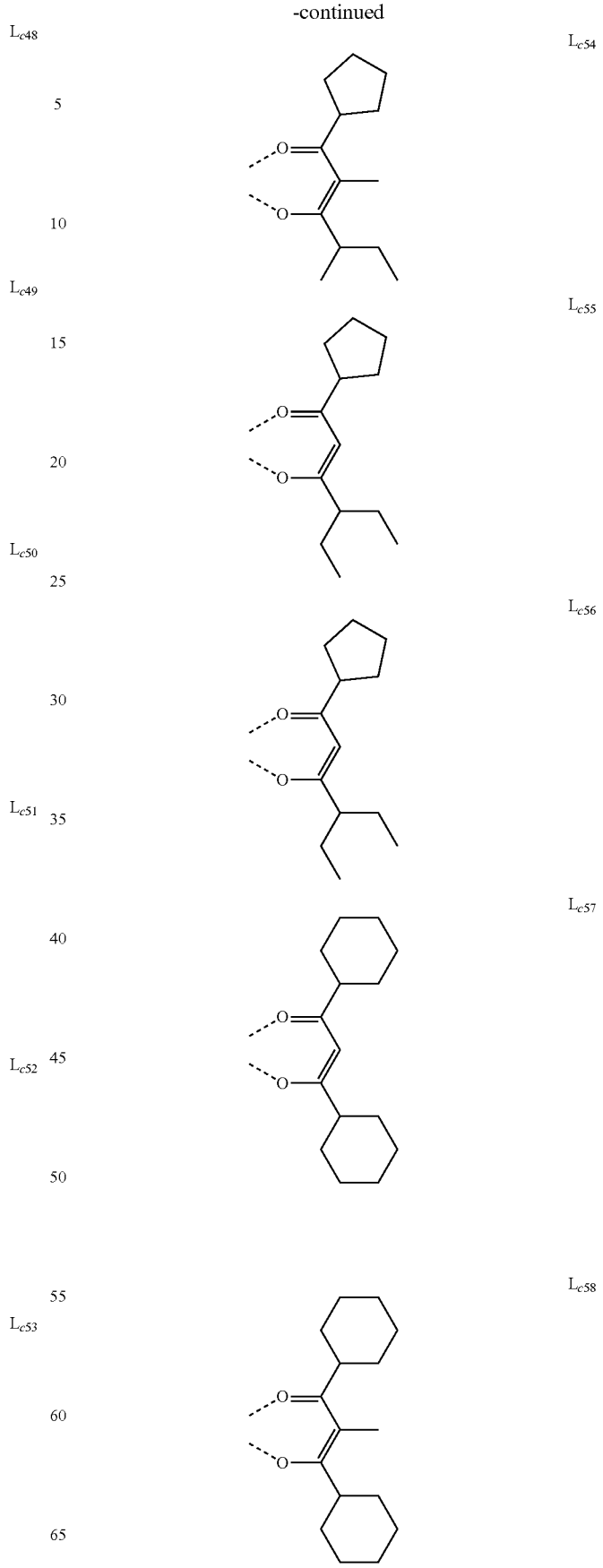

L_{c59}
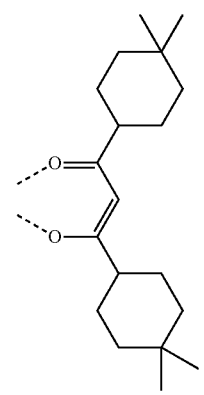
L_{c60}
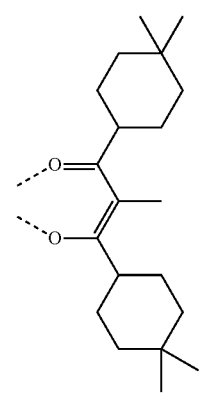
L_{c61}
L_{c62}
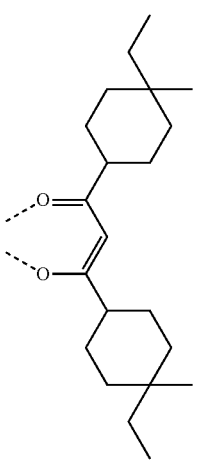
L_{c63}
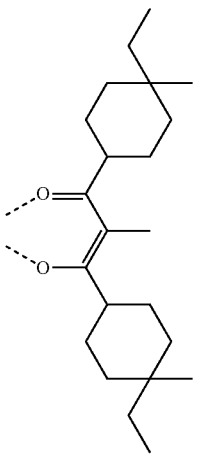
L_{c64}
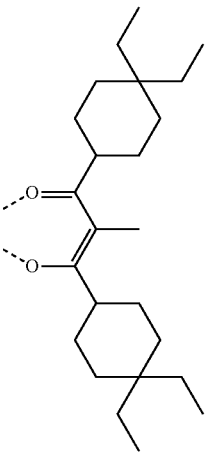
L_{c65}
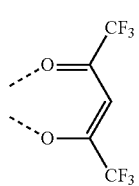

-continued
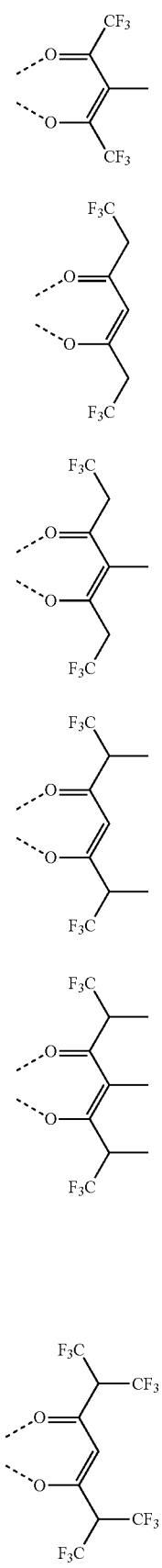
L_{c66}
L_{c67}
L_{c68}
L_{c69}
L_{c70}
L_{c71}
-continued
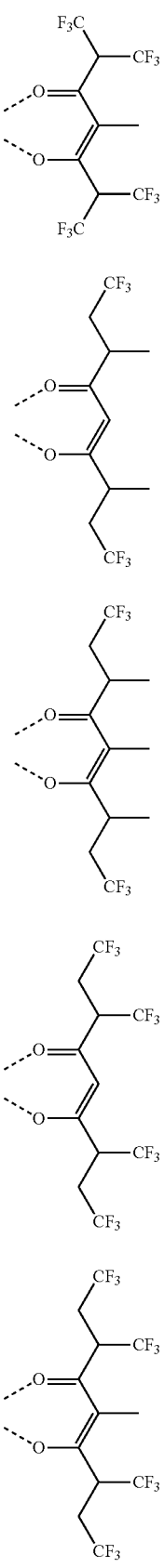
L_{c72}
L_{c73}
L_{c74}
L_{c75}
L_{c76}

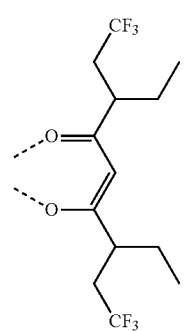 L_{c77}
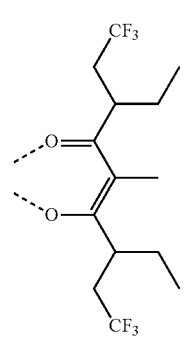 L_{c78}
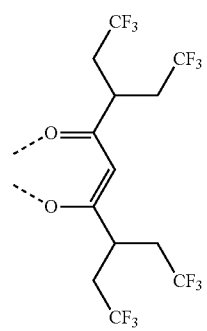 L_{c79}
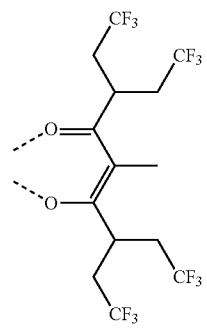 L_{c80}
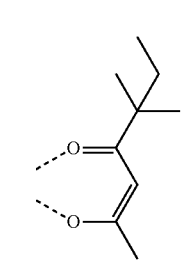 L_{c81}
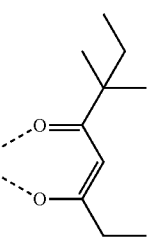 L_{c82}
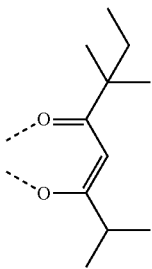 L_{c83}
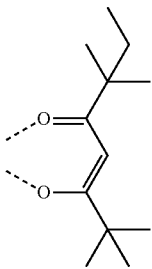 L_{c84}
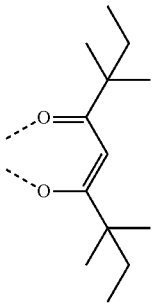 L_{c85}
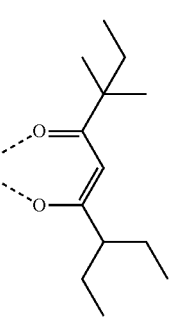 L_{c86}

-continued
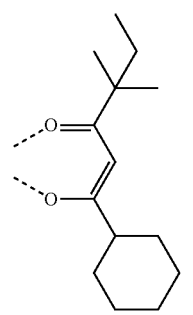 L$_{c87}$
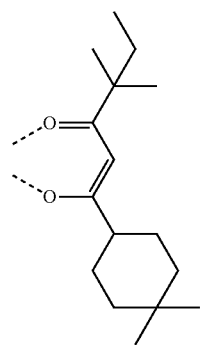 L$_{c88}$
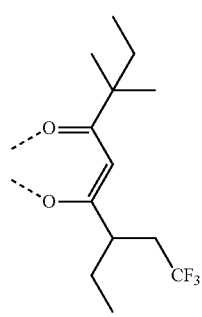 L$_{c89}$
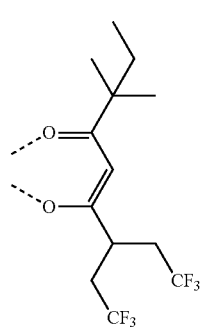 L$_{c90}$
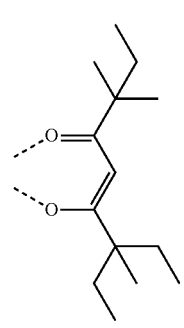 L$_{c91}$
-continued
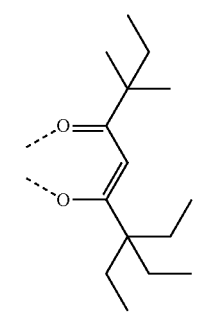 L$_{c92}$
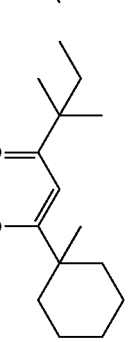 L$_{c93}$
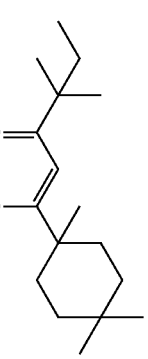 L$_{c94}$
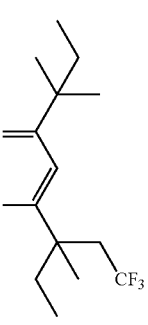 L$_{c95}$
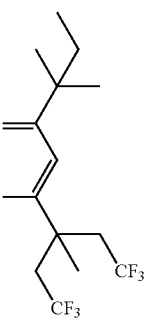 L$_{c96}$

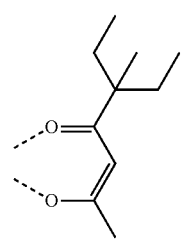 L_{c97}
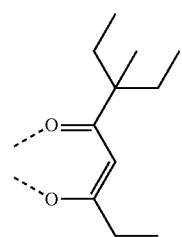 L_{c98}
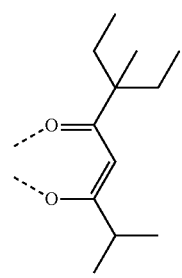 L_{c99}
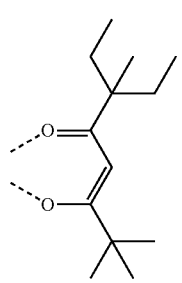 L_{c100}
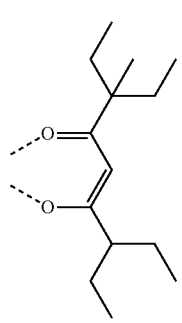 L_{c101}
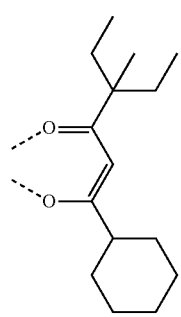 L_{c102}
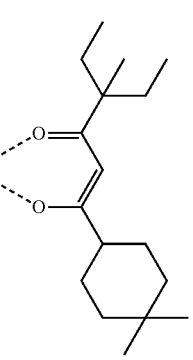 L_{c103}
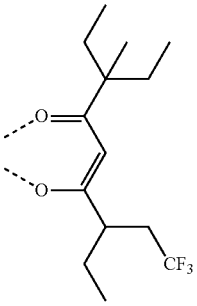 L_{c104}
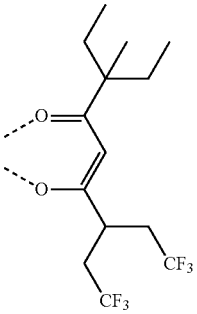 L_{c105}
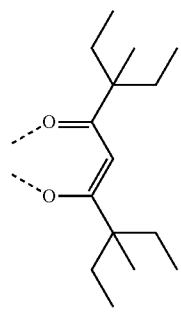 L_{c106}

L$_{c107}$ 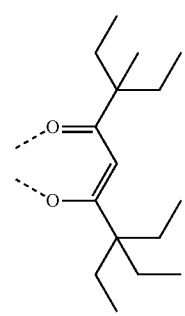
L$_{c108}$ 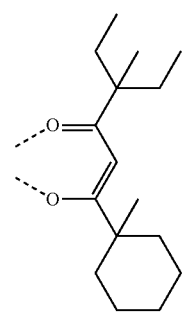
L$_{c109}$ 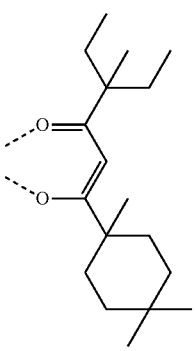
L$_{c110}$ 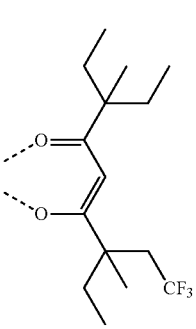
L$_{c111}$ 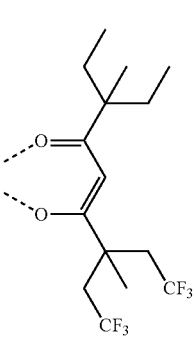
L$_{c112}$ 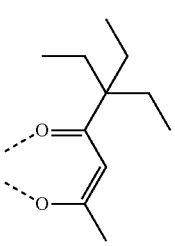
L$_{c113}$ 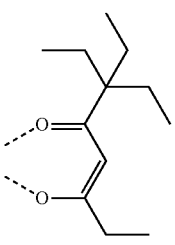
L$_{c114}$ 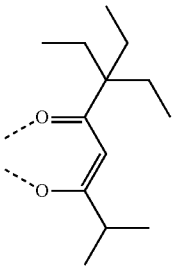
L$_{c115}$ 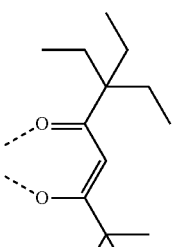
L$_{c116}$ 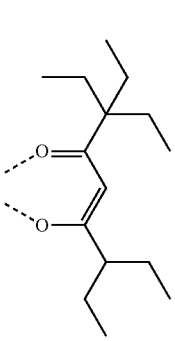

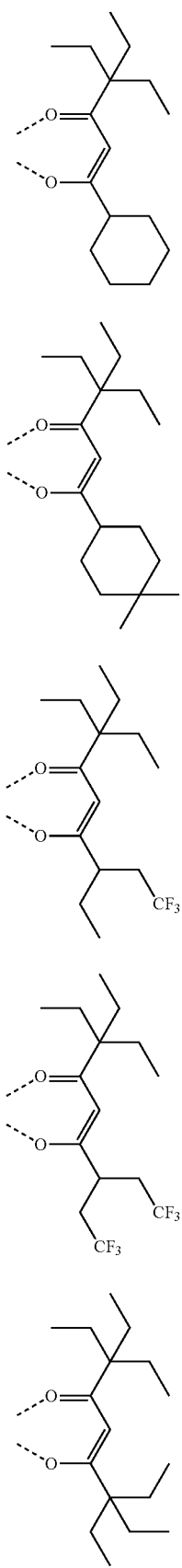
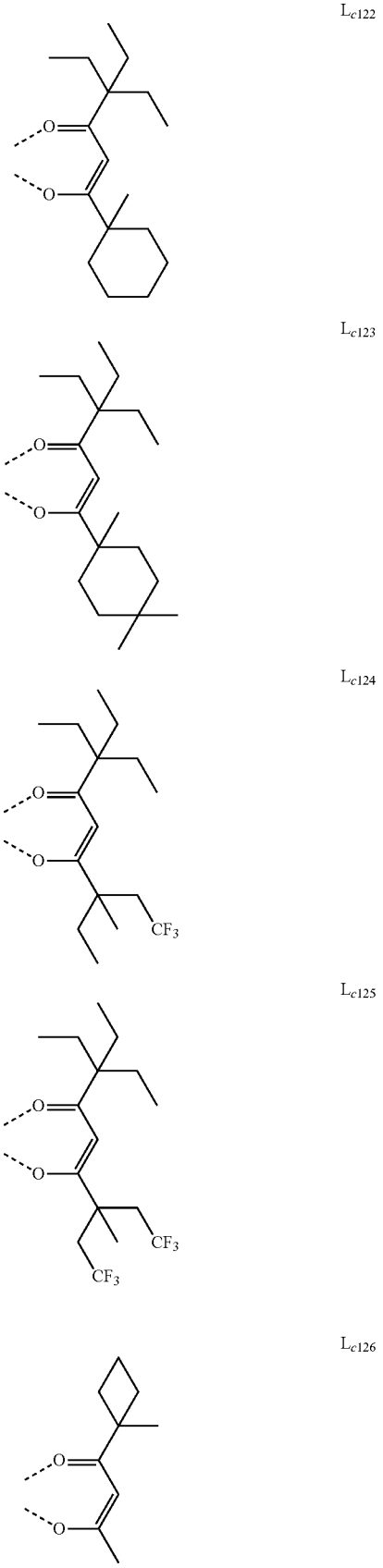

L_{c127}
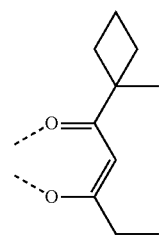
L_{c128}
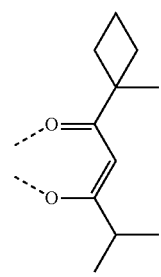
L_{c129}
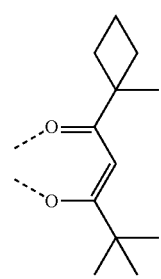
L_{c130}
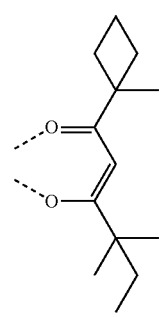
L_{c131}
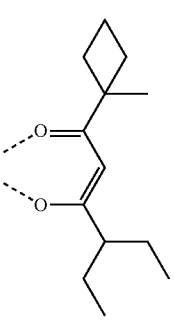
L_{c132}
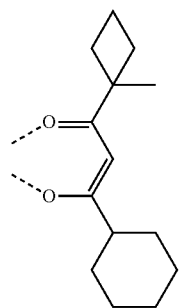
L_{c133}
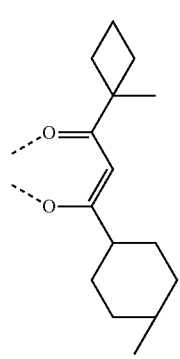
L_{c134}
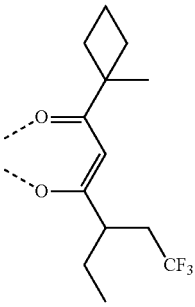
L_{c135}
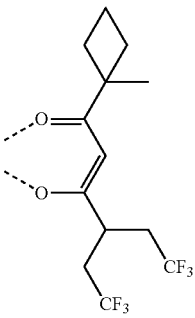
L_{c136}
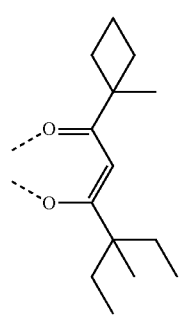

| | |
|---|---|
| $L_{c137}$ | |
| $L_{c138}$ | $L_{c142}$ |
| $L_{c139}$ | $L_{c143}$ |
| $L_{c140}$ | $L_{c144}$ |
| $L_{c141}$ | $L_{c145}$ |
| | $L_{c146}$ |

-continued
$L_{c147}$
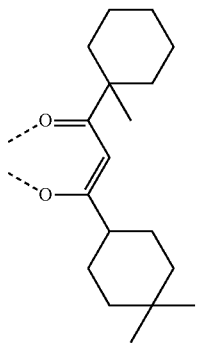
$L_{c148}$
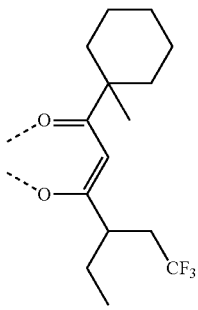
$L_{c149}$
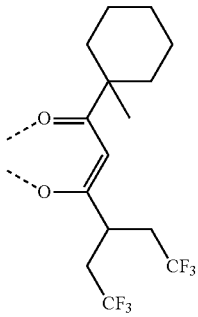
$L_{c150}$
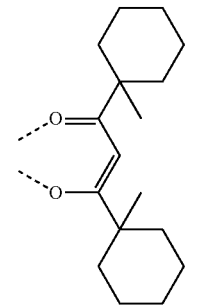
$L_{c151}$
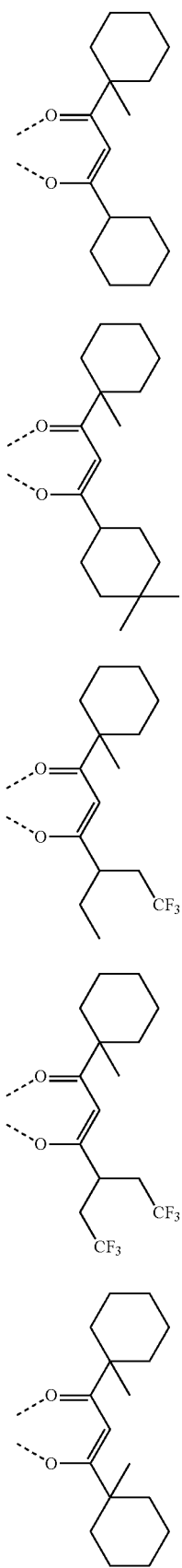
-continued
$L_{c152}$
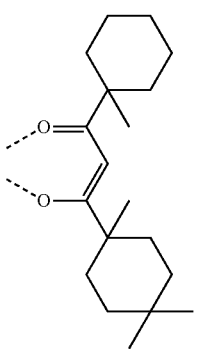
$L_{c153}$
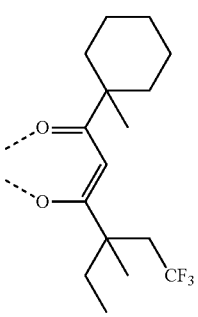
$L_{c154}$
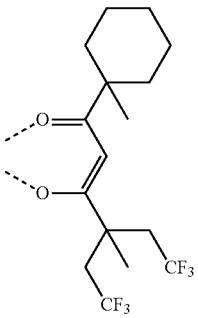
$L_{c155}$
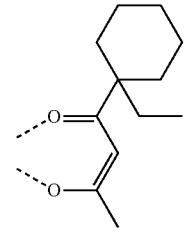
$L_{c156}$
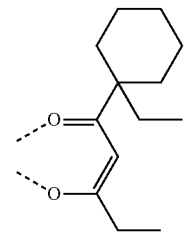

-continued
L$_{c157}$
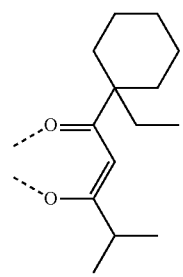
L$_{c158}$
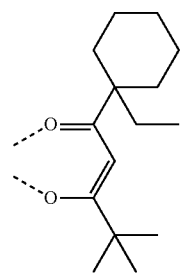
L$_{c159}$
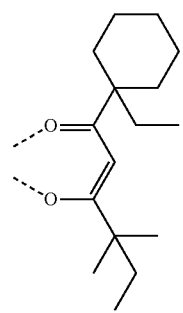
L$_{c160}$
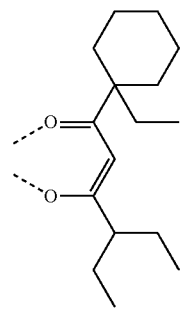
L$_{c161}$
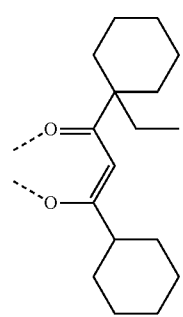
-continued
L$_{c162}$
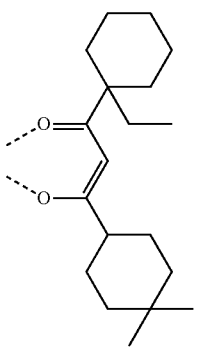
L$_{c163}$
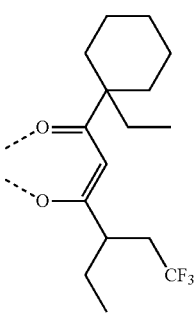
L$_{c164}$
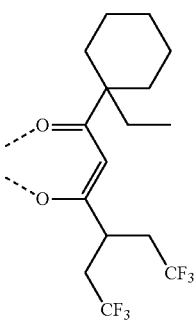
L$_{c165}$
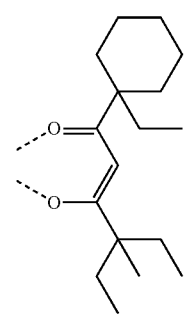
L$_{c166}$
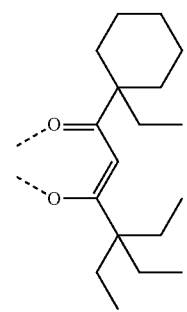

L_{c167}
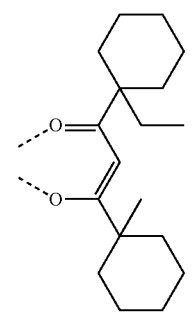
L_{c168}
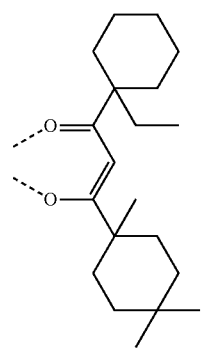
L_{c169}
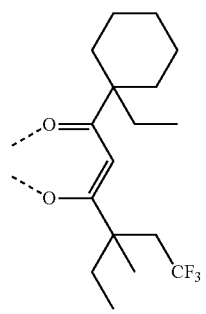
L_{c170}
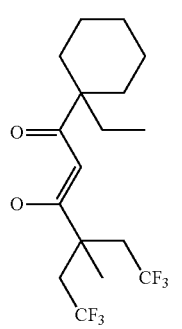
L_{c171}
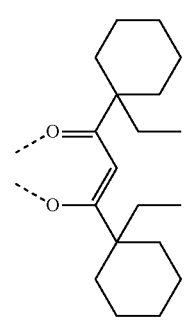
L_{c172}
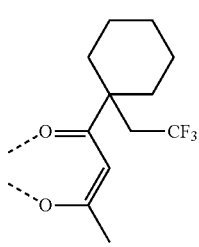
L_{c173}
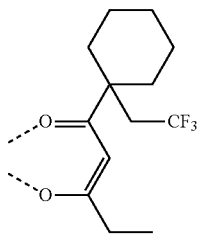
L_{c174}
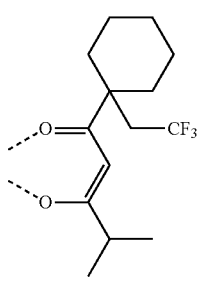
L_{c175}
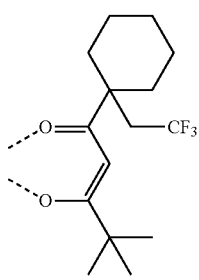
L_{c176}
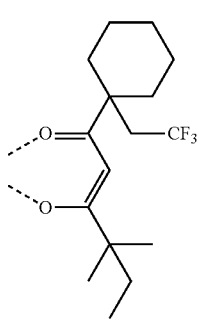

L_{c177}
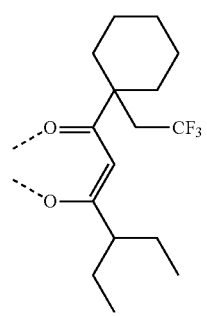
L_{c178}
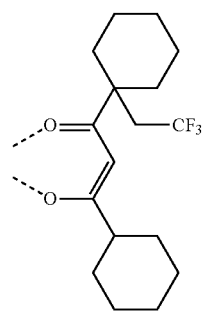
L_{c179}
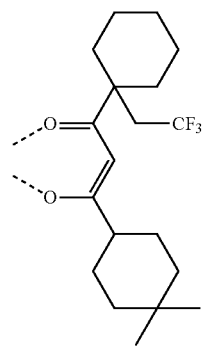
L_{c180}
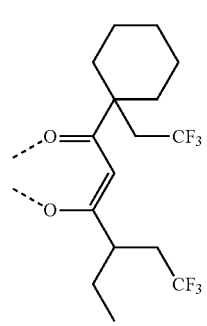
L_{c181}
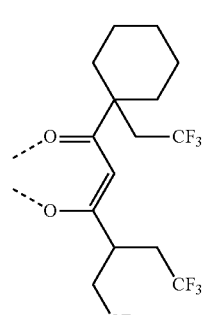
L_{c182}
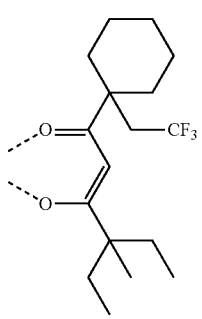
L_{c183}
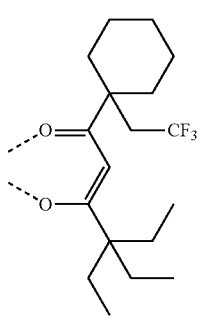
L_{c184}
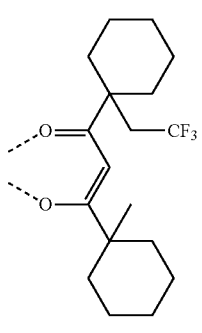
L_{c185}
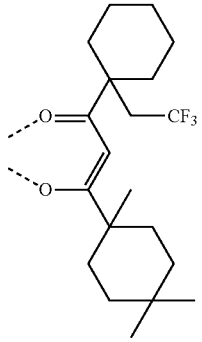
L_{c186}
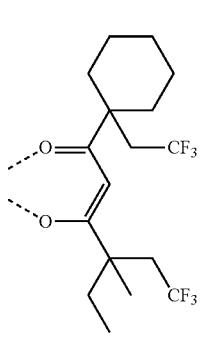

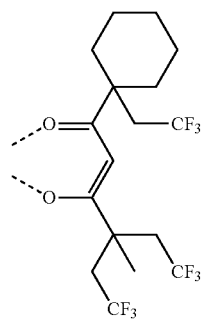 L<sub>c187</sub>
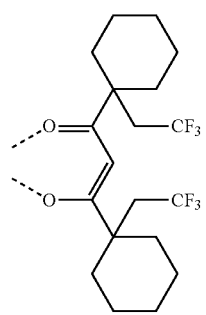 L<sub>c188</sub>
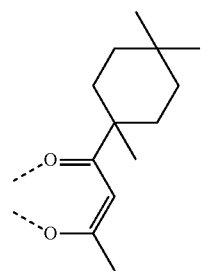 L<sub>c189</sub>
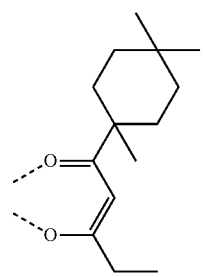 L<sub>c190</sub>
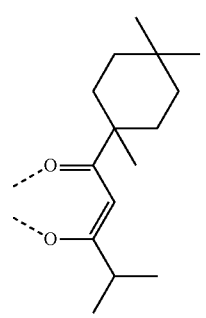 L<sub>c191</sub>
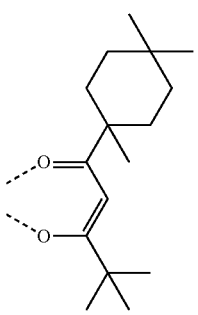 L<sub>c192</sub>
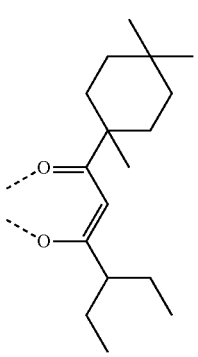 L<sub>c193</sub>
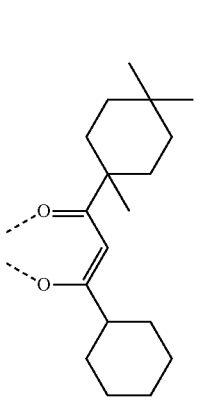 L<sub>c194</sub>
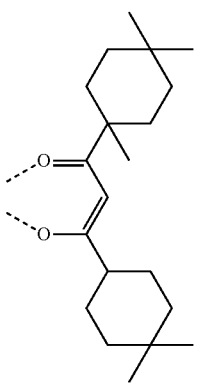 L<sub>c195</sub>

| | |
|---|---|
| 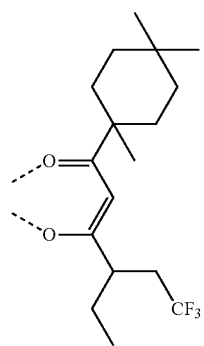 $L_{c196}$ | 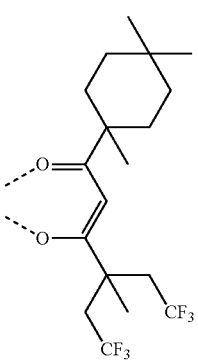 $L_{c200}$ |
| 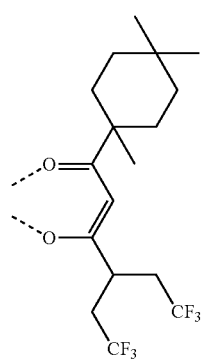 $L_{c197}$ | 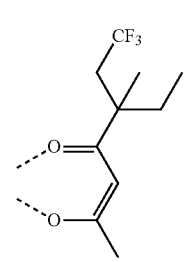 $L_{c201}$ |
| 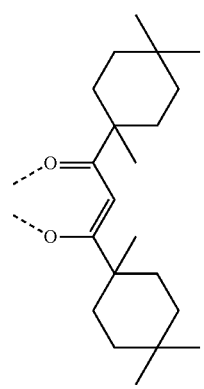 $L_{c198}$ | 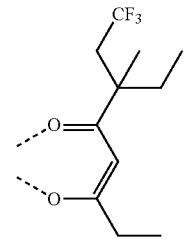 $L_{c202}$ |
| | 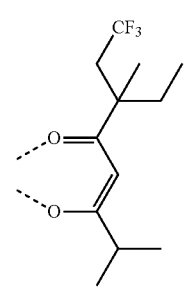 $L_{c203}$ |
| 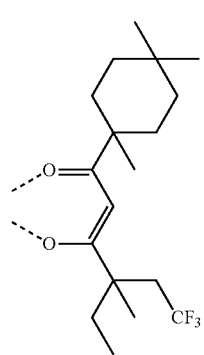 $L_{c199}$ | 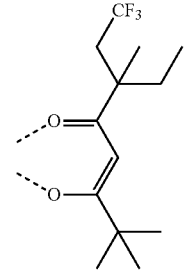 $L_{c204}$ |

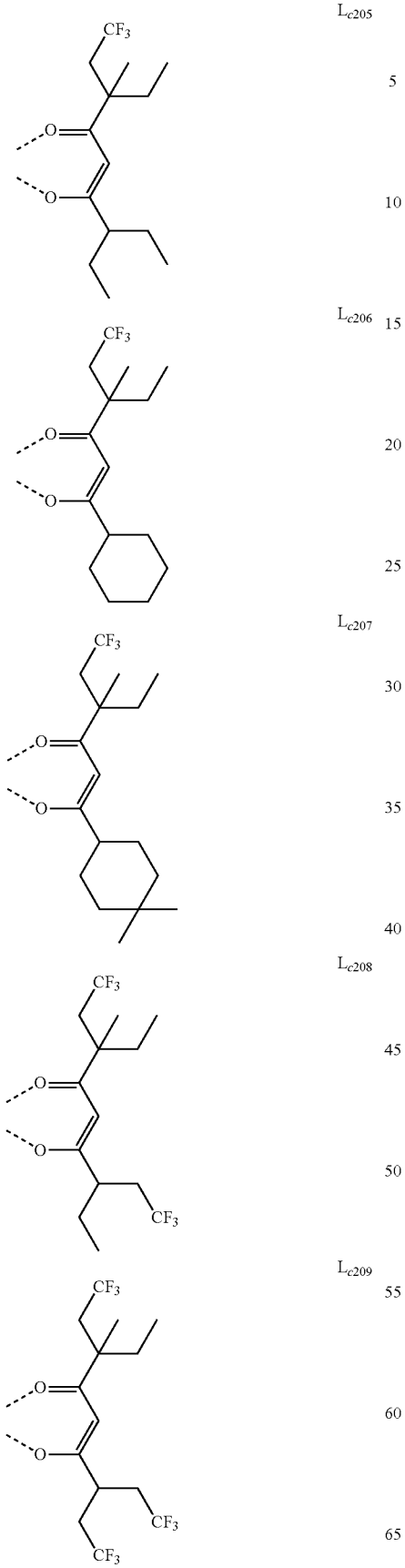
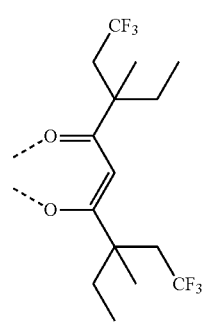
L$_{c210}$
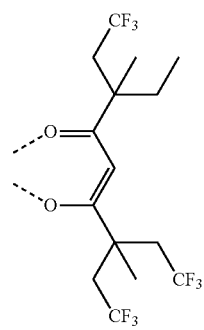
L$_{c211}$
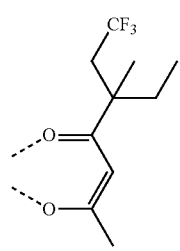
L$_{c212}$
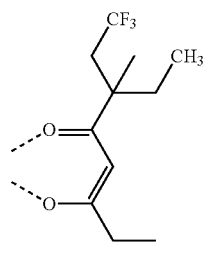
L$_{c213}$
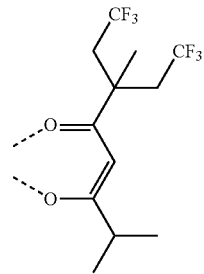
L$_{c214}$

| | |
|---|---|
| 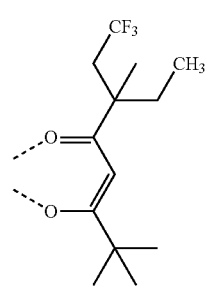 | $L_{c215}$ |
| 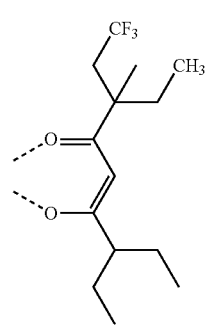 | $L_{c216}$ |
| 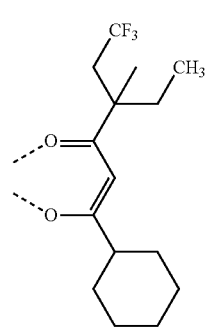 | $L_{c217}$ |
| 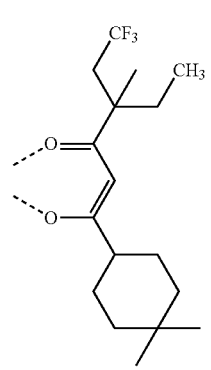 | $L_{c218}$ |
| 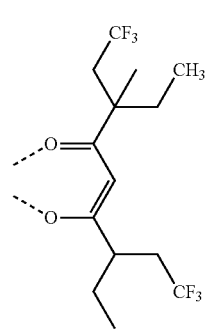 | $L_{c219}$ |
| | |
|---|---|
| 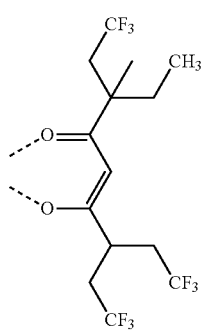 | $L_{c220}$ |
| 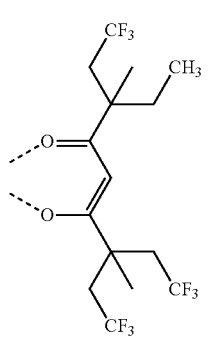 | $L_{c221}$ |
| 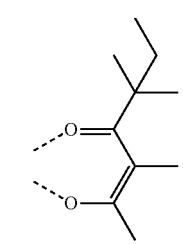 | $L_{c222}$ |
| 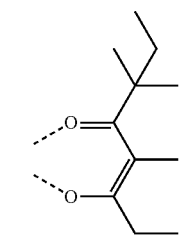 | $L_{c223}$ |
| 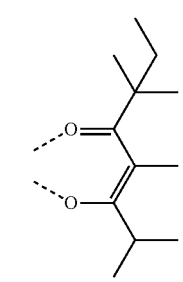 | $L_{c224}$ |

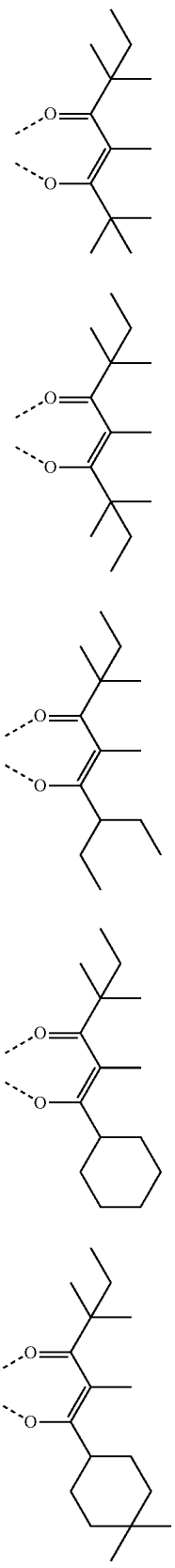
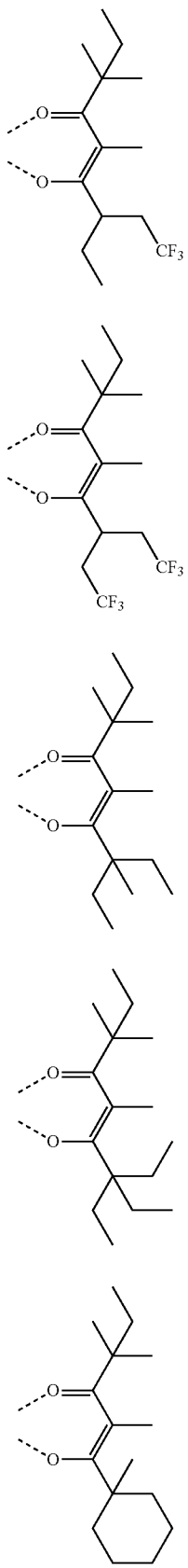

| | |
|---|---|
| 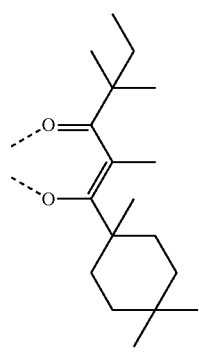 | $L_{c235}$ |
| 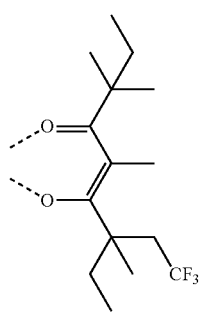 | $L_{c236}$ |
| 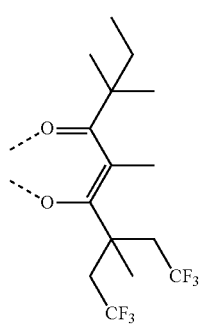 | $L_{c237}$ |
| 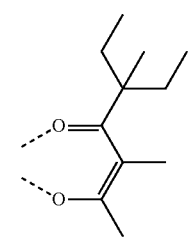 | $L_{c238}$ |
| 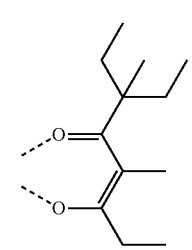 | $L_{c239}$ |
| 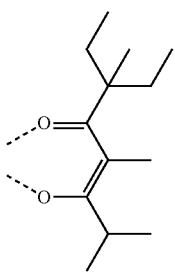 | $L_{c240}$ |
| 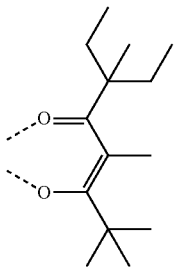 | $L_{c241}$ |
| 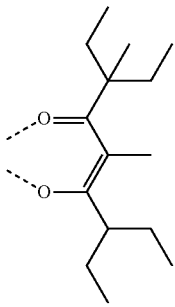 | $L_{c242}$ |
| 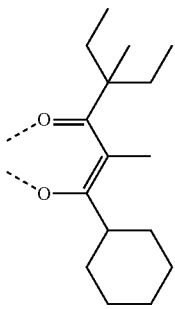 | $L_{c243}$ |
| 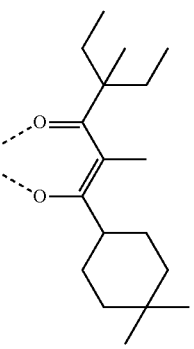 | $L_{c244}$ |

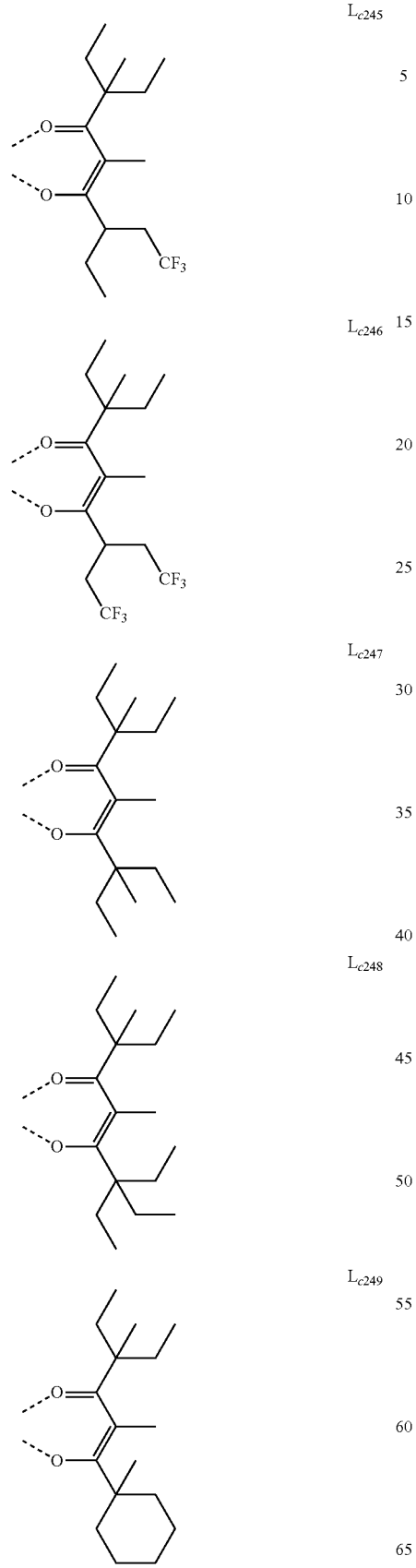
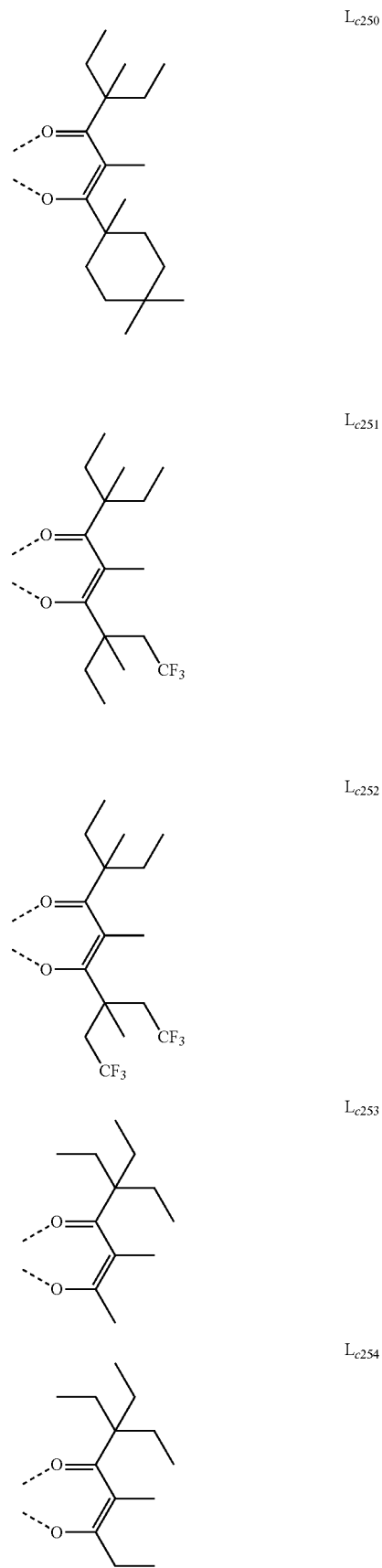

L_{c255} 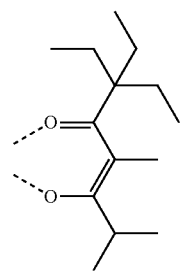
L_{c256} 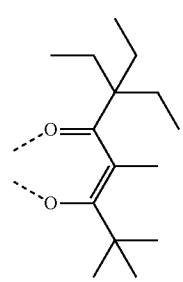
L_{c257} 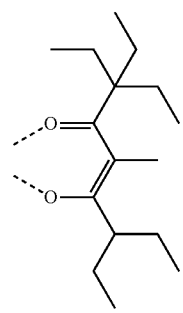
L_{c258} 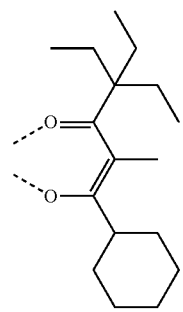
L_{c259} 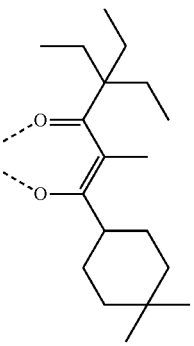
L_{c260} 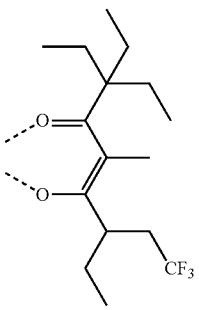
L_{c261} 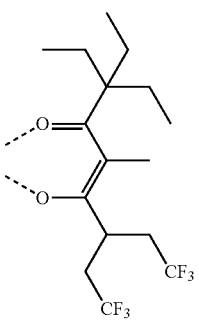
L_{c262} 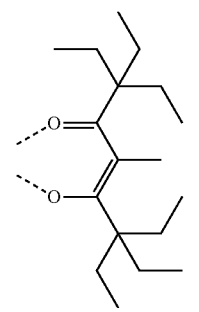
L_{c263} 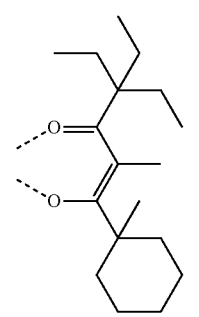
L_{c264} 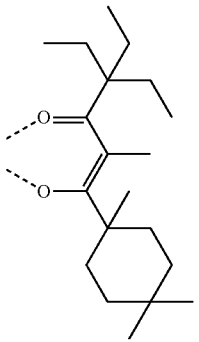

L_{c265}
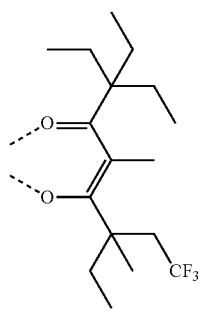
L_{c266}
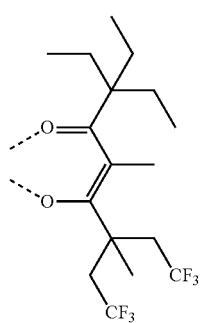
L_{c267}
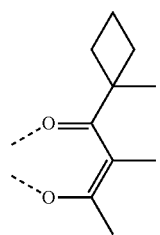
L_{c268}
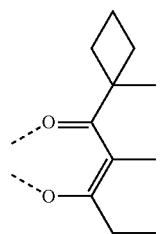
L_{c269}
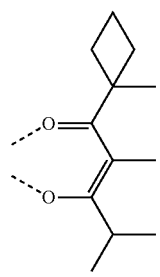
L_{c270}
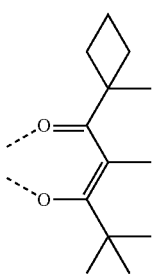
L_{c271}
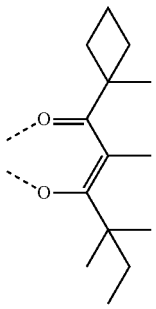
L_{c272}
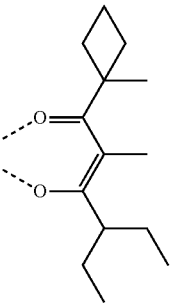
L_{c273}
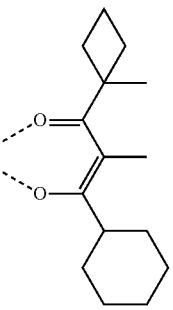
L_{c274}
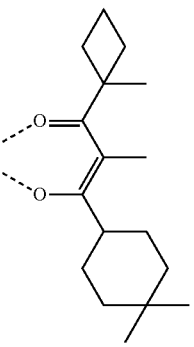

L*c275*
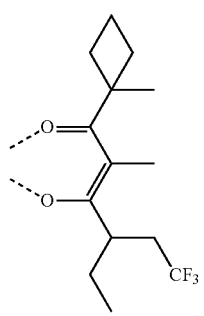
L*c276*
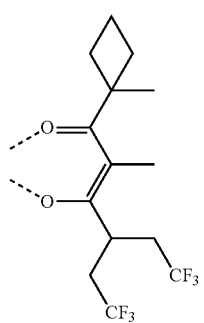
L*c277*
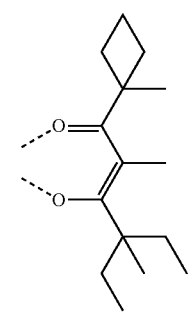
L*c278*
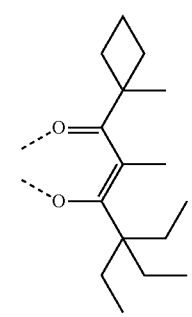
L*c279*
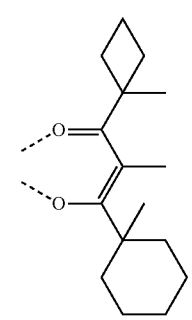
L*c280*
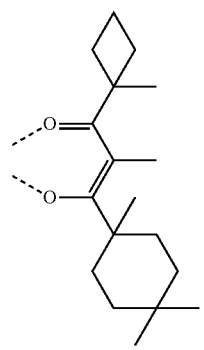
L*c281*
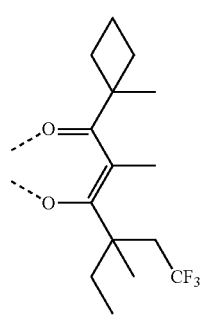
L*c282*
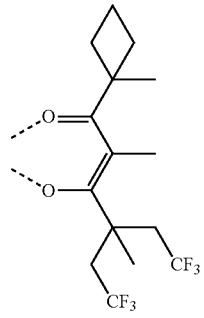
L*c283*
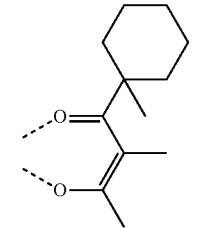
L*c284*
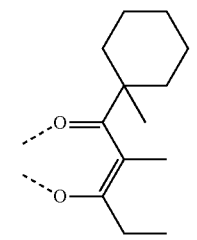

L_{c285}
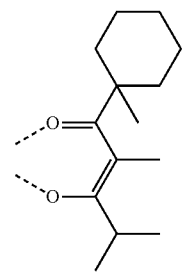
L_{c286}
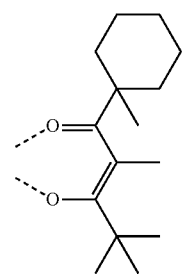
L_{c287}
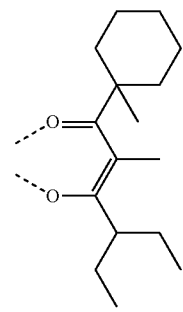
L_{c288}
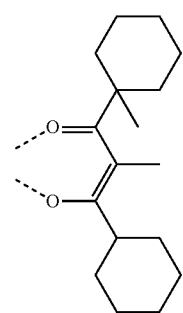
L_{c289}
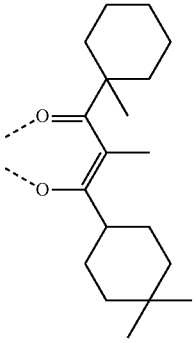
L_{c290}
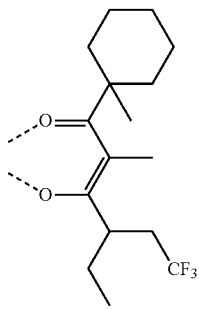
L_{c291}
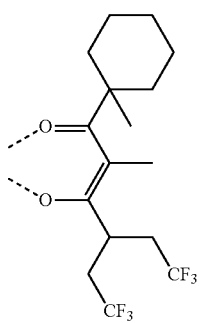
L_{c292}
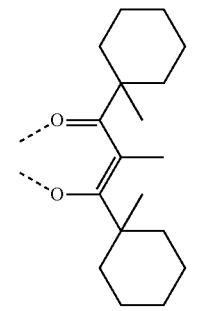
L_{c293}
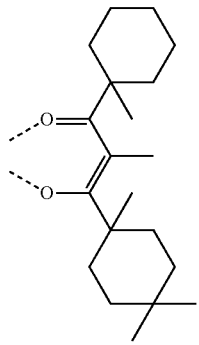
L_{c294}
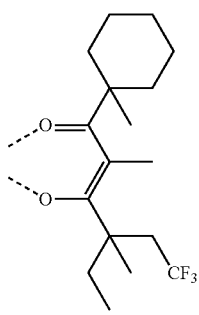

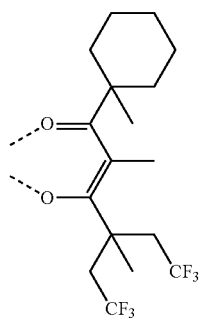
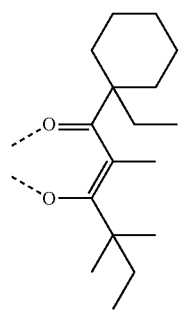
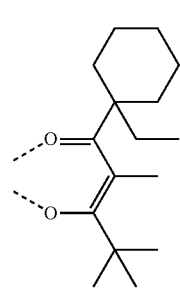

L_{c305}
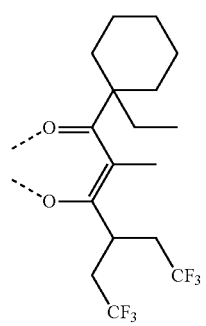
L_{c306}
L_{c307}
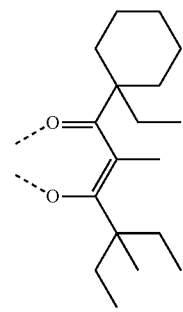
L_{c308}
L_{c309}
L_{c310}
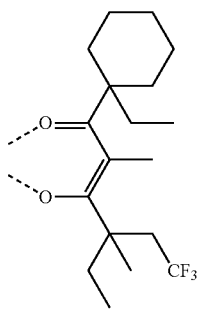
L_{c311}
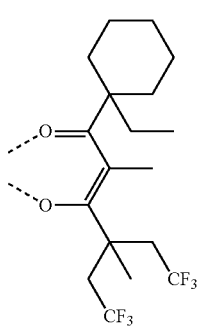
L_{c312}
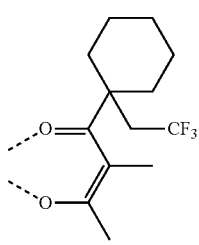
L_{c313}
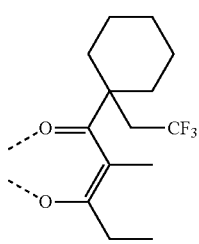
L_{c314}
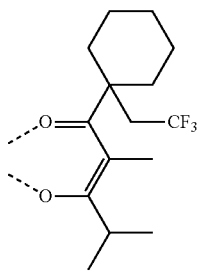

$L_{c315}$
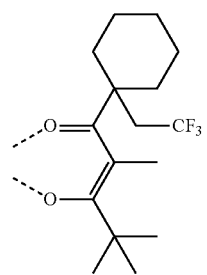
$L_{c316}$
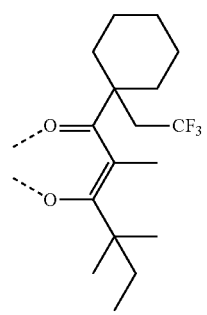
$L_{c317}$
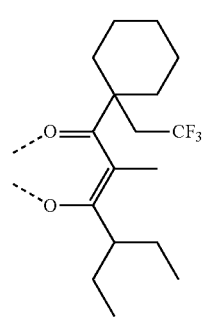
$L_{c318}$
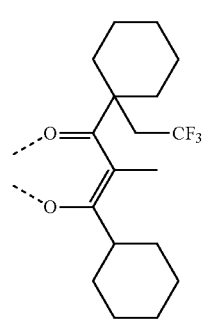
$L_{c319}$
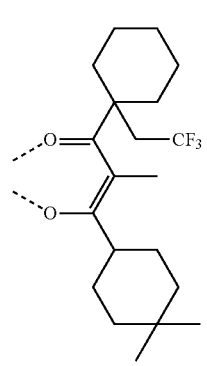
$L_{c320}$
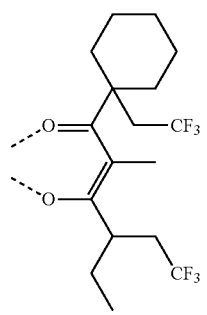
$L_{c321}$
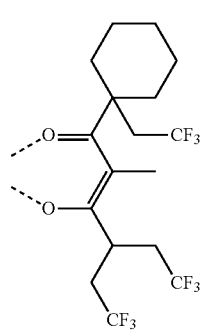
$L_{c322}$
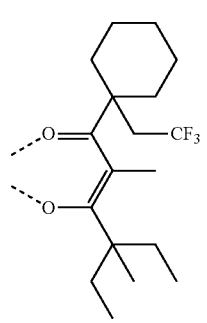
$L_{c323}$
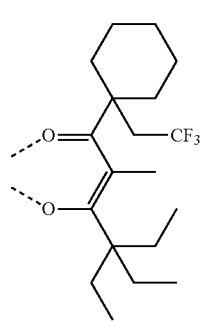
$L_{c324}$
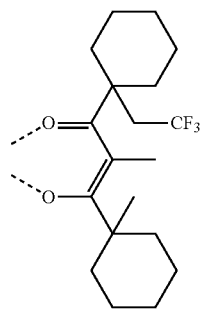

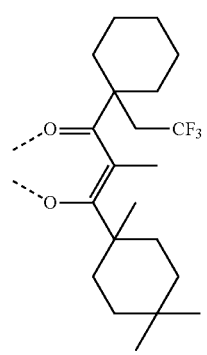 L$_{c325}$
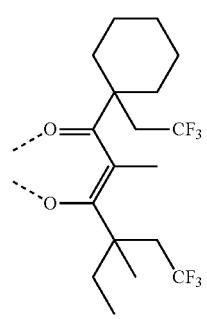 L$_{c326}$
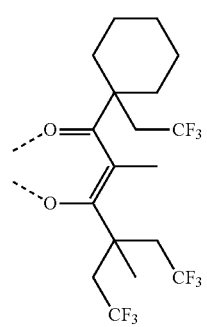 L$_{c327}$
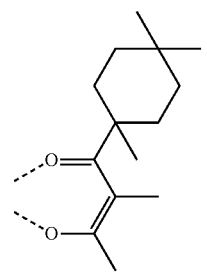 L$_{c328}$
L$_{c329}$
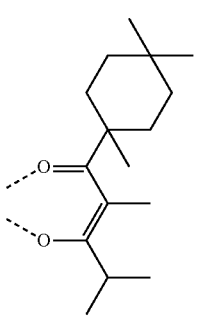 L$_{c330}$
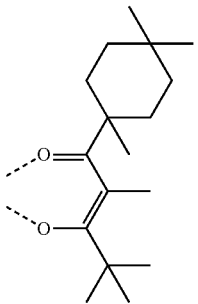 L$_{c331}$
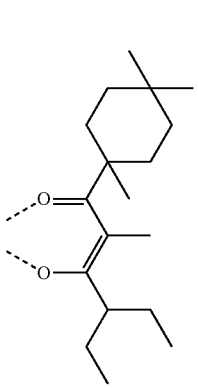 L$_{c332}$
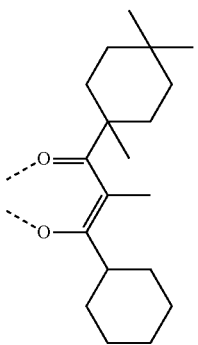 L$_{c333}$ 411
-continued
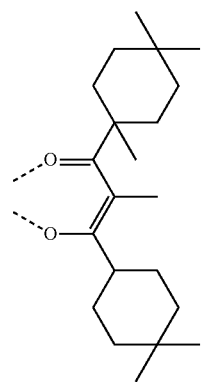
L<sub>c334</sub>
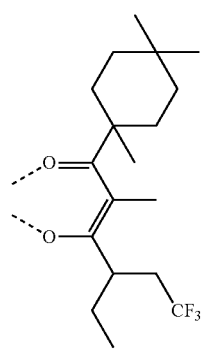
L<sub>c335</sub>
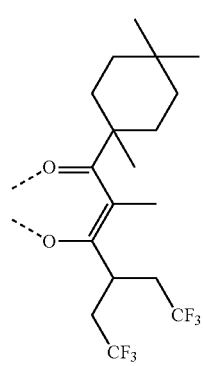
L<sub>c336</sub>
412
-continued
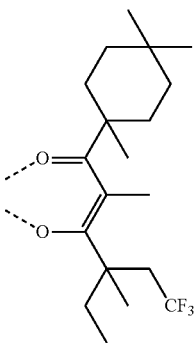
L<sub>c338</sub>
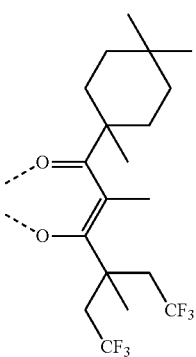
L<sub>c339</sub>
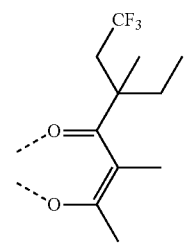
L<sub>c340</sub>
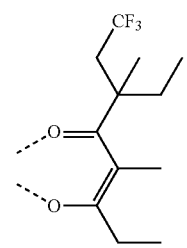
L<sub>c341</sub>
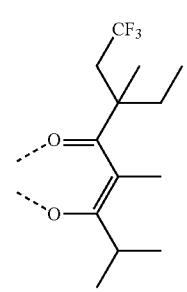
L<sub>c342</sub>

-continued
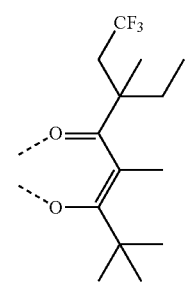
L<sub>c343</sub>
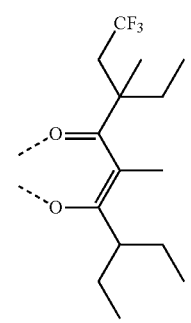
L<sub>c344</sub>
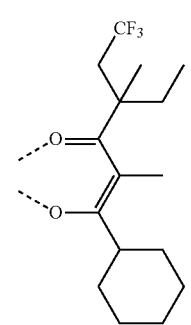
L<sub>c345</sub>
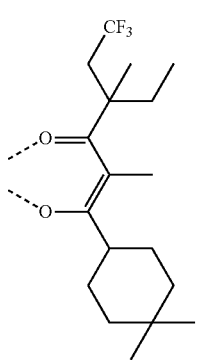
L<sub>c346</sub>
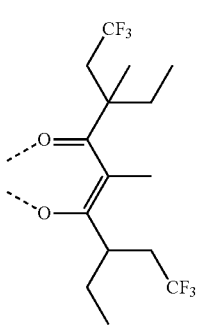
L<sub>c347</sub>
-continued
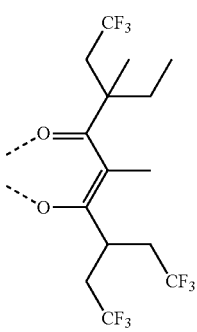
L<sub>c348</sub>
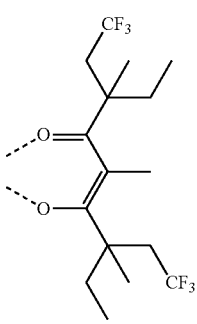
L<sub>c349</sub>
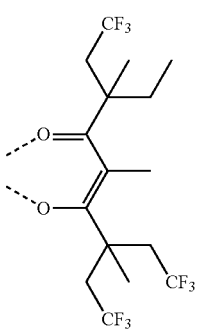
L<sub>c350</sub>
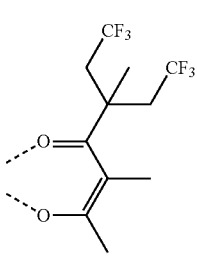
L<sub>c351</sub>
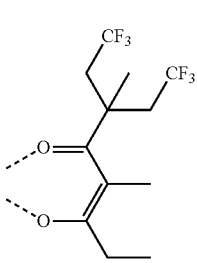
L<sub>c352</sub>

L_{c353} 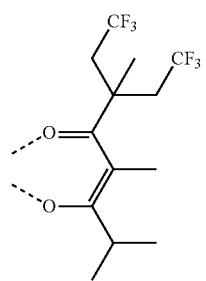

L_{c354} 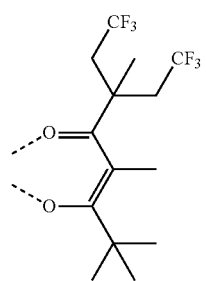

L_{c355} 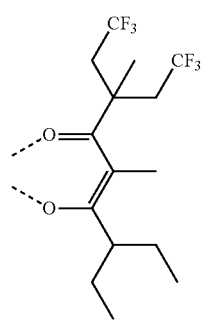

L_{c356} 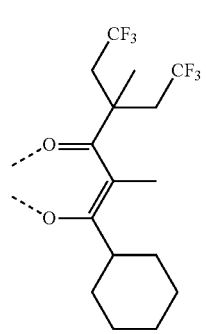

L_{c357} 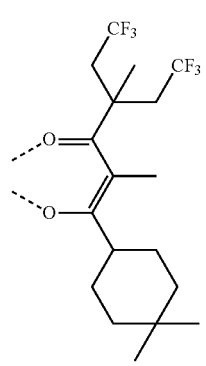

L_{c358} 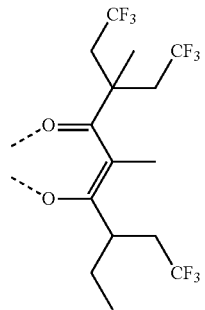

L_{c359} 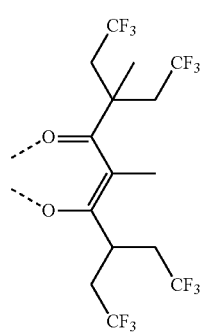

L_{c360} 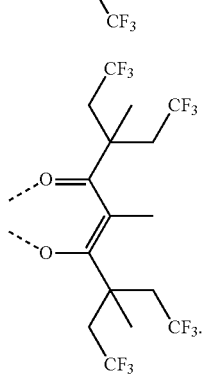

13. The metal complex according to claim 1, wherein the metal complex has a structure represented by any one selected from the group consisting of Metal complex 1 to Metal complex 316:

wherein, Metal complex 1 to Metal complex 226 have the structure of $IrL_a(L_b)_2$, wherein two $L_b$ are the same, wherein $L_a$ and $L_b$ correspond to the structures as shown in the following table, respectively:

| Metal complex | $L_a$ | $L_b$ | Metal complex | $L_a$ | $L_b$ |
|---|---|---|---|---|---|
| 1 | $L_{a1}$ | $L_{b1}$ | 2 | $L_{a2}$ | $L_{b1}$ |
| 3 | $L_{a3}$ | $L_{b1}$ | 4 | $L_{a4}$ | $L_{b1}$ |
| 5 | $L_{a121}$ | $L_{b1}$ | 6 | $L_{a122}$ | $L_{b1}$ |
| 7 | $L_{a123}$ | $L_{b1}$ | 8 | $L_{a137}$ | $L_{b1}$ |
| 9 | $L_{a138}$ | $L_{b1}$ | 10 | $L_{a139}$ | $L_{b1}$ |
| 11 | $L_{a153}$ | $L_{b1}$ | 12 | $L_{a154}$ | $L_{b1}$ |
| 13 | $L_{a155}$ | $L_{b1}$ | 14 | $L_{a169}$ | $L_{b1}$ |
| 15 | $L_{a170}$ | $L_{b1}$ | 16 | $L_{a171}$ | $L_{b1}$ |
| 17 | $L_{a221}$ | $L_{b1}$ | 18 | $L_{a222}$ | $L_{b1}$ |
| 19 | $L_{a293}$ | $L_{b1}$ | 20 | $L_{a294}$ | $L_{b1}$ |
| 21 | $L_{a295}$ | $L_{b1}$ | 22 | $L_{a297}$ | $L_{b1}$ |
| 23 | $L_{a298}$ | $L_{b1}$ | 24 | $L_{a299}$ | $L_{b1}$ |
| 25 | $L_{a313}$ | $L_{b1}$ | 26 | $L_{a314}$ | $L_{b1}$ |
| 27 | $L_{a415}$ | $L_{b1}$ | 28 | $L_{a416}$ | $L_{b1}$ |
| 29 | $L_{a467}$ | $L_{b1}$ | 30 | $L_{a468}$ | $L_{b1}$ |
| 31 | $L_{a487}$ | $L_{b1}$ | 32 | $L_{a488}$ | $L_{b1}$ |

-continued

| Metal complex | $L_a$ | $L_b$ | Metal complex | $L_a$ | $L_b$ |
|---|---|---|---|---|---|
| 33 | $L_{a507}$ | $L_{b1}$ | 34 | $L_{a508}$ | $L_{b1}$ |
| 35 | $L_{a516}$ | $L_{b1}$ | 36 | $L_{a517}$ | $L_{b1}$ |
| 37 | $L_{a527}$ | $L_{b1}$ | 38 | $L_{a528}$ | $L_{b1}$ |
| 39 | $L_{a547}$ | $L_{b1}$ | 40 | $L_{a548}$ | $L_{b1}$ |
| 41 | $L_{a576}$ | $L_{b1}$ | 42 | $L_{a577}$ | $L_{b1}$ |
| 43 | $L_{a592}$ | $L_{b1}$ | 44 | $L_{a593}$ | $L_{b1}$ |
| 45 | $L_{a640}$ | $L_{b1}$ | 46 | $L_{a652}$ | $L_{b1}$ |
| 47 | $L_{a692}$ | $L_{b1}$ | 48 | $L_{a693}$ | $L_{b1}$ |
| 49 | $L_{a704}$ | $L_{b1}$ | 50 | $L_{a842}$ | $L_{b1}$ |
| 51 | $L_{a854}$ | $L_{b1}$ | 52 | $L_{a896}$ | $L_{b1}$ |
| 53 | $L_{a962}$ | $L_{b1}$ | 54 | $L_{a966}$ | $L_{b1}$ |
| 55 | $L_{a970}$ | $L_{b1}$ | 56 | $L_{a973}$ | $L_{b1}$ |
| 57 | $L_{a974}$ | $L_{b1}$ | 58 | $L_{a975}$ | $L_{b1}$ |
| 59 | $L_{a976}$ | $L_{b1}$ | 60 | $L_{a978}$ | $L_{b1}$ |
| 61 | $L_{a985}$ | $L_{b1}$ | 62 | $L_{a987}$ | $L_{b1}$ |
| 63 | $L_{a988}$ | $L_{b1}$ | 64 | $L_{a999}$ | $L_{b1}$ |
| 65 | $L_{a1003}$ | $L_{b1}$ | 66 | $L_{a1010}$ | $L_{b1}$ |
| 67 | $L_{a1}$ | $L_{b3}$ | 68 | $L_{a2}$ | $L_{b3}$ |
| 69 | $L_{a3}$ | $L_{b3}$ | 70 | $L_{a4}$ | $L_{b3}$ |
| 71 | $L_{a121}$ | $L_{b3}$ | 72 | $L_{a122}$ | $L_{b3}$ |
| 73 | $L_{a123}$ | $L_{b3}$ | 74 | $L_{a137}$ | $L_{b3}$ |
| 75 | $L_{a138}$ | $L_{b3}$ | 76 | $L_{a139}$ | $L_{b3}$ |
| 77 | $L_{a293}$ | $L_{b3}$ | 78 | $L_{a294}$ | $L_{b3}$ |
| 79 | $L_{a297}$ | $L_{b3}$ | 80 | $L_{a298}$ | $L_{b3}$ |
| 81 | $L_{a576}$ | $L_{b3}$ | 82 | $L_{a577}$ | $L_{b3}$ |
| 83 | $L_{a592}$ | $L_{b3}$ | 84 | $L_{a593}$ | $L_{b3}$ |
| 85 | $L_{a640}$ | $L_{b3}$ | 86 | $L_{a652}$ | $L_{b3}$ |
| 87 | $L_{a692}$ | $L_{b3}$ | 88 | $L_{a693}$ | $L_{b3}$ |
| 89 | $L_{a704}$ | $L_{b3}$ | 90 | $L_{a842}$ | $L_{b3}$ |
| 91 | $L_{a854}$ | $L_{b3}$ | 92 | $L_{a896}$ | $L_{b3}$ |
| 93 | $L_{a962}$ | $L_{b3}$ | 94 | $L_{a966}$ | $L_{b3}$ |
| 95 | $L_{a970}$ | $L_{b3}$ | 96 | $L_{a973}$ | $L_{b3}$ |
| 97 | $L_{a974}$ | $L_{b3}$ | 98 | $L_{a975}$ | $L_{b3}$ |
| 99 | $L_{a976}$ | $L_{b3}$ | 100 | $L_{a978}$ | $L_{b3}$ |
| 101 | $L_{a985}$ | $L_{b3}$ | 102 | $L_{a987}$ | $L_{b3}$ |
| 103 | $L_{a988}$ | $L_{b3}$ | 104 | $L_{a999}$ | $L_{b3}$ |
| 105 | $L_{a1003}$ | $L_{b3}$ | 106 | $L_{a1010}$ | $L_{b3}$ |
| 107 | $L_{a1}$ | $L_{b4}$ | 108 | $L_{a2}$ | $L_{b4}$ |
| 109 | $L_{a3}$ | $L_{b4}$ | 110 | $L_{a4}$ | $L_{b4}$ |
| 111 | $L_{a121}$ | $L_{b4}$ | 112 | $L_{a122}$ | $L_{b4}$ |
| 113 | $L_{a123}$ | $L_{b4}$ | 114 | $L_{a137}$ | $L_{b4}$ |
| 115 | $L_{a138}$ | $L_{b4}$ | 116 | $L_{a139}$ | $L_{b4}$ |
| 117 | $L_{a293}$ | $L_{b4}$ | 118 | $L_{a294}$ | $L_{b4}$ |
| 119 | $L_{a297}$ | $L_{b4}$ | 120 | $L_{a298}$ | $L_{b4}$ |
| 121 | $L_{a576}$ | $L_{b4}$ | 122 | $L_{a577}$ | $L_{b4}$ |
| 123 | $L_{a592}$ | $L_{b4}$ | 124 | $L_{a593}$ | $L_{b4}$ |
| 125 | $L_{a640}$ | $L_{b4}$ | 126 | $L_{a652}$ | $L_{b4}$ |
| 127 | $L_{a692}$ | $L_{b4}$ | 128 | $L_{a693}$ | $L_{b4}$ |
| 129 | $L_{a704}$ | $L_{b4}$ | 130 | $L_{a842}$ | $L_{b4}$ |
| 131 | $L_{a854}$ | $L_{b4}$ | 132 | $L_{a896}$ | $L_{b4}$ |
| 133 | $L_{a962}$ | $L_{b4}$ | 134 | $L_{a966}$ | $L_{b4}$ |
| 135 | $L_{a970}$ | $L_{b4}$ | 136 | $L_{a973}$ | $L_{b4}$ |
| 137 | $L_{a974}$ | $L_{b4}$ | 138 | $L_{a975}$ | $L_{b4}$ |
| 139 | $L_{a976}$ | $L_{b4}$ | 140 | $L_{a978}$ | $L_{b4}$ |
| 141 | $L_{a985}$ | $L_{b4}$ | 142 | $L_{a987}$ | $L_{b4}$ |
| 143 | $L_{a988}$ | $L_{b4}$ | 144 | $L_{a999}$ | $L_{b4}$ |
| 145 | $L_{a1003}$ | $L_{b4}$ | 146 | $L_{a1010}$ | $L_{b4}$ |
| 147 | $L_{a1}$ | $L_{b8}$ | 148 | $L_{a2}$ | $L_{b8}$ |
| 149 | $L_{a3}$ | $L_{b8}$ | 150 | $L_{a4}$ | $L_{b8}$ |
| 151 | $L_{a121}$ | $L_{b8}$ | 152 | $L_{a122}$ | $L_{b8}$ |
| 153 | $L_{a123}$ | $L_{b8}$ | 154 | $L_{a137}$ | $L_{b8}$ |
| 155 | $L_{a138}$ | $L_{b8}$ | 156 | $L_{a139}$ | $L_{b8}$ |
| 157 | $L_{a293}$ | $L_{b8}$ | 158 | $L_{a294}$ | $L_{b8}$ |
| 159 | $L_{a297}$ | $L_{b8}$ | 160 | $L_{a298}$ | $L_{b8}$ |
| 161 | $L_{a576}$ | $L_{b8}$ | 162 | $L_{a577}$ | $L_{b8}$ |
| 163 | $L_{a592}$ | $L_{b8}$ | 164 | $L_{a593}$ | $L_{b8}$ |
| 165 | $L_{a640}$ | $L_{b8}$ | 166 | $L_{a652}$ | $L_{b8}$ |
| 167 | $L_{a692}$ | $L_{b8}$ | 168 | $L_{a693}$ | $L_{b8}$ |
| 169 | $L_{a704}$ | $L_{b8}$ | 170 | $L_{a842}$ | $L_{b8}$ |
| 171 | $L_{a854}$ | $L_{b8}$ | 172 | $L_{a896}$ | $L_{b8}$ |
| 173 | $L_{a962}$ | $L_{b8}$ | 174 | $L_{a966}$ | $L_{b8}$ |
| 175 | $L_{a970}$ | $L_{b8}$ | 176 | $L_{a973}$ | $L_{b8}$ |
| 177 | $L_{a974}$ | $L_{b8}$ | 178 | $L_{a975}$ | $L_{b8}$ |
| 179 | $L_{a976}$ | $L_{b8}$ | 180 | $L_{a978}$ | $L_{b8}$ |
| 181 | $L_{a985}$ | $L_{b8}$ | 182 | $L_{a987}$ | $L_{b8}$ |
| 183 | $L_{a988}$ | $L_{b8}$ | 184 | $L_{a999}$ | $L_{b8}$ |
| 185 | $L_{a1003}$ | $L_{b8}$ | 186 | $L_{a1010}$ | $L_{b8}$ |
| 187 | $L_{a1}$ | $L_{b30}$ | 188 | $L_{a2}$ | $L_{b30}$ |
| 189 | $L_{a3}$ | $L_{b30}$ | 110 | $L_{a4}$ | $L_{b30}$ |
| 191 | $L_{a121}$ | $L_{b30}$ | 192 | $L_{a122}$ | $L_{b30}$ |
| 193 | $L_{a123}$ | $L_{b30}$ | 194 | $L_{a137}$ | $L_{b30}$ |
| 195 | $L_{a138}$ | $L_{b30}$ | 196 | $L_{a139}$ | $L_{b30}$ |
| 197 | $L_{a293}$ | $L_{b30}$ | 198 | $L_{a294}$ | $L_{b30}$ |
| 199 | $L_{a297}$ | $L_{b30}$ | 200 | $L_{a298}$ | $L_{b30}$ |
| 201 | $L_{a576}$ | $L_{b30}$ | 202 | $L_{a577}$ | $L_{b30}$ |
| 203 | $L_{a592}$ | $L_{b30}$ | 204 | $L_{a593}$ | $L_{b30}$ |
| 205 | $L_{a640}$ | $L_{b30}$ | 206 | $L_{a652}$ | $L_{b30}$ |
| 207 | $L_{a692}$ | $L_{b30}$ | 208 | $L_{a693}$ | $L_{b30}$ |
| 209 | $L_{a704}$ | $L_{b30}$ | 210 | $L_{a842}$ | $L_{b30}$ |
| 211 | $L_{a854}$ | $L_{b30}$ | 212 | $L_{a896}$ | $L_{b30}$ |
| 213 | $L_{a962}$ | $L_{b30}$ | 214 | $L_{a966}$ | $L_{b30}$ |
| 215 | $L_{a970}$ | $L_{b30}$ | 216 | $L_{a973}$ | $L_{b30}$ |
| 217 | $L_{a974}$ | $L_{b30}$ | 218 | $L_{a975}$ | $L_{b30}$ |
| 219 | $L_{a976}$ | $L_{b30}$ | 220 | $L_{a978}$ | $L_{b30}$ |
| 221 | $L_{a985}$ | $L_{b30}$ | 222 | $L_{a987}$ | $L_{b30}$ |
| 223 | $L_{a988}$ | $L_{b30}$ | 224 | $L_{a999}$ | $L_{b30}$ |
| 225 | $L_{a1003}$ | $L_{b30}$ | 226 | $L_{a1010}$ | $L_{b30}$ | wherein, Metal complex 227 to Metal complex 274 have the structure of $Ir(L_a)_2L_c$, wherein two $L_a$ are the same, wherein $L_a$ and $L_c$ correspond to the structures as shown in the following table, respectively:

| Metal complex | $L_a$ | $L_c$ | Metal complex | $L_a$ | $L_c$ |
|---|---|---|---|---|---|
| 227 | $L_{a323}$ | $L_{c1}$ | 228 | $L_{a324}$ | $L_{c1}$ |
| 229 | $L_{a328}$ | $L_{c1}$ | 230 | $L_{a329}$ | $L_{c1}$ |
| 231 | $L_{a333}$ | $L_{c1}$ | 232 | $L_{a334}$ | $L_{c1}$ |
| 233 | $L_{a338}$ | $L_{c1}$ | 234 | $L_{a339}$ | $L_{c1}$ |
| 235 | $L_{a343}$ | $L_{c1}$ | 236 | $L_{a344}$ | $L_{c1}$ |
| 237 | $L_{a348}$ | $L_{c1}$ | 238 | $L_{a349}$ | $L_{c1}$ |
| 239 | $L_{a353}$ | $L_{c1}$ | 240 | $L_{a354}$ | $L_{c1}$ |
| 241 | $L_{a358}$ | $L_{c1}$ | 242 | $L_{a359}$ | $L_{c1}$ |
| 243 | $L_{a363}$ | $L_{c1}$ | 244 | $L_{a364}$ | $L_{c1}$ |
| 245 | $L_{a368}$ | $L_{c1}$ | 246 | $L_{a369}$ | $L_{c1}$ |
| 247 | $L_{a373}$ | $L_{c1}$ | 248 | $L_{a374}$ | $L_{c1}$ |
| 249 | $L_{a388}$ | $L_{c1}$ | 250 | $L_{a389}$ | $L_{c1}$ |
| 251 | $L_{a323}$ | $L_{31}$ | 252 | $L_{a324}$ | $L_{31}$ |
| 253 | $L_{a328}$ | $L_{31}$ | 254 | $L_{a329}$ | $L_{31}$ |
| 255 | $L_{a333}$ | $L_{31}$ | 256 | $L_{a334}$ | $L_{31}$ |
| 257 | $L_{a338}$ | $L_{31}$ | 258 | $L_{a339}$ | $L_{31}$ |
| 259 | $L_{a343}$ | $L_{31}$ | 260 | $L_{a344}$ | $L_{31}$ |
| 261 | $L_{a348}$ | $L_{31}$ | 262 | $L_{a349}$ | $L_{31}$ |
| 263 | $L_{a353}$ | $L_{31}$ | 264 | $L_{a354}$ | $L_{31}$ |
| 265 | $L_{a358}$ | $L_{31}$ | 266 | $L_{a359}$ | $L_{31}$ |
| 267 | $L_{a363}$ | $L_{31}$ | 268 | $L_{a364}$ | $L_{31}$ |
| 269 | $L_{a368}$ | $L_{31}$ | 270 | $L_{a369}$ | $L_{31}$ |
| 271 | $L_{a373}$ | $L_{31}$ | 272 | $L_{a374}$ | $L_{31}$ |
| 273 | $L_{a388}$ | $L_{31}$ | 274 | $L_{a389}$ | $L_{31}$ | wherein, Metal complex 275 to Metal complex 316 have the structure of $Ir(L_a)_3$, wherein three $L_a$ are the same, wherein $L_a$ corresponds to the structures as shown in the following table:

| Metal complex | $L_a$ |
|---|---|
| 275 | $L_{a1}$ |
| 276 | $L_{a2}$ |
| 277 | $L_{a3}$ |
| 278 | $L_{a121}$ |
| 279 | $L_{a122}$ |
| 280 | $L_{a137}$ |
| 281 | $L_{a138}$ |

-continued
| Metal complex | $L_a$ |
|---|---|
| 282 | $L_{a293}$ |
| 283 | $L_{a297}$ |
| 284 | $L_{a298}$ |
| 285 | $L_{a487}$ |
| 286 | $L_{a488}$ |
| 287 | $L_{a507}$ |
| 288 | $L_{a508}$ |
| 289 | $L_{a547}$ |
| 290 | $L_{a548}$ |
| 291 | $L_{a576}$ |
| 292 | $L_{a577}$ |
| 293 | $L_{a640}$ |
| 294 | $L_{a641}$ |
| 295 | $L_{a652}$ |
| 296 | $L_{a653}$ |
| 297 | $L_{a692}$ |
| 298 | $L_{a693}$ |
| 299 | $L_{a704}$ |
| 300 | $L_{a842}$ |
| 301 | $L_{a854}$ |
| 302 | $L_{a896}$ |
| 303 | $L_{a962}$ |
| 304 | $L_{a966}$ |
| 305 | $L_{a970}$ |
| 306 | $L_{a973}$ |
| 307 | $L_{a974}$ |
| 308 | $L_{a975}$ |
| 309 | $L_{a976}$ |
| 310 | $L_{a978}$ |
| 311 | $L_{a985}$ |
| 312 | $L_{a987}$ |
| 313 | $L_{a988}$ |
| 314 | $L_{a999}$ |
| 315 | $L_{a1003}$ |
| 316 | $L_{a1010}$. |
14. A compound selected from the group consisting of:
Compound 1
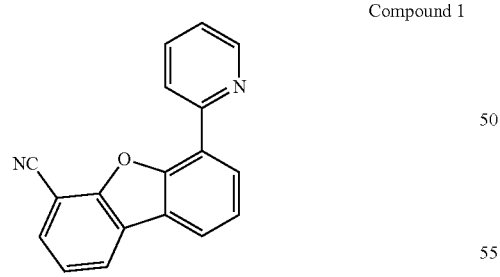
Compound 2
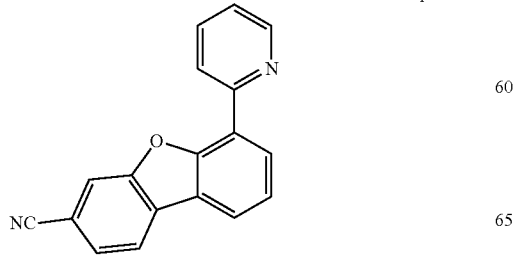
Compound 3
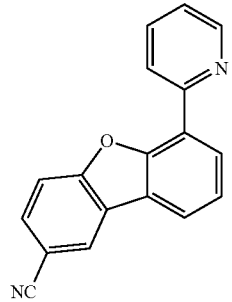
Compound 4
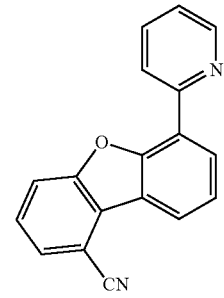
Compound 5
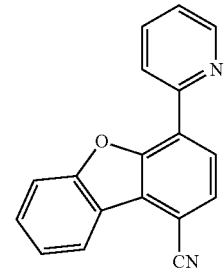
Compound 6
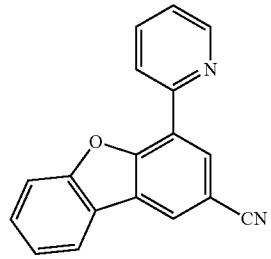
Compound 7
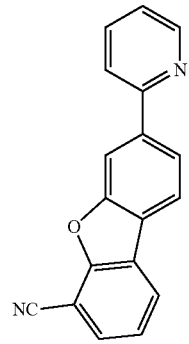

-continued
Compound 8
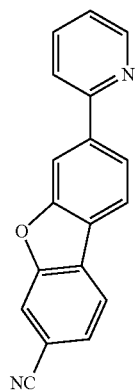
Compound 9
Compound 10
Compound 11
Compound 12
-continued
Compound 13
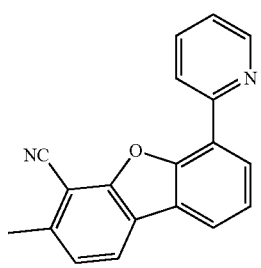
Compound 14
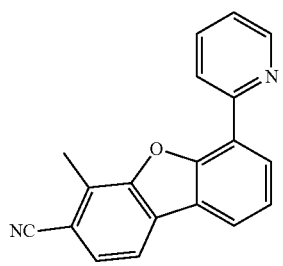
Compound 15
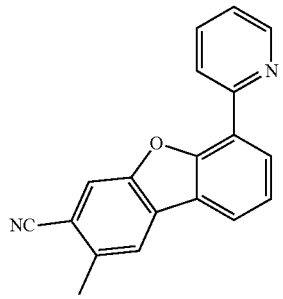
Compound 16
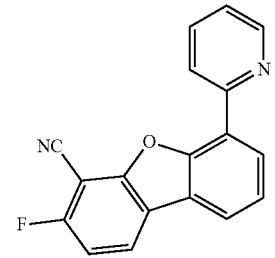
Compound 17
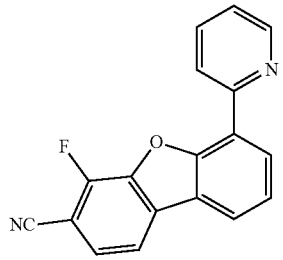

Compound 18
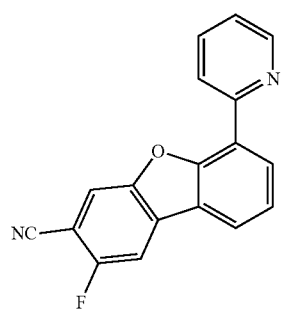
Compound 19
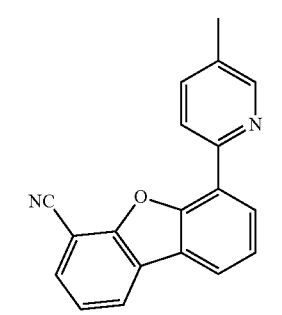
Compound 20
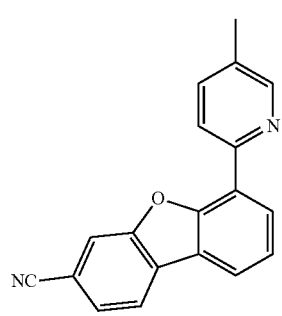
Compound 21
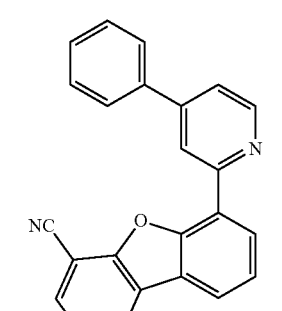
Compound 22
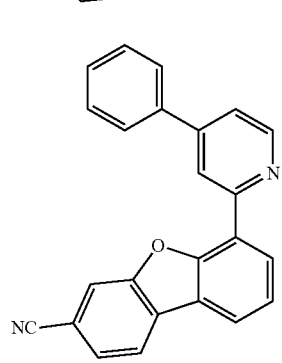
Compound 23
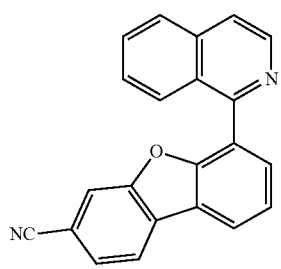
Compound 24
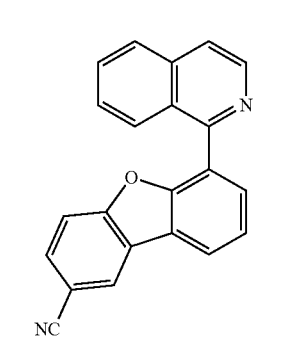
Compound 25
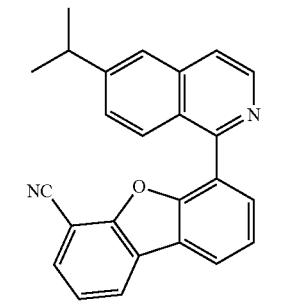
Compound 26
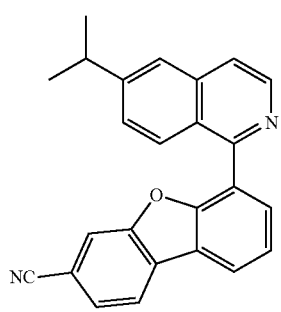
Compound 27
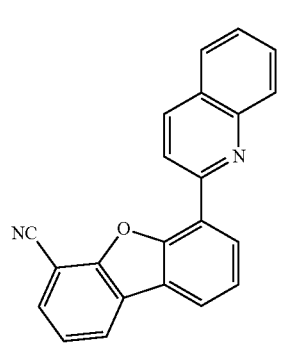

Compound 28
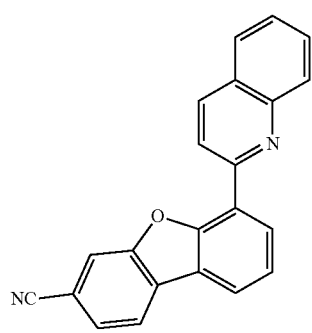
Compound 29
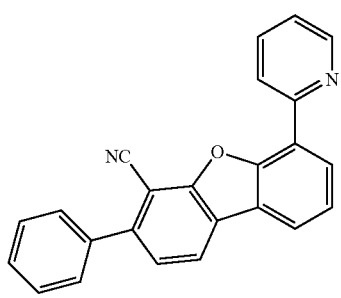
Compound 30
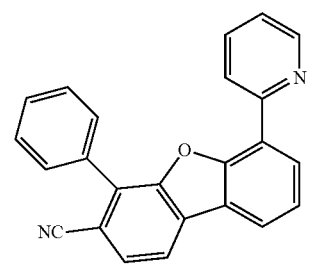
Compound 31
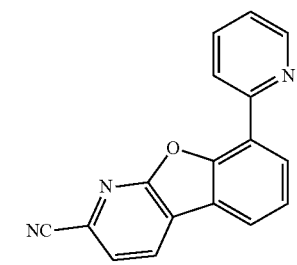
Compound 32
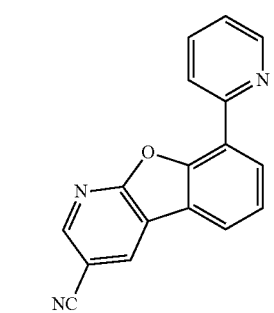
Compound 33
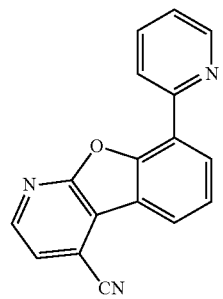
Compound 34
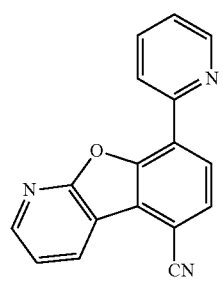
Compound 35
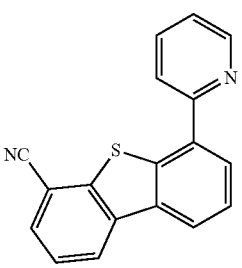
Compound 36
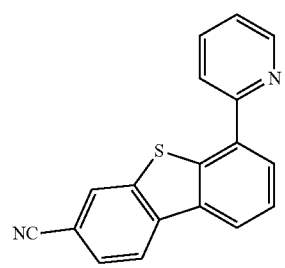
Compound 37
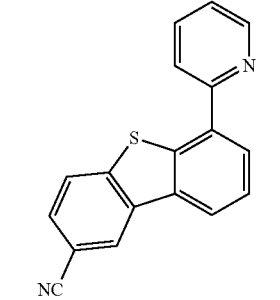

-continued
Compound 38
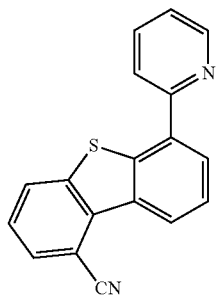
Compound 39
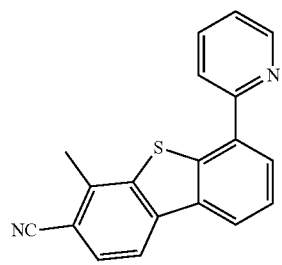
Compound 40
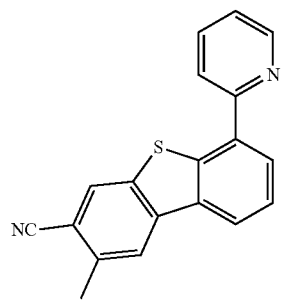
Compound 41
Compound 42
-continued
Compound 43
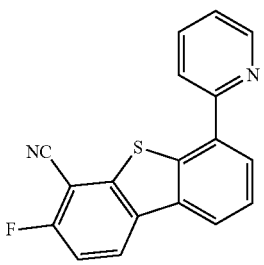
Compound 44
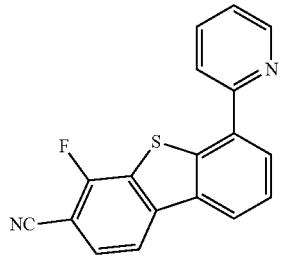
Compound 45
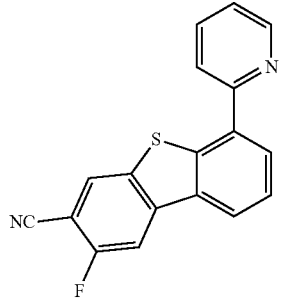
Compound 46
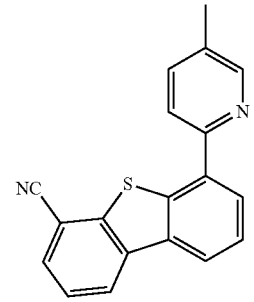
Compound 47
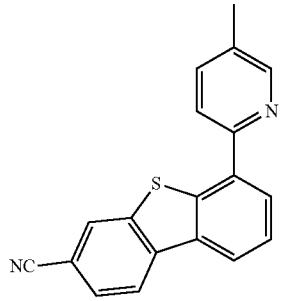

-continued
Compound 48
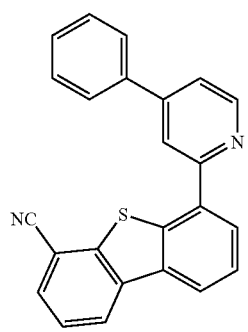
Compound 49
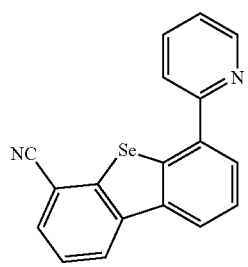
Compound 50
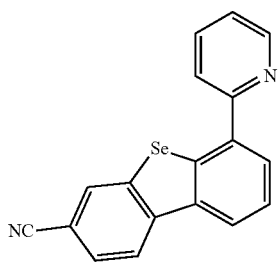
Compound 51
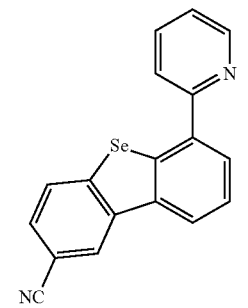
Compound 52
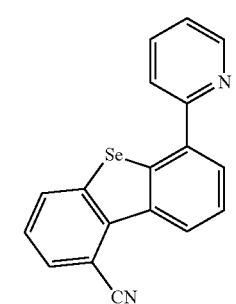
-continued
Compound 53
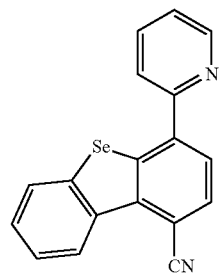
Compound 54
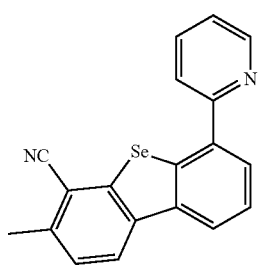
Compound 55
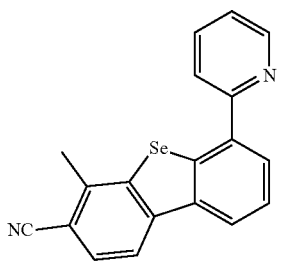
Compound 56
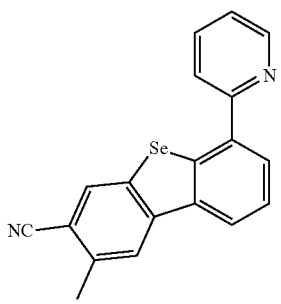
Compound 57
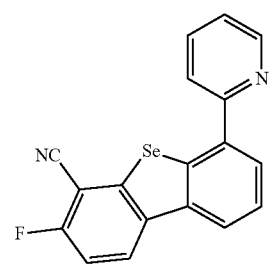
Compound 58
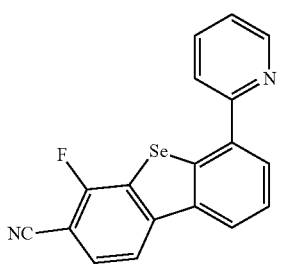

Compound 59
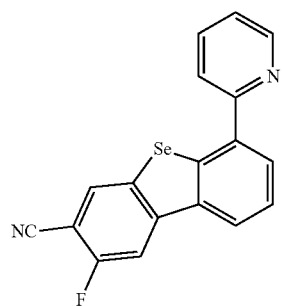
Compound 60
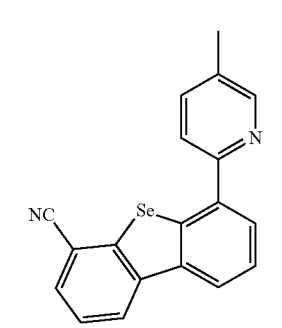
Compound 61
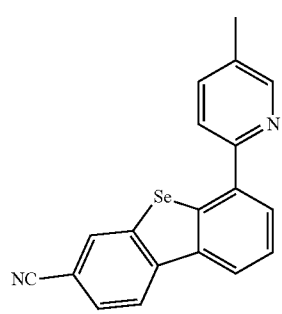
Compound 62
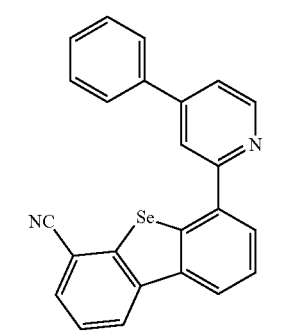
Compound 63
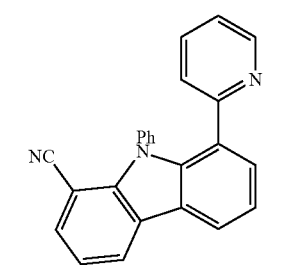
Compound 64
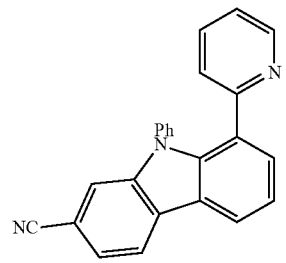
Compound 65
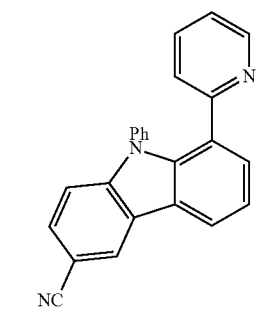
Compound 66
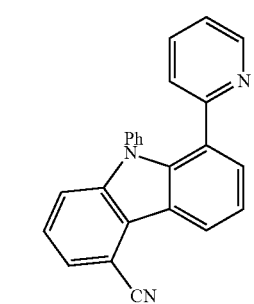
Compound 67
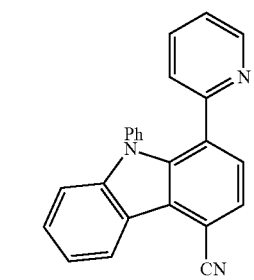
Compound 68
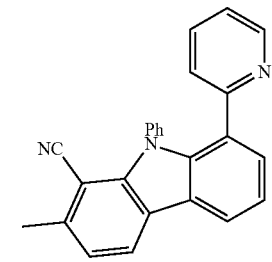

-continued
Compound 69
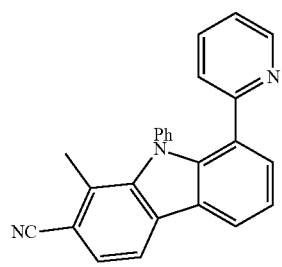
Compound 70
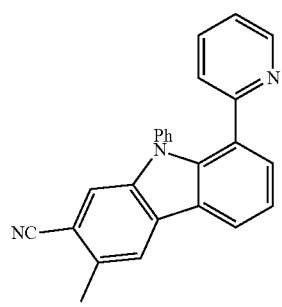
Compound 71
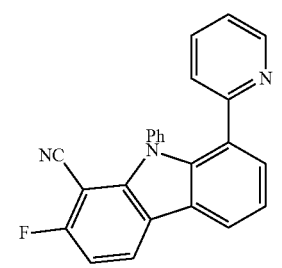
Compound 72
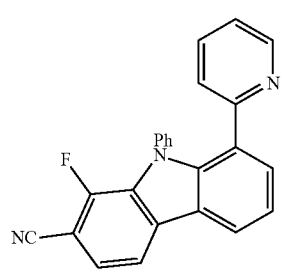
Compound 73
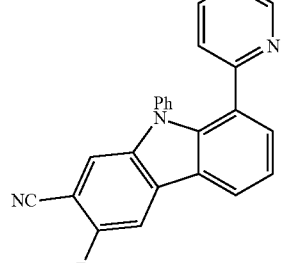
-continued
Compound 74
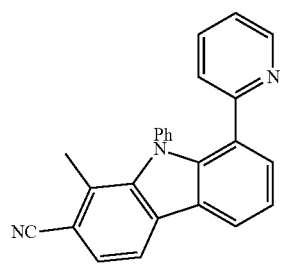
Compound 75
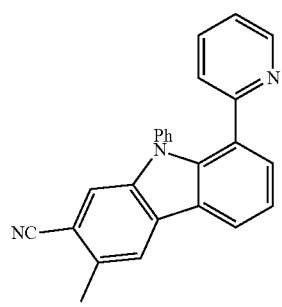
Compound 76
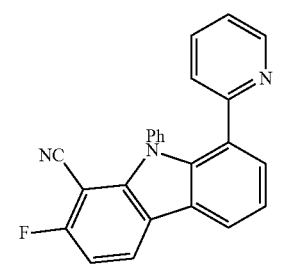
Compound 77
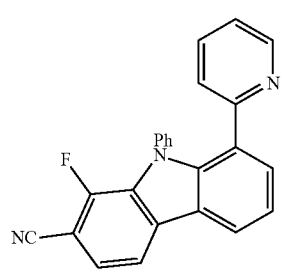
Compound 78
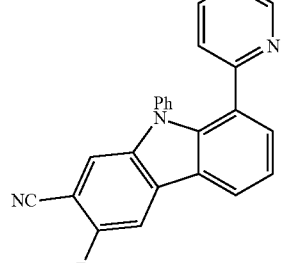

Compound 79
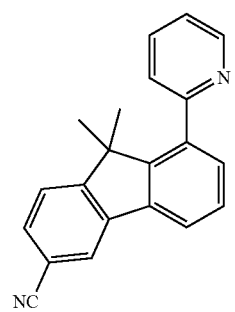
Compound 80
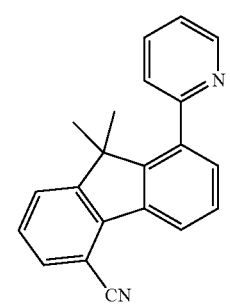
Compound 81
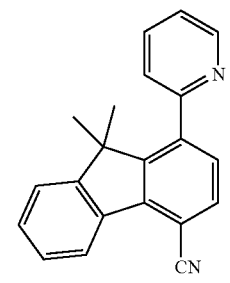
Compound 82
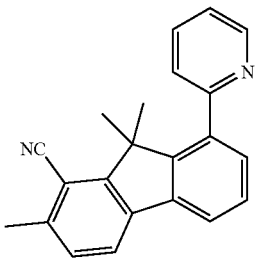
Compound 83
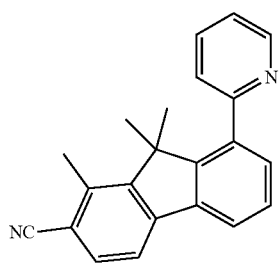
Compound 84
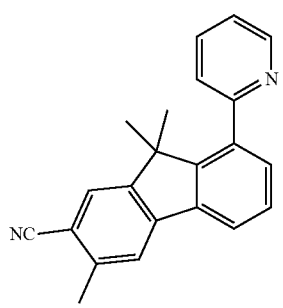
Compound 85
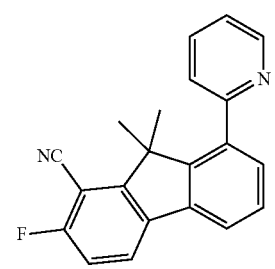
Compound 86
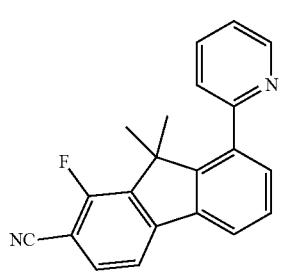
Compound 87
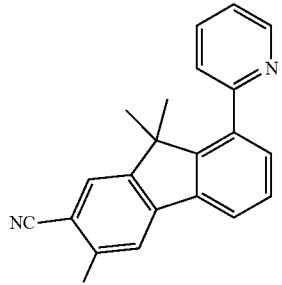
Compound 88
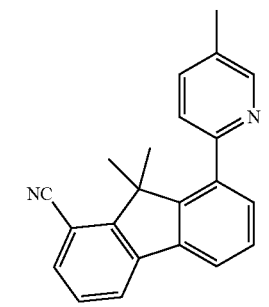

-continued

Compound 89

Compound 90

Compound 91

Compound 92

Compound 93

Compound 94

Compound 95

Compound 96

Compound 97

Compound 98

-continued

Compound 99

Compound 100

Compound 101

Compound 102

Compound 103

-continued

Compound 104

Compound 105

Compound 106

Compound 107

Compound 108

Compound 109
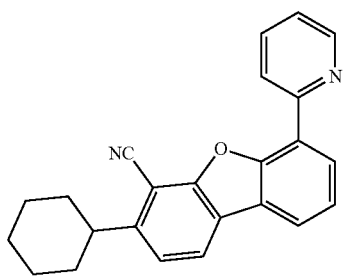
Compound 110
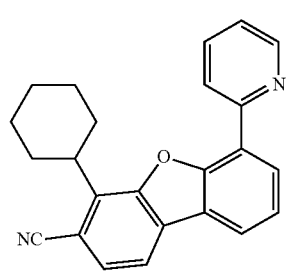
Compound 111
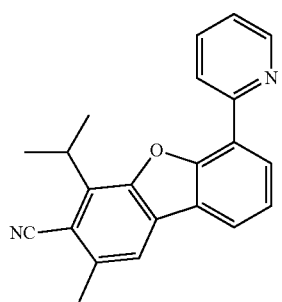
Compound 112
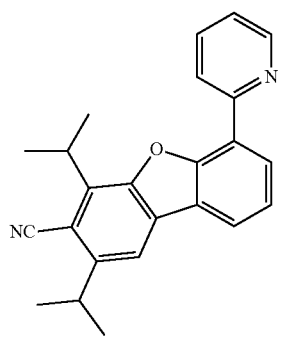
Compound 113
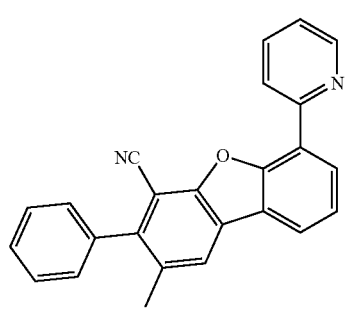
Compound 114
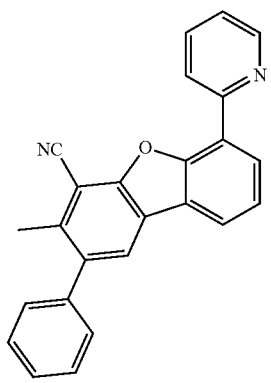
Compound 115
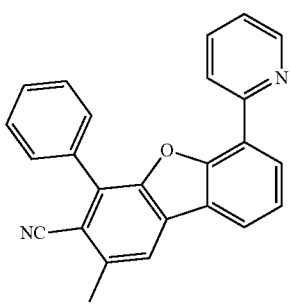
Compound 116
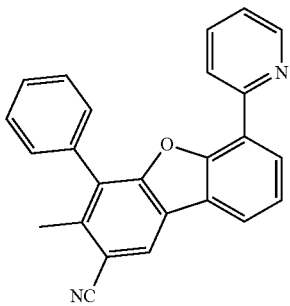
Compound 117
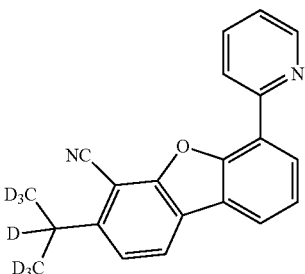
Compound 118
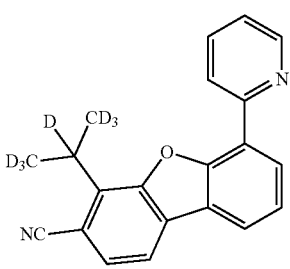

Compound 119
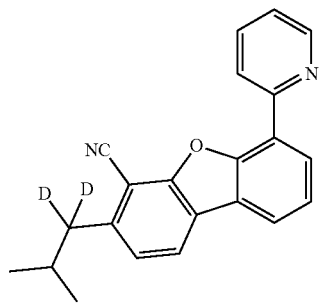
Compound 120
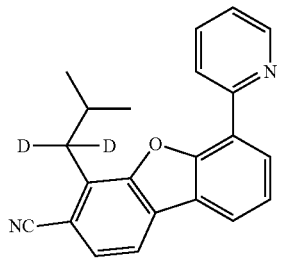
Compound 121
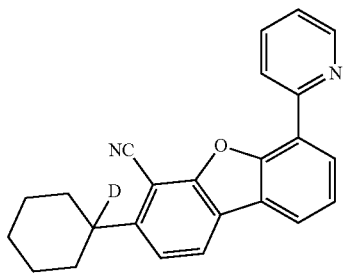
Compound 122
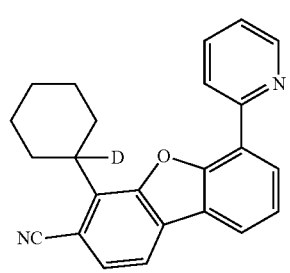
Compound 123
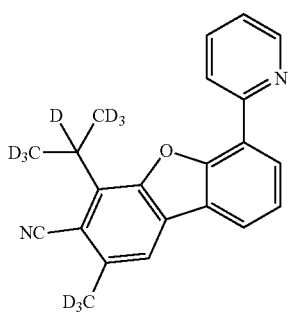
Compound 124
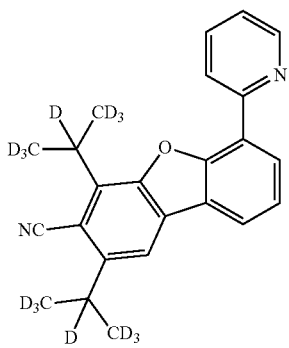
Compound 125
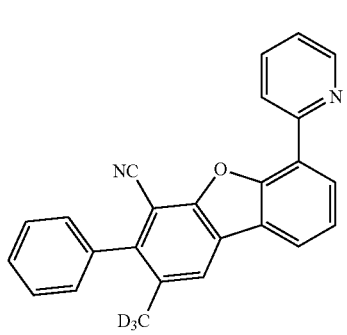
Compound 126
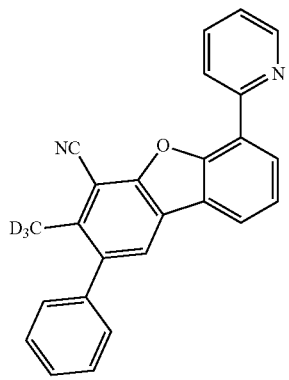
Compound 127
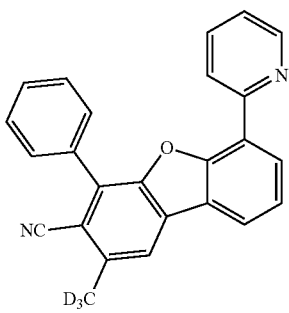

Compound 128
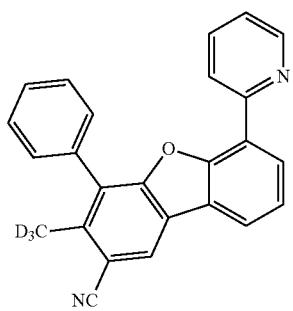

Compound 129
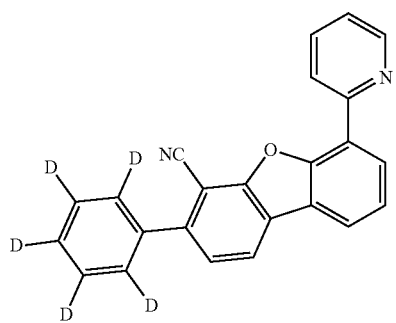

Compound 130
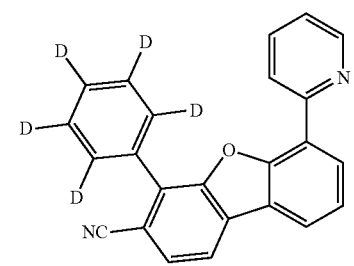

Compound 131
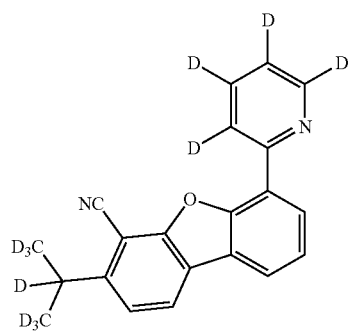

Compound 132
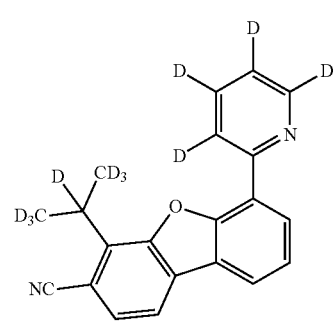

Compound 133
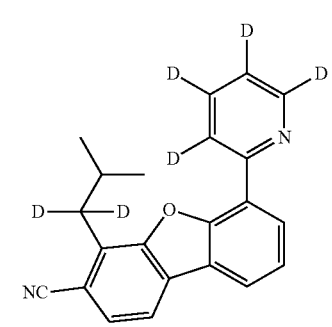

Compound 134
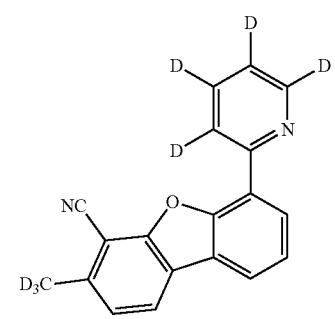

Compound 135
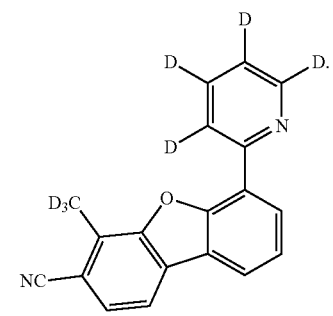

Compound 136
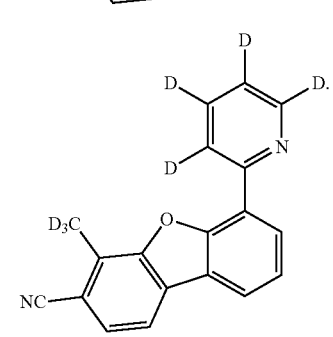

15. An electroluminescent device comprising:
an anode,
a cathode, and
an organic layer disposed between the anode and the cathode, wherein the organic layer includes the metal complex according to claim 1.

16. The electroluminescent device according to claim 15, wherein the organic layer is a light emitting layer, and the metal complex is a light emitting material.

17. The electroluminescent device according to claim 16, wherein the organic layer further comprises a host material; or wherein the organic layer contains at least two host materials.

18. The electroluminescent device according to claim 17, wherein the host material comprises at least one chemical group selected from the group consisting of benzene, biphenyl, pyridine, pyrimidine, triazine, carbazole, azacarbazole, indolocarbazole, dibenzothiophene, azadibenzothiophen, dibenzofuran, azadibenzofuran, dibenzoselenophene, azadibenzoselenophene, triphenylene, azatriphenylene, fluorene, silicon-fluorene, naphthalene, quinoline, isoquinoline, quinazoline, quinoxaline, phenanthrene, azaphenanthrene, and combinations thereof.

19. The electroluminescent device according to claim 15, wherein the electroluminescent device is incorporated into a device selected from the group consisting of a consumption product, an electronic component module, an organic light-emitting device and a lighting panel.

20. A compound formulation comprising the metal complex according to claim 1.

21. The metal complex according to claim 5, when $R_{11}$ and $R_{14}$ are both hydrogen, $R_{12}$ and $R_{13}$ are each independently selected from the group consisting of hydrogen, deuterium, halogen, a substituted or unsubstituted alkyl group having 1-20 carbon atoms, a substituted or unsubstituted heteroalkyl group having 1-20 carbon atoms, a substituted or unsubstituted alkoxy group having 1-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof, and the sum of carbon atoms in $R_{12}$ and $R_{13}$ is less than or equal to 1; alternatively, when at least one of $R_{11}$ and $R_{14}$ is not hydrogen, $R_{12}$ and $R_{13}$ are each independently selected from the group consisting of hydrogen, deuterium, halogen, a substituted or unsubstituted alkyl group having 1-20 carbon atoms, a substituted or unsubstituted cycloalkyl group having 3-20 ring carbon atoms, a substituted or unsubstituted heteroalkyl group having 1-20 carbon atoms, a substituted or unsubstituted arylalkyl group having 7-30 carbon atoms, a substituted or unsubstituted alkoxy group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amino group having 0-20 carbon atoms, an acyl group, a carbonyl group, a carboxylic acid group, an ester group, a cyano group, an isocyano group, thioalkyl, sulfinyl, sulfonyl, phosphino, and combinations thereof.

22. The metal complex according to claim 9, wherein the hydrogen on the aryl group in the $L_a$ can be partially or fully deuterated; or the hydrogen on the alkyl group in the $L_a$ may be partially or fully deuterated.

* * * * *